US010675267B2

(12) United States Patent
Jamieson et al.

(10) Patent No.: US 10,675,267 B2
(45) Date of Patent: Jun. 9, 2020

(54) METHODS FOR DETECTION AND ERADICATION OF MYELOID LEUKEMIA STEM CELLS

(71) Applicant: The Regents Of The University Of California, San Francisco, CA (US)

(72) Inventors: Catriona H.m. Jamieson, La Jolla, CA (US); Leslie C. Robertson, La Jolla, CA (US); Larisa Balaian, San Diego, CA (US); James J. La Clair, San Diego, CA (US); Reymundo Villa, San Mateo, CA (US); Heather Leu, Walnut, CA (US); Nathaniel Delos Santos, San Diego, CA (US); Michael D. Burkart, La Jolla, CA (US)

(73) Assignee: The Regents Of The University Of California, Oakland, CA (US)

( * ) Notice: Subject to any disclaimer, the term of this patent is extended or adjusted under 35 U.S.C. 154(b) by 0 days.

(21) Appl. No.: 15/761,983

(22) PCT Filed: Sep. 23, 2016

(86) PCT No.: PCT/US2016/053575
§ 371 (c)(1),
(2) Date: Mar. 21, 2018

(87) PCT Pub. No.: WO2017/053887
PCT Pub. Date: Mar. 30, 2017

(65) Prior Publication Data
US 2018/0296524 A1    Oct. 18, 2018

Related U.S. Application Data

(60) Provisional application No. 62/222,421, filed on Sep. 23, 2015, provisional application No. 62/232,414, filed on Sep. 24, 2015.

(51) Int. Cl.
| | | |
|---|---|---|
| *A61K 31/365* | (2006.01) |
| *G01N 33/574* | (2006.01) |
| *A61P 35/02* | (2006.01) |
| *C12N 5/095* | (2010.01) |
| *C12Q 1/6886* | (2018.01) |

(52) U.S. Cl.
CPC ............ *A61K 31/365* (2013.01); *A61P 35/02* (2018.01); *C12N 5/0695* (2013.01); *C12Q 1/6886* (2013.01); *G01N 33/57484* (2013.01); *C12N 2501/999* (2013.01); *G01N 2333/70585* (2013.01); *G01N 2333/912* (2013.01)

(58) Field of Classification Search
CPC . A61K 31/365; A61P 35/02; C12N 2501/999; C12N 5/0695; C12Q 1/6886; G01N 2333/70585; G01N 2333/912; G01N 33/57484
See application file for complete search history.

(56) References Cited

FOREIGN PATENT DOCUMENTS

WO    WO 2013/148324    * 10/2013

OTHER PUBLICATIONS

UC San Diego, https://techtransfer.universityofcalifornia.edu/NCD/28845.html, 2016 (Year: 2016).*
Villa et al. (J Med Chem Sep. 2013, 12, 56, 17, p. 1-19) (Year: 2013).*
Advances in understanding genetic changes in Cancer (Research Briefing, Policy Institute of Medicine, National Academy Press, 1992). (Year: 1992).*
Balaian, L. et al. (Dec. 5, 2013). "A Highly Selective SF3B1-Targeted Splicing Reduces Human CD34+ Cell Survival and Self-Renewal in Acute Myeloid Leukemia," *Blood* 122(21):Abstract No. 1653. 5 pages.
Kashyap. M.K. et al. (Jul. 2015, e-published Apr. 10, 2015). "Targeting the spliceosome in chronic lymphocytic leukemia with the macrolides FD-895 and pladienolide-B," *Haematologica* 100(7):945-954.
International Search Report dated Feb. 3, 2017, for PCT Application No. PCT/US2016/053575, filed Sep. 23, 2016, 6 pages.
Written Opinion dated Feb. 3, 2017, for PCT Application No. PCT/US2016/053575, filed Sep. 23, 2016, 7 pages.

* cited by examiner

*Primary Examiner* — Umamaheswari Ramachandran
(74) *Attorney, Agent, or Firm* — Edward D. Grieff; Mintz, Levin, Cohn, Ferris, Glovsky and Popeo, P.C.

(57)    ABSTRACT

There are provided, inter alia, methods and compositions for diagnosis and treatment of acute myeloid leukemia (AML), secondary acute myeloid leukemia (sAML), and age-related diseases.

17 Claims, 83 Drawing Sheets
Specification includes a Sequence Listing.

FIGF. 4G

Normal BM

AML-41

▲ sAML, p=0.0023
■ de novo AML, p=0.0026

Primary Transplant

Serial Transplant
BM

Spleen

FIG. 11D

| transcript_id | transcript_name | L2FC | ABS L2FC | PVAL | QVAL | Volcano Vector |
|---|---|---|---|---|---|---|
| ENST00000486554 | TSC22D3-006 | 2.847 | 2.847 | 0.000 | 0.039 | 4.591 |
| ENST00000248673 | ZFP36-201 | 2.842 | 2.842 | 0.000 | 0.041 | 4.363 |
| ENST00000586113 | FOSB-009 | 2.744 | 2.744 | 0.000 | 0.039 | 4.672 |
| ENST00000343677 | HIST1H1C-001 | 2.183 | 2.183 | 0.000 | 0.039 | 4.129 |
| ENST00000555242 | FOS-008 | 2.031 | 2.031 | 0.000 | 0.039 | 4.029 |
| ENST00000592811 | FOSB-008 | 1.985 | 1.985 | 0.000 | 0.039 | 4.090 |
| ENST00000528443 | TOR1AIP1-001 | 1.564 | 1.564 | 0.000 | 0.039 | 3.785 |
| ENST00000554617 | FOS-005 | 1.390 | 1.390 | 0.001 | 0.044 | 3.451 |
| ENST00000499732 | NEAT1-002 | 1.297 | 1.297 | 0.001 | 0.044 | 3.411 |
| ENST00000379953 | LY86-001 | -1.112 | 1.112 | 0.000 | 0.039 | 3.538 |
| ENST00000495215 | TRNAU1AP-008 | -1.327 | 1.327 | 0.000 | 0.039 | 3.723 |
| ENST00000354291 | DDX55-012 | -1.363 | 1.363 | 0.000 | 0.039 | 4.158 |
| ENST00000429859 | RP4-717I23.3-011 | -1.414 | 1.414 | 0.000 | 0.036 | 4.812 |
| ENST00000375972 | YME1L1-201 | -1.423 | 1.423 | 0.000 | 0.039 | 3.671 |
| ENST00000462189 | MOGS-004 | -1.448 | 1.448 | 0.001 | 0.047 | 3.425 |
| ENST00000481007 | LYPLAL1-012 | -1.477 | 1.477 | 0.000 | 0.039 | 4.029 |
| ENST00000359301 | ZC3H14-201 | -1.489 | 1.489 | 0.000 | 0.039 | 3.698 |
| ENST00000607660 | INTS10-019 | -1.494 | 1.494 | 0.000 | 0.039 | 3.882 |
| ENST00000569770 | MBTPS1-015 | -1.495 | 1.495 | 0.001 | 0.041 | 3.554 |
| ENST00000506789 | CDK7-010 | -1.509 | 1.509 | 0.001 | 0.041 | 3.595 |
| ENST00000561855 | MAZ-012 | -1.690 | 1.690 | 0.000 | 0.039 | 4.077 |
| ENST00000447713 | ANKRD44-012 | -1.956 | 1.956 | 0.000 | 0.039 | 4.019 |
| ENST00000447740 | CARD8-204 | -2.212 | 2.212 | 0.001 | 0.041 | 3.913 |
| ENST00000552606 | CCDC59-005 | -2.341 | 2.341 | 0.001 | 0.041 | 3.995 |

FIG. 11E

| transcript_id (Ensembl GRCh37) | transcript_name | L2FC | ABS L2FC | PVAL | QVAL | Volcano Vector |
|---|---|---|---|---|---|---|
| ENST00000365645 | VTRNA1-3-201 | 4.223 | 4.223 | 0.003 | 0.032 | 4.912 |
| ENST00000364931 | RNU5E-4P-201 | 3.797 | 3.797 | 0.003 | 0.030 | 4.586 |
| ENST00000307365 | DDIT4-001 | 3.615 | 3.615 | 0.011 | 0.046 | 4.112 |
| ENST00000242152 | NPY-001 | 3.535 | 3.535 | 0.008 | 0.043 | 4.115 |
| ENST00000314332 | HIST1H2BC-003 | 3.449 | 3.449 | 0.002 | 0.029 | 4.372 |
| ENST00000462639 | SAT1-007 | 3.393 | 3.393 | 0.002 | 0.028 | 4.372 |
| ENST00000548363 | TUBA1A-015 | 3.316 | 3.316 | 0.009 | 0.044 | 3.906 |
| ENST00000244601 | HIST1H2BG-001 | 3.168 | 3.168 | 0.001 | 0.028 | 4.552 |
| ENST00000303910 | HIST1H2AE-001 | 3.053 | 3.053 | 0.001 | 0.028 | 4.362 |
| ENST00000508487 | CXCL2-001 | 3.042 | 3.042 | 0.002 | 0.030 | 4.011 |
| ENST00000379251 | SAT1-004 | 2.957 | 2.957 | 0.002 | 0.028 | 4.062 |
| ENST00000588696 | SEC14L1-007 | 2.884 | 2.884 | 0.012 | 0.048 | 3.459 |
| ENST00000248673 | ZFP36-201 | 2.861 | 2.861 | 0.008 | 0.043 | 3.544 |
| ENST00000396984 | HIST1H2BC-002 | 2.798 | 2.798 | 0.002 | 0.028 | 3.962 |
| ENST00000474223 | SAT1-006 | 2.698 | 2.698 | 0.004 | 0.033 | 3.590 |
| ENST00000365574 | RNU5E-6P-201 | 2.696 | 2.696 | 0.008 | 0.044 | 3.400 |
| ENST00000356476 | HIST1H3D-001 | 2.616 | 2.616 | 0.001 | 0.028 | 3.899 |
| ENST00000534719 | FTH1-009 | 2.602 | 2.602 | 0.005 | 0.034 | 3.465 |
| ENST00000365626 | RNVU1-20-201 | 2.555 | 2.555 | 0.007 | 0.040 | 3.350 |
| ENST00000364688 | RNVU1-6-201 | 2.522 | 2.522 | 0.004 | 0.032 | 3.506 |
| ENST00000602277 | RP6-99M1.3-001 | 2.389 | 2.389 | 0.003 | 0.032 | 3.456 |
| ENST00000228434 | CD69-001 | 2.387 | 2.387 | 0.001 | 0.028 | 3.918 |
| ENST00000377777 | HIST1H2BD-002 | 2.341 | 2.341 | 0.002 | 0.028 | 3.661 |
| ENST00000607315 | RP11-51J9.5-001 | 2.286 | 2.286 | 0.004 | 0.033 | 3.314 |
| ENST00000379253 | SAT1-003 | 2.280 | 2.280 | 0.010 | 0.044 | 3.043 |
| ENST00000608684 | RP11-386I14.4-001 | 2.218 | 2.218 | 0.000 | 0.024 | 4.142 |
| ENST00000416624 | CD69-002 | 2.201 | 2.201 | 0.000 | 0.028 | 3.984 |
| ENST00000536709 | CD69-003 | 2.190 | 2.190 | 0.000 | 0.016 | 4.450 |
| ENST00000370986 | GADD45A-001 | 2.181 | 2.181 | 0.006 | 0.039 | 3.096 |
| ENST00000495813 | SLC2A3-002 | 2.150 | 2.150 | 0.005 | 0.034 | 3.162 |
| ENST00000369155 | HIST2H2BE-001 | 2.136 | 2.136 | 0.001 | 0.028 | 3.662 |
| ENST00000289577 | TMED4-005 | 2.115 | 2.115 | 0.000 | 0.020 | 4.203 |
| ENST00000411315 | RNU2-64P-201 | 2.096 | 2.096 | 0.010 | 0.045 | 2.896 |
| ENST00000367577 | IER5-001 | 2.092 | 2.092 | 0.011 | 0.045 | 2.879 |
| ENST00000589949 | H3F3B-008 | 2.068 | 2.068 | 0.004 | 0.032 | 3.204 |
| ENST00000239223 | DUSP1-001 | 2.064 | 2.064 | 0.001 | 0.028 | 3.579 |
| ENST00000520420 | CREBRF-004 | 2.032 | 2.032 | 0.009 | 0.044 | 2.872 |
| ENST00000601309 | HNRNPUL1-019 | 2.018 | 2.018 | 0.010 | 0.045 | 2.838 |
| ENST00000509150 | ATP2C1-023 | 2.011 | 2.011 | 0.009 | 0.044 | 2.877 |
| ENST00000357647 | HIST1H3A-001 | 1.958 | 1.958 | 0.001 | 0.028 | 3.694 |

FIG. 11E - cont.

| transcript_id (Ensembl GRCh37) | transcript_name | L2FC | ABS L2FC | PVAL | QVAL | Volcano Vector |
|---|---|---|---|---|---|---|
| ENST00000343677 | HIST1H1C-001 | 1.950 | 1.950 | 0.009 | 0.044 | 2.813 |
| ENST00000482091 | IDI1-001 | 1.930 | 1.930 | 0.007 | 0.040 | 2.902 |
| ENST00000507022 | MRPS36-006 | 1.927 | 1.927 | 0.004 | 0.032 | 3.120 |
| ENST00000369163 | HIST1H3H-001 | 1.891 | 1.891 | 0.005 | 0.034 | 2.972 |
| ENST00000515833 | MATR3-036 | 1.797 | 1.797 | 0.003 | 0.030 | 3.150 |
| ENST00000511207 | CCNH-009 | 1.795 | 1.795 | 0.002 | 0.029 | 3.212 |
| ENST00000409769 | CLK1-005 | 1.780 | 1.780 | 0.004 | 0.033 | 2.990 |
| ENST00000560274 | RPLP1-006 | 1.779 | 1.779 | 0.001 | 0.028 | 3.411 |
| ENST00000377364 | HIST1H4B-001 | 1.757 | 1.757 | 0.001 | 0.028 | 3.504 |
| ENST00000534470 | EIF4G2-032 | 1.739 | 1.739 | 0.002 | 0.030 | 3.132 |
| ENST00000421512 | TBP-004 | 1.736 | 1.736 | 0.002 | 0.029 | 3.205 |
| ENST00000409685 | FAM124B-003 | 1.722 | 1.722 | 0.006 | 0.039 | 2.801 |
| ENST00000545027 | ETV6-004 | 1.713 | 1.713 | 0.004 | 0.032 | 2.986 |
| ENST00000377831 | HIST1H3D-201 | 1.616 | 1.616 | 0.004 | 0.033 | 2.857 |
| ENST00000438169 | KRR1-003 | 1.575 | 1.575 | 0.005 | 0.034 | 2.807 |
| ENST00000459299 | SNORD13-201 | 1.568 | 1.568 | 0.005 | 0.034 | 2.816 |
| ENST00000369159 | HIST2H2AA4-001 | 1.527 | 1.527 | 0.001 | 0.028 | 3.351 |
| ENST00000476634 | SLC2A3-004 | 1.484 | 1.484 | 0.002 | 0.028 | 3.173 |
| ENST00000486554 | TSC22D3-006 | 1.483 | 1.483 | 0.000 | 0.024 | 3.774 |
| ENST00000590335 | FOSB-006 | 1.473 | 1.473 | 0.003 | 0.031 | 2.936 |
| ENST00000377745 | HIST1H4F-001 | 1.457 | 1.457 | 0.000 | 0.016 | 4.163 |
| ENST00000554988 | RPPH1-001 | 1.435 | 1.435 | 0.002 | 0.028 | 3.106 |
| ENST00000243806 | FAM124B-001 | 1.421 | 1.421 | 0.001 | 0.028 | 3.179 |
| ENST00000511865 | REEP5-006 | 1.411 | 1.411 | 0.002 | 0.029 | 3.046 |
| ENST00000549490 | UBE2N-005 | 1.391 | 1.391 | 0.001 | 0.028 | 3.396 |
| ENST00000565108 | CMC2-021 | 1.377 | 1.377 | 0.002 | 0.028 | 3.137 |
| ENST00000377401 | HIST1H2BL-001 | 1.339 | 1.339 | 0.002 | 0.029 | 2.993 |
| ENST00000321356 | CLK1-001 | 1.334 | 1.334 | 0.001 | 0.028 | 3.183 |
| ENST00000484921 | ARL6IP5-006 | 1.285 | 1.285 | 0.002 | 0.028 | 3.051 |
| ENST00000520618 | SNX16-012 | 1.260 | 1.260 | 0.000 | 0.016 | 4.396 |
| ENST00000541694 | AC084018.1-011 | 1.228 | 1.228 | 0.001 | 0.028 | 3.268 |
| ENST00000601837 | EID2B-002 | 1.197 | 1.197 | 0.002 | 0.028 | 3.031 |
| ENST00000282388 | ZFP36L2-001 | 1.193 | 1.193 | 0.002 | 0.029 | 2.923 |
| ENST00000465085 | ABCD4-017 | 1.175 | 1.175 | 0.002 | 0.030 | 2.857 |
| ENST00000453677 | KMT2E-AS1-001 | 1.168 | 1.168 | 0.003 | 0.030 | 2.833 |
| ENST00000596355 | RP11-315I20.1-018 | 1.163 | 1.163 | 0.001 | 0.028 | 3.066 |
| ENST00000460600 | PNISR-004 | 1.157 | 1.157 | 0.000 | 0.020 | 3.833 |
| ENST00000243189 | C1orf63-001 | 1.148 | 1.148 | 0.003 | 0.030 | 2.825 |
| ENST00000517805 | RPL30-012 | 1.145 | 1.145 | 0.002 | 0.028 | 2.979 |
| ENST00000202017 | PDRG1-001 | 1.141 | 1.141 | 0.001 | 0.028 | 3.161 |

FIG. 11E - cont.

| transcript_id (Ensembl GRCh37) | transcript_name | L2FC | ABS L2FC | PVAL | QVAL | Volcano Vector |
|---|---|---|---|---|---|---|
| ENST00000431446 | RBMX-003 | 1.019 | 1.019 | 0.001 | 0.028 | 3.301 |
| ENST00000453018 | HGF-006 | 1.013 | 1.013 | 0.000 | 0.016 | 4.043 |
| ENST00000521889 | C8orf44-005 | 1.001 | 1.001 | 0.002 | 0.029 | 2.838 |
| ENST00000423368 | CNOT4-001 | -1.023 | 1.023 | 0.000 | 0.027 | 3.518 |
| ENST00000580571 | MIF4GD-005 | -1.025 | 1.025 | 0.001 | 0.028 | 3.407 |
| ENST00000462069 | C3orf14-004 | -1.032 | 1.032 | 0.000 | 0.016 | 4.417 |
| ENST00000574128 | MED31-004 | -1.107 | 1.107 | 0.003 | 0.030 | 2.827 |
| ENST00000391742 | LAIR1-001 | -1.184 | 1.184 | 0.001 | 0.028 | 3.129 |
| ENST00000361785 | RNF13-002 | -1.219 | 1.219 | 0.002 | 0.029 | 2.910 |
| ENST00000367367 | PTPRC-005 | -1.290 | 1.290 | 0.001 | 0.028 | 3.334 |
| ENST00000376557 | PRR3-002 | -1.374 | 1.374 | 0.003 | 0.032 | 2.822 |
| ENST00000355499 | YY1AP1-034 | -1.446 | 1.446 | 0.002 | 0.028 | 3.170 |
| ENST00000420503 | LINC00339-003 | -1.524 | 1.524 | 0.001 | 0.028 | 3.525 |
| ENST00000509081 | RASGEF1B-002 | -1.534 | 1.534 | 0.000 | 0.016 | 4.156 |
| ENST00000479041 | AOX3P-002 | -1.589 | 1.589 | 0.003 | 0.032 | 2.927 |
| ENST00000436911 | TRGC2-001 | -1.625 | 1.625 | 0.005 | 0.034 | 2.827 |
| ENST00000243347 | TNFAIP6-001 | -1.680 | 1.680 | 0.002 | 0.028 | 3.214 |
| ENST00000325074 | RUNX1-201 | -1.970 | 1.970 | 0.005 | 0.034 | 3.015 |
| ENST00000394223 | NDUFC1-004 | -2.010 | 2.010 | 0.003 | 0.032 | 3.222 |
| ENST00000410457 | RNU2-28P-201 | -2.226 | 2.226 | 0.001 | 0.028 | 3.658 |

FIG. 11F

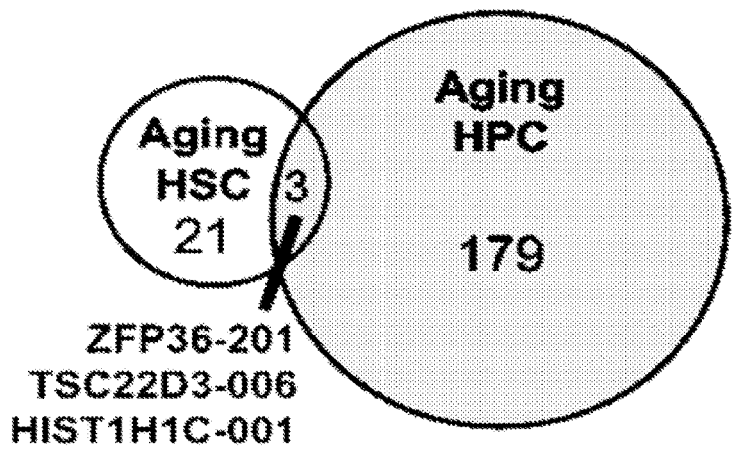

Common differentially expressed isoforms in human HSPC aging (FDR<5%)

Aging HSC 21
Aging HPC 179
3
ZFP36-201
TSC22D3-006
HIST1H1C-001

FIG. 12D

| transcript_id (Ensembl GRCh37) | transcript_name | L2FC | ABS L2FC | PVAL | QVAL | Volcano Vector |
|---|---|---|---|---|---|---|
| ENST00000586925 | FXYD5-009 | 4.439 | 4.439 | 0.000 | 0.005 | 5.559 |
| ENST00000525690 | RPS3-023 | 4.299 | 4.299 | 0.001 | 0.007 | 5.170 |
| ENST00000485708 | RPS24-002 | 4.065 | 4.065 | 0.001 | 0.007 | 4.973 |
| ENST00000547479 | NAP1L1-018 | 4.018 | 4.018 | 0.000 | 0.001 | 6.303 |
| ENST00000436911 | TRGC2-001 | 3.869 | 3.869 | 0.001 | 0.007 | 4.816 |
| ENST00000528086 | CD44-012 | 3.815 | 3.815 | 0.003 | 0.011 | 4.557 |
| ENST00000570382 | ACTG1-014 | 3.278 | 3.278 | 0.000 | 0.005 | 4.688 |
| ENST00000368811 | S100A10-001 | 3.071 | 3.071 | 0.000 | 0.004 | 4.652 |
| ENST00000541549 | EIF3A-201 | 2.910 | 2.910 | 0.000 | 0.003 | 5.009 |
| ENST00000576544 | ACTG1-006 | 2.895 | 2.895 | 0.001 | 0.006 | 4.221 |
| ENST00000491410 | NRD1-005 | 2.855 | 2.855 | 0.000 | 0.000 | 6.840 |
| ENST00000302347 | ITGB2-201 | 2.848 | 2.848 | 0.001 | 0.005 | 4.347 |
| ENST00000416215 | PTPN6-003 | 2.623 | 2.623 | 0.000 | 0.003 | 4.915 |
| ENST00000589517 | TYROBP-002 | 2.616 | 2.616 | 0.000 | 0.005 | 4.219 |
| ENST00000252725 | ARPC1B-001 | 2.269 | 2.269 | 0.000 | 0.004 | 4.290 |
| ENST00000300060 | ANPEP-001 | 2.212 | 2.212 | 0.000 | 0.004 | 4.265 |
| ENST00000587561 | LMAN1-005 | 2.136 | 2.136 | 0.000 | 0.003 | 4.595 |
| ENST00000415231 | TAC3-010 | 2.052 | 2.052 | 0.000 | 0.000 | 7.670 |
| ENST00000568406 | C1orf228-020 | 2.034 | 2.034 | 0.000 | 0.004 | 4.371 |
| ENST00000541365 | CEP57-011 | 2.019 | 2.019 | 0.000 | 0.003 | 4.597 |
| ENST00000305533 | TWF2-001 | 2.013 | 2.013 | 0.000 | 0.004 | 4.226 |
| ENST00000572457 | ARRB2-003 | 1.940 | 1.940 | 0.000 | 0.003 | 4.514 |
| ENST00000420218 | PTK2B-202 | 1.912 | 1.912 | 0.000 | 0.003 | 4.536 |
| ENST00000427321 | C1orf228-011 | 1.863 | 1.863 | 0.000 | 0.003 | 4.539 |
| ENST00000502635 | DCP2-008 | 1.807 | 1.807 | 0.000 | 0.004 | 4.235 |
| ENST00000488324 | PPP1R18-003 | 1.769 | 1.769 | 0.000 | 0.003 | 4.469 |
| ENST00000472498 | RPL37P2-001 | 1.762 | 1.762 | 0.000 | 0.000 | 6.418 |
| ENST00000319511 | TMUB2-002 | 1.723 | 1.723 | 0.000 | 0.004 | 4.148 |
| ENST00000326005 | OAZ2-001 | 1.718 | 1.718 | 0.000 | 0.003 | 4.459 |
| ENST00000346049 | PTK2B-001 | 1.663 | 1.663 | 0.000 | 0.004 | 4.134 |
| ENST00000441658 | RP11-77O7.1-001 | 1.624 | 1.624 | 0.000 | 0.002 | 4.691 |
| ENST00000511155 | XPC-007 | 1.619 | 1.619 | 0.000 | 0.004 | 4.224 |
| ENST00000544691 | SDR39U1-003 | 1.551 | 1.551 | 0.000 | 0.002 | 4.764 |
| ENST00000480624 | MACF1-014 | 1.504 | 1.504 | 0.000 | 0.002 | 5.006 |
| ENST00000312423 | SWSAP1-001 | 1.443 | 1.443 | 0.000 | 0.003 | 4.404 |
| ENST00000563576 | MGA-002 | 1.443 | 1.443 | 0.000 | 0.003 | 4.327 |
| ENST00000485803 | FHL3-002 | 1.438 | 1.438 | 0.000 | 0.001 | 5.726 |
| ENST00000496289 | ZC3H15-005 | 1.404 | 1.404 | 0.000 | 0.004 | 4.157 |
| ENST00000375040 | GPSM3-001 | 1.380 | 1.380 | 0.000 | 0.002 | 4.797 |
| ENST00000459726 | RBM28-003 | 1.378 | 1.378 | 0.000 | 0.002 | 4.802 |

FIG. 12D - cont.

| transcript_id (Ensembl GRCh37) | transcript_name | L2FC | ABS L2FC | PVAL | QVAL | Volcano Vector |
|---|---|---|---|---|---|---|
| ENST00000584294 | LPIN2-002 | 1.372 | 1.372 | 0.000 | 0.001 | 5.720 |
| ENST00000424649 | PXN-002 | 1.292 | 1.292 | 0.000 | 0.000 | 6.531 |
| ENST00000430629 | WASF2-001 | 1.270 | 1.270 | 0.000 | 0.001 | 5.366 |
| ENST00000293831 | EIF4A1-001 | 1.175 | 1.175 | 0.000 | 0.003 | 4.171 |
| ENST00000496499 | RN7SL182P-201 | 1.161 | 1.161 | 0.000 | 0.001 | 5.470 |
| ENST00000600628 | SSBP4-008 | 1.120 | 1.120 | 0.000 | 0.001 | 5.192 |
| ENST00000418929 | PRR12-001 | 1.084 | 1.084 | 0.000 | 0.002 | 4.793 |
| ENST00000450863 | GOLGA4-004 | 1.063 | 1.063 | 0.000 | 0.001 | 5.577 |
| ENST00000330736 | ANKRD11-011 | 1.021 | 1.021 | 0.000 | 0.003 | 4.175 |
| ENST00000357508 | C1orf228-005 | 1.017 | 1.017 | 0.000 | 0.001 | 5.410 |
| ENST00000550146 | TMEM106C-007 | -1.061 | 1.061 | 0.000 | 0.002 | 4.600 |
| ENST00000498704 | RABL5-007 | -1.087 | 1.087 | 0.000 | 0.003 | 4.363 |
| ENST00000532152 | EIF4G2-022 | -1.110 | 1.110 | 0.000 | 0.003 | 4.331 |
| ENST00000521273 | HNRNPA1P7-001 | -1.119 | 1.119 | 0.000 | 0.001 | 5.815 |
| ENST00000546989 | RPLP0-008 | -1.257 | 1.257 | 0.000 | 0.003 | 4.389 |
| ENST00000452673 | CANX-005 | -1.316 | 1.316 | 0.000 | 0.002 | 4.617 |
| ENST00000548355 | TMEM106C-020 | -1.316 | 1.316 | 0.000 | 0.003 | 4.345 |
| ENST00000374594 | CTNNAL1-003 | -1.319 | 1.319 | 0.000 | 0.003 | 4.212 |
| ENST00000502784 | NPM1P27-001 | -1.366 | 1.366 | 0.000 | 0.003 | 4.175 |
| ENST00000522304 | NCAPH2-016 | -1.399 | 1.399 | 0.000 | 0.003 | 4.204 |
| ENST00000461768 | SRRM1-017 | -1.410 | 1.410 | 0.000 | 0.003 | 4.261 |
| ENST00000600519 | FAM129C-007 | -1.515 | 1.515 | 0.000 | 0.003 | 4.268 |
| ENST00000405805 | HMGB1-012 | -1.554 | 1.554 | 0.000 | 0.004 | 4.175 |
| ENST00000258349 | RC3H1-201 | -1.588 | 1.588 | 0.000 | 0.003 | 4.414 |
| ENST00000282507 | UGT3A2-001 | -1.702 | 1.702 | 0.000 | 0.003 | 4.362 |
| ENST00000409290 | WIPF3-002 | -1.777 | 1.777 | 0.000 | 0.004 | 4.147 |
| ENST00000505636 | RP11-315A17.1-001 | -1.815 | 1.815 | 0.000 | 0.004 | 4.315 |
| ENST00000431467 | ING3-006 | -1.843 | 1.843 | 0.000 | 0.003 | 4.628 |
| ENST00000427726 | ING3-005 | -1.868 | 1.868 | 0.000 | 0.003 | 4.520 |
| ENST00000520990 | CA1-009 | -1.871 | 1.871 | 0.000 | 0.004 | 4.238 |
| ENST00000450948 | IGHV5-78-001 | -2.035 | 2.035 | 0.000 | 0.004 | 4.386 |
| ENST00000503828 | CAST-038 | -2.320 | 2.320 | 0.000 | 0.004 | 4.303 |
| ENST00000261769 | CDH1-001 | -2.359 | 2.359 | 0.000 | 0.002 | 5.210 |
| ENST00000339121 | ING3-002 | -2.360 | 2.360 | 0.000 | 0.002 | 5.103 |
| ENST00000284878 | CXADR-001 | -2.412 | 2.412 | 0.000 | 0.004 | 4.390 |
| ENST00000289448 | HMHB1-001 | -2.439 | 2.439 | 0.000 | 0.004 | 4.415 |
| ENST00000416501 | AC015987.2-201 | -2.465 | 2.465 | 0.000 | 0.001 | 5.488 |
| ENST00000323224 | TYMS-002 | -2.570 | 2.570 | 0.000 | 0.005 | 4.190 |
| ENST00000282388 | ZFP36L2-001 | -2.724 | 2.724 | 0.000 | 0.001 | 6.090 |
| ENST00000509259 | CAST-039 | -2.780 | 2.780 | 0.001 | 0.006 | 4.199 |

FIG. 12D - cont.

| transcript_id (Ensembl GRCh37) | transcript_name | L2FC | ABS L2FC | PVAL | QVAL | Volcano Vector |
|---|---|---|---|---|---|---|
| ENST00000302273 | VPREB1-002 | -2.817 | 2.817 | 0.001 | 0.006 | 4.235 |
| ENST00000360091 | EWSR1-019 | -2.827 | 2.827 | 0.000 | 0.004 | 4.550 |
| ENST00000420189 | FAM134A-004 | -2.830 | 2.830 | 0.000 | 0.005 | 4.369 |
| ENST00000430694 | AC096579.7-001 | -2.964 | 2.964 | 0.000 | 0.005 | 4.485 |
| ENST00000391248 | RNU1-78P-201 | -2.977 | 2.977 | 0.000 | 0.004 | 4.703 |
| ENST00000368868 | SELENBP1-001 | -3.017 | 3.017 | 0.000 | 0.002 | 5.577 |
| ENST00000335295 | HBB-001 | -3.091 | 3.091 | 0.002 | 0.008 | 4.157 |
| ENST00000313708 | EBF1-001 | -3.209 | 3.209 | 0.001 | 0.006 | 4.411 |
| ENST00000221804 | CLC-001 | -3.247 | 3.247 | 0.001 | 0.007 | 4.413 |
| ENST00000235382 | RGS2-001 | -3.298 | 3.298 | 0.001 | 0.007 | 4.430 |
| ENST00000397381 | UCA1-001 | -3.481 | 3.481 | 0.000 | 0.001 | 6.067 |
| ENST00000534180 | FTH1-002 | -3.547 | 3.547 | 0.002 | 0.008 | 4.515 |
| ENST00000302312 | AHSP-001 | -3.563 | 3.563 | 0.000 | 0.004 | 5.051 |
| ENST00000383907 | SNORA22-201 | -3.631 | 3.631 | 0.000 | 0.000 | 7.088 |
| ENST00000547798 | TMBIM6-006 | -4.629 | 4.629 | 0.000 | 0.002 | 6.381 |
| ENST00000242152 | NPY-001 | -4.888 | 4.888 | 0.001 | 0.006 | 5.780 |
| ENST00000367459 | RGS1-001 | -5.000 | 5.000 | 0.002 | 0.008 | 5.719 |
| ENST00000548925 | BLOC1S1-001 | -5.755 | 5.755 | 0.000 | 0.001 | 7.877 |
| ENST00000248948 | VPREB3-001 | -6.280 | 6.280 | 0.000 | 0.000 | 8.639 |
| ENST00000479563 | RPL14-003 | -7.357 | 7.357 | 0.000 | 0.005 | 8.135 |

FIG. 18A

| Sample Code | Gender | Age |
|---|---|---|
| Young-2130§ | M | 27 |
| Young-4018^* | M | 26 |
| Young-4040^ | M | 24 |
| Young-4066^* | M | 28 |
| Young-4188^ | M | 19 |
| Young-4215^ | F | 27 |
| Young-4218^ | M | 28 |
| Young-4259^ | M | 27 |
| Young-4279^ | M | 27 |
| Young-4532§ | M | 26 |
| Young-4698§ | F | 33 |
| Young-4742§ | F | 27 |
| Aged-368^§ | F | 61 |
| Aged-380^* | F | 65 |
| Aged-401^§ | F | 64 |
| Aged-402^* | F | 82 |
| Aged-410^§ | M | 66 |
| Aged-415^ | F | 66 |
| Aged-416^ | M | 62 |
| Aged-426^ | F | 61 |
| Aged-439§ | F | N/A (>60) |
| Aged-457§* | F | 77 |
| Aged-620§* | M | 68 |
| Aged-654§* | F | 61 |

FIG. 18B

| NAME | SIZE | NES | NOM p-val | FDR q-val |
|---|---|---|---|---|
| KEGG_OXIDATIVE_PHOSPHORYLATION | 106 | -2.18 | <0.001 | <0.001 |
| KEGG_HUNTINGTONS_DISEASE | 161 | -2.08 | <0.001 | 0.002 |
| KEGG_RIBOSOME | 86 | -1.96 | <0.001 | 0.006 |
| KEGG_DNA_REPLICATION | 36 | -1.94 | 0.002 | 0.007 |
| KEGG_PROTEASOME | 43 | -1.9 | <0.001 | 0.009 |

FIG. 18C

| NAME | SIZE | NES | NOM p-val | FDR q-val |
|---|---|---|---|---|
| KEGG_SYSTEMIC_LUPUS_ERYTHEMATOSUS | 132 | 2.978 | <0.001 | <0.001 |
| KEGG_MISMATCH_REPAIR | 23 | -2.14 | <0.001 | <0.001 |
| KEGG_HOMOLOGOUS_RECOMBINATION | 28 | -2.1 | <0.001 | <0.001 |
| KEGG_GLYCOSAMINOGLYCAN_BIOSYNTHESIS_HEPARAN_SULFATE | 26 | -2.01 | <0.001 | 0.001 |
| KEGG_AMINOACYL_TRNA_BIOSYNTHESIS | 41 | -1.87 | <0.001 | 0.009 |

FIG. 18D

| SYMBOL | LOG2((Average_Aged.Stem_FPKM+1)/(Average_Young.Stem_FPKM+1)) | PVAL |
|---|---|---|
| RP11-386I14.4 | 5.678 | 0.017 |
| ID1 | 5.613 | 0.040 |
| SOCS3 | 3.381 | 0.042 |
| ZFP36 | 3.113 | 0.002 |
| SOCS1 | 2.871 | 0.033 |
| CXCL2 | 2.871 | 0.004 |
| LINC-PINT | 2.730 | 0.048 |
| C10orf10 | 2.617 | 0.003 |
| EGR1 | 2.612 | 0.033 |
| ATF3 | 2.366 | 0.037 |
| RHOB | 2.314 | 0.005 |
| HIST1H2BC | 2.184 | 0.035 |
| HIST1H1C | 2.183 | 0.000 |
| JUNB | 2.159 | 0.001 |
| FOSB | 2.130 | 0.002 |
| TSC22D3 | 2.106 | 0.000 |
| JUN | 2.103 | 0.008 |
| HIST1H2BO | -2.205 | 0.048 |
| BRD2-IT1 | -2.604 | 0.026 |
| CLC | -2.836 | 0.039 |
| NDUFC2-KCTD14 | -4.318 | 0.007 |

FIG. 18E

| SYMBOL | LOG2((Average_Aged.Stem_FPKM+1)/(Average_Young.Stem_FPKM+1)) | PVAL |
|---|---|---|
| MT-TR | 6.890 | 0.026 |
| VTRNA1-3 | 4.223 | 0.003 |
| IL8 | 3.910 | 0.029 |
| RNU5E-4P | 3.797 | 0.003 |
| GADD45B | 3.669 | 0.026 |
| AL031602.1 | 3.667 | 0.025 |
| DDIT4 | 3.635 | 0.012 |
| IGHG1 | 3.620 | 0.038 |
| RNU6-33P | 3.592 | 0.025 |
| NPY | 3.551 | 0.007 |
| RGS16 | 3.545 | 0.014 |
| ID2 | 3.420 | 0.031 |
| RNU1-85P | 3.376 | 0.016 |
| RGS1 | 3.341 | 0.019 |
| RP11-1100L3.8 | 3.325 | 0.017 |
| HIST1H2BC | 3.279 | 0.001 |
| HIST1H2BG | 3.168 | 0.001 |
| CDKN1A | 3.058 | 0.032 |
| HIST1H2AE | 3.053 | 0.001 |
| TNFAIP3 | 2.987 | 0.030 |
| NR4A1 | 2.946 | 0.039 |
| ZFP36 | 2.890 | 0.016 |
| CXCL2 | 2.884 | 0.003 |
| GRASP | 2.872 | 0.036 |
| IGHA1 | 2.826 | 0.019 |
| TSC22D3 | 2.817 | 0.024 |
| C12orf79 | 2.787 | 0.043 |
| RNU2-2P | 2.741 | 0.037 |
| RNU5E-6P | 2.696 | 0.008 |
| RNU3P3 | 2.646 | 0.029 |
| RNU12 | 2.626 | 0.048 |
| RNA5SP464 | 2.613 | 0.016 |
| PER1 | 2.596 | 0.021 |
| NFKBIA | 2.572 | 0.020 |
| RNVU1-20 | 2.555 | 0.007 |
| SEC14L1 | 2.528 | 0.040 |
| HIST1H3D | 2.526 | 0.002 |
| RNVU1-6 | 2.522 | 0.004 |

FIG. 18E - cont.

| SYMBOL | LOG2((Average_Aged.Stem_FPKM+1)/(Average_Young.Stem_FPKM+1)) | PVAL |
|---|---|---|
| CTA-29F11.1 | 2.518 | 0.031 |
| RNU5B-1 | 2.459 | 0.013 |
| RNU5F-1 | 2.407 | 0.026 |
| SCARNA17 | 2.392 | 0.027 |
| RP6-99M1.3 | 2.389 | 0.003 |
| CD69 | 2.386 | 0.001 |
| CSRNP1 | 2.354 | 0.041 |
| RNU2-59P | 2.321 | 0.038 |
| LINC00910 | 2.314 | 0.032 |
| RP11-51J9.5 | 2.286 | 0.004 |
| ETV3 | 2.279 | 0.026 |
| SAT1 | 2.246 | 0.006 |
| SLC2A3 | 2.233 | 0.042 |
| RNU5A-1 | 2.232 | 0.034 |
| PHTF1 | 2.220 | 0.049 |
| RP11-386I14.4 | 2.218 | 0.000 |
| GADD45A | 2.163 | 0.007 |
| PLIN2 | 2.148 | 0.022 |
| HIST2H2BE | 2.136 | 0.001 |
| JUNB | 2.106 | 0.048 |
| RNU2-64P | 2.096 | 0.010 |
| IER5 | 2.092 | 0.011 |
| HIST1H2BD | 2.083 | 0.002 |
| DUSP1 | 2.064 | 0.001 |
| RNVU1-18 | 2.048 | 0.039 |
| ID1 | 2.015 | 0.033 |
| PIM2 | 2.012 | 0.038 |
| RNU2-28P | -2.226 | 0.001 |
| RP11-145M9.6 | -2.569 | 0.025 |
| MIR4425 | -5.098 | 0.025 |

FIG. 19A

| SYMBOL | LOG2((Average_Aged.Stem_FPKM+1)/(Average_Young.Stem_FPKM+1)) | PVAL |
|---|---|---|
| MIR1234 | 7.182 | 0.002 |
| SNORD105 | 5.853 | 0.037 |
| RNU6-125P | 4.206 | 0.031 |
| MEG3 | 3.929 | 0.043 |
| TRGC2 | 3.869 | 0.001 |
| RNU6-384P | 3.786 | 0.035 |
| TMEM176B | 3.762 | 0.004 |
| MIR221 | 3.253 | 0.031 |
| AC083862.1 | 3.244 | 0.039 |
| LY6E | 3.117 | 0.014 |
| MAMDC2 | 3.029 | 0.032 |
| AC008914.1 | 3.021 | 0.046 |
| RNU6-5P | 3.005 | 0.031 |
| C10orf54 | 2.972 | 0.001 |
| TYROBP | 2.952 | 0.001 |
| CEACAM4 | 2.940 | 0.016 |
| TSPAN2 | 2.905 | 0.014 |
| TRBVB | 2.861 | 0.026 |
| CCL5 | 2.820 | 0.048 |
| LPAR6 | 2.775 | 0.016 |
| CRIP1 | 2.738 | 0.002 |
| HLA-DRB5 | 2.725 | 0.018 |
| HCG9 | 2.710 | 0.042 |
| IL1RAP | 2.685 | 0.001 |
| S100A10 | 2.639 | 0.000 |
| RP11-38J22.6 | 2.635 | 0.004 |
| RP11-110G21.2 | 2.627 | 0.004 |
| AL512428.1 | 2.602 | 0.042 |
| PRSS21 | 2.595 | 0.040 |
| HCK | 2.540 | 0.000 |
| TRGC1 | 2.446 | 0.002 |
| NPM2 | 2.395 | 0.001 |
| SNORA70G | 2.366 | 0.002 |
| S100Z | 2.297 | 0.041 |
| MIF | 2.283 | 0.046 |
| TPPP3 | 2.271 | 0.005 |
| HGF | 2.269 | 0.020 |
| GNPDA1 | 2.249 | 0.027 |
| HPGD | 2.248 | 0.032 |

FIG. 19A - cont.

| | | |
|---|---|---|
| CALCRL | 2.231 | 0.003 |
| RAB5C | 2.217 | 0.015 |
| AC069200.1 | 2.200 | 0.030 |
| WDR6 | 2.199 | 0.000 |
| ANPEP | 2.176 | 0.000 |
| CCDC144B | 2.149 | 0.043 |
| CYTH4 | 2.111 | 0.005 |
| DUSP3 | 2.102 | 0.000 |
| AC020550.7 | 2.083 | 0.031 |
| RP1-249H1.4 | 2.072 | 0.001 |
| ITGB2 | 2.069 | 0.001 |
| PRAM1 | 2.069 | 0.002 |
| GPR97 | 2.063 | 0.012 |
| CSGALNACT1 | 2.049 | 0.048 |
| PTK2B | 2.035 | 0.000 |
| FES | 2.015 | 0.001 |
| CD99 | 2.013 | 0.005 |
| WDR49 | 2.010 | 0.001 |
| SLC17A9 | 2.009 | 0.001 |
| CTSA | 2.007 | 0.000 |
| ING3 | -2.008 | 0.000 |
| IGHV5-78 | -2.035 | 0.000 |
| ARRDC3 | -2.042 | 0.006 |
| CAST | -2.044 | 0.001 |
| TYMS | -2.048 | 0.000 |
| RNU4-47P | -2.064 | 0.017 |
| KRBOX1 | -2.076 | 0.002 |
| TGFBI | -2.086 | 0.007 |
| RP11-467L13.4 | -2.090 | 0.016 |
| DNTT | -2.094 | 0.011 |
| SERPINB10 | -2.127 | 0.002 |
| CA2 | -2.147 | 0.009 |
| RNU6-485P | -2.151 | 0.011 |
| NR4A2 | -2.163 | 0.028 |
| ST6GAL2 | -2.171 | 0.000 |
| SGK1 | -2.179 | 0.011 |
| SNORA12 | -2.186 | 0.001 |
| RAG2 | -2.228 | 0.008 |
| RGCC | -2.232 | 0.035 |
| EREG | -2.289 | 0.007 |
| ID3 | -2.305 | 0.037 |
| CDH1 | -2.325 | 0.000 |

FIG. 19A - cont.

| | | |
|---|---|---|
| VPREB1 | -2.331 | 0.004 |
| U1 | -2.334 | 0.006 |
| MT1X | -2.342 | 0.006 |
| CXADR | -2.365 | 0.000 |
| LINC01013 | -2.410 | 0.001 |
| EPCAM | -2.411 | 0.002 |
| KLF4 | -2.422 | 0.014 |
| MME | -2.423 | 0.000 |
| HMHB1 | -2.439 | 0.000 |
| APOC1 | -2.459 | 0.003 |
| AC015987.2 | -2.465 | 0.000 |
| DUSP1 | -2.523 | 0.001 |
| TNFAIP3 | -2.537 | 0.049 |
| RP11-392P7.6 | -2.554 | 0.028 |
| CXCR4 | -2.623 | 0.001 |
| RNU3P3 | -2.646 | 0.029 |
| SLC2A3 | -2.706 | 0.015 |
| ZFP36L2 | -2.724 | 0.000 |
| FOSB | -2.771 | 0.004 |
| GRASP | -2.851 | 0.038 |
| IGHV1-69 | -2.892 | 0.005 |
| RNU5E-4P | -2.913 | 0.008 |
| SELENBP1 | -2.946 | 0.000 |
| AC096579.7 | -2.967 | 0.000 |
| RNU1-78P | -2.977 | 0.000 |
| SKIL | -3.013 | 0.008 |
| NR4A1 | -3.023 | 0.033 |
| SHISA2 | -3.027 | 0.018 |
| HBB | -3.061 | 0.002 |
| SNORA22 | -3.116 | 0.000 |
| IRF4 | -3.230 | 0.015 |
| RGS16 | -3.230 | 0.019 |
| CLC | -3.247 | 0.001 |
| SIK1 | -3.259 | 0.014 |
| RGS2 | -3.299 | 0.001 |
| AHSP | -3.544 | 0.000 |
| UCA1 | -3.632 | 0.000 |
| HAMP | -3.824 | 0.048 |
| EBF1 | -3.881 | 0.000 |
| RP11-1100L3.8 | -3.885 | 0.009 |
| TRNAI2 | -4.279 | 0.027 |
| RGS1 | -4.823 | 0.002 |
| NPY | -4.884 | 0.001 |
| VPREB3 | -6.285 | 0.000 |

FIG. 20B

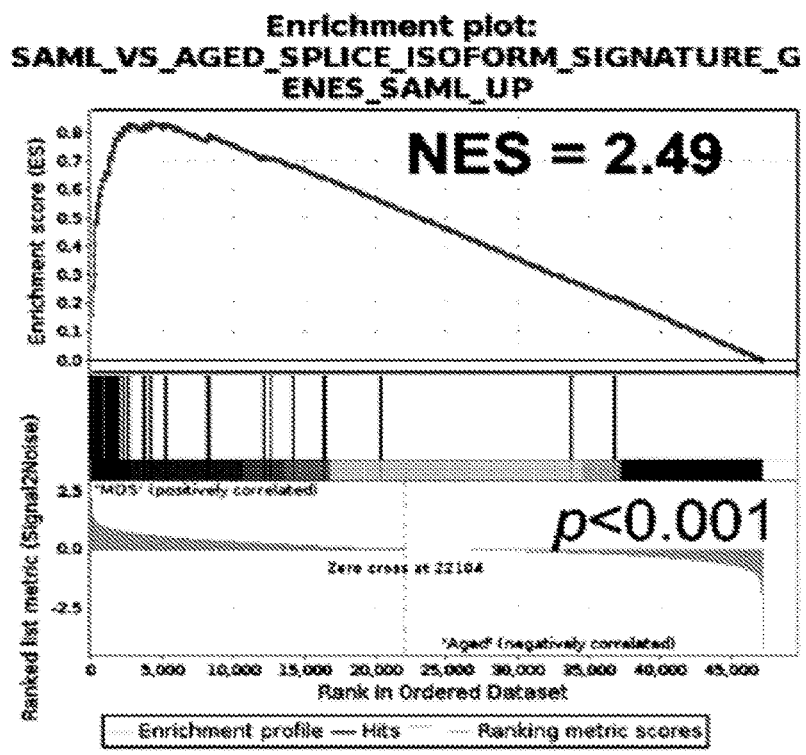

FIG. 20C

| NAME | SIZE | NES | NOM p-val | FDR q-val |
|---|---|---|---|---|
| KEGG_CYTOKINE_CYTOKINE_RECEPTOR_INTERACTION | 256 | 2.00 | <0.001 | 0.002 |
| AGED_VS_YOUNG_SPLICE_ISOFORM_SIGNATURE_GENES_AGED_UP | 55 | 1.92 | <0.001 | 0.002 |
| KEGG_TOLL_LIKE_RECEPTOR_SIGNALING_PATHWAY | 97 | 1.96 | <0.001 | 0.002 |
| KEGG_FC_GAMMA_R_MEDIATED_PHAGOCYTOSIS | 96 | 1.87 | <0.001 | 0.004 |
| KEGG_SYSTEMIC_LUPUS_ERYTHEMATOSUS | 134 | 1.88 | <0.001 | 0.005 |
| KEGG_ERBB_SIGNALING_PATHWAY | 87 | 1.84 | <0.001 | 0.006 |
| KEGG_COLORECTAL_CANCER | 62 | 1.83 | <0.001 | 0.006 |
| KEGG_FC_EPSILON_RI_SIGNALING_PATHWAY | 79 | 1.82 | <0.001 | 0.007 |
| KEGG_B_CELL_RECEPTOR_SIGNALING_PATHWAY | 74 | 1.81 | <0.001 | 0.007 |
| KEGG_PEROXISOME | 78 | -1.95 | <0.001 | 0.008 |

FIG. 23C

| Primary sample | # Mice transplanted with primary sample | # Mice serially transplanted | Range of weeks to engraftment (sac) | 17S-FD-895 treatment |
|---|---|---|---|---|
| AML-37 (PB) | 12 mice (Rag2-/-γc-/-) | 59 mice (41 Rag2-/-γc-/-, 18 NSGS) | 16-28 | IV, 3 doses of 5-10 mg/kg, 2 weeks, n=4-5 mice per group |
| AML-08 (BM) | 7 mice (3 Rag2-/-γc-/-, 4 NSGS) | 20 mice (NSGS) | 7-12 | IV, 3 doses of 5 mg/kg, 2 weeks, n=4 mice per group |
| AML-12 (BM) | 6 mice (2 Rag2-/-γc-/-, 4 NSGS) | 32 mice (19 Rag2-/-γc-/-, 13 NSGS) | 7-13 | Not used (no further compound available) |

METHODS FOR DETECTION AND ERADICATION OF MYELOID LEUKEMIA STEM CELLS

CROSS-REFERENCES TO RELATED APPLICATIONS

This applications claims the benefit of U.S. Provisional Application No. 62/222,421, filed Sep. 23, 2015, and U.S. Provisional Application No. 62/232,414, filed Sep. 24, 2015, the content of each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant W81XWH-14-1-0121 awarded by the Department of Defense, grant CA023100 awarded by the National Institutes of Health, and grant P30-CA-023100 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48537-568001WO_ST25.TXT, created on Sep. 22, 2016, 5,274 bytes, machine format IBM-PC, MS Windows operating system, is hereby incorporated by reference.

BACKGROUND

Recent evidence suggests that mutations in RNA splicing genes occur in a variety of human cancers. These mutations are particularly prevalent in hematopoietic malignancies such as acute myeloid leukemia (AML) (Hahn and Scott, *Nat Genetics* 2012; Yoshida et al., *Nature* 2011), which arises de novo or secondary to myeloproliferative neoplasms (MPNs) or myelodysplastic syndromes (MDS). However, the role of RNA splicing alterations and targeted modulation of splicing activity in maintenance of leukemia stem cells (LSC), which contribute to disease relapse and drug resistance, has been unclear. To address these questions, we performed comparative splice isoform profiling of FACS-purified hematopoietic progenitors from secondary AML (sAML) and normal bone marrow. We then investigated the LSC inhibitory efficacy of a stable and potent splicing modulatory agent, 17S-FD-895.

There are provided herewith solutions and these and other problems in the art.

SUMMARY

In a first aspect, there is provided a for treating acute myeloid leukemia in a subject in need thereof, the method comprising administering to the subject an effective amount of a splicing modulator, thereby treating the acute myeloid leukemia.

In another aspect, there is provided a method for modulating acute myeloid leukemia stem cells, the method comprising contacting the acute myeloid leukemia stem cells with an effective amount of a splicing modulator, thereby modulating the acute myeloid leukemia stem cells.

In another aspect, there is provided a method of detecting a protein level in a subject having acute myeloid leukemia, the method comprising (i) obtaining a biological sample from the subject; (ii) contacting the biological sample with a detection agent capable of binding at least one protein encoded by at least one RNA set forth in Table 13A and/or Table 13B, thereby forming a detectable complex; (iii) detecting and quantitating the detectable complex; and (iv) comparing to a standard control, thereby detecting the protein level of the protein in the subject.

In another aspect, there is provided a method of detecting an RNA level in a subject having acute myeloid leukemia, the method comprising (i) obtaining a biological sample from the subject; (ii) contacting the biological sample with a probe capable of hybridizing to the RNA set forth in Table 13A and/or Table 13B, thereby forming a hybridized complex; (iii) detecting and quantitating the hybridized complex; and (iv) comparing to a standard control, thereby detecting the protein level of the protein in the subject.

In another aspect, there is provided a solid support comprising a plurality of detection agents that each bind to a protein encoded by the RNA set forth in Table 13A and/or 13B.

In another aspect, there is provided a solid support comprising one or more probes that hybridize to one or more RNA sequences selected from the group consisting of Table 13A and/or Table 13B.

In another aspect, there is provided a method for modulating stem cells and progenitor cells, the method comprising contacting stem cells and progenitor cells with an effective amount of a splicing modulator, thereby modulating the stem cells and progenitor cells.

In another aspect, there is provided a method for treating an age-related disease in a subject in need thereof, the method comprising administering to the subject an effective amount of a splicing modulator, thereby treating the age-related disease.

In another aspect, there is provided a method of detecting a protein level in a subject having an age-related disorder, the method comprising (i) obtaining a biological sample from the subject; (ii) contacting the biological sample with a detection agent capable of binding a protein encoded by at least one RNA set forth in Table 12A and/or Table 12B, thereby forming a detectable complex; (iii) detecting and quantitating the detectable complex; and (iv) comparing to a standard control, thereby detecting the protein level of the protein in the subject.

In another aspect, there is provided a method of detecting an RNA level in a subject having an age-related disease, the method comprising (i) obtaining a biological sample from the subject; (ii) contacting the biological sample with a probe capable of hybridizing to the RNA set forth in Table 12A and Table 12B, thereby forming a hybridized complex; (iii) detecting and quantitating the hybridized complex; and (iv) comparing to a standard control, thereby detecting the protein level of the protein in the subject.

In another aspect, there is provided a method of detecting a long-coding RNA level in a subject having an age-related disease, the method comprising (i) obtaining a biological sample from the subject; (ii) contacting the biological sample with a probe capable of hybridizing to the RNA set forth in Table 7A and/or Table 7B and/or Table 10, thereby forming a hybridized complex; (iii) detecting and quantitating the hybridized complex; and (iv) comparing to a standard control, thereby detecting the protein level of the protein in the subject.

In another aspect, there is provided a solid support comprising a plurality of detection agents that each bind to a protein encoded by the RNA set forth in Table 12A and/or 12B.

In another aspect, there is provided a solid support comprising one or more probes that hybridize to one or more RNA sequences selected from the group consisting of: Table 12A and/or Table 12B.

In another aspect, there is provided a solid support comprising a plurality of detection agents that each bind to a protein encoded by the RNA set forth in Table 7A and/or Table 7B and/or Table 10.

In another aspect, there is provided a solid support comprising one or more probes that hybridize to one or more RNA sequences selected from the group consisting of: Table 7A and/or Table 7B and/or Table 10.

In another aspect, there is provided a method for modulating bone marrow stromal cells, the method comprising contacting bone marrow stromal cells with an effective amount of a splicing modulator, thereby modulating the bone marrow stromal cells.

In another aspect, there is provided a method of correcting human stem cell function in an aged microenvironment, the method comprising increasing production of one or more proteins encoded by the RNA in Table 15B in bone marrow stromal cells; and optionally further administering an effective amount of a splicing modulator to the aged microenvironment.

In another aspect, there is provided a method of detecting a protein level in a subject having an age-related disorder, the method comprising (i) obtaining a biological sample from the subject; (ii) contacting the biological sample with a detection agent capable of binding a protein encoded by an RNA in Table 15A and/or Table 15B, thereby forming a detectable complex; (iii) detecting and quantitating the detectable complex; and (iv) comparing to a standard control, thereby detecting the protein level of the protein in the subject.

In another aspect, there is provided a method of detecting an RNA level in a subject having an age-related disease, the method comprising (i) obtaining a biological sample from the subject; (ii) contacting the biological sample with a probe capable of hybridizing to the RNA set forth in Table 15A and/or Table 15B, thereby forming a hybridized complex; (iii) detecting and quantitating the hybridized complex; and (iv) comparing to a standard control, thereby detecting the protein level of the protein in the subject.

In another aspect, there is provided a method of detecting a protein level in a subject having an age-related disorder, the method comprising (i) obtaining a biological sample from the subject; (ii) contacting the biological sample with a detection agent capable of binding a cytokines selected from the group consisting of BDNF, IL-17, IL-12p40, IL-23, ICAM-1, Eotaxin-1, B2M, AAT, SCF, MCP-1, VEGF, C3, RANTES, and IL-4, thereby forming a detectable complex; (iii) detecting and quantitating the detectable complex; and (iv) comparing to a standard control, thereby detecting the protein level of the protein in the subject.

In another aspect, there is provided a method of correcting human stem cell function in an aged microenvironment, the method comprising increasing production of one or more cytokines selected from the group consisting of BDNF, IL-17, IL-12p40, IL-23, ICAM-1, Eotaxin-1, B2M, AAT, SCF, MCP-1, VEGF, C3, RANTES, and IL-4 in bone marrow stromal cells; and optionally further administering an effective amount of a splicing modulator to the aged microenvironment.

In another aspect, there is provided a solid support comprising a plurality of detection agents that each bind to a protein encoded by the RNA set forth in Table 15A and/or Table 15B.

In another aspect, there is provided a solid support comprising a plurality of detection agents that each bind to a cytokines selected from the group consisting of BDNF, IL-17, IL-12p40, IL-23, ICAM-1, Eotaxin-1, B2M, AAT, SCF, MCP-1, VEGF, C3, RANTES, and IL-4.

In another aspect, there is provided a solid support comprising one or more probes that hybridize to one or more RNA sequences selected from the group consisting of: Table 15A and/or Table 15B.

BRIEF DESCRIPTION OF THE DRAWINGS

(FIG. 1A) Top gene sets deregulated in sAML versus normal progenitors (false discovery rate, FDR<25%). NES=normalized enrichment score. (FIG. 1B) Relative expression of SF3B1 by qRT-PCR in FACS-purified AML versus normal progenitors (p<0.05 by unpaired, two-tailed Student's t-test; § =primary sample harboring a point mutation in exon 14 of SF3B1).

(FIG. 2A) A heat map was made using GENE-E and expression data for the top 50 isoforms ranked by absolute Log 2 fold change for transcripts with a median FPKM of at least 10 in one condition, p value <0.01, and absolute Log 2 fold change >1. Transcript names correspond to the identifiers used in Ensembl GRCh37. (FIG. 2B) Volcano plot analysis using isoform Log 2 fold change and p values for all isoforms with FPKM≥1, highlighting transcripts with absolute Log 2 fold change >1 and p value <0.05. (FIG. 2C) Expression levels (FPKM) of top significantly differentially expressed isoforms generated from AML-associated genes. p<0.01 compared to normal bone marrow (BM) controls by unpaired, two-tailed Student's t-test.

(FIG. 3A) Chemical structures of FD-895 and 17S-FD-895. (FIG. 3B) Left: summary of the predicted fluorescence readout using a dual fluorescence (RFP and GFP) alternative splicing reporter (pFlare) assay in HEK293 cells [42]. Middle and right: live-cell confocal microscopy images showing increased RFP/GFP expression in reporter-transfected, 17S-FD-895-treated (10 μM) HEK293 cells. Scale bar=50 μm. (FIG. 3C) RT-PCR analysis of HEK293 and MOLM-13 cells treated with 17S-FD-895 for 4 hrs. Gel analysis of PCR products amplified using primers flanking MCL1 exon 2 show increased intron retention predominantly in sAML cells (MOLM-13). L=100-bp ladder (L); arrowhead represents 500 bp. (D-G) CD34$^+$ AML (n=4), normal bone marrow (BM, n=3) or cord blood (CB, n=3) cells were co-cultured with SL/M2 stroma for two weeks in the presence of FD-895, 17S-FD-895 or vehicle controls (DMSO), then plated in methylcellulose. Colony formation assays (FIG. 3D and FIG. 3E) after treatment with FD-895 or 17S-FD-895 showed reduced AML LSC survival that was significantly lower with 17S-FD-895 than FD-895 at the 1 μM dose (p=0.020). Individual colonies were transferred to fresh methylcellulose and counted after an additional 14 days as a measure of normal or leukemic progenitor self-renewal (FIG. 3F and FIG. 3G). Colony replating assays showing reduced AML LSC self-renewal that was significantly lower with 17S-FD-895 than FD-895 at the 0.1 and 1 μM doses (p=0.001). Statistical values represent comparisons between each dose and the next lowest dose for each compound (*p<0.001 by one-way ANOVA). In addition, at all doses tested for each compound, AML LSC survival and self-renewal were significantly less than DMSO-treated controls. # p<0.001 for AML compared with 1 and 10 μM-treated normal controls (one-way ANOVA).

FIGS. 4A-4H. In vivo splicing modulation and splice isoform switching in AML PRIMAGRAFT™ assays. (FIG. 4A) Schematic diagram showing in vivo 17S-FD-895 treatment regimen, tissues analyzed (spleen; bone marrow, BM; peripheral blood, PB), and analytical endpoints of the study. (FIG. 4B) FACS analysis of human CD45$^+$ cell engraftment in hematopoietic tissues from mice transplanted with AML-37 and treated with vehicle (DMSO, n=5), 17S-FD-895 (5 mg/kg, n=4; 10 mg/kg, n=5). (FIG. 4C) Frequency of human stem (CD34$^+$CD38$^-$Lin$^-$) cell engraftment in 17S-FD-895-treated AML-37 mice compared with vehicle-treated controls. (FIG. 4D) Frequency of human progenitor (CD34$^+$ CD38$^+$ Lin$^-$) cell engraftment in 17S-FD-895-treated AML-37 mice compared with vehicle-treated controls. (FIG. 4E) Human CD45$^+$ cell engraftment in serial transplant recipients of CD34$^+$ cells from 17S-FD-895-treated mice compared with vehicle controls. One additional mouse in the vehicle group was excluded from this analysis because of development of a femoral mass not typical of AML PRIMAGRAFT™ models, but suggestive of an infection occurring in the context of the immunocompromised status of the mouse. (FIG. 4F-4H) For qRT-PCR analysis of in vivo splicing alterations, single cell suspensions from hematopoietic tissues of 17S-FD-895-treated mice were CD34-selected and processed for RNA extraction and cDNA preparation. Quantification of DNAJB1 intron 2 retention (FIG. 4F) and MCL1-L/S (FIG. 4G) and BCL2-L/S (FIG. 4H) ratios in CD34$^+$ cells from the spleens of individual AML-37 mice treated with vehicle or 17S-FD-895. All graphs show mean values and statistical analysis by unpaired, two-tailed Student's t-test (p<0.05 compared to vehicle-treated controls).

(FIG. 5A) A heat map was made using GENE-E for analysis of significantly differentially expressed genes (p<0.05) in sAML versus normal progenitors for the KEGG Spliceosome gene set. (FIG. 5B) Sanger sequencing-based verification of one coding SNV in SF3B1 in leukemic progenitors from one sAML patient sample. (FIG. 5C) qRT-PCR analysis of PTK2B-202 isoform (ENST00000420218) expression in FACS-purified normal BM versus AML progenitors. Graphs shows mean values and statistical analysis by unpaired, two-tailed Student's t-test (p<0.01 compared to normal BM controls).

(FIG. 6A) Dynamic range of the splicing reporter assay. HEK293 cells were transfected with GFP (pFlare5A) or RFP (pFlare5G) vector controls, or the pFlare reporter vector (n=2-3 separate wells per condition). Forty-eight hours after transfection, cells were dissociated and analyzed by flow cytometry to determine the transfection efficiency and mean fluorescence intensity (MFI) of transfected cells. (FIG. 6B) Fluorescent microscopy images of HEK293 cells transfected with pFlare vectors (no treatment). pFlare5A represents the GFP-expressing control, while pFlare5G represents the RFP-expressing control. Cells were imaged 24 h after transfection. Scale bar=75 μm. (FIG. 6C) For in vitro fluorescence reporter-based validation of splicing attenuation, HEK293 cells were treated with 17S-FD-895 at doses from 0.01-10 μM starting 24 h after transfection with the pFlare splicing reporter [42]. After 24 hrs of treatment with 17S-FD-895, cells were analyzed by flow cytometry and splicing activity was calculated as the ratio of RFP/GFP MFI. (FIG. 6D) HEK293 and MOLM-13 cells treated with increasing doses of 17S-FD-895 and analyzed by qRT-PCR to assess relative DNAJB1 intron 2 expression levels. (FIG. 6E) RT-PCR analysis using primers flanking DNAJB1 intron 2 showed a dose-dependent increase in intron 2 retention after treatment with 17S-FD-895 as visualized by gel analysis. 100-bp ladder (L) shows estimated length of PCR products, with the arrowhead representing 500 bp. (FIG. 6F) qRT-PCR analysis using splice isoform-specific primers detecting MCL1 exon 2 skipping showed an increase in MCL1-S transcripts at low doses of 17S-FD-895. (FIG. 6G) Splice isoform-specific qRT-PCR analysis of PTK2B-202 expression in MOLM-13 cells (n=2) after 17S-FD-895 treatment as for (F). PTK2B-202 was undetectable in HEK293 cells.

(FIG. 7A) Reduced AML LSC survival and self-renewal compared to normal controls in a validation cohort of separate patient samples treated with the optimal dose and time of the compound that was functionally more potent in dose response assays (1 μM 17S-FD-895). (FIG. 7B) Survival and self-renewal assays for CD34-selected normal cord blood (CB, n=3) and AML LSC (n=4) after one or two weeks of co-culture with SL/M2 bone marrow stroma and treatment with 17S-FD-895 (1 μM, p<0.01 compared to one week co-cultures by one-way ANOVA). (FIG. 7C) Hematopoietic progenitor assays showing that FD-895 and 17S-FD-895 reduces myeloid colony formation, with no effect on erythroid colonies (p<0.05 for CFU-GM compared to DMSO-treated controls by one-way ANOVA).

(FIG. 8A) Summary of AML patient samples used to establish AML PRIMAGRAFT™ models in immunocompromised mice (n=136 mice transplanted). All primary and serial transplantations were performed using $1\text{-}2\times10^5$ $CD34^+$ (LSC-enriched) cells. (FIG. 8B) FACS plots showing live, lineage-negative stem ($CD34^+CD38^-$) and progenitor ($CD34^+CD38^+$) cell populations in AML-37. (FIGS. 8C-8D) Representative FACS plots showing robust primary engraftment (FIG. 8C) and serial transplantation (FIG. 8D) capacity of AML LSC into immunocompromised mice.

(FIG. 9A) Mouse weights over the two-week treatment period. (FIGS. 9B-9D) FACS analysis of human GMP ($CD34^+CD38^+CD123^+CD45RA^+$, FIG. 9B), CMP ($CD34^+CD38^+CD123^+CD45RA^-$, FIG. 9C), and MEP ($CD34^+CD38^+CD123^-CD45RA^-$, FIG. 9D) engraftment in mouse hematopoietic tissues following treatment of AML-37 mice with vehicle (DMSO, n=5) or 17S-FD-895 at 5 mg/kg (n=4) or 10 mg/kg (n=5). All graphs show mean values and statistical analysis by Student's t-test. (FIG. 9E) FACS analysis of human $CD45^+$ cell engraftment in hematopoietic tissues from mice transplanted with AML-08 and treated with vehicle (DMSO, n=5), 17S-FD-895 (5 mg/kg, n=4; 10 mg/kg, n=5). (FIG. 9F) Frequency of human stem ($CD34^+CD38^-$ $Lin^-$) cell engraftment in 17S-FD-895-treated AML-08 mice compared with vehicle-treated controls. (FIG. 9G) Frequency of human progenitor ($CD34^+CD38^+$ $Lin^-$) cell engraftment in 17S-FD-895-treated AML-08 mice compared with vehicle-treated controls. (FIG. 9H) For serial transplantation experiments, CD34-selected cells from AML-08 PRIMAGRAFT™ assays were pooled from the individual hematopoietic tissues from mice in each treatment group (n=4-5 per group) and transplanted intravenously into serial transplant recipients. Human cell engraftment (CD45) was analyzed by flow cytometry 11 weeks after transplant. All graphs show mean values and statistical analysis by unpaired, two-tailed Student's t-test ($p<0.05$ compared to vehicle-treated controls).

(FIG. 10A-10C) For qRT-PCR analysis of in vivo splicing alterations, single cell suspensions from hematopoietic tissues of 17S-FD-895-treated mice were CD34-selected and processed for RNA extraction and cDNA preparation. Quantification of DNAJB1 intron 2 retention (FIG. 10A) and MCL1-L/S (FIG. 10B) and BCL2-L/S (FIG. 10C) ratios in $CD34^+$ cells from the spleens of individual AML-08 mice treated with vehicle or 17S-FD-895. All graphs show mean values and statistical analysis by unpaired, two-tailed Student's t-test ($p<0.01$ compared to vehicle-treated controls). (FIGS. 10D-10E) qRT-PCR analysis of SF3B1 mRNA expression in 17S-FD-895-treated AML PRIMAGRAFT™ samples. (FIGS. 10F-10H) Aliquots of pooled $CD34^+$ cells prepared for serial transplantation studies were analyzed by RT-PCR to evaluate MCL1 exon 1-3 splicing patterns (FIG. 10F) or qRT-PCR to verify MCL1-L/S (FIG. 10G) and SF3B1 expression levels (FIG. 10H) in transplanted cells. For RT-PCR analyses, 1000-bp ladder (L) shows estimated length of PCR products, with the arrowhead representing 500 bp.

FIGS. 11A-11H. Splice Isoform Signatures of Human Hematopoietic Stem and Progenitor Cell Aging. Whole transcriptome sequencing was performed on RNA from FACS-purified HSC ($CD34^+CD38^-$ $Lin^-$) and HPC ($CD34^+CD38^+$ $Lin^-$) cells from normal young and aged samples (HSC: n=4 young, n=4 aged; HPC: n=6 per group plus a validation set of 2 additional samples per group). Gene and isoform expression data in FPKM were used to calculate average log 2 fold change (L2FC) and p values and FDR correction. (FIG. 11A) Schematic diagram of pre-mRNA splicing, adapted from the KEGG splicing pathway. (FIG. 11B) GSEA spliceosome enrichment plots for human aged versus young HSC and HPC. (FIG. 11C) Volcano plot analysis of all transcripts (FPKM>1) in aged versus young HSC (upper panel) or HPC (lower panel). L2FC was calculated for each transcript using FPKM+1 values. (FIGS. 11D-11E) Splice isoform heat maps (not shown) were made using GENE-E and expression data (Ensembl GFCh37) for the top differentially expressed isoforms (FPKM>1, FDR<5%, absolute L2FC>1) comparing samples in each discovery sample set, ranked by Volcano Vector Value. (FIG. 11D) Tabulation of significantly differentially expressed isoforms (FDR<5%) in aged versus young normal HSC (n=4 per group). Log 2 fold change (L2FC) values are calculated from FPKM values for all isoforms with average FPKM>1 in aged or young HSC, absolute L2FC>1, FDR<5% (q<0.05). (FIG. 11E) Tabulation of top 100 significantly differentially expressed isoforms (FDR<5%) in aged versus young normal HPC (n=6 per group). Log 2 fold change (L2FC) values are calculated from FPKM values for all isoforms with average FPKM>1 in aged or young HPC, absolute L2FC>1, FDR<5% (q<0.05). (FIG. 11F) Intersection of FDR-corrected differentially expressed isoforms in aging HSC and HPC. (FIG. 11G) All significantly differentially expressed genes (FPKM>1, p<0.05, L2FC>1) in discovery sets of normal aged versus young HSC and HPC were probed for human transcription factors, and commonly DE transcription factors were identified. (FIG. 11H) LncRNA signatures of human HSC (upper) and HPC (lower) aging (FPKM>1, p<0.05, L2FC>).

FIGS. 12A-12K. Splicing Deregulation Distinguishes sAML, MDS and Normal Aged Progenitors. Whole transcriptome sequencing data (gene and isoform FPKMs) was analyzed for FACS-purified progenitors from 7 secondary (s)AML, 2 de novo AML, 5 MDS patients, and 6 normal age-matched control samples (aging HPC discovery sample set). (FIG. 12A) GSEA spliceosome enrichment plot showing significant disruption of splicing genes in sAML. (FIG. 12B) Waterfall plot showing average L2FC of all significantly differentially expressed (FDR<5%) KEGG spliceosome components comparing RNA-Seq data from sAML versus normal age-matched HPC. (FIG. 12C) Volcano plot analysis of all transcripts (FPKM>1) in sAML or normal age-matched progenitors. L2FC was calculated for each transcript using FPKM+1 values. (FIG. 12D) Tabulated are top significantly differentially expressed isoforms (FDR<5%) in sAML LSC (n=7) versus aged normal HPC (n=6). Log 2 fold change (L2FC) values are calculated from FPKM values for all isoforms with average FPKM>1 in normal or sAML progenitors, absolute L2FC>1, FDR<5% (q<0.05). Using these data, a heat map (not shown) was made using GENE-E for the top isoforms (sAML versus aged normal HPC) ranked by Volcano Vector Value for transcripts with FPKM>1, FDR<5%, p<0.05, and absolute L2FC>1. Comparative expression profiles in MDS progenitors were obtained for clustering analysis. (FIG. 12E) Cytoscape network analysis of gene interactions between the top differentially expressed (DE) isoforms (p<0.05) in sAML LSC versus aged normal HPC. (FIG. 12F) RNA-Seq-based quantification of CD44-012 expression levels (FDR<5%). (FIGS. 12G-12H) RNA-Seq-based (FIG. 12G, FDR<5%) and splice isoform-specific qRT-PCR (FIG. 12H)

quantification of PTK2B-202 expression levels. **p<0.01 by unpaired, two-tailed Student's t-test. (FIG. 12I) Overall survival (OS) of AML patients (n=156) separated into six subgroups based on expression profiles of sAML splice isoform signature transcripts that mapped to UCSC identifiers in TCGA isoform datasets from RNA-Seq studies performed on unsorted AML leukemic cells. *p—0.0045 (log rank test for trend). (FIG. 12J) All significantly differentially expressed genes in sAML versus normal age-matched HPC were probed for human transcription factors, and the most common families are shown. Differential expression of additional transcription factors is calculated. (FIG. 12K) LncRNA signature of sAML (FPKM>1, p<0.05, L2FC>1).

(FIG. 13A) Enrichment plot showing disruption of HPC aging-associated transcript genes (AGED_VS_YOUNG_SPLICE_ISOFORM_SIGNATURE_GENES_AGED_UP) in sAML progenitors. (FIG. 13B) Principal components analysis showing separation of all samples on the basis of expression values (log 2 (FPKM+1)) of aged versus young HPC splice isoform signature transcripts. (FIG. 13C) GSEA KEGG apoptosis pathway enrichment plot showing disruption of apoptosis regulatory genes in sAML. (FIG. 13D) RNA-Seq-based analysis (Log 2 (FPKM+1)) showing increased expression of pro-survival BCL2L1-001 (BCL-XL) in AML (p<0.05 by two-tailed, unpaired Student's t-test). (FIGS. 13E-13F) RNA-Seq-based (FIG. 13E) and splice isoform-specific qRT-PCR (FIG. 13F) quantification showing decreased expression of the pro-survival BCL2-001 long isoform (BCL2-L) in normal progenitor aging (p<0.01 by unpaired, two-tailed Student's t-test).

(FIG. 14A) Time course (hrs) of MOLM-13 (sAML, n=2) cells treated with 17S-FD-895 for 30 mins-24 hrs and analyzed by qRT-PCR for DNAJB1 intron 2 retention (EC50 of the 1 µM treatment condition at 4.5 hrs was 3.2-6.5 hrs, with a 95% C.I.). (FIG. 14B) HEK293 (n=2), MOLM-13 (sAML, n=2) and KG1a (AML, n=3) cells treated with increasing doses of 17S-FD-895 for 4 hrs and analyzed by qRT-PCR for DNAJB1 intron 2 retention. (FIG. 14C) RT-PCR analysis of HEK293 and MOLM-13 cells using primers flanking DNAJB1 intron 2, or MCL1 exon 2 (FIG. 3C), after 4 hrs of 17S-FD-895 treatment. 100-bp ladder (L) shows estimated length of PCR products; arrowhead=500 bp. (FIG. 14D) MCL1-S isoform-specific qRT-PCR analysis of 17S-FD-895-treated HEK293, MOLM-13 and KG1a cells. (FIG. 14E) Splice isoform-specific qRT-PCR analysis of PTK2B-202 expression in MOLM-13 cells (n=2) and KG1a (n=3) cells after 17S-FD-895 treatment as for FIGS. 14B-14D. PTK2B-202 was undetectable in HEK293 cells. *p=0.004 (unpaired, two-tailed Student's t-test) for KG1a cells compared to DMSO-treated control at 1 µM.

(FIG. 15A) Schematic cartoon diagram of co-culture assay using mouse SL/M2 bone marrow stromal cells that express human interleukin-3 (IL-3), granulocyte colony stimulating factor (G-CSF) and stem cell factor (SCF). (FIG. 15B) Reduced LSC survival and self-renewal compared to normal controls in a validation cohort including relapsed de novo AML and sAML samples treated with 1 µM 17S-FD-895 (*p<0.001 by one-way ANOVA).

(FIG. 16D) Human CD45$^+$ cell engraftment in serial transplant recipients of CD34$^+$ cells from 17S-FD-895-treated mice. For statistical analyses in all graphs, p<0.05 by unpaired, two-tailed Student's t-test compared to vehicle-treated controls. Histogram bins in order left to right: FIGS. 16A and 16D (spleen, bone marrow, peripheral blood); FIGS. 16B-16C (spleen, bone marrow).

(FIGS. 17A-17D) Quantification of DNAJB1 intron 2 retention (FIG. 17A) and MCL1-L/S (FIG. 17B), BCLX-L/S (FIG. 17C) and BCL2-L/S (FIG. 17D) expression ratios in CD34$^+$ cells isolated from the spleens and bone marrows of individual AML-37 mice treated with vehicle or 17S-FD-895. p<0.05 by unpaired, two-tailed Student's t-test compared to vehicle-treated controls. (FIGS. 17E-17G) Aliquots of pooled CD34$^+$ cells prepared for serial transplantation studies were analyzed by RT-PCR to evaluate MCL1 exon 1-3 splicing patterns (FIG. 17E) or RNA-Seq-based splice isoform expression profiles (FIGS. 17F-17G). In FIG. 17E, 1000-bp ladder (L) shows estimated length of PCR products, arrowhead=500 bp. (FIG. 17F) Cytoscape network analysis showing reversion of aberrant expression patterns of genes associated with sAML signature transcripts quantified by RNA-Seq in human CD34$^+$ cells pooled from the bone marrow (BM) of 17S-FD-895 versus vehicle-treated mice (compare to FIG. 12E showing sAML versus aged normal BM). (FIG. 17G) RNA-Seq-based analysis showing expression of sAML-associated splice isoforms in human CD34$^+$ fractions pooled from hematopoietic tissues after in vivo treatment of AML-37 xenografted (X) mice with vehicle (Veh) or 17S-FD-895 (5 or 10 mg/kg, n=4-5 mice pooled per tissue, per condition). (FIG. 17H) Overall survival (OS) of AML patients (n=84) separated into two subgroups based on high (upper quartile of 168 samples) and low (bottom quartile of 168 samples) expression of PTK2B-001 (UCSC transcript uc003xfp.1, GRCh37) in publicly available TCGA isoform datasets from RNA-Seq studies performed on unsorted AML leukemic cells (*p<0.05 by Gehan-Breslow-Wilcoxon test).

FIGS. 18A-18G. Primary Samples, Gene Set Enrichment Analyses and Whole Gene Expression Signatures of Human HSC and HPC Aging. (FIG. 18A) Primary patient bone marrow samples used in RNA-sequencing studies of normal HSC and HPC. ^Used in HPC RNA-Seq, § Used in HSC RNA-Seq, *Validation cohorts, N/A=not available. (FIGS. 18B-18C) For FACS-purified hematopoietic stem (CD34+ CD38− Lin−, n=4 per group) and progenitor (CD34+CD38+ Lin−, n=6 per group) cells from normal young and aged BM samples, gene and isoform expression data in FPKM was obtained from RNA-Seq datasets. Gene set enrichment analyses (GSEA) were performed to identify significant KEGG pathways. Top gene sets deregulated in aged versus young normal HSC (FIG. 18B) and HPC (FIG. 18C) are shown (false discovery rate, FDR<1%). NES=normalized enrichment score. (FIGS. 18D-18E) FIG. 18D tabulates significantly differentially expressed genes in aged versus young normal HSC (n=4 per group). Log 2 fold change (L2FC) values are calculated from FPKM values for all genes with average FPKM>1 in aged or young HSC, absolute L2FC>2. FIG. 18E tabulates significantly differentially expressed genes in aged versus young normal HPC (n=6 per group). Log 2 fold change (L2FC) values are calculated from FPKM values for all isoforms with average FPKM>1 in aged or young HPC, absolute L2FC>2. Profiles of all differentially expressed genes (p<0.05) in human HSC (FIG. 18D) and HPC (FIG. 18E) aging (absolute L2FC>1) were calculated. (FIG. 18F) Heatmap depicting comparison of HPC aging isoform signature with transcript expression levels in cord blood (CB) progenitors (n=3) (Jiang et al., 2013). (FIG. 18G) Figures depicts validation of common isoforms in HSC and HPC. Histograms depict validation across all sequenced patient samples showing relative expression levels (log 2 FPKM+1) of abundant transcripts that were commonly differentially expressed in young versus aged HSC and HPC in the discovery sample sets. For this analysis, three additional HSC samples were included (run on NextSeq platform as compared to HiSeq platform used in discovery sets), and four additional HPC samples were used for validation (*p<0.05). Histogram order (left to right): ZFP36-201, TSC22D3-006, and HIST1H1C-001.

FIGS. 19A-19B. Whole Gene Expression Signatures of sAML LSC. For FACS-purified sAML and normal progenitor (CD34+CD38+ Lid) cells, gene expression data in FPKM was obtained from RNA-sequencing data by aligning paired end unstranded 100 bp poly-A reads using STAR and quantifying genes using Cufflinks. (FIG. 19A) The figure tabulates significantly differentially expressed genes in sAML LSC (n=7) versus aged normal HPC (n=6). Log 2 fold change (L2FC) values are calculated from FPKM values for all isoforms with average FPKM>1 in normal or sAML progenitors, absolute L2FC>2. (FIG. 19B) The gene expression data was submitted for gene set enrichment analysis (GSEA) to determine enriched KEGG pathways in benign versus malignant progenitor cell aging. Venn diagram summarizes the unique and intersecting enriched KEGG pathways (FDR<25% for gene sets with positive normalized enrichment scores) in aged versus young normal progenitors and sAML versus aged progenitors. Relative expression of SF3B1 was assessed by qRT-PCR in FACS-purified AML versus normal progenitors (p<0.05 by unpaired, two-tailed Student's t-test, § =primary sample harboring a point mutation in exon 14 of SF3B1). Sanger sequencing (FIG. 5B) verified one coding SNV in SF3B1 in progenitors from AML-41. sAML-specific splice isoform expression patterns were evaluated in an additional cohort of aged and young progenitors (n=2 per group) and cord blood progenitors (n=3), and a heatmap (not shown) was calculated. Expression profiles of sAML splice isoform signature transcripts that mapped to UCSC identifiers in publicly available TCGA isoform datasets from RNA-Seq studies were conducted on unsorted AML leukemic cells (n=164 samples), and a heatmap (not shown) was calculated. Samples (n=156) clustered into six dominant subgroups (n=9-55 per group) based on sAML-associated transcript expression (log 2 TPM+1).

FIGS. 20A-20C. Gene set enrichment analyses of normal, MDS and sAML progenitors. Gene set enrichment analyses (GSEA) were performed using all KEGG pathways plus custom gene sets including genes associated with the top differentially expressed transcript signatures in aged ("aged up") versus young ("young up") HPC, and sAML ("sAML up") versus aged ("aged up") HPC to identify significant pathways enriched in MDS versus age-matched control HPC, and in sAML versus MDS progenitors. (FIG. 20A) Enrichment plot showing moderate disruption of spliceosome components in MDS progenitors versus aged HPC. (FIG. 20B) Enrichment plot showing that genes associated with upregulated splice isoforms in sAML represents the top enriched gene set in MDS progenitors versus aged HPC. (FIG. 20C) Top gene sets deregulated in sAML versus MDS progenitors are shown (false discovery rate, FDR<1%). NES=normalized enrichment score.

(FIG. 21A) Dynamic range of the splicing reporter assay. HEK293 cells were transfected with GFP (pFlare5A) or RFP (pFlare5G) vector controls (Stoilov et al., 2008), or the pFlare reporter vector (n=2-3 separate wells per condition). Forty-eight hours after transfection, cells were dissociated and analyzed by flow cytometry to determine the transfection efficiency and mean fluorescence intensity (MFI) of transfected cells. (FIG. 21B) Fluorescent microscopy images of HEK293 cells transfected with pFlare vectors (no treatment). pFlare5A represents the GFP-expressing control, while pFlare5G represents the RFP-expressing control. Cells were imaged 24 h after transfection. Scale bar=75 um. (FIG. 21C) For in vitro fluorescence reporter-based validation of splicing attenuation, HEK293 cells were treated with 17S-FD-895 at doses from 0.01-10 uM starting 24 h after transfection with the pFlare splicing reporter. After 24 hrs of treatment with 17S-FD-895, cells were analyzed by flow cytometry, and splicing activity was calculated as the ratio of RFP/GFP MFI.

(FIG. 22A) Viability of CD34-selected normal cord blood (CB, n=3) and AML LSC (n=4) after two weeks of co-culture with SL/M2 bone marrow stroma in the presence of DMSO control, FD-895 or 17S-FD-895 (0.1-10 uM). (FIG. 22B) Survival and self-renewal assays for CD34-selected normal cord blood (CB, n=3) and AML LSC (n-=4) after one or two weeks of co-culture with SI/M2 bone marrow stroma and treatment with 17S-FD-895 (1 uM, p<0.01 compared to one week co-cultures by one-way ANOVA). (FIG. 22C) Hematopoietic progenitor assays showing that FD-895 and 17S-FD-895 reduces myeloid colony formation of normal aged bone marrow samples (n=3), with no effect on erythroid colonies (p<0.05 for CFU-GM compared to DMSO-treated controls by one-way ANOVA). (FIGS. 22D-22G) Lentiviral-shRNA knockdown of SF3B1 in aged bone marrow samples, sAML, or MOLM-13 cells. For in vitro survival and self-renewal assays, CD34+ cells from primary patient samples or unselected MOLM-13 cells were transduced with lentiviral vectors (shCtrl-GFP or shSF3B1-GFP, MOI=100) and subsequently transferred to MethoCult for replating assays. (FIG. 22D) Fluorescence microscopy images of lentivirally-transduced normal aged bone marrow (n=4) and sAML (n=1) samples. Scale bar=200 um. (FIGS. 22E-22F) Survival and self-renewal of normal HSPC (FIG. 22E) and AML LSC (FIG. 22F) in replating assays. (FIG. 22G) Fluorescence microscopy images of lentivirally-transduced MOLM-13 cells (48 hrs after transduction, upper panels) and overall reduction in cell viability (lower panel, left) 5 days after transduction with shSF3B1 lentivirus (n=2) and cell survival in colony formation assays (lower panel, right). Scale bar=200 um.

FIGS. 23A-23I. Normal HSPC In Vivo Models, Serially Transplantable AML PRIMAGRAFT™ Models, and Human Stem and Progenitor Cell Analyses After In Vivo 17S-FD-895 Treatment. (FIG. 23A) Representative FACS plots showing engraftment of normal cord blood-derived hematopoietic cells in immunocompromised mice. (FIG. 23B) Figure depicts histograms of results of FACS analysis of human total CD45+ cells and hematopoietic stem and progenitor cell engraftment in hematopoietic tissues from mice transplanted with CD34+ cord blood cells followed by treatment with vehicle (DMSO, n=4), 17S-FD-895 (10 mg/kg, n=4). Histogram bins for FIG. 23B (left to right): Normal HSPC transplant—CD45+ cell engraftment (spleen, bone marrow, peripheral blood); Normal HSPC transplant—CD34+ cell engraftment (spleen, bone marrow); Normal HSPC transplant—frequency of progenitors (spleen, bone marrow). (FIG. 23C) Summary of AML patient samples used to establish AML PRIMAGRAFT™ models in immuno-compromised mice (n=136 mice transplanted). All primary and serial transplantations were performed using 1-2×10⁵ CD34+(LSC enriched) cells. (FIG. 23D) FACS plots showing live, lineage-negative stem (CD34+CD38−) and progenitor (CD34+CD384) cell populations in AML-37. (FIG. 23E) Representative FACS plots showing robust engraftment of AML LSC in immunocompromised mice. (FIG. 23F) Mouse weights over the two-week treatment period in AML PRIMAGRAFT™ studies. (FIG. 23G) FACS analysis of human hematopoietic stem (CD34+CD38− Lin), CMP (CD34+CD38+CD123+CD45RA), MEP (CD34+CD38+CD123−CD45RA−) cell engraftment, and leukemic blast burden (CD45+CD334) in hematopoietic tissues of mice transplanted with AML-37 and treated with vehicle (DMSO, n=5) or 17S-FD-895 (5 mg/kg, n=4; 10 mg/kg, n=5). All graphs show mean values and statistical analysis by Student's t-test. (FIG. 23H) FACS analysis of human total CD45+ cells and hematopoietic stem and progenitor cell engraftment in hematopoietic tissues from mice transplanted with AML-08 and treated with vehicle (DMSO, n=5), 17S-FD-895 (5 mg/kg, n=4; 10 mg/kg, n=5). (FIG. 23I) For serial transplantation experiments, CD34-selected cells from AML-08 PRIMAGRAFT™ results were pooled from the individual hematopoietic tissues from mice in each treatment group (n=4-5 per group) and transplanted intravenously into serial transplant recipients. Human cell engraftment (CD45+) was analyzed by flow cytometry 11 weeks after transplant. All graphs show mean values and statistical analysis by unpaired, two-tailed Student's t-test (p<0.05 compared to vehicle-treated controls).

(FIGS. 24A-24C) Quantification of DNAJB1 intron 2 retention (FIG. 24A) and MCL1-L/S (FIG. 24B) and BCL2-L/S (FIG. 24C) ratios in CD34+ cells from the spleens of individual AML-08 mice treated with vehicle or 17S-FD-895. (FIGS. 24D-24F) Aliquots of pooled CD34+ cells prepared for serial transplantation studies were analyzed by qRT-PCR and RNA-Seq. (FIG. 24D) Reduced MCL1-US expression ratios in pooled CD34+ cells from 17S-FD-895-treated mice, (FIG. 24E) GSEA enrichment plot showing genes associated with upregulated splice isoforms in sAML ("sAML up") and downregulated splice isoforms in sAML ("aged up") were depleted and enriched, respectively, in the 10 mg/kg 17S-FD-895 treated mice compared with vehicle-treated controls. The "aged up" genes represented the third most enriched gene set in the spleens of pooled CD34+ cells from mice that received splicing modulator treatment. (FIG. 24F) RNA-Seq-based splicing factor gene expression changes in the spleens of treated mice. (FIGS. 24G-24I) qRT-PCR analysis of SF3B1 mRNA expression in 17S-FD-895-treated AML PRIMAGRAFT™ models (individual mice, FIG. 24G, 24H) or pooled cells used in serial transplantation assays (FIG. 24I). All graphs show mean values and statistical analysis by unpaired, two-tailed Student's t-test (p<0.01 compared to vehicle-treated controls).

DETAILED DESCRIPTION

Definitions

Figure 1A:
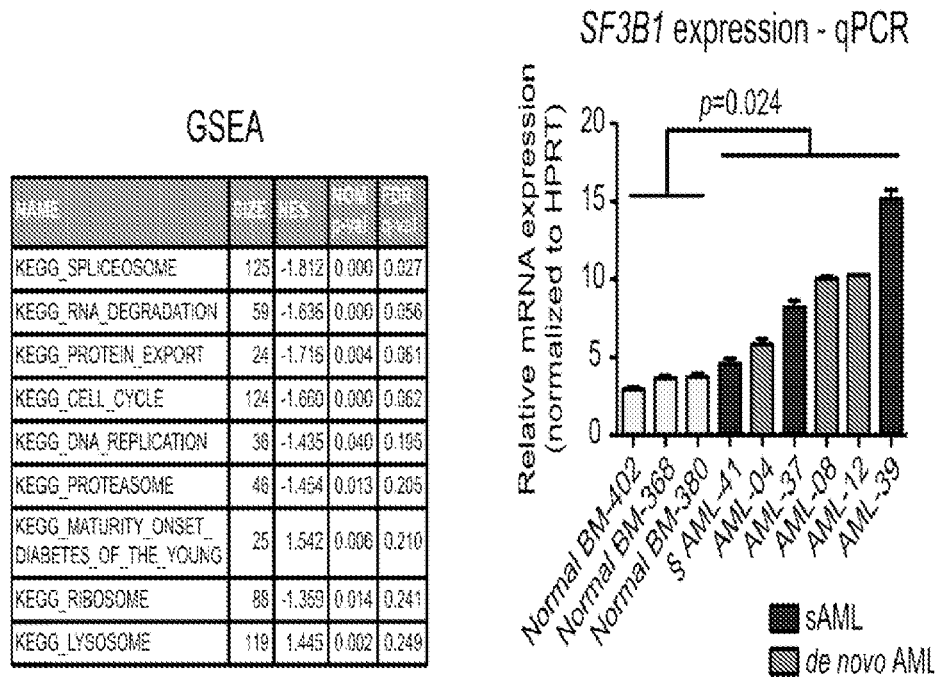
FIGS. 1A-1B. Global disruption of spliceosome gene expression in AML. For FACS-purified hematopoietic progenitors (CD34$^+$CD38$^+$ Lin$^-$) from 7 secondary (s)AML and 6 age-matched normal bone marrow (BM) samples, gene expression data in FPKM was obtained from RNA-sequencing data by aligning paired end unstranded 100 bp poly-A reads using STAR and quantifying transcripts using Cufflinks [56]. The resulting gene expression data was submitted to GSEA to determine significant KEGG pathways and enrichment plots describing ranked gene expression in those pathways.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_1$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, and/or each substituted or unsubstituted heterocycloalkylene is a substituted or unsubstituted 3 to 7 membered heterocycloalkylene.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "⁓" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "biological sample" refers to a material of biological origin (e.g., blood, plasma, cells, tissues, organs, fluids).

"Detection agent" refers to (i) a compound that is capable of binding (covalently or non-covalently) a protein and (ii) a detectable label. The "detection agent" can be an "indirect detection agent" or a "direct detection agent." An "indirect detection agent" refers to a compound that is capable of binding (covalently or non-covalently) a protein that cannot be detected itself, but is detected using a separate, distinct detectable label that specifically binds (covalently or non-covalently) to the compound that is capable of binding the protein. A "direct detection agent" refers to a compound that is capable of binding (covalently or non-covalently) a protein and is also a detectable label (e.g., whether the compound and detectable label are the same compound or whether the compound and detectable label are separate, bound compounds). Exemplary detection agents that can interact with a protein include antibodies (monoclonal or polyclonal), RNA, DNA, biotin, and the like. In one embodiment, the detection agent that interacts with the protein is, or includes, an antibody. In embodiments, the detection agent comprises an antibody bound to an enzyme. In embodiments, the detection agent includes a primary antibody bound to a secondary antibody that is bound to an enzyme. In embodiments, the detection agent comprises biotin and streptavidin. In embodiments, the detection agent comprises biotin, streptavidin, and an enzyme. In embodiments, the detection agent comprises biotin and avidin. In embodiments, the detection agent comprises biotin, avidin, and an enzyme.

"Detectable label" refers to a moiety that indicates the presence of a corresponding molecule (e.g., probe) to which it is bound. A "detectable label" can be an indirect or direct label. An "indirect label" refers to a moiety, or ligand, that is detected using a labeled secondary agent, or ligand-binding partner, that specifically binds to the indirect label. A "direct label" refers to a moiety that is detectable in the absence of a ligand-binding partner interaction. Exemplary labels include fluorescent labels (including, e.g., quenchers or absorbers), non-fluorescent labels, colorimetric labels, chemiluminescent labels, bioluminescent labels, radioactive labels (such as $^3$H, $^{35}$S, $^{32}$P, $^{125}$I, $^{57}$Co or $^{14}$C), mass-modifying groups, antibodies, antigens, biotin, haptens, digoxigenin, enzymes (including, e.g., peroxidase, phosphatase, etc.), and the like.

"Detectable complex" refers to a composition comprising (i) a detection agent and (ii) a protein bound, where the detection agent and protein are bound (covalently or non-covalently) together, and where the detectable complex can be identified and/or quantified by methods known in the art.

"Hybridization complex" refers to a composition containing (i) a probe and (ii) a target nucleic acid, where the probe and target nucleic acid are bound (e.g., hybridized) together, and where the hybridization complex can be identified and/or quantified by methods known in the art.

"Probe" refers to a nucleotide that includes a target-binding region that is substantially complementary to a target sequence in a target nucleic acid (e.g., RNA) and, thus, is capable of forming a hydrogen-bonded duplex with the target nucleic acid. Typically, the probe is a single-stranded probe, having one or more detectable labels to permit the detection of the probe following hybridization to its complementary target.

"Complementary" refers to sequence complementarity between two different nucleic acid strands or between two regions of the same nucleic acid strand. A first region of a nucleic acid is complementary to a second region of the same or a different nucleic acid if, when the two regions are arranged in an anti-parallel fashion, at least one nucleotide residue of the first region is capable of base pairing (i.e., hydrogen bonding) with a residue of the second region, thus forming a hydrogen-bonded duplex.

"Substantially complementary" refers to two nucleic acid strands (e.g., a strand of a target nucleic acid and a complementary single-stranded oligonucleotide probe) that are capable of base pairing with one another to form a stable hydrogen-bonded duplex under stringent hybridization conditions, including the isothermal hybridization conditions described herein. In general, "substantially complementary" refers to two nucleic acids having at least 75%, for example, about 80%, 85%, 90%, 95%, 97%, 98%, 99% or 100% complementarity. The term "stringent" refers to hybridization conditions that affect the stability of hybrids, e.g., temperature, salt concentration, pH, formamide concentration, and the like. These conditions are empirically optimized to maximize specific binding, and minimize nonspecific binding, of a probe to a target nucleic acid (e.g., RNA).

Hybridization assays are well known in the art, and include, for example, sandwich hybridization assays, competitive hybridization assays, hybridization-ligation assays, dual ligation hybridization assays, nuclease hybridization assays, and the like. Nucleic acids "hybridize" when they associate, typically in solution. Nucleic acids hybridize due to a variety of well-characterized physicochemical forces, such as hydrogen bonding, solvent exclusion, base stacking and the like. In certain embodiments, hybridization occurs under conventional hybridization conditions, such as under stringent conditions as described, for example, in Sambrook et al., in "Molecular Cloning: A Laboratory Manual" (1989), Eds. J. Sambrook, E. F. Fritsch and T. Maniatis, Cold Spring Harbour Laboratory Press, Cold Spring Harbour, N.Y., which is incorporated by reference. Such conditions are, for example, hybridization in 6×SSC, pH 7.0/0.1% SDS at about 45° C. for 18-23 hours, followed by a washing step with 2×SSC/1% SDS at 50° C. In order to select the stringency, the salt concentration in the washing step can, for example, be chosen between 2×SSC/0.1% SDS at room temperature for low stringency and 0.2×SSC/0.1% SDS at 50° C. for high stringency. In addition, the temperature of the washing step can be varied between room temperature (ca. 22° C.), for low stringency, and 65° C. to 70° C. for high stringency. Also contemplated are polynucleotides that hybridize at lower stringency hybridization conditions. Changes in the stringency of hybridization and signal detection are primarily accomplished through the manipulation of, e.g., formamide concentration (lower percentages of formamide result in lowered stringency), salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 mg/mL salmon sperm blocking DNA, followed by washes at 50° C. with 1×SSPE, 0.1% SDS. In addition, to achieve even lower stringency, washes performed following stringent hybridization can be done at higher salt concentrations (e.g., 5×SSC). Variations in the above conditions may be accomplished through the inclusion and/or substitution of alternate blocking reagents used to suppress background in hybridization experiments. The inclusion of specific blocking reagents may require modification of the hybridization conditions described herein, due to problems with compatibility. An extensive guide to the hybridization of nucleic acids is found in Tijssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, New York), as well as in Ausubel (Ed.) Current Protocols in Molecular Biology, Volumes I, II, and III, (1997), which are each incorporated by reference. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis; labeling, detection and quantification of DNA and RNA, including oligonucleotides. Both Hames and Higgins 1 and 2 are incorporated by reference.

"Nucleic acid" refers to a polymer having multiple nucleotide monomers. A nucleic acid can be single- or double-stranded, and can be DNA (e.g., cDNA or genomic DNA), RNA, or hybrid polymers (e.g., DNA/RNA). Nucleic acids can be chemically or biochemically modified and/or can contain non-natural or derivatized nucleotide bases. Nucleic acid modifications include, for example, methylation, substitution of one or more of the naturally occurring nucleotides with an analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). Nucleic acids also include synthetic molecules that mimic nucleic acids in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids (also referred to herein as "PNAs. Nucleic acids can also include, for example, conformationally restricted nucleic acids (e.g., "locked nucleic acids" or "LNAs."

The terms "DNA" and "RNA" refer to deoxyribonucleic acid and ribonucleic acid, respectively.

Where a method disclosed herein refers to "amplifying" a nucleic acid, the term "amplifying" refers to a process in which the nucleic acid is exposed to at least one round of extension, replication, or transcription in order to increase (e.g., exponentially increase) the number of copies (including complimentary copies) of the nucleic acid. The process can be iterative including multiple rounds of extension, replication, or transcription. Various nucleic acid amplification techniques are known in the art, such as PCR amplification or rolling circle amplification.

A "primer" as used herein refers to a nucleic acid that is capable of hybridizing to a complimentary nucleic acid sequence in order to facilitate enzymatic extension, replication or transcription.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The sensitivity of the hybridization assays may be enhanced through use of a nucleic acid amplification system that multiplies the target nucleic acid being detected. Amplification can also be used for direct detection techniques. Examples of such systems include the polymerase chain reaction (PCR) system and the ligase chain reaction (LCR) system. Other methods include the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including TAQMAN® and molecular beacon probes can be used to monitor amplification reaction products in real time.

"Solid support" refers to a physical structure which can bind detection agents, probes, analytes, and/or reagents, covalently or non-covalently, in a device or method disclosed herein and embodiments thereof. Use of solid supports can facilitate detection and/or separation of analytes, e.g., splice isoforms, proteins coded by splice isoforms, RNA, nucleic acids, and the like. The choice of solid support for use in the present devices and methods is based upon the desired assay format and performance characteristics. Acceptable solid supports for use in the present devices and methods can vary widely. A solid support can be porous or nonporous. It can be continuous or non-continuous, and flexible or nonflexible. A solid support can be made of a variety of materials including ceramic, glass, silicon, metal, organic polymeric materials, or combinations thereof. In embodiments, the solid support is a resin or a bead. In embodiments, an antibody can be immobilized on a solid support, e.g., magnetic or chromatographic matrix particles, the surface of an assay plate (e.g., microtiter wells), pieces of a solid substrate material or membrane (e.g., plastic, nylon, paper), and the like. In embodiments, the solid support is a micro-titer plate. In embodiments, the micro-titer plate is a polystyrene micro-titer plate. In embodiments, the solid support can be a microchip upon which nucleic acid reagent is affixed. In embodiments, binding of a portion of an analyte (e.g., splice isoform sample) to a nucleic acid reagent affixed on a microchip results in formation of a detectable duplex nucleic acid. In embodiments, the solid support is a nitrocellulose or PVDF membrane. In embodiments, the solid support includes a protein binding surface which can be a microtiter plate, a colloidal metal particle, an iron oxide particle, a latex particle, a polymeric bead, and any combination thereof. In embodiments, antibodies or other polypeptides can be immobilized onto a solid support for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TENTAGEL®, AGROGEL®, PEGA gels, SPOCC gels, and multiple-well plates.

The terms "spliceosome" or "spliceosomal" are used according to their common and ordinary meaning and refer to the process or complex involved in removal of introns from transcribed pre-mRNA. A spliceosome may include a complex of small nuclear RNA (snRNA) and protein subunits.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

"Diagnosis" as used herein generally includes determination of a subject's susceptibility to a disease or disorder, determination as to whether a subject is presently affected by a disease or disorder, prognosis of a subject affected by a disease or disorder (e.g., identification of cancerous states, stages of cancer, or responsiveness of cancer to therapy), and use of therametrics (e.g., monitoring a subject's condition to provide information as to the effect or efficacy of therapy).

A "therapeutically effective amount" or "an effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" or "standard" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

A "test compound" as used herein refers to an experimental compound used in a screening process to identify activity, non-activity, or other modulation of a particularized biological target or pathway.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Patient" or "subject" in need thereof refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "associated" or "associated with" in the context of a substance or substance activity or function associated with a disease means that the disease is caused by (in whole or in part), or a symptom of the disease is caused by (in whole or in part) the substance or substance activity or function.

"Leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Leukemias are generally classified into four different groups or types: acute myeloid (AML), acute lymphatic (ALL), chronic myeloid (CML) and chronic lymphatic leukemia (CLL). These different categories of leukemia are associated with varying clinical outcomes and therefore can serve as guides to the selection of different treatment strategies.

Blood cancers such as acute myeloid leukemia (AML) are particularly heterogeneous, and represent a collection of hematopoietic malignancies characterized by clonal diversity, chromosomal abnormalities, DNA mutations, and widespread epigenetic alterations. Acute myeloid leukemia arises de novo or secondary to myeloproliferative neoplasms (MPNs) or myelodysplastic syndromes (MDS). A myeloid leukemia that arises secondary to MPNs or MDS is referred to as a secondary acute myeloid leukemia (sAML). Despite extensive clinical use of DNA-modifying hypomethylating agents in the treatment of AML, bone marrow transplantation remains the only potential cure for this aggressive disease. A major clinical obstacle in the treatment of patients with sAML is that many individuals are ineligible for hematopoietic stem cell (HSC) transplantation procedures due to advanced age. Moreover, disease relapse, the leading cause of death in sAML, is driven in part by a dormant leukemia stem cell (LSC) population that harbors enhanced survival and self-renewal capacity. Studies involving mouse transgenic AML models and in human intermediate and high-risk MDS demonstrate that hematopoietic stem cells (HSC) have a myeloid lineage bias that leads to expansion of the granulocyte-macrophage progenitor (GMP) population that can give rise to self-renewing LSC. Frequent activation of stem cell regulatory pathways, combined with mutations in splicing regulatory genes and alterations in the epigenetic landscape, influence clinical outcomes in sAML. Consequently, a central goal of therapeutic strategies is to eradicate LSCs by selectively targeting molecular pathways that typify LSC expression patterns and are essential to their function.

"Age-related disease" refers to any disease associated with the aging process, and that is more frequently seen in elderly patients. Exemplary age-related diseases include atherosclerosis, cardiovascular disease, cancer (e.g., AML, sAML), arthritis, cataracts, osteoporosis, type 2 diabetes, hypertension, Alzheimer's disease, and bone marrow failure. In embodiments, the "age-related disease" is AML or sAML. In embodiments, the "age-related disease" is bone marrow failure.

"Bone marrow failure" refers to diseases of the hematopoietic stem cells and occur when the body is incapable of making enough blood, such as red cells, white cells, or platelets. Exemplary diseases of bone marrow failure are aplastic anemia, myelodysplastic syndrome, and paroxysmal nocturnal hemoglobinuria.

Rationale and Experimental Description

Through whole transcriptome analyses, we identified a splicing profile that distinguishes secondary acute myeloid leukemia (AML) stem cells from normal progenitors. Pharmacological spliceosome modulation disrupted AML leukemia stem cell (LSC) maintenance in humanized LSC stromal co-culture and PRIMAGRAFT™ assays by promoting intron retention and altering splicing of pro-survival and other AML-associated transcripts. Thus, detection and targeted modulation of aberrant splicing provides an innovative strategy for AML LSC eradication with implications for treatment of other aggressive malignancies.

Thus, we have identified the first hematopoietic progenitor-cell-specific splice isoform signature that discriminates sAML LSC from normal progenitors. This signature is based on whole transcriptome analyses to identify splice isoforms that are differentially expressed in sAML compared with normal controls. Previous studies have evaluated whole gene expression in related premalignant disorders (MDS, Dolatshad et al., *Leukemia* 2015) and differential exon usage in de novo AML (Adamia et al., *Clin Cancer Res* 2014), but none have specifically identified sAML biomarkers at the isoform level. sAML is typified by complex cytogenetics and is notoriously difficult to treat with current therapies. Therefore, new strategies to diagnose and treat this disease will have significant clinical impact.

Although the spliceosome has emerged as a promising target of novel anti-tumor drugs that include several families of splicing modulatory agents derived from natural products (Bonnal et al., *Nat Rev Drug Discov* 2012), structural complexity and poor compound stability under biological conditions has constrained clinical research and development. For example, the macrolide pladienolide B targets splicing factor 3b (SF3B)—a core component of the U2 pre-mRNA splicing complex—but this, along with its analogues including FD-895, demonstrate poor stability in aqueous and biological media, with short half-lives ($t_{1/2} \leq 15$ min) and potential off-target toxicity arising from hydrolyzed seco-acids. These decomposition products have been implicated in the discontinuation of clinical trials with the pladienolide B analogue E7107 in solid tumors (Hong et al., *Invest New Drugs* 2014), highlighting the need for development of stabilized and selective spliceosome-targeted compounds with reduced toxicity.

Our collaborative team recently described a series of synthetic derivatives of FD-895 that demonstrate enhanced activity and metabolic stability, including one analogue, 17S-FD-895, that exhibited 25-fold increased activity over FD-895 (Villa et al., *Org Lett* 2012). Therefore, we evaluated this splicing modulatory agent in humanized AML LSC stromal co-culture and PRIMAGRAFT™ assays. Our results show for the first time that splicing modulation reverts sAML-specific and stem cell regulatory splice isoform expression patterns. Moreover, 17S-FD-895 treatment impaired AML LSC survival and self-renewal in AML PRIMAGRAFT™ models and in humanized stromal co-cultures at doses that spared normal hematopoietic progenitors. Thus, splicing modulation provides a viable approach to reprogramming sAML splicing activity and targets AML LSC with a favorable therapeutic index.

Leukemia relapse is driven, at least in part, by malignant reprogramming of preleukemic progenitors into self-renewing LSC ) [1-3]. Previously, we showed that RNA editing-induced mis-splicing of a stem cell regulatory gene, GSK3β, promoted therapy-resistant LSC generation in chronic myeloid leukemia (CML) [4-7]. In addition, MDS[8] and de novo AML[9] gene expression studies demonstrate differential exon usage of epigenetic modifier and tumor suppressor transcripts, including EZH1 and TP53. Here we sought to establish global gene and splice isoform expression signatures that distinguish sAML from normal age-matched progenitors. Comparative RNA-Seq and gene set enrichment analyses of FACS-purified sAML and normal progenitors revealed significant alterations in splicing factor expression. While one sAML sample had a mutation in the splicing factor SF3B1, numerous spliceosome-related genes were transcriptionally deregulated in sAML, and quantitative real-time (qRT)-PCR showed increased SF3B1 expression in AML progenitors.

To further examine splice isoform changes associated with sAML, an isoform-specific alignment algorithm was applied[5]. Analysis of moderate-to-highly expressed isoforms, and transcripts with a median FPKM≥1, revealed a splice isoform expression signature that included genes associated with AML (NPM1, TP53, CD82 and PTK2B) [10, 11]. Nucleophosmin (NPM1) is an AML prognostic marker, and the tumor suppressor TP53 has been widely studied in cancer. Integrins—key regulators of tumor progression—interact with select CD82 (KAI1) isoforms[12] and regulate cell-adhesion associated activation of the focal adhesion kinase-related tyrosine kinase PTK2B (PYK2) [13]. These transcripts—in particular PTK2B-202, which was upregulated in AML progenitors—may represent prognostic isoform-specific biomarkers and therapeutic targets.

Considering the splice isoform expression patterns that distinguished sAML LSC from normal progenitors, we hypothesized that pharmacological spliceosome modulation might have LSC inhibitory effects. The SF3B subunit of the spliceosome is a target of several natural products with anti-tumor properties, including the macrolide pladienolide B[14]. However, structural complexity has to date constrained clinical research and development. The natural product pladienolide B and related analogues including FD-895 [15] demonstrate poor stability in aqueous and biological media, with short half-lives ($t_{1/2} \leq 15$ min) and potential off-target toxicity arising from hydrolyzed seco-acids. These decomposition products have been implicated in the discontinuation of clinical trials with the pladienolide B analogue E7107 in solid tumors[16], highlighting the need for development of stabilized and selective spliceosome-targeted compounds with reduced toxicity. We recently described a series of synthetic analogues of FD-895 that demonstrate enhanced activity and metabolic stability [15]. Here we evaluated FD-895 and 17S-FD-895[15], a stereoisomer with 25-fold higher activity, in splicing reporter activity, PCR, and functional hematopoietic progenitor assays [4, 5].

To assess the splicing modulatory activity of 17S-FD-895, cell-based assays were performed using a dual fluorescence splicing reporter (pFlare [17]). Analysis showed a dose-dependent increase in RFP/GFP ratios in HEK293 cells. Time-lapse confocal fluorescence microscopy confirmed an increase in RFP fluorescence following 17S-FD-895 treatment. In keeping with previous work showing that pladienolide B derivatives alter intron retention of DnaJ (Hsp40) homolog, Subfamily B, Member 1 (DNAJB1) [14], PCR analyses demonstrated a rapid and dose-dependent increase in DNAJB1 intron 2 retention following 17S-FD-895 treatment of MOLM-13 sAML cells. These data suggest that sAML cells harbor marked sensitivity to splicing modulation.

Previous studies involving genetic and pharmacologic modulation show that SF3B1 inhibition alters splicing and pre-mRNA nuclear retention[19] of vital cancer-related transcripts, including cell-cycle, angiogenesis and apoptosis[20] (e.g. MCL1[18]). Quantitative RT-PCR studies in HEK293 and MOLM-13 cells revealed that while low doses of 17S-FD-895 increased MCL11S expression, this effect was reversed at high doses. Additional RT-PCR analysis revealed that splicing modulation triggered MCL1 exon 2 skipping (producing MCL1-S) as well as production of an array of other intron-retained and completely unspliced products specific to sAML cells. In addition, short-term 17S-FD-895 treatment reduced expression of the sAML-associated transcript PTK2B-202, suggesting that splicing modulation could normalize AML-specific splice isoform expression patterns.

Previous studies identified a therapeutic index for FD-895 in primary chronic lymphocytic leukemia cells compared with normal B cells, which was independent of SF3B1 mutational status[18]. However, LSC inhibitory efficacy had not been established. Thus, we evaluated FD-895 and 17S-FD-895 in a LSC-supportive stromal co-culture model that recapitulates key aspects of the human bone marrow microenvironment[4,6] and in newly-established AML PRIMAGRAFT™ models. Since 17S-FD-895 showed a favorable therapeutic index and greater functional potency than FD-895 in in vitro LSC assays, we performed additional pre-clinical 17S-FD-895 studies in AML PRIMAGRAFT™ assays. Transplantation of CD34' LSC-enriched fractions from three patient samples resulted in engraftment of serially transplantable human LSC after 7-28 weeks. Two sets of engrafted mice were treated with 17S-FD-895 or vehicle control, followed by FACS and splice isoform analyses in $CD34^+$ LSC-enriched fractions. The treatment was well tolerated, with no significant weight changes detected.

Self-renewing AML LSC reside in the hematopoietic stem ($CD34^+CD38^-$) or progenitor ($CD34^+CD38^+$) compartments[21], and resemble multipotent hematopoietic progenitors including granulocyte-macrophage progenitors (GMP), which are the dominant $CD34^+CD38^+$ population in 80% of sAML cases[1]. Therefore, we analyzed the hematopoietic stem and progenitor cell frequencies in a sAML PRIMAGRAFT™ model treated with 5 or 10 mg/kg of 17S-FD-895. Flow cytometry revealed a dose-dependent decrease in human stem ($CD45^+CD34^+CD38^-$ Lin$^-$, 68% reduction in the spleens of the 10 mg/kg group versus vehicle controls, p<0.05) and progenitor cells ($CD45^+CD34^+CD38^+$ Lin$^-$, 80% reduction to nearly zero in the spleens of the 10 mg/kg group versus vehicle controls, p=0.08) in the hematopoietic tissues of treated mice. Among progenitor cell subpopulations, there was reduced GMP frequency and a slight increase in common myeloid progenitor (CMP) frequency in 17S-FD-895-treated mice. In an AML PRIMAGRAFT™ model with high disease burden, serial transplantation studies showed a 49% decrease (p=0.07) in circulating leukemic burden in secondary recipients of $CD34^+$ cells from 17S-FD-895-treated mice.

Notably, AML LSC functional capacity to propagate leukemia is dictated by stem cell gene expression[21]. We hypothesized that stem cell isoform-specific expression profiles could be reprogrammed through splicing modulation. To assess in vivo splice isoform-targeted activity of 17S-FD-895, CD34-selected human cells from treated mice were analyzed by PCR. Consistent with our in vitro studies, there was increased DNAJB1 intron 2 expression in human $CD34^+$ cells from 17S-FD-895-treated mice. Notably, splice isoform-specific qRT-PCR showed a significant reduction in MCL1-/S and BCL2-L/S expression ratios compared to vehicle-treated controls. Consistent with a functional reduction in activity of SF3B1—the putative target of FD-895, SF3B1 mRNA expression was unchanged after 17S-FD-895 treatment. Pooled $CD34^+$ cells from 17S-FD-895-treated mice displayed MCL1 exon skipping and intron inclusion, along with dramatically reduced MCL1-L/S expression ratios, and, as expected, SF3B1 expression was unaffected. Together, pharmacological splicing modulation with 17S-FD-895 restored normal ratios of MCL1-L/S and BCL2-L/S expression, suggesting that reprogramming splicing of stem cell pro-survival genes may contribute to this agent's functional impact on AML LSC maintenance.

Here we provide the first evidence that splicing modulation impairs AML LSC maintenance in part by promoting pro-apoptotic splice isoform expression and intron inclusion in MCL1. Our RNA-Seq results suggest that widespread changes in spliceosome components sensitize self-renewing AML LSC to pharmacological splicing modulation by 17S-FD-895. This potent and stable FD-895 analogue reverted sAML-specific splice isoform (PTK2B-202) expression patterns and MCL1-L/S and BLC2-LS ratios, and impaired AML LSC survival and self-renewal. Notably, drug resistance in AML has been attributed to high levels of MCL1 [22], and genetic and epigenetic alterations typical of AML can induce dependence on BCL2 pro-survival activity[23]. Because splicing modulation effectively reduced sAML-associated and stem cell pro-survival splice isoform expression and impaired LSC maintenance, it may represent a key component of combination therapeutic strategies aimed at eradicating therapy-resistant AML LSC. This will be highly relevant to other hematopoietic malignancies and solid tumors[24,25] typified by cancer stem cell-associated aberrant RNA splicing.

Accordingly, in a first aspect, there is provided a for diagnosis of secondary acute myeloid leukemia (sAML). The method includes obtaining a splice isoform signature from a subject, and comparing the splice isoform signature with a normal control, thereby providing diagnosis of sAML.

In another aspect, there is provided a method for treating secondary acute myeloid leukemia (sAML). The method includes administering to a subject in need an effective amount of a splicing modulator, thereby treating sAML.

In embodiments, the splicing modulator is 17S-FD-895, which is a compound of Formula (XI).

REFERENCES

[1] Goardon, N., et al. Coexistence of LMPP-like and GMP-like leukemia stem cells in acute myeloid leukemia. Cancer Cell 19, 138-152 (2011); [2] Bonnet, D. & Dick, J. E. Human acute myeloid leukemia is organized as a hierarchy that originates from a primitive hematopoietic cell. Nat Med 3, 730-737 (1997); [3] Shlush, L. I., et al. Identification of pre-leukaemic haematopoietic stem cells in acute leukaemia. Nature 506, 328-333 (2014); [4] Goff, D. J., et al. A Pan-BCL2 inhibitor renders bone-marrow-resident human leukemia stem cells sensitive to tyrosine kinase inhibition. Cell Stem Cell 12, 316-328 (2013); [5] Jiang, Q., et al. ADAR1 promotes malignant progenitor reprogramming in chronic myeloid leukemia. Proc Natl Acad Sci USA 110, 1041-1046 (2013); [6] Crews, L. A., et al. An RNA editing fingerprint of cancer stem cell reprogramming. Journal of translational medicine 13 (2015); [7] Abrahamsson, A. E., et al. Glycogen synthase kinase 3beta missplicing contributes to leukemia stem cell generation. Proc Natl Acad Sci USA 106, 3925-3929 (2009); [8] Dolatshad, H., et al. Disruption of SF3B1 results in deregulated expression and splicing of key genes and pathways in myelodysplastic syndrome hematopoietic stem and progenitor cells. Leukemia 29, 1092-1103 (2015); [9] Adamia, S., et al. A genome-wide aberrant RNA splicing in patients with acute myeloid leukemia identifies novel potential disease markers and therapeutic targets. Clin Cancer Res 20, 1135-1145 (2014); [10] Burchert, A., et al. CD82 (KAI1), a member of the tetraspan family, is expressed on early hemopoietic progenitor cells and up-regulated in distinct human leukaemias. Br J Haematol 107, 494-504 (1999); [11] Miller, P. G., et al. In Vivo RNAi screening identifies a leukemia-specific dependence on integrin beta 3 signaling. Cancer Cell 24, 45-58 (2013); [12] Lee, J. H., Seo, Y. W., Park, S. R., Kim, Y. J. & Kim, K. K. Expression of a splice variant of KAI1, a tumor metastasis suppressor gene, influences tumor invasion and progression. Cancer Res 63, 7247-7255 (2003); [13] Weis, S. M., et al. Compensatory role for Pyk2 during angiogenesis in adult mice lacking endothelial cell FAK. The Journal of cell biology 181, 43-50 (2008); [14] Kotake, Y., et al. Splicing factor SF3b as a target of the antitumor natural product pladienolide. Nat Chem Biol 3, 570-575 (2007); [15] Villa, R., Mandel, A. L., Jones, B. D., La Clair, J. J. & Burkart, M. D. Structure of FD-895 revealed through total synthesis. Org Lett 14, 5396-5399 (2012); [16] Hong, D. S., et al. A phase I, open-label, single-arm, dose-escalation study of E7107, a precursor messenger ribonucleic acid (pre-mRNA) spliceosome inhibitor administered intravenously on days 1 and 8 every 21 days to patients with solid tumors. Investigational new drugs 32, 436-444 (2014); [17] Stoilov, P., Lin, C. H., Damoiseaux, R., Nikolic, J. & Black, D. L. A high-throughput screening strategy identifies cardiotonic steroids as alternative splicing modulators. Proc Natl Acad Sci USA 105, 11218-11223 (2008); [18] Kashyap, M. K., et al. Targeting the spliceosome in chronic lymphocytic leukemia with the macrolides FD-895 and pladienolide B. Haematologica (2015); [19] Kaida, D., et al. Spliceostatin A targets SF3b and inhibits both splicing and nuclear retention of pre-mRNA. Nat Chem Biol 3, 576-583 (2007); [20] Wang, L., et al. SF3B1 and other novel cancer genes in chronic lymphocytic leukemia. N Engl J Med 365, 2497-2506 (2011); [21] Eppert, K., et al. Stem cell gene expression programs influence clinical outcome in human leukemia. Nat Med 17, 1086-1093 (2011); [22] Glaser, S. P., et al. Anti-apoptotic Mcl-1 is essential for the development and sustained growth of acute myeloid leukemia. Genes Dev 26, 120-125 (2012); [23] Chan, S. M., et al. Isocitrate dehydrogenase 1 and 2 mutations induce BCL-2 dependence in acute myeloid leukemia. Nat Med 21, 178-184 (2015); [24] DeBoever, C., et al. Transcriptome sequencing reveals potential mechanism of cryptic 3' splice site selection in SF3B1-mutated cancers. PLoS computational biology 11, e1004105 (2015); [25] Salton, M., et al. Inhibition of vemurafenib-resistant melanoma by interference with pre-mRNA splicing. Nat Commun 6, 7103 (2015).

Methods and Compositions

In a first aspect, there is provided a for treating acute myeloid leukemia in a subject in need thereof, the method comprising administering to the subject an effective amount of a splicing modulator, thereby treating the acute myeloid leukemia.

In another aspect, there is provided a method for modulating acute myeloid leukemia stem cells, the method comprising contacting the acute myeloid leukemia stem cells with an effective amount of a splicing modulator, thereby modulating the acute myeloid leukemia stem cells.

In embodiments, normal progenitor cells are not substantially modulated.

In another aspect, there is provided a method of detecting a protein level in a subject having acute myeloid leukemia, the method comprising (i) obtaining a biological sample from the subject; (ii) contacting the biological sample with a detection agent capable of binding at least one protein encoded by at least one RNA set forth in Table 13A and/or Table 13B, thereby forming a detectable complex; (iii) detecting and quantitating the detectable complex; and (iv) comparing to a standard control, thereby detecting the protein level of the protein in the subject.

In embodiments, the protein is PTK2B, CD44, or a combination thereof. In embodiments, the method further includes detecting additional protein levels for a plurality of additional proteins encoded by RNA set forth in Table 13A and/or Table 13B by further contacting the biological sample with a plurality of additional different detection agents, each additional different detection agent capable of binding to one of the plurality of additional proteins to form a plurality of additional different detectable complexes; and further detecting and quantitating the plurality of additional different detectable complexes and comparing to a standard control, thereby detecting additional protein levels the protein in the additional proteins in the subject.

In embodiments, the protein and the plurality of additional proteins comprise all the proteins encoded by RNA set forth in Table 13A and/or Table 13B.

In embodiments, the protein and the plurality of additional proteins comprise at least 50 of the proteins encoded by RNA set forth in Table 13A and/or Table 13B. In embodiments, the protein and the plurality of additional proteins comprise at least 5, 10, 15, 20, 25, 30, 35, 40, 45 or even 50 of the proteins encoded by RNA set forth in Table 13A and/or Table 13B.

In embodiments, the protein levels of the proteins encoded by the RNA set forth in Table 13B are lower than in a subject that does not have acute myeloid leukemia; and the protein levels of the proteins encoded by the RNA set forth in Table 13A are higher than in a subject that does not have acute myeloid leukemia.

In another aspect, there is provided a method of detecting an RNA level in a subject having acute myeloid leukemia, the method comprising (i) obtaining a biological sample from the subject; (ii) contacting the biological sample with a probe capable of hybridizing to the RNA set forth in Table 13A and/or Table 13B, thereby forming a hybridized complex; (iii) detecting and quantitating the hybridized complex; and (iv) comparing to a standard control, thereby detecting the protein level of the protein in the subject.

In embodiments, the method further includes detecting additional RNA levels for a plurality of additional RNAs set forth in Table 13A and/or Table 13B by further contacting the biological sample with a plurality of additional different probes, each additional different probe capable of hybridizing to one of the plurality of additional RNAs to form a plurality of additional different hybridized complexes; and further detecting and quantitating the plurality of additional different hybridized complexes and comparing to a standard control, thereby detecting additional RNA levels in the additional RNAs in the subject.

In embodiments, the RNA and the plurality of additional RNAs comprise all the RNA set forth in Table 13A and Table 13B.

In embodiments, the RNA and the plurality of additional RNAs comprise at least 50 of the RNA set forth in Table 13A and/or Table 13B. In embodiments, the RNA and the plurality of additional RNAs comprise at least 5, 10, 15, 20, 25, 30, 35, 40, 45 or even 50 of the RNA set forth in Table 13A and/or Table 13B.

In embodiments, the RNA levels of the RNAs set forth in Table 13B are lower than in a subject that does not have acute myeloid leukemia; and the RNA levels of the RNAs set forth in Table 13A are higher than in a subject that does not have acute myeloid leukemia.

Further to any method above and embodiments thereof, in embodiments the acute myeloid leukemia is secondary acute myeloid leukemia. In embodiments, the acute myeloid leukemia is refractory acute myeloid leukemia. In embodiments, the acute myeloid leukemia is relapsed acute myeloid leukemia.

Further to any method above and embodiments thereof, in embodiments the method further includes administering to the subject an effective amount of a splicing modulator.

In another aspect, there is provided a solid support comprising a plurality of detection agents that each bind to a protein encoded by the RNA set forth in Table 13A and/or 13B.

In another aspect, there is provided a solid support comprising one or more probes that hybridize to one or more RNA sequences selected from the group consisting of Table 13A and/or Table 13B.

In another aspect, there is provided a method for modulating stem cells and progenitor cells, the method comprising contacting stem cells and progenitor cells with an effective amount of a splicing modulator, thereby modulating the stem cells and progenitor cells.

In another aspect, there is provided a method for treating an age-related disease in a subject in need thereof, the method comprising administering to the subject an effective amount of a splicing modulator, thereby treating the age-related disease.

In another aspect, there is provided a method of detecting a protein level in a subject having an age-related disorder, the method comprising (i) obtaining a biological sample from the subject; (ii) contacting the biological sample with a detection agent capable of binding a protein encoded by at least one RNA set forth in Table 12A and/or Table 12B, thereby forming a detectable complex; (iii) detecting and quantitating the detectable complex; and (iv) comparing to a standard control, thereby detecting the protein level of the protein in the subject.

In embodiments, the method further includes detecting additional protein levels for a plurality of additional proteins encoded by at least one RNA set forth in Table 12A and/or Table 12B by further contacting the biological sample with a plurality of additional different detection agents, each additional different detection agent capable of binding to one of the plurality of additional proteins to form a plurality of additional different detectable complexes; and further detecting and quantitating the plurality of additional different detectable complexes and comparing to a standard control, thereby detecting additional protein levels the protein in the additional proteins in the subject.

In embodiments, the protein and the plurality of additional proteins comprise all the proteins encoded by the RNA set forth in Table 12A and Table 12B.

In embodiments, the protein and the plurality of additional proteins comprise at least 50 of the proteins encoded the RNA set forth in Table 12A and/or Table 12B. In embodiments, the protein and the plurality of additional proteins comprise at least 5, 10, 15, 20, 25, 30, 35, 40, 45 or even 50 of the proteins encoded the RNA set forth in Table 12A and/or Table 12B.

In embodiments, the protein levels of the proteins encoded by at least one RNA set forth in Table 12B are lower than in a subject that does not have acute myeloid leukemia; and the protein levels of the proteins encoded by at least one RNA set forth in Table 12A are higher than in a subject that does not have acute myeloid leukemia.

In another aspect, there is provided a method of detecting an RNA level in a subject having an age-related disease, the method comprising (i) obtaining a biological sample from the subject; (ii) contacting the biological sample with a probe capable of hybridizing to the RNA set forth in Table 12A and Table 12B, thereby forming a hybridized complex; (iii) detecting and quantitating the hybridized complex; and (iv) comparing to a standard control, thereby detecting the protein level of the protein in the subject.

In embodiments, the method further includes detecting additional RNA levels for a plurality of additional RNAs set forth in Table 12A and Table 12B by further contacting the biological sample with a plurality of additional different probes, each additional different probe capable of hybridizing to one of the plurality of additional RNAs to form a plurality of additional different hybridized complexes; and further detecting and quantitating the plurality of additional different hybridized complexes and comparing to a standard control, thereby detecting additional RNA levels in the additional RNAs in the subject.

In embodiments, the RNA and the plurality of additional RNAs comprise all the proteins set forth in Table 12A and Table 12B.

In embodiments, the RNA and the plurality of additional RNAs comprise at least 50 of the RNA set forth in Table 12A and Table 12B. In embodiments, the RNA and the plurality of additional RNAs comprise at least 5, 10, 15, 20, 25, 30, 35, 40, 45 or even 50 of the RNA set forth in Table 12A and Table 12B.

In embodiments, the RNA levels of the RNAs set forth in Table 12B are lower than in a subject that does not have acute myeloid leukemia; and the RNA levels of the RNA set forth in Table 12A are higher than in a subject that does not have acute myeloid leukemia.

In another aspect, there is provided a method of detecting a long-coding RNA level in a subject having an age-related disease, the method comprising (i) obtaining a biological sample from the subject; (ii) contacting the biological sample with a probe capable of hybridizing to the RNA set forth in Table 7A and/or Table 7B and/or Table 10, thereby forming a hybridized complex; (iii) detecting and quantitating the hybridized complex; and (iv) comparing to a standard control, thereby detecting the protein level of the protein in the subject.

In embodiments, the method further includes detecting additional RNA levels for a plurality of additional RNAs set forth in Table 7A and/or Table 7B and/or Table 10 by further contacting the biological sample with a plurality of additional different probes, each additional different probe capable of hybridizing to one of the plurality of additional RNAs to form a plurality of additional different hybridized complexes; and further detecting and quantitating the plurality of additional different hybridized complexes and comparing to a standard control, thereby detecting additional RNA levels in the additional RNAs in the subject.

In embodiments, the RNA and the plurality of additional RNAs comprise all the RNAs set forth in Table 7A, Table 7B, and Table 10.

In embodiments, the RNA and the plurality of additional RNAs comprise at least 25 of the RNAs set forth in Table 7A and/or Table 7B and/or Table 10.

In embodiments, the age-related disease is bone marrow failure. In embodiments, the age-related disease is aplastic anemia, myelodysplastic syndrome, paroxysmal nocturnal hemoglobinuria, or large granular lymphocytic leukemia.

Further to the method, in embodiment the method further includes administering an effective amount of a splicing modulator.

In another aspect, there is provided a solid support comprising a plurality of detection agents that each bind to a protein encoded by the RNA set forth in Table 12A and/or 12B.

In another aspect, there is provided a solid support comprising one or more probes that hybridize to one or more RNA sequences selected from the group consisting of: Table 12A and/or Table 12B.

In another aspect, there is provided a solid support comprising a plurality of detection agents that each bind to a protein encoded by the RNA set forth in Table 7A and/or Table 7B and/or Table 10.

In another aspect, there is provided a solid support comprising one or more probes that hybridize to one or more RNA sequences selected from the group consisting of: Table 7A and/or Table 7B and/or Table 10.

In another aspect, there is provided a method for modulating bone marrow stromal cells, the method comprising contacting bone marrow stromal cells with an effective amount of a splicing modulator, thereby modulating the bone marrow stromal cells.

In another aspect, there is provided a method of correcting human stem cell function in an aged microenvironment, the method comprising increasing production of one or more proteins encoded by the RNA in Table 15B in bone marrow stromal cells; and optionally further administering an effective amount of a splicing modulator to the aged microenvironment.

In another aspect, there is provided a method of detecting a protein level in a subject having an age-related disorder, the method comprising (i) obtaining a biological sample from the subject; (ii) contacting the biological sample with a detection agent capable of binding a protein encoded by an RNA in Table 15A and/or Table 15B, thereby forming a detectable complex; (iii) detecting and quantitating the detectable complex; and (iv) comparing to a standard control, thereby detecting the protein level of the protein in the subject.

In embodiments, the method further includes detecting additional protein levels for a plurality of additional proteins encoded by RNA in Table 15A and/or Table 15B by further contacting the biological sample with a plurality of additional different detection agents, each additional different detection agent capable of binding to one of the plurality of additional proteins to form a plurality of additional different detectable complexes; and further detecting and quantitating the plurality of additional different detectable complexes and comparing to a standard control, thereby detecting additional protein levels the protein in the additional proteins in the subject.

In embodiments, the protein and the plurality of additional proteins comprise all the proteins encoded by RNA in Table 15A and Table 15.

In embodiments, the protein levels of the proteins set forth in Table 15B are lower than in a subject that does not have acute myeloid leukemia; and the protein levels of the proteins set forth in Table 15A are higher than in a subject that does not have acute myeloid leukemia.

In another aspect, there is provided a method of detecting an RNA level in a subject having an age-related disease, the method comprising (i) obtaining a biological sample from the subject; (ii) contacting the biological sample with a probe capable of hybridizing to the RNA set forth in Table 15A and/or Table 15B, thereby forming a hybridized complex; (iii) detecting and quantitating the hybridized complex; and (iv) comparing to a standard control, thereby detecting the protein level of the protein in the subject.

In embodiments, the method further includes detecting additional RNA levels for a plurality of additional RNAs set forth in Table 15A and/or Table 15B by further contacting the biological sample with a plurality of additional different probes, each additional different probe capable of hybridizing to one of the plurality of additional RNAs to form a plurality of additional different hybridized complexes; and further detecting and quantitating the plurality of additional different hybridized complexes and comparing to a standard control, thereby detecting additional RNA levels in the additional RNAs in the subject.

In embodiments, the RNA and the plurality of additional RNAs comprise all the RNA set forth in Table 15A and Table 15B. In embodiments, the RNA and the plurality of additional RNAs comprise at least 20 of the RNA set forth in Table 15A and/or Table 15B. In embodiments, the RNA and the plurality of additional RNAs comprise at least 5, 10, 15 or even 20 of the RNA set forth in Table 15A and/or Table 15B.

In embodiments, the RNA levels of the RNAs set forth in Table 15B are lower than in a subject that does not have acute myeloid leukemia; and the RNA levels of the RNAs set forth in Table 15A are higher than in a subject that does not have acute myeloid leukemia.

In another aspect, there is provided a method of detecting a protein level in a subject having an age-related disorder, the method comprising (i) obtaining a biological sample from the subject; (ii) contacting the biological sample with a detection agent capable of binding a cytokines selected from the group consisting of BDNF, IL-17, IL-12p40, IL-23, ICAM-1, Eotaxin-1, B2M, AAT, SCF, MCP-1, VEGF, C3, RANTES, and IL-4, thereby forming a detectable complex; (iii) detecting and quantitating the detectable complex; and (iv) comparing to a standard control, thereby detecting the protein level of the protein in the subject.

In embodiments, the age-related disease is bone marrow failure. In embodiments, the age-related disease is aplastic anemia, myelodysplastic syndrome, or paroxysmal nocturnal hemoglobinuria.

In another aspect, there is provided a method of correcting human stem cell function in an aged microenvironment, the method comprising increasing production of one or more cytokines selected from the group consisting of BDNF, IL-17, IL-12p40, IL-23, ICAM-1, Eotaxin-1, B2M, AAT, SCF, MCP-1, VEGF, C3, RANTES, and IL-4 in bone marrow stromal cells; and optionally further administering an effective amount of a splicing modulator to the aged microenvironment.

In embodiments, the aged microenvironment is the area adjacent to the bone marrow stromal cells and/or the area in which the bone marrow stromal cells originate and grow.

In embodiments, the method further includes administering to the subject an effective amount of a splicing modulator.

In another aspect, there is provided a solid support comprising a plurality of detection agents that each bind to a protein encoded by the RNA set forth in Table 15A and/or Table 15B.

In another aspect, there is provided a solid support comprising a plurality of detection agents that each bind to a cytokines selected from the group consisting of BDNF, IL-17, IL-12p40, IL-23, ICAM-1, Eotaxin-1, B2M, AAT, SCF, MCP-1, VEGF, C3, RANTES, and IL-4.

In another aspect, there is provided a solid support comprising one or more probes that hybridize to one or more RNA sequences selected from the group consisting of: Table 15A and/or Table 15B.

Further to any aspect above and embodiments thereof, in embodiments the splicing modulator is a compound of Formula (I):

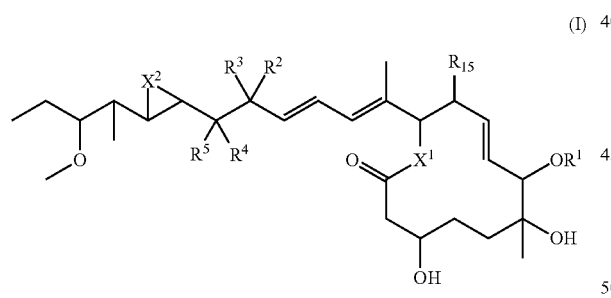

wherein, $X^1$ is N, O, or $CH_2$; $X^2$ is O or $C(R^6)(R^7)$; $R^6$ and $R^7$ are independently hydrogen, halogen, substituted or unsubstituted alkyl, substituted or unsubstituted aryl, —$OR^{12}$, —$OC(O)R^{12}$, —$OC(O)OR^{12}$, or —$OC(O)NR^{13}R^{14}$; $R^1$ is hydrogen, —$C(O)R^8$, —$OC(O)R^8$, —$OC(O)OR^8$, or —$NHC(O)NHR^8$; $R^2$, $R^3$, $R^4$, and $R^5$ are each independently selected from hydrogen, substituted or unsubstituted alkyl, —$OR^9$, —$OC(O)R^9$, —$OC(O)OR^9$, or —$OC(O)NR^{10}R^{11}$; $R^8$, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{15}$ is hydrogen, halogen, $CF_3$, $CCl_3$, $CBr_3$, $CI_3$, substituted or unsubstituted alkyl.

In embodiments, $X^2$ is O and the chiral carbon at $R^2$ has (R) stereochemistry and the chiral carbon at $R^4$ has (S) stereochemistry. In embodiments, $X^2$ is O and the chiral carbon at $R^2$ has (S) stereochemistry and the chiral carbon at $R^4$ has (R) stereochemistry. In embodiments, when $R^2$ is attached to a chiral carbon having (S) stereochemistry, $R^4$ is attached to a chiral carbon having (S) or (R) stereochemistry. In embodiments, $X^2$ is $C(R^6)(R^7)$ and the chiral carbon at $R^2$ has (R) stereochemistry and the chiral carbon at $R^4$ has (S) stereochemistry. In embodiments, $X^2$ is $C(R^6)(R^7)$ and the chiral carbon at $R^2$ has (S) stereochemistry and the chiral carbon at $R^4$ has (R) stereochemistry.

In embodiments, the compound of Formula (I) is a compound selected from the group consisting of:

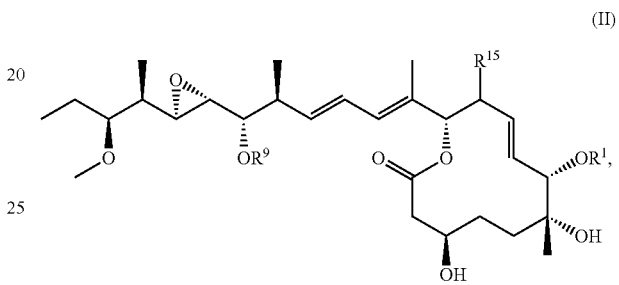

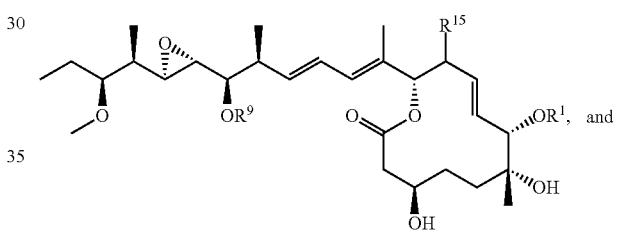

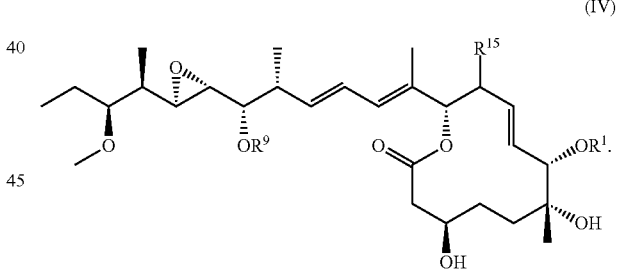

In embodiments, the compound of Formula (I)

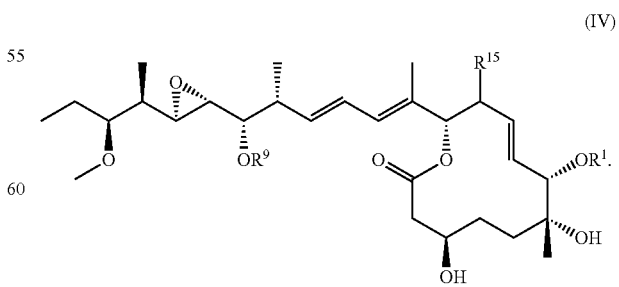

In embodiments, the compound of Formula (I) is a compound selected from the group consisting of:

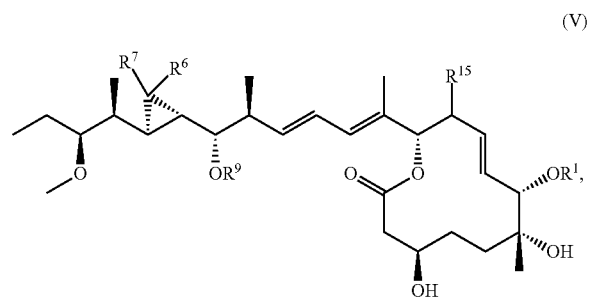

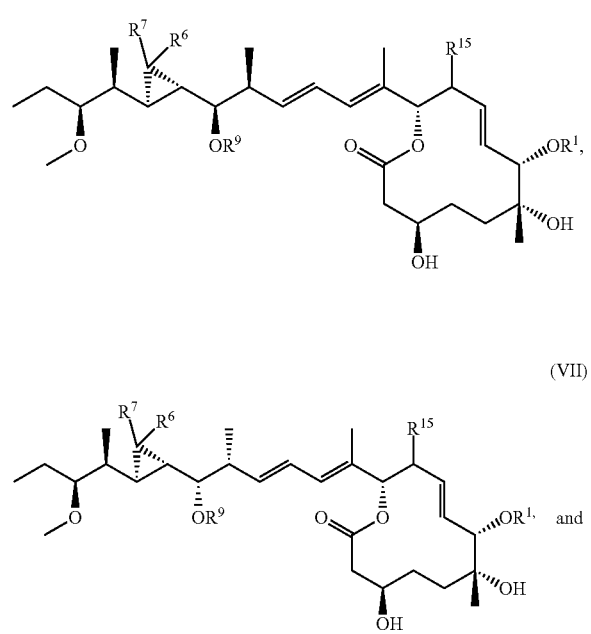

In embodiments, the compound of Formula (I) is:

In embodiments, $R^{15}$ is hydrogen or $C_1$-$C_4$ unsubstituted alkyl.

In embodiments, $R^{15}$ is hydrogen or methyl. In embodiments, $R^{15}$ is methyl.

In embodiments, $R^9$ is hydrogen.

In embodiments, $X^2$ is O. In embodiments, $X^2$ is $C(R^6)(R^7)$.

In embodiments, $R^6$ and $R^7$ are independently hydrogen, halogen, or methyl. In embodiments, $R^6$ and $R^7$ are hydrogen. In embodiments, $R^6$ and $R^7$ are fluoride.

In embodiments, the compound of Formula (is selected from the group consisting of:

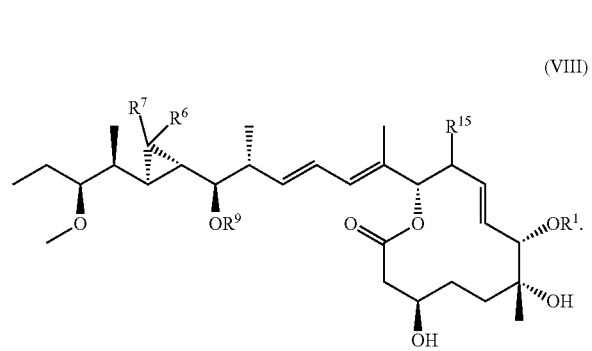

In embodiments, the compound of Formula (I) is selected from the group consisting of:

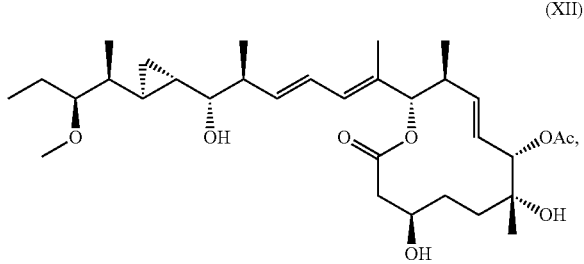 [SMILES: CC[C@H](OC)[C@@H](C)[C@H]1C[C@@H]1[C@H](O)[C@@H](C)/C=C/C=C(\C)[C@H]1OC(=O)C[C@H](O)CC[C@@](C)(O)[C@@H](OC(C)=O)/C=C/[C@@H]1C]

-continued (XIII)

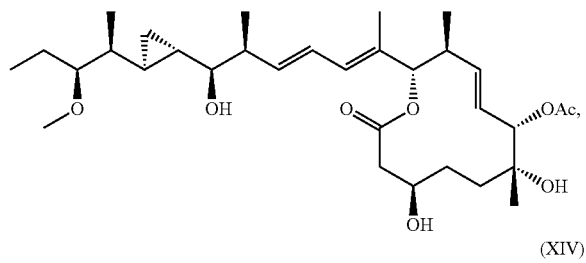

(XIV)

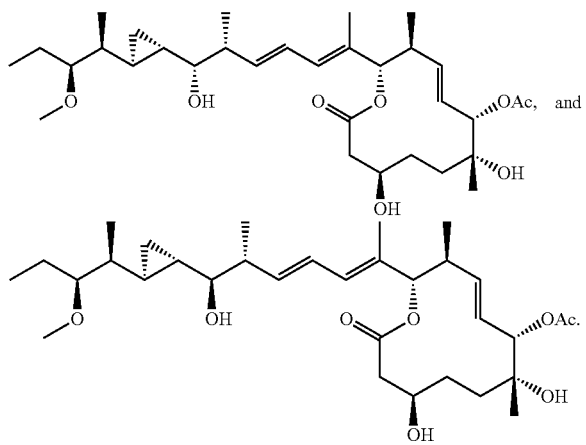

Further to any aspect above or embodiment thereof, the compounds used in the methods of the invention are splicing modulators. A "splicing modulator" refers to an agent (e.g., small molecule, peptide, protein) that modulates (e.g., increases or decreases) the production of full-length mRNA undergoing splice processing. In embodiments, a splicing modulator can interact with a spliceosome, or components thereof, to increase production of mRNA, which after release of the mRNA leads to increased protein synthesis encoded by the mRNA. In embodiments, a splicing modulator can decrease production of mRNA, leading to decreased protein synthesis. In embodiments, a splicing modulator is a compound of formula (I), and all the variations, embodiments, and derivatives thereof, as described herein.

In embodiments, a splicing modulator useful in the methods disclosed herein, and embodiments thereof, is a compound having formula (I):

(I)

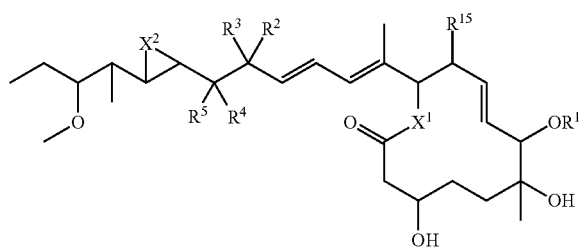

wherein $X^1$ is N, O, or $CH_2$. $X^2$ is O or $C(R^6)(R^7)$. $R^6$ and $R^7$ are independently hydrogen, halogen, substituted or unsubstituted alkyl, substituted or unsubstituted aryl, —$OR^{12}$, —$OC(O)R^2$, —$OC(O)OR^{12}$, or —$OC(O)NR^{13}R^{14}$.

$R^1$ is hydrogen, —$C(O)R^8$, —$OC(O)R^8$, —$OC(O)OR^8$, or —$NHC(O)NHR^8$. $R^2$, $R^3$, $R^4$, and $R^5$ are each independently selected from hydrogen, substituted or unsubstituted alkyl, —$OR^9$, —$OC(O)R^9$, —$OC(O)OR^9$, or —$OC(O)NR^{10}R^{11}$. $R^8$, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, $CF_3$, $CCl_3$, $CBr_3$, $CI_3$, or substituted or unsubstituted alkyl.

In embodiments $X^1$ is O. In certain embodiments $R^2$ is methyl. In certain embodiments $R^4$ is —$OR^9$ where $R^9$ may be hydrogen or $C_1$-$C_4$ unsubstituted alkyl. $R^9$ may be hydrogen. When $X^1$ is O, $R^2$ is attached to a chiral carbon having (S) stereochemistry, and $R^4$ may be attached to a carbon having (S) or (R) stereochemistry. When $R^2$ is attached to a carbon having (S) stereochemistry, $R^4$ may be attached to a carbon having (S) stereochemistry. The compound may have formula (II). When $R^2$ is attached to a carbon having (S) stereochemistry, $R^4$ may be attached to a carbon having (R) stereochemistry. The compound may have formula (III). When $X^1$ is O, $R^2$ may be attached to a chiral carbon having (R) stereochemistry, and $R^4$ may be attached to a carbon having (S) stereochemistry. The compound may have formula (IV).

In embodiments, a splicing modulator useful in the methods disclosed herein and embodiments thereof, has the formula:

(II)

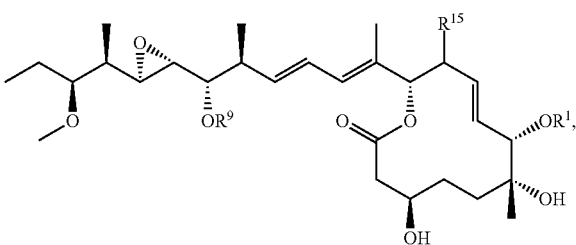

(III)

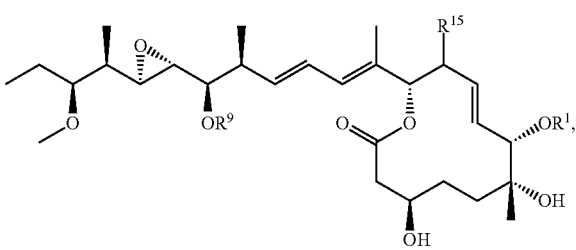

(IV)

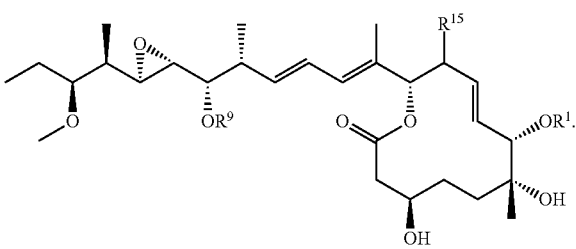

-continued (V)
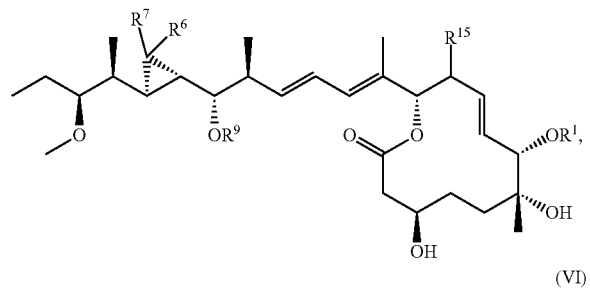

(VI)
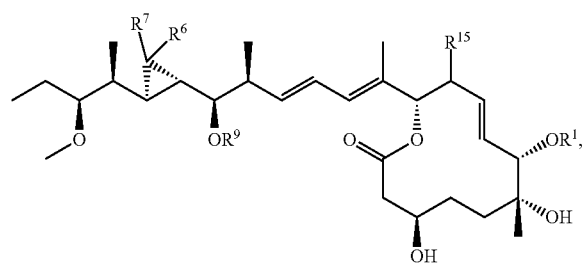

(VII)
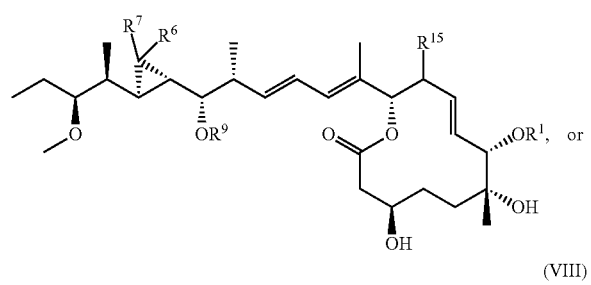

(VIII)
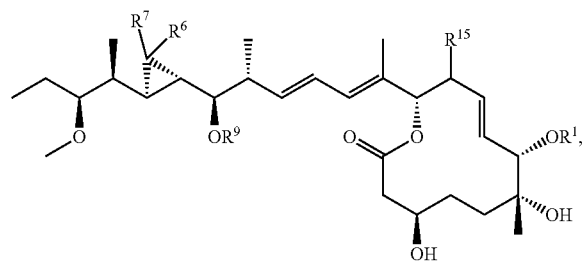

wherein $R^1$, $R^6$, $R^7$, and $R^{15}$ are as defined herein.

$R^1$ may be acetyl or hydrogen. $R^1$ may be acetyl. $R^{15}$ may be hydrogen or $C_1$-$C_4$ unsubstituted alkyl. $R^{15}$ may be $C_1$-$C_4$ unsubstituted alkyl. $R^{15}$ may be $C_1$-$C_4$ unsubstituted alkyne or $C_1$-$C_4$ alkene. $R^{15}$ may be methyl. $R^{15}$ may be hydrogen. $R^9$ may be hydrogen or $C_1$-$C_4$ unsubstituted alkyl. $R^9$ may be hydrogen. $R^9$ may be acetyl. $X^2$ may be $C(R^6)(R^7)$, as exemplified by formula (V), (VI), (VII), or (VIII). $R^6$ and $R^7$ may independently be hydrogen, halogen, or methyl. $R^6$ and $R^7$ may both be hydrogen. $R^6$ and $R^7$ may both be fluoride.

When $X^2$ is $C(R^6)(R^7)$, $R^2$ may be attached to a chiral carbon having (S) stereochemistry, and $R^4$ may be attached to a carbon having (S) or (R) stereochemistry. $R^2$ and $R^4$ may both be attached to a chiral carbon having (S) stereochemistry. The compound may have formula (V). When $R^2$ is attached to a carbon having (S) stereochemistry, $R^4$ may be attached to a carbon having (R) stereochemistry. The compound may have formula (VI). When $X^2$ is $C(R^6)(R^7)$, and $R^2$ is attached to a chiral carbon having (R) stereochemistry, $R^4$ may be attached to a carbon having (S) or (R) stereochemistry. Both $R^2$ and $R^4$ may be attached to a chiral carbon having (R) stereochemistry. When $R^2$ is attached to a carbon having (R) stereochemistry and $R^4$ may be attached to a carbon having (S) stereochemistry. The compound may have formula (VIII).

The splicing modulator of formula (I) may have formula:

(IX)
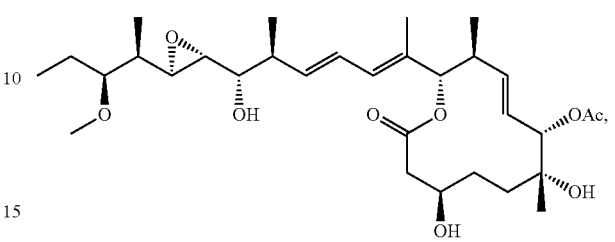

(X)
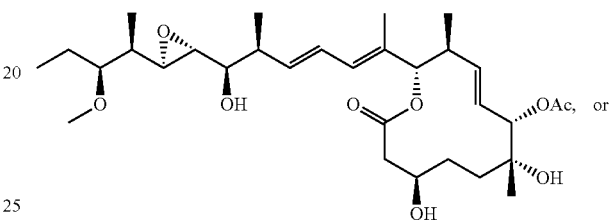

(XI)
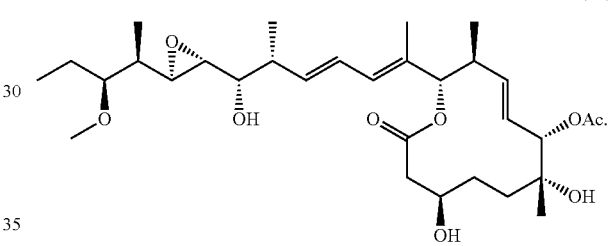

The splicing modulator may have formula:

(X)
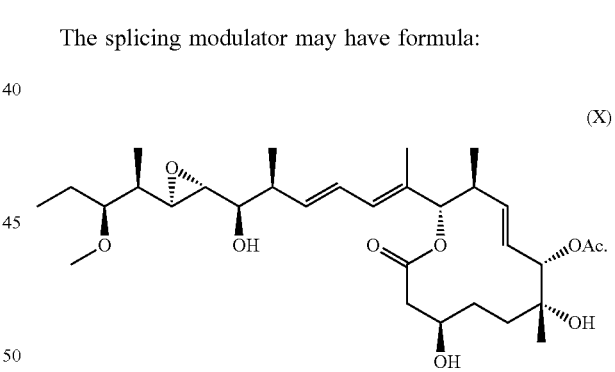

In embodiment, the splicing modulator of formula (I) has formula:

(XII)
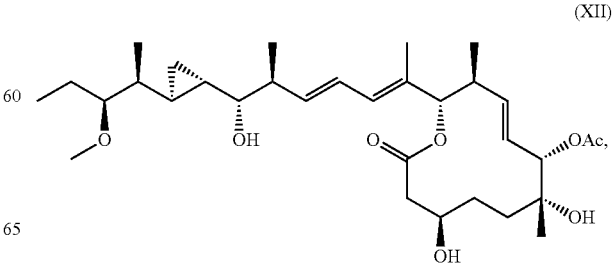

(XIII)

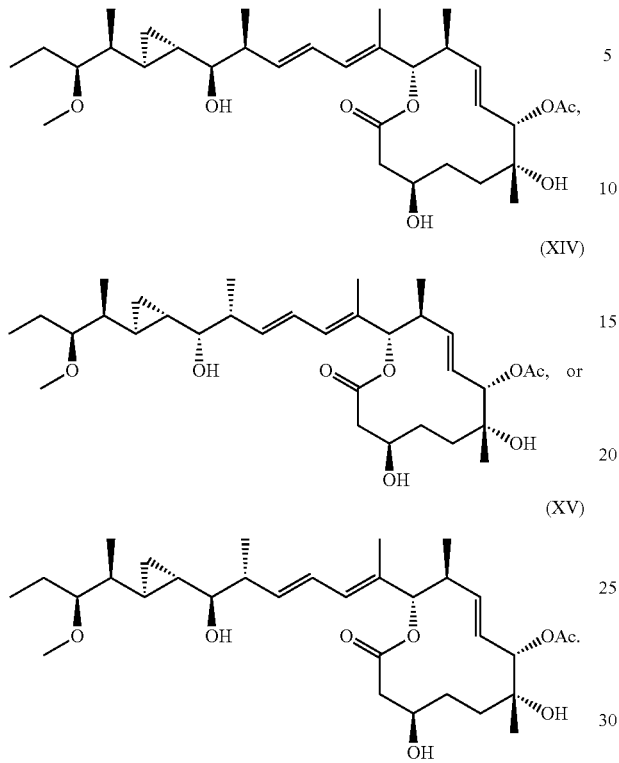

(XIV)

(XV)

The splicing modulator may have formula:

(XIII)

In embodiments, a splicing modulator useful in the methods disclosed herein and embodiments thereof has formula:

(XVI)

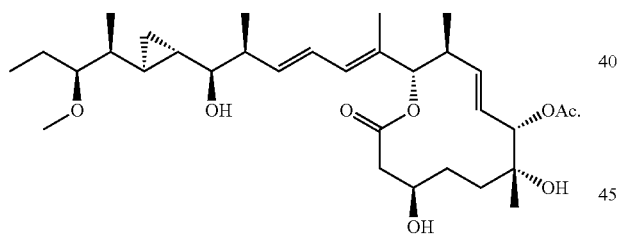

$X^1$ and $R^1$ are defined herein. $R^{20}$ is halogen, $SO_3CF_3$, or $SO_3(C_6H_6)CH_3$. $R^{21}$ is hydrogen, $C(O)R^8$, $OCO(O)R^8$, $OC(O)OR^8$, $NHC(O)NHR^8$.

The splicing modulator of formula (XVI) may have formula:

(XVIa)

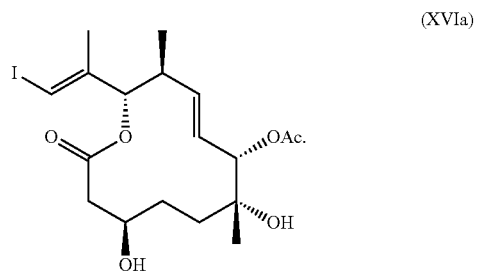 [SMILES: CC(=O)O[C@H]1/C=C/[C@H](C)[C@@H](/C(C)=C/I)OC(=O)C[C@H](O)CC[C@@]1(C)O]

In another aspect is a splicing modulator having formula:

(XVII)

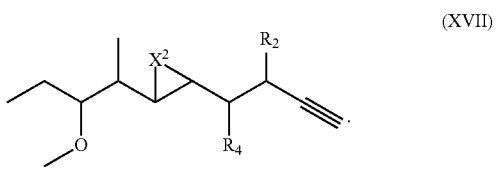

$X^1$, $R^2$, and $R^4$ are as defined herein.

$X^2$ may be O. In such instances, when $R^2$ is attached to a chiral carbon having (S) stereochemistry, $R^4$ may be attached to a carbon having (S) or (R) stereochemistry. When $R^2$ is attached to a carbon having (S) stereochemistry, $R^4$ may be attached to a carbon having (S) stereochemistry. When $R^2$ is attached to a carbon having (S) stereochemistry, $R^4$ may be attached to a carbon having (R) stereochemistry. In another embodiment, when $X^1$ is O, $R^2$ is attached to a chiral carbon having (R) stereochemistry, and $R^4$ is attached to a carbon having (S) stereochemistry. $R^2$ and $R^4$ may be methyl.

A splicing modulator may be a compound have formula:

(XVIIa)

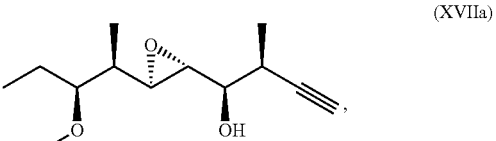

(XVIIb)

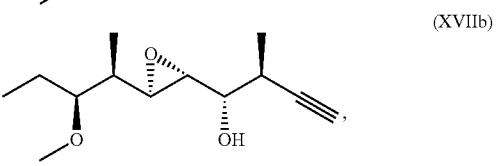

(XVIIc)

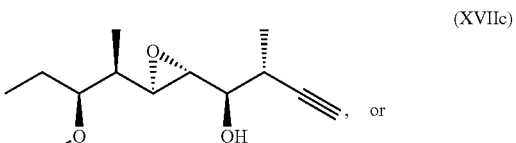

, or (XVIId)

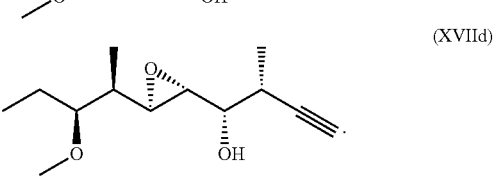

In embodiments, $X^2$ may be $C(R^6)(R^7)$. In such instances, $R^6$ and $R^7$ may independently be hydrogen, halogen, or methyl. Both $R^6$ and $R^7$ may be hydrogen. Both $R^6$ and $R^7$ may be fluoride. When $X^2$ is $C(R^6)(R^7)$, $R^2$ may be attached to a chiral carbon having (S) stereochemistry, and $R^4$ may be attached to a carbon having (S) or (R) stereochemistry. Both $R^2$ and $R^4$ may be attached to a chiral carbon having (S) stereochemistry. When $R^2$ is attached to a carbon having (S) stereochemistry, $R^4$ may be attached to a carbon having (R) stereochemistry. In another embodiment, when $R^2$ is attached to a chiral carbon having (R) stereochemistry, $R^4$ may be attached to a carbon having (S) or (R) stereochemistry. Both $R^2$ and $R^4$ may be attached to a chiral carbon having (R) stereochemistry. When $R^2$ is attached to a carbon having (R) stereochemistry and $R^4$ may be attached to a carbon having (S) stereochemistry. $R^2$ and $R^4$ may be methyl.

A splicing modulator may be a compound have formula:

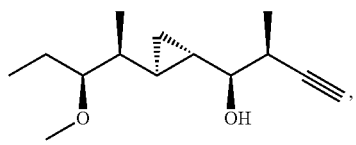
(XVIIe)

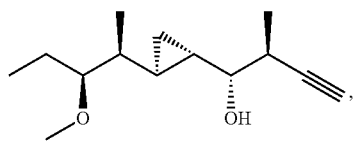
(XVIIf)

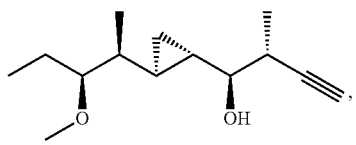
(XVIIg)

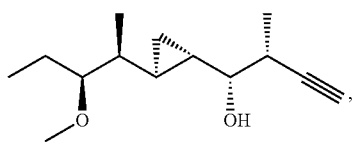
(XVIIh)

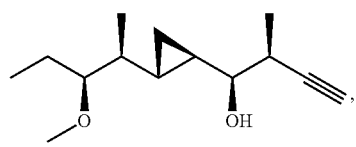
(XVIIi)

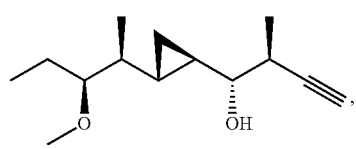
(XVIIj)

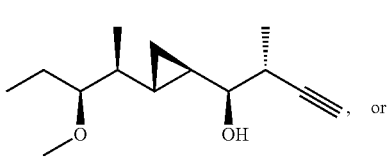
(XVIIk)
, or

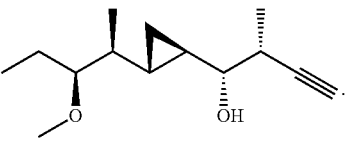
(XVIII)
.

Pharmaceutical Compositions

In another aspect is provided a pharmaceutical composition. The composition includes a splicing modulator, which is a compound having formula (I), (II), (III), (IV), (V), (VI), (VII), or (VIII), and a pharmaceutically acceptable excipient. The compound may have formula (IX), (X), or (XI). Alternatively the compound may have formula (XII), (XIII), (XIV), or (XV). The pharmaceutical composition may include more than one compound having formula (I), (II), (III), (IV), (V), (VI), (VII), or (VIII). The pharmaceutical composition may contain dosages of the compounds in a therapeutically effective amount. The pharmaceutical composition may include one amount of a compound having formula (I), (II), (III), (IV), (V), (VI), (VII), or (VIII) and a second amount of a second compound having (I), (II), (III), (IV), (V), (VI), (VII), or (VIII). The pharmaceutical composition may include at least one compound having formula (IX), (X), (XI), (XII), (XIII), (XIV), or (XV). The pharmaceutical composition may include one amount of a compound having formula (IX), (X), (XI), (XII), (XIII), (XIV), or (XV) and a second amount of a second compound having formula (IX), (X), (XI), (XII), (XIII), (XIV), or (XV).

Formulations

The pharmaceutical composition may be prepared and administered in a wide variety of dosage formulations. Compounds having formula (I), (II), (III), (IV), (V), (VI), (VII), or (VIII) may be administered orally, rectally, or by injection (e.g. intravenously, intramuscularly, intracutaneously, subcutaneously, intraduodenally, or intraperitoneally).

For preparing pharmaceutical compositions from compounds having formula (I), (II), (III), (IV), (V), (VI), (VII), or (VIII), pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; PLURONIC® F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutics composition may be intended for intravenous use. The pharmaceutically acceptable excipient can include buffers to adjust the pH to a desirable range for intravenous use. Many buffers including salts of inorganic acids such as phosphate, borate, and sulfate are known.

Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat AML, sAML, and aging-related diseases, such compositions will contain amounts of active ingredients effective to achieve the desired result (e.g. increasing the extent of cancer cell death in the patient).

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For any compound described herein or combination thereof, the therapeutically effective amounts can be initially determined from cell culture assays. Target concentrations will be those concentrations of active compound(s) that are capable of increasing the extent of cancer cell death as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring response of the AML, sAML, or age-related disease to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

EXAMPLES

Example 1. RNA Splicing Modulation Impairs Acute Myeloid Leukemia Stem Cell Maintenance Abstract.

Mutations in pre-mRNA splicing regulatory genes and alterations in the epigenetic landscape predict poor clinical outcomes in several human malignancies including acute myeloid leukemia (AML), however whether aberrant splicing contributes to cancer progression and relapse, and if splicing-targeted treatments may have therapeutic efficacy, has been unclear. Acute myeloid leukemia arises de novo or secondary to myeloproliferative neoplasms (MPNs) or myelodysplastic syndromes (MDS). Disease relapse is the leading cause of death in secondary AML (sAML) and is driven, in part, by therapy-resistant leukemia stem cells (LSC) harboring enhanced survival and self-renewal capacity. To identify alternative splicing patterns that distinguish sAML LSC, here we performed comparative splice isoform profiling of purified hematopoietic progenitors from sAML and normal bone marrow. We then investigated the LSC inhibitory efficacy of a stable and potent analogue of a splicing modulatory agent, FD-895, in humanized LSC stromal co-culture and primary xenograft assays. Whole transcriptome analyses revealed a splice isoform expression profile that distinguished sAML LSC from normal progenitors. Pharmacological spliceosome modulation disrupted AML LSC maintenance by promoting intron retention and altering splicing of pro-survival and other AML-associated transcripts. Thus, detection and targeted modulation of aberrant splicing provides an innovative strategy for AML LSC eradication with implications for treatment of a variety of human malignancies and other age-related disorders.

Introduction

Rapid advances in next-generation sequencing technologies in recent years have dramatically increased the known catalog of molecular abnormalities occurring in human malignancies. Blood cancers such as acute myeloid leukemia (AML) are particularly heterogeneous, and represent a collection of hematopoietic malignancies characterized by clonal diversity [1], chromosomal abnormalities, DNA mutations [2], and widespread epigenetic alterations [3]. Acute myeloid leukemia arises de novo or secondary to myeloproliferative neoplasms (MPNs) or myelodysplastic syndromes (MDS) [4-6]. It is estimated that there will be over 20,000 new cases of AML in the U.S. in 2015 (SEER Fact Sheets). Despite extensive clinical use of DNA-modifying hypomethylating agents [4,7,8] in the treatment of AML, bone marrow transplantation remains the only potential cure for this aggressive disease. A major clinical obstacle in the treatment of patients with sAML is that many individuals are ineligible for hematopoietic stem cell (HSC) transplantation procedures due to advanced age. Moreover, disease relapse, the leading cause of death in sAML, is driven in part by a dormant leukemia stem cell (LSC) population that harbors enhanced survival and self-renewal capacity [9-11]. Studies involving mouse transgenic AML models and in human intermediate and high-risk MDS demonstrate that hematopoietic stem cells (HSC) have a myeloid lineage bias that leads to expansion of the granulocyte-macrophage progenitor (GMP) population that can give rise to self-renewing LSC [12, 13]. Frequent activation of stem cell regulatory pathways [10, 14], combined with mutations in splicing regulatory genes and alterations in the epigenetic landscape [2, 6, 10, 15-17], influence clinical outcomes in sAML. Consequently, a central goal of future therapeutic strategies is to eradicate LSCs by selectively targeting molecular pathways that typify LSC expression patterns and are essential to their function.

Transcriptomic analyses reveal widespread splice isoform alterations in splicing factor-mutated cancers [18] and MPN progenitors [19, 20]. Together with deregulated RNA editing [21, 22] and non-coding RNA expression [23, 24], transcriptome remodeling has emerged as a hallmark of leukemic transformation and therapeutic resistance. Previously, we showed that RNA editing-induced misspcling of a stem cell regulatory gene, GSK3β, promoted therapy-resistant LSC generation [19-22]. In addition, MDS [25] and de novo AML [26] gene expression studies demonstrate differential exon usage of epigenetic modifier and tumor suppressor transcripts, including EZH1 and TP53. However, the splice isoform expression profiles of sAML LSC had not been established.

Alternative splicing occurs in up to 95% of human multi-exon genes during human development and aging [27,28]. Widespread changes in pre-mRNA splicing have been implicated in a variety of age-related disorders including neurological diseases and cancer [29], however regulation of pre-mRNA splicing is a highly intricate process that remains rather poorly defined. Numerous multi-protein complexes participate in post-transcriptional processing of RNA to form mature spliced transcripts. However, the functional effects of imbalances in the expression and activity of splicing factors remains unclear. Seminal DNA sequencing and microarray gene expression studies suggest risk for transformation to AML is governed by mutations in splicing-related genes (SF3B1, U2AF1 [15,30,31]) and epigenetic modifiers of gene expression (RPS14, E12, EZH2, ASXL1, DNMT3A [31]) [17]. Recently, the presence of mutations in SF3B1, SRSF2, U2AF1, ZRSR2, ASXL1, EZH2, BCOR, or STAG2 was shown to be >95% specific for diagnosis of sAML [6]. Four of these eight genes are key regulators of RNA splicing function, suggesting a common theme of splicing de-regulation occurring during the initiation and progression of leukemia.

Whether aberrant RNA splicing promotes LSC generation, and whether RNA splicing modulation may represent a viable therapeutic strategy for sAML and other hematopoietic malignancies that respond poorly to current treatments is unknown, and is currently a subject of great interest for cancer treatment development [32,33]. To address these questions, we performed comparative splice isoform profiling of FAC S-purified hematopoietic progenitors from sAML and normal bone marrow. We then investigated the LSC inhibitory efficacy of a stable and potent analogue [34] of a splicing modulatory agent, FD-895, in humanized LSC stromal co-culture and PRIMAGRAFT™ assays. Global gene and whole transcriptome expression signatures distinguished sAML from normal progenitors and revealed sAML-specific splice isoform biomarkers. Pre-clinical spliceosome modulation studies in primary AML models demonstrated LSC inhibitory efficacy with a favorable therapeutic index. Thus, detection and targeted modulation of aberrant splicing provides an innovative strategy for AML LSC eradication with broad implications for treatment of other therapy-resistant cancers [18] and a variety of other age-related diseases typified by aberrant RNA splicing [29]. Effective therapeutic modulation of pre-mRNA splicing would provide new clinical tools for correcting malignant gene expression programs, as a powerful complement or alternative strategy to existing cancer treatment regimens.

Results.

Global Disruption of Splicing Factor Gene Expression in sAML LSC.

Figure 5A:
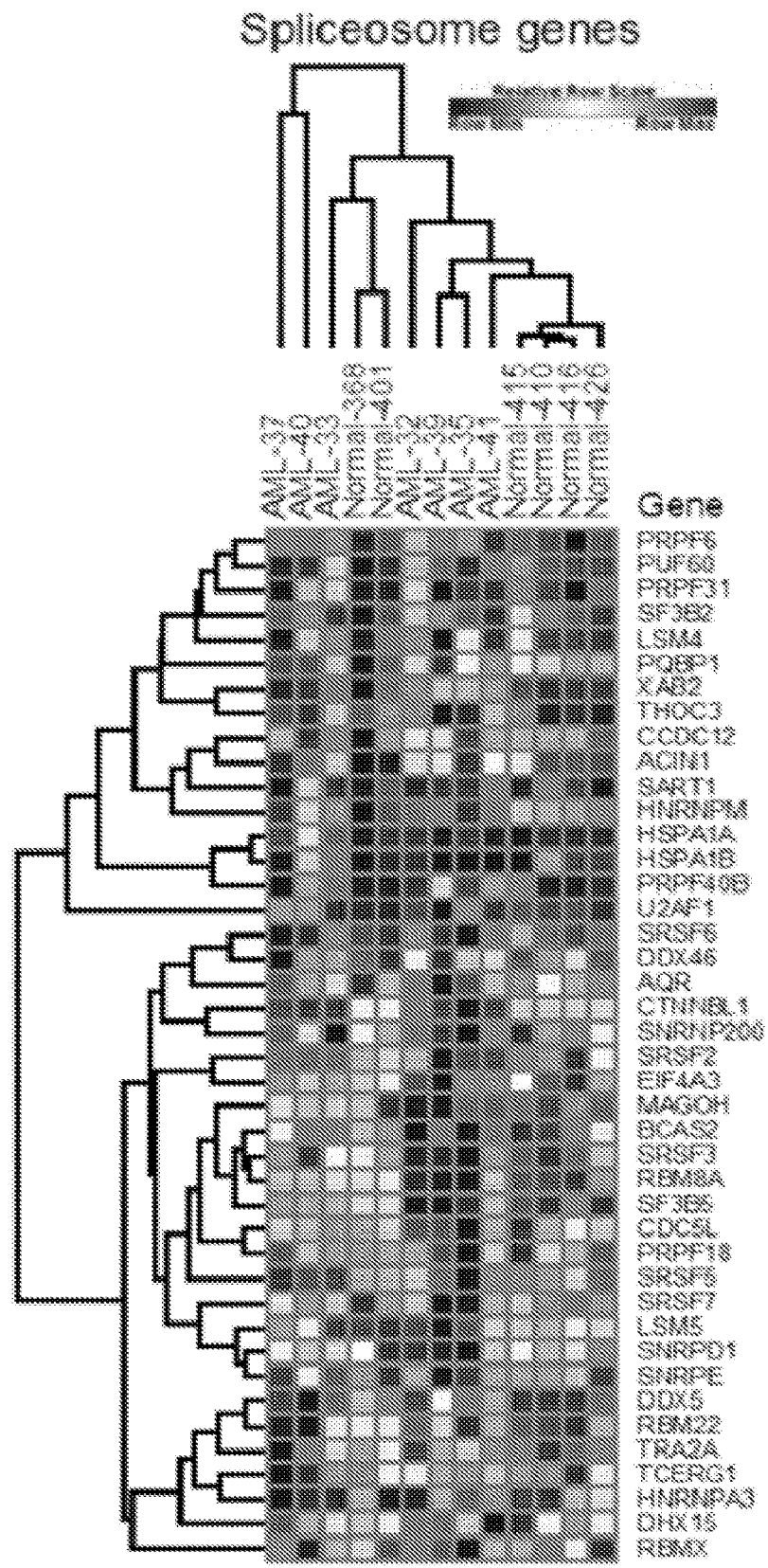
FIGS. 5A-5C. Gene expression changes in spliceosome machinery, mutational analyses in SF3B1, and PTK2B isoform expression. For FACS-purified hematopoietic progenitors (CD34$^+$CD38$^+$ Lin$^-$) from 7 secondary (s)AML and 6 normal age-matched bone marrow (BM) samples, gene expression data in FPKM was obtained from RNA-sequencing data by aligning paired end unstranded 100 bp poly-A reads using STAR and quantifying transcripts using Cufflinks. The resulting gene expression data was submitted to GSEA to determine significant KEGG pathways and enrichment plots describing ranked gene expression in those pathways. Additional targeted analysis was performed to search for single nucleotide variants (SNV) in spliceosome gene products in which mutations have been previously described in hematopoietic malignancies and pre-malignant bone marrow disorders (e.g. MDS) [17].
Figure 11A:
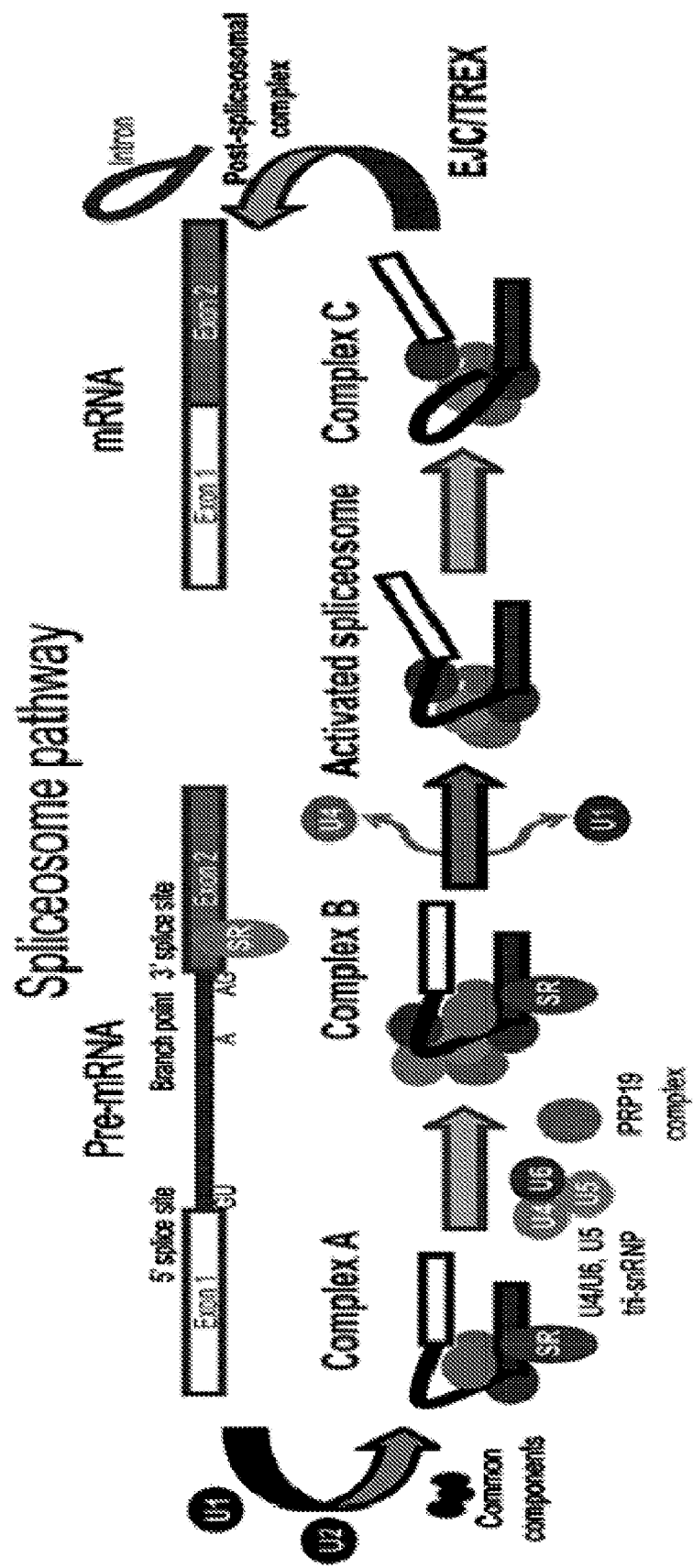

We performed whole transcriptome analyses of FACS-purified hematopoietic progenitor cells (CD34$^+$CD38$^+$Lin$^-$) to analyze overall patterns of gene expression in sAML LSC compared with normal controls. Comparative RNA-Seq and gene set enrichment analyses of purified progenitor cells isolated from seven sAML patient samples (see Table 1 for patient clinical characteristics) and six normal age-matched controls (average age=63 y/o) revealed significant alterations in splicing factor expression (FIGS. 1A, 5A). Notably, spliceosome-associated pathways represented the most significantly de-regulated gene set in sAML progenitors compared with normal controls (see e.g., FIG. 11A). While one sAML sample had a mutation in the splicing factor SF3B1 (FIG. 5B), numerous spliceosome-related genes were transcriptionally deregulated in sAML (FIG. 5A). Furthermore, quantitative real-time (qRT)-PCR showed increased SF3B1 expression in AML progenitors.

TABLE 1

AML and MDS patient samples used for RNA-sequencing, qRT-PCR, functional studies and to establish in vivo AML PRIMAGRAFT ™ models.

| Sample Code | Gender | Age | Cell Source | Blast % | Diagnosis | Prior Disease | Treatment | Cytogenetics |
|---|---|---|---|---|---|---|---|---|
| AML-04 | M | 76 | BM | M = 88%, F = 95% | AML | AML | None | 46, XY, del(7)(q22)[3]/46, XY [6] |
| *AML-08 | F | 52 | BM | M = 37%, F = 42.1% | AML | AML | None | 46, XX[20] |
| *AML-12 | M | 51 | BM | M = 38%, F = 31% | AML | AML | None | 46, XY[20] |
| AML-22 | F | 60 | BM | M = 14%, C = 7% | AML (NOS) | 1st relapse | N/A | N/A |
| AML-23 | M | 66 | BM | M = 50%, C = 70% | AML (M0) | 1st relapse | N/A | N/A |
| AML-24 | M | 70 | BM | M = 13%, C < 5% | AML | 1st relapse | N/A | N/A |
| AML-25 | M | 66 | BM | M < 5%, C = 0 | AML (M1) | 1st relapse | N/A | N/A |
| AML-26 | F | 47 | BM | M = 60.3%, C < 1% | AML (NOS) | 1st relapse | N/A | N/A |
| AML-27 | F | 73 | BM | M = 0% - relapse quantified by monocytoid cells | AML (M5b) | 1st relapse | N/A | N/A |
| AML-28 | M | 72 | PB | M = 41%, C = 6% | AML (NOS) | 1st relapse | N/A | N/A |
| AML-29 | M | 61 | PB | M = 90%, C = 45% | AML (M1) | 1st relapse | N/A | N/A |
| AML-31 | M | 59 | PB | PB = 10% | sAML | MDS | None | N/A |
| *AML-32 | M | 68 | PB | 50% | sAML | MDS | None | 47, XY, +8[2]/46, XY[18] |
| *AML-33 | F | 63 | BM | M = 21%, F = 5.8% | sAML | MDS | None | 47, XX +21[14]/46, XX, +mar1 [2]/46, XX[4] |
| *AML-35 | M | 82 | BM | M = 12%, F = 28.2% | sAML | MDS | None | 45, X, −Y[20] |
| *AML-37 | F | 72 | PB | PB = 63% | sAML | MDS | None | 46, XX, 1, inv(3)(q21q26.2), del(5)(q14q34), der(12)t(1; 12)(q21; p11.2), 20, +r, +mar1[9]/46, sl, der(7)t(7; 9)(p13; q13)[4]/46, sl, i(21)(q10)[3]/46, sl, add(2)(q31)[2]/46], sl, add(2)(q33)[2] |
| *AML-39 | F | 69 | PB | PB = 79.8% | sAML | MPD | None | 46, XX[10] |
| *AML-40 | F | 63 | PB | 5% CD34+, 19% promonocytes | sAML | MDS | None | 5q−, +8, possible 7q− |

TABLE 1-continued

AML and MDS patient samples used for RNA-sequencing, qRT-PCR, functional studies and to establish in vivo AML PRIMAGRAFT ™ models.

| Sample Code | Gender | Age | Cell Source | Blast % | Diagnosis | Prior Disease | Treatment | Cytogenetics |
|---|---|---|---|---|---|---|---|---|
| *AML-41 | M | 82 | BM | N/A | sAML | MDS (RARS) | Hydroxyurea | N/A |
| AML-42 | M | 73 | BM | 92% | sAML | CMML | None | N/A |
| AML-43 | M | 72 | PB | 14% in BM | sAML-M6 | MDS | None | N/A |
| AML-44 | M | 74 | BM | N/A | sAML | MF | Revlimid | N/A |
| *MDS-06 | F | 62 | PB | M = <5%, F = 14% | MDS/MF | None known | None | 5q deletion; JAK2V617F negative |
| *MDS-07 | M | 74 | PB | M = 4.5%, F = 1.7-2.3% | MDS/MF | None known | G-CSF | Normal FISH results in bone marrow, JAK2V617F negative |
| *MDS-10 | M | 71 | BM | M = <1% | MDS | None known | None | Normal FISH results in bone marrow, JAK2V617F negative |
| *^MDS-12 | M | 48 | PB | F = 9% | MDS-RAEB2 | Newly diagnosed | None | 45~47, X, add(Y)(q11.23), add(4)(q12), der(5; 17)(p10; q10), −6, del(7)(q22q34), +8, −18, add(18)(q11.2), −20, −22, +1~3r, +mar1, +2~4mar[cp20] |
| *^MDS-13 | M | 48 | BM | M = 13%, F = 4.4% | MDS-RAEB2 | Newly diagnosed | None | 45~47, X, add(Y)(q11.23), add(4)(q12), der(5; 17)(p10; q10), −6, del(7) (q22q34), +8, −18, add(18)(q11.2), −20, −22, +1~3r, +mar1, +2~4mar[cp20] |

M = morphology, F = flow (peripheral blood), C = circulating blasts (peripheral blood), BM = bone marrow, PB = peripheral blood, NOS = not otherwise specified, N/A = not available.
*Samples used in RNA-seq studies;
^from same sample donor Identification of an AML LSC-Specific Splice Isoform Expression Signature.

Figure 2A:
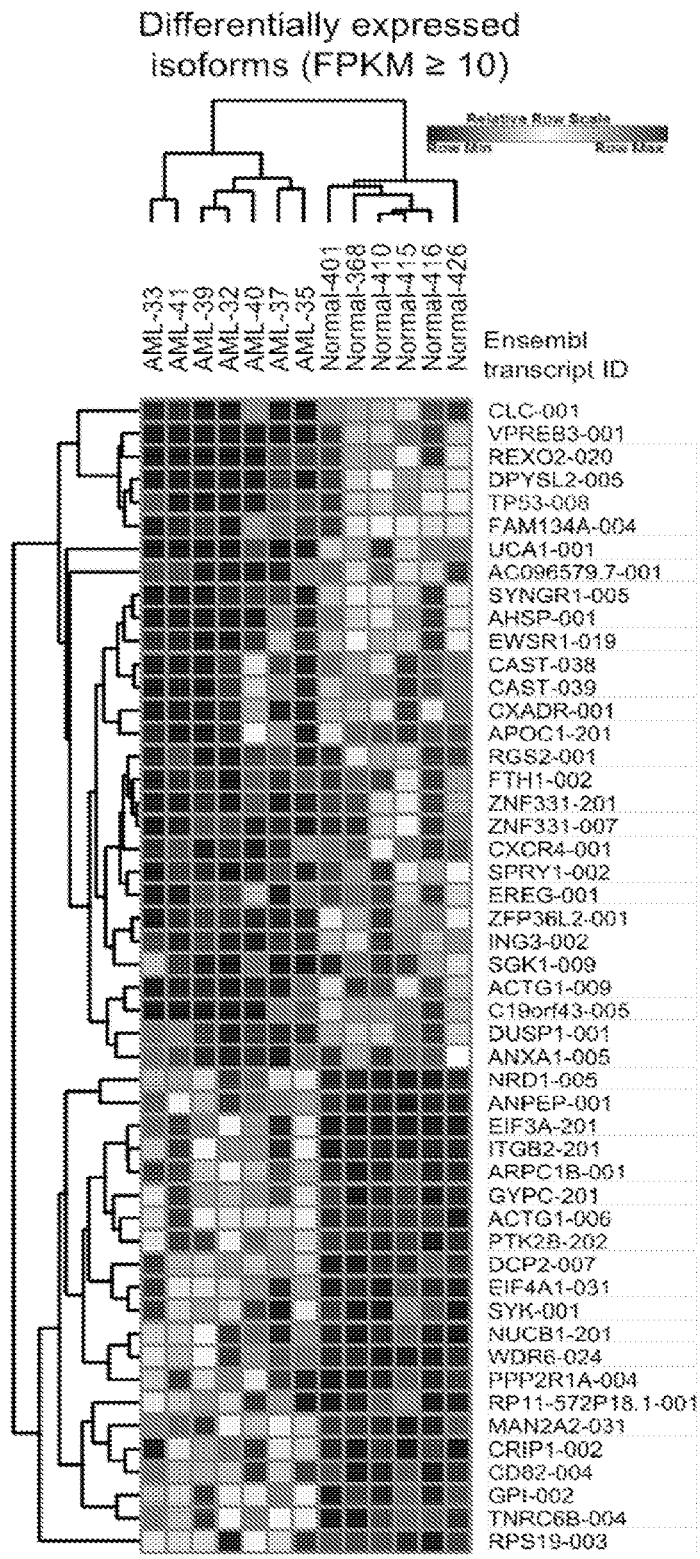
FIGS. 2A-2C. Splice isoform expression signature distinguishes sAML progenitors. For FACS-purified hematopoietic progenitors (CD34$^+$CD38$^+$ Lin$^-$) from 7 secondary (s)AML and 6 normal age-matched BM samples, isoform expression data in FPKM was obtained from RNA-sequencing data by aligning paired end unstranded 100 bp poly-A reads using STAR and quantifying transcripts using Cufflinks [56]. Log 2 fold change (L2FC) and p values for comparison between sAML and normal progenitors were computed from gene and isoform expression data (FPKM+1).
Figure 2B:
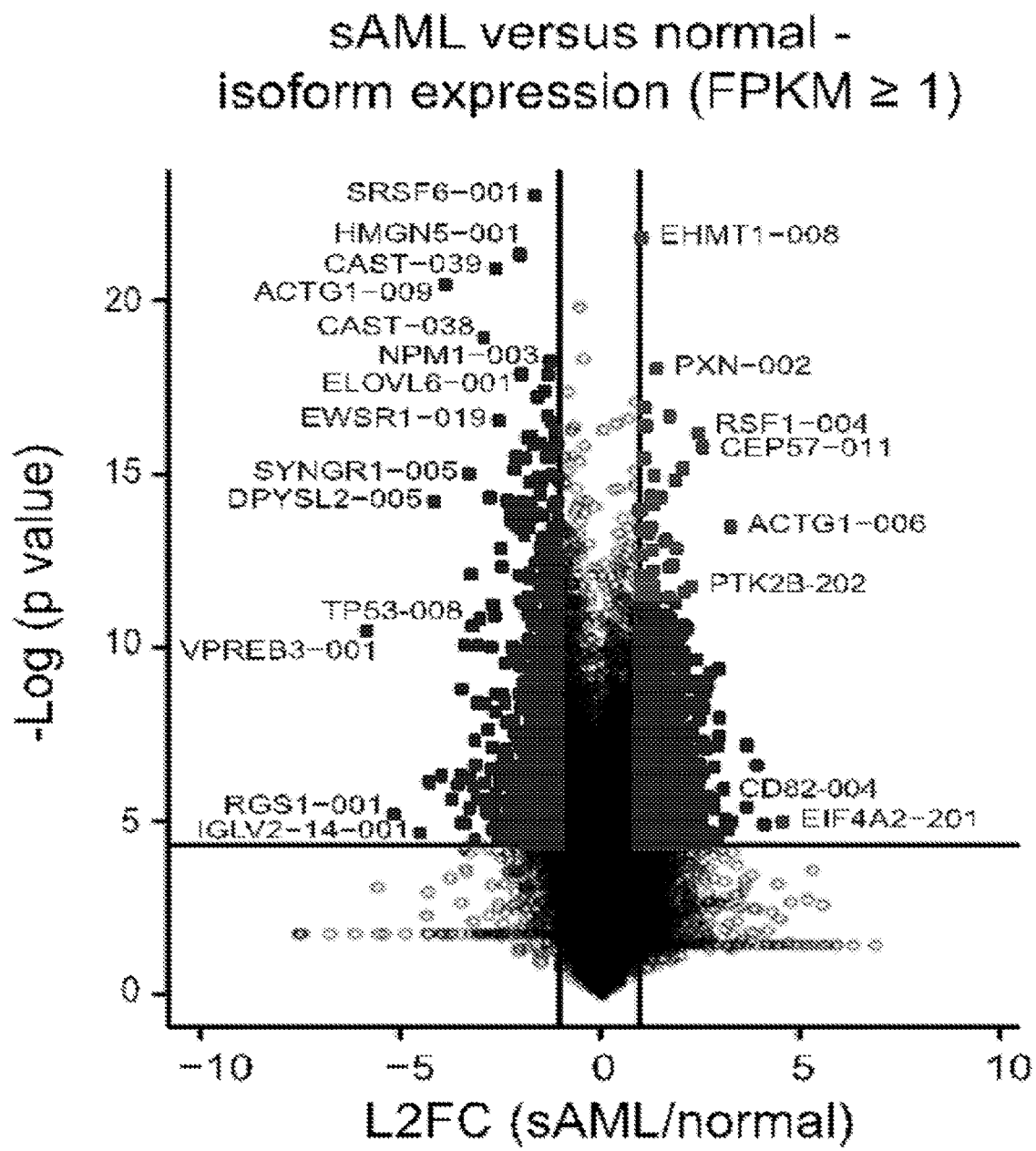
Figure 2C:
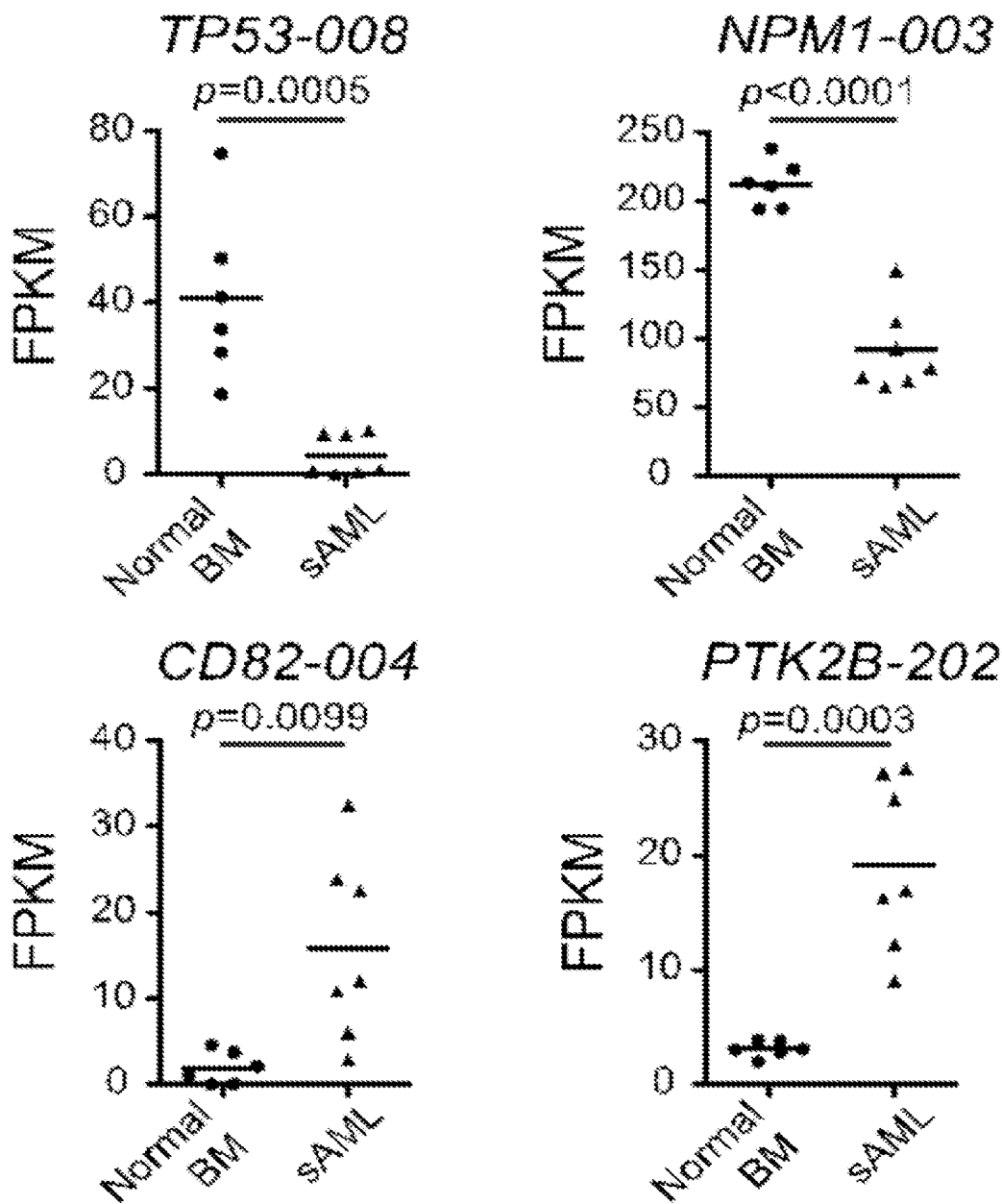

Next, we examined splice isoform changes associated with sAML using an isoform-specific alignment algorithm that incorporates known transcript sequences from UCSC, NCBI, and Ensembl [21,35]. Analysis of moderate-to-highly expressed isoforms (FPKM≥10), and all transcripts with a median FPKM≥1, revealed a splice isoform expression signature that included specific transcripts of genes associated with AML (NPM1, TP53, CD82 and PTK2B) [36, 37] (FIGS. 2A-2C). Nucleophosmin (NPM1) is an AML prognostic marker, and the tumor suppressor TP53 has been widely studied in cancer. Integrins, key regulators of tumor progression, interact with select CD82 (KAI1) isoforms [38] and regulate cell adhesion-mediated activation of the focal adhesion kinase-related tyrosine kinase PTK2B (PYK2) [39]. These transcripts may represent splice isoform-specific diagnostic biomarkers and therapeutic targets. RNA-Seq based analysis showing increased expression of PTK2B-202 in AML progenitors (FIG. 2C) was validated by splice isoform-specific qRT-PCR (FIG. 5C), suggesting that AML-specific transcripts could be translated into clinical assays for LSC detection.

Rapid and Potent Alterations in Splicing Following 17S-FD-895 Treatment.

Figure 3A:
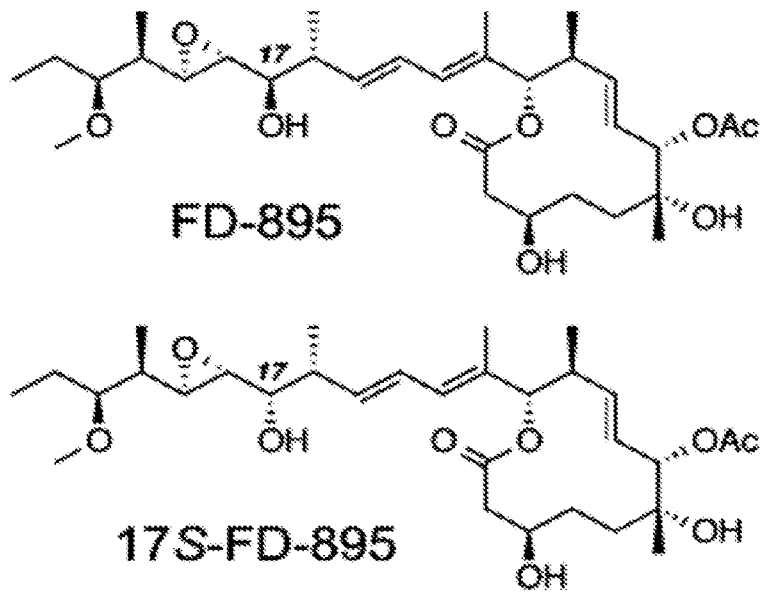
FIGS. 3A-3G. Chemical structures, splicing reporter and AML LSC assays.

Considering the alterations in splicing factor gene expression and de-regulated splice isoform expression patterns that distinguished sAML LSC from normal progenitors, we hypothesized that pharmacological spliceosome modulation might have LSC inhibitory effects. The SF3B subunit of the spliceosome is a target of several natural products with anti-tumor properties, including the macrolide pladienolide B [40]. However, structural complexity has to date constrained clinical research and development. The natural product pladienolide B and related analogues including FD-895 (FIG. 3A) [34] demonstrate poor stability in aqueous and biological media. The short half-lives ($t_{1/2}$≤15 min) of these compounds and potential off-target toxicity [41] arising from hydrolyzed seco-acids highlights the need for development of stabilized and selective spliceosome-targeted compounds. We recently described a series of synthetic analogues of FD-895 that demonstrate enhanced activity and metabolic stability [34]. Here we evaluated FD-895 and 17S-FD-895 [34] (FIG. 3A), a stereoisomer with 25-fold higher activity, in splicing reporter activity, PCR, and functional hematopoietic progenitor assays [19,21].

Figure 3B:
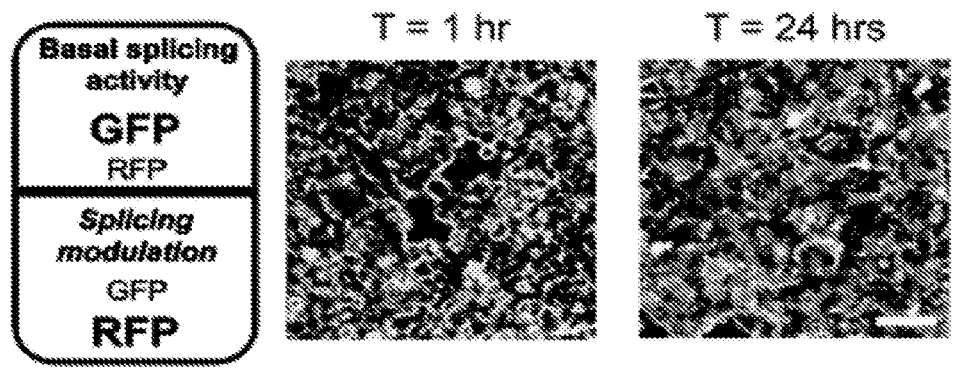
Figure 3C:
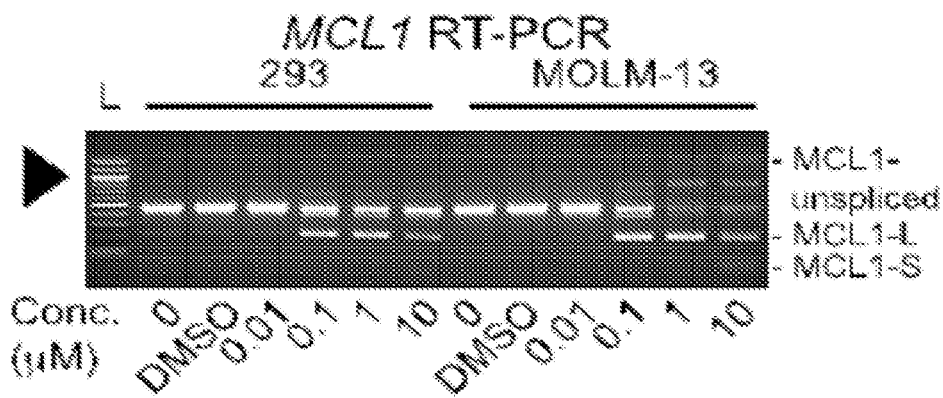
Figure 3D:
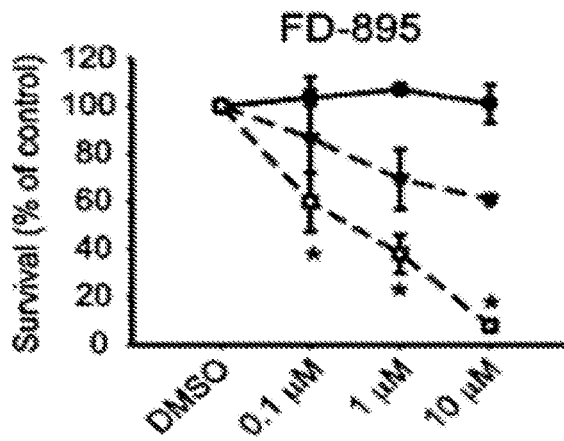
Figure 3E:
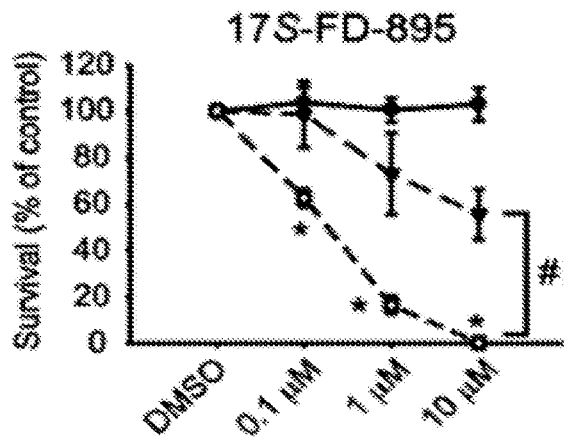
Figure 3F:
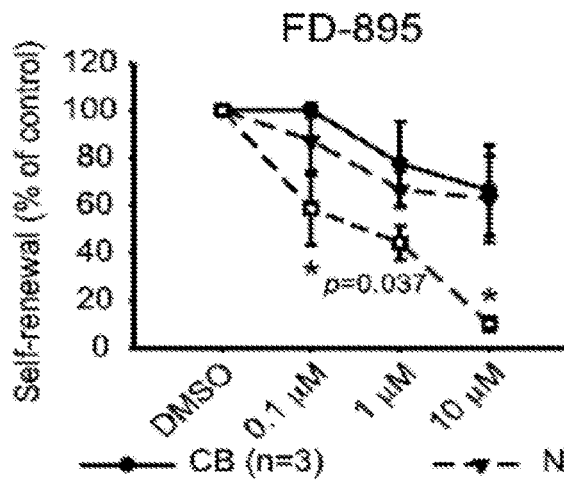
Figure 3G:
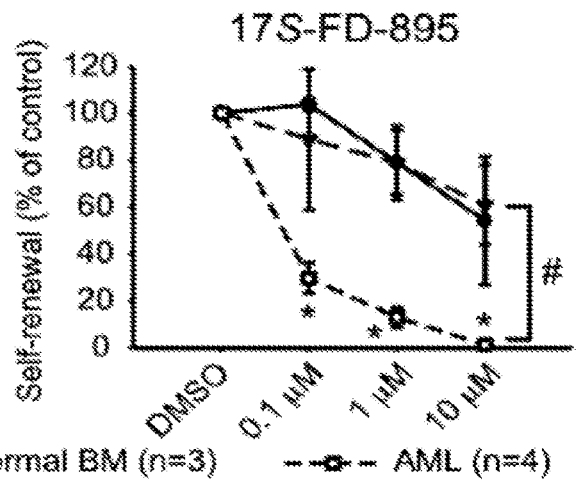
Figure 6A:
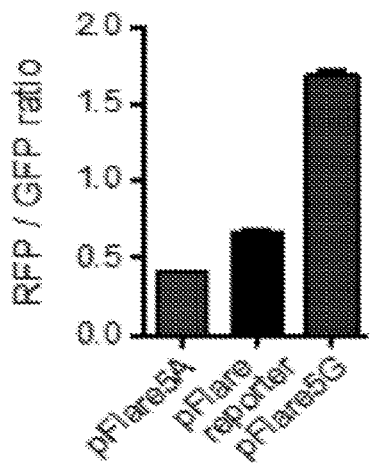
FIGS. 6A-6G. Splicing reporter and RT-PCR assays in HEK293 and sAML MOLM-13 cells treated with FD-895 or 17S-FD-895.
Figure 6B:
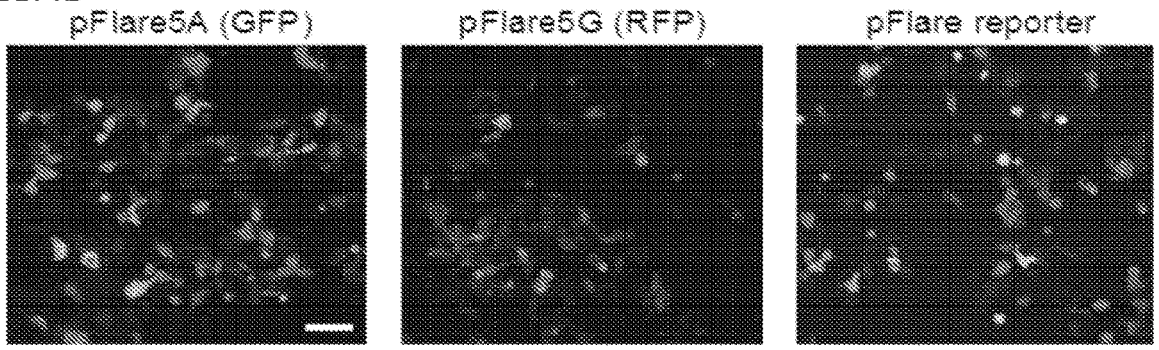
Figure 6C:
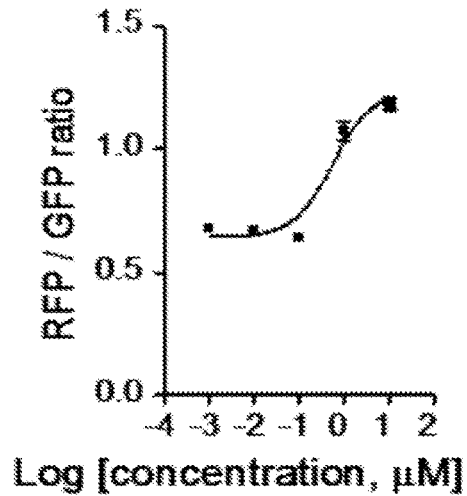
Figure 6D:
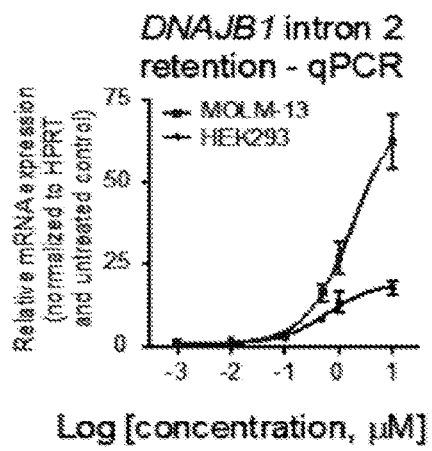
Figure 6E:
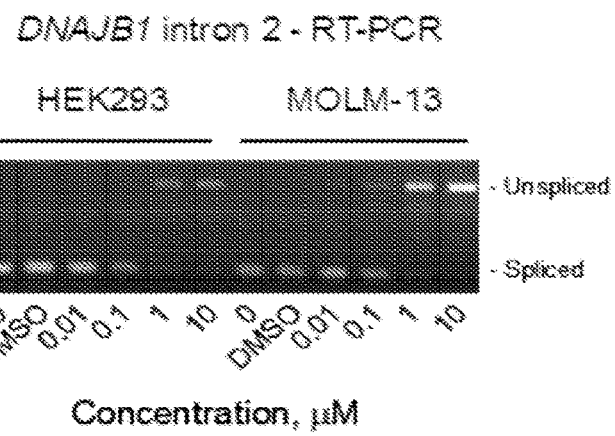
Figure 6F:
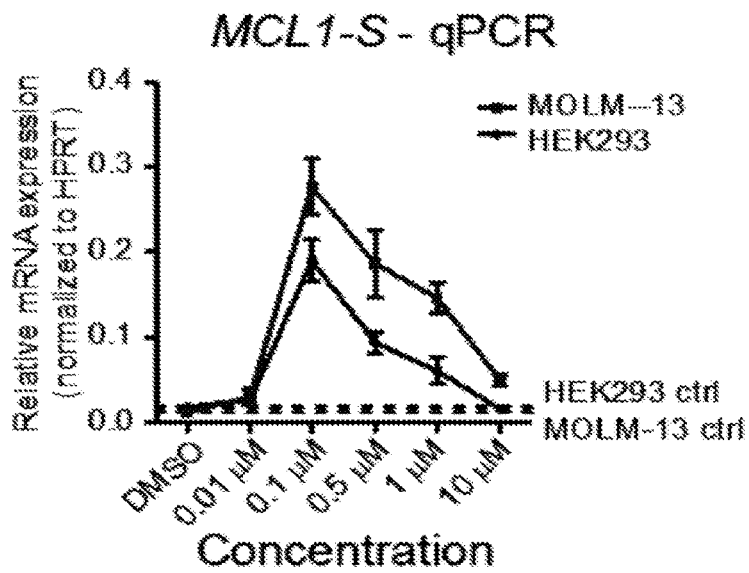
Figure 6G:
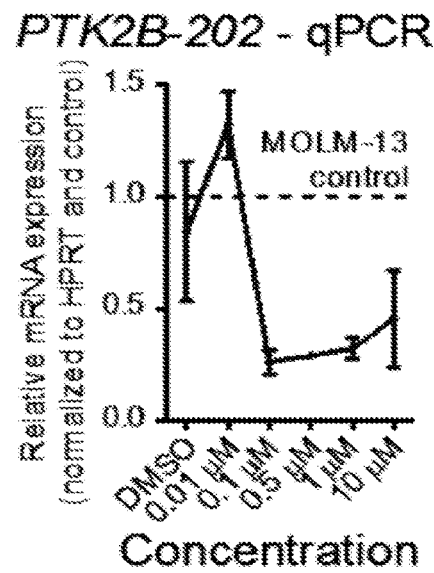

To assess the splicing modulatory activity of 17S-FD-895, cell-based assays were performed using a dual fluorescence splicing reporter (pFlare [42], FIG. 3B, FIGS. 6A-6B). Analysis showed a dose-dependent increase in RFP/GFP ratios in HEK293 cells (FIG. 3B, FIG. 6C). Time-lapse confocal fluorescence microscopy confirmed an increase in RFP fluorescence following 17S-FD-895 treatment. In keeping with previous work showing that pladienolide derivatives alter intron retention of DnaJ (Hsp40) homolog, Subfamily B, Member 1 (DNAJB1) [40], PCR analyses demonstrated a rapid and dose-dependent increase in DNAJB1 intron 2 retention following 17S-FD-895 treatment of MOLM-13 sAML cells (FIGS. 6D-6E). Notably, previous studies involving genetic and pharmacologic modulation show that SF3B1 inhibition alters splicing and pre-mRNA nuclear retention [43] of vital cancer-related transcripts regulating cell-cycle, angiogenesis and apoptosis [44], such as MCL1 [45]. Interestingly, quantitative RT-PCR analyses of HEK293 and MOLM-13 cells revealed that while low doses of 17S-FD-895 increased MCL1-S expression, this effect was reversed at high doses (FIG. 6F). Additional RT-PCR analysis revealed that splicing modulation triggered MCL1 exon 2 skipping, producing MCL1-S, as well as production of an array of other intron-retained and completely unspliced products specific to sAML cells. These data suggest that sAML cells harbor marked sensitivity to splicing modulation. In addition, short-term 17S-FD-895 treatment reduced expression of the sAML-associated transcript PTK2B-202 (FIG. 6G), suggesting that splicing modulation could restore normal splice isoform expression patterns.

Impaired AML LSC Maintenance with In Vitro Pharmacological Splicing Modulation.

Figure 7A:
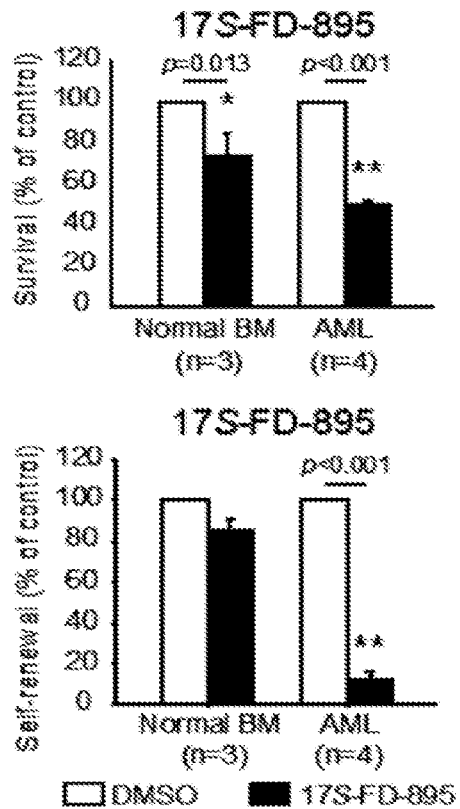
FIGS. 7A-7C. Validation, time course and hematopoietic progenitor cell fate studies in bone marrow stromal co-cultures treated with 17S-FD-895.
Figure 7B:
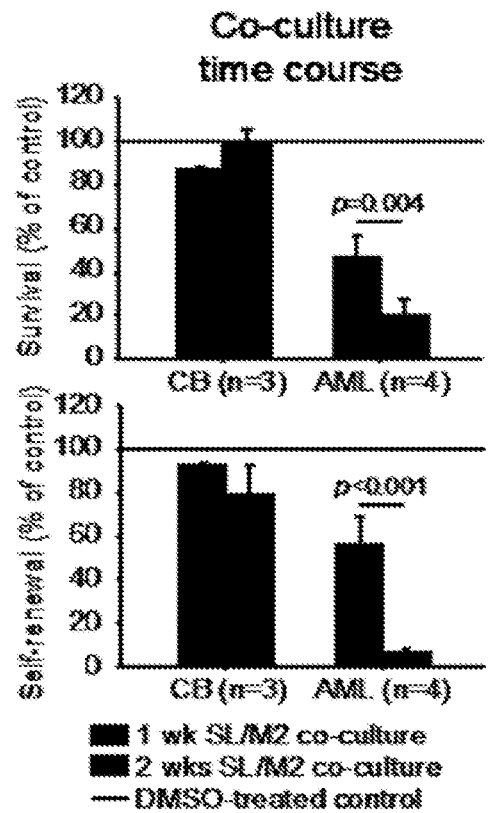
Figure 7C:
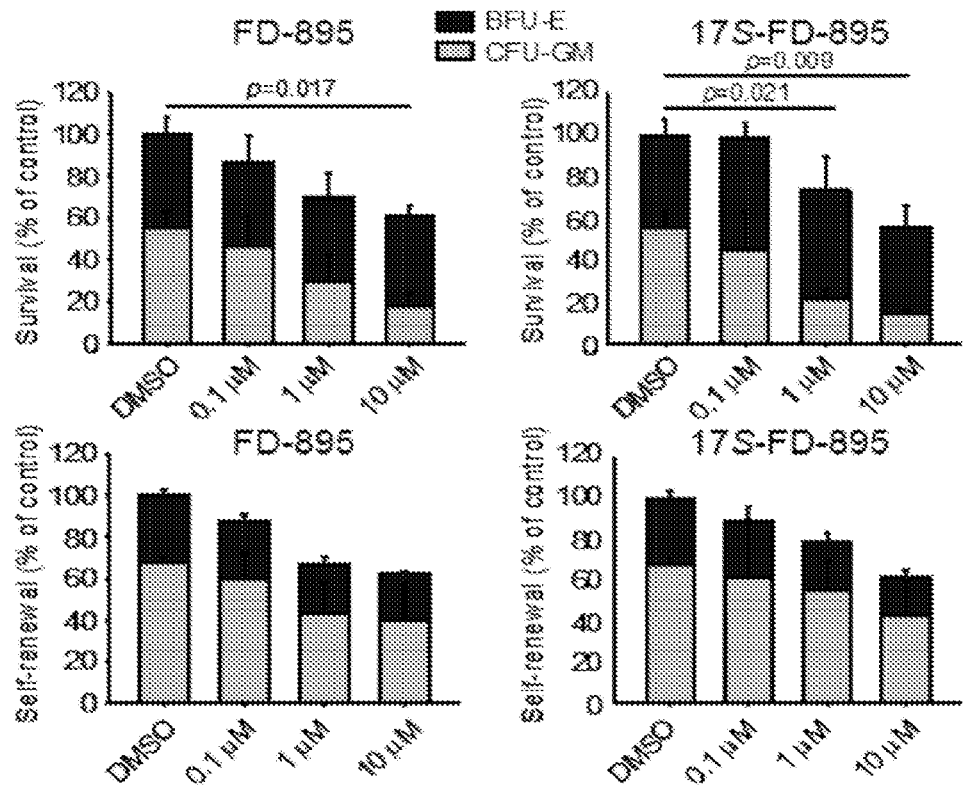

Previous studies identified a therapeutic index for FD-895 in primary chronic lymphocytic leukemia cells compared with normal B cells, which was independent of SF3B1 mutational status [45]. However, LSC inhibitory efficacy had not been established. Thus, we evaluated FD-895 and 17S-FD-895 in a LSC-supportive stromal co-culture model that recapitulates key aspects of the human bone marrow microenvironment [19,22]. In hematopoietic progenitor assays, performed following stromal co-culture of CD34+ cells from AML, cord blood (CB) and normal bone marrow with FD-895 or 17S-FD-895, there was a dose-dependent reduction in AML LSC survival and self-renewal (FIGS. 3D-3G, FIG. 7A) with a favorable therapeutic index. Notably, effects were more pronounced with 17S-FD-895. In keeping with reduced LSC maintenance, significantly fewer colonies formed after two weeks of stromal co-culture (FIG. 7B). While there was a slight decrease in granulocyte-macrophage colony survival in aged bone marrow samples treated with FD-895 or 17S-FD-895, erythroid colony formation and self-renewal were not significantly changed (FIG. 7C).

Splicing Modulation Impairs AML LSC Maintenance In Vivo.

Figure 4A:
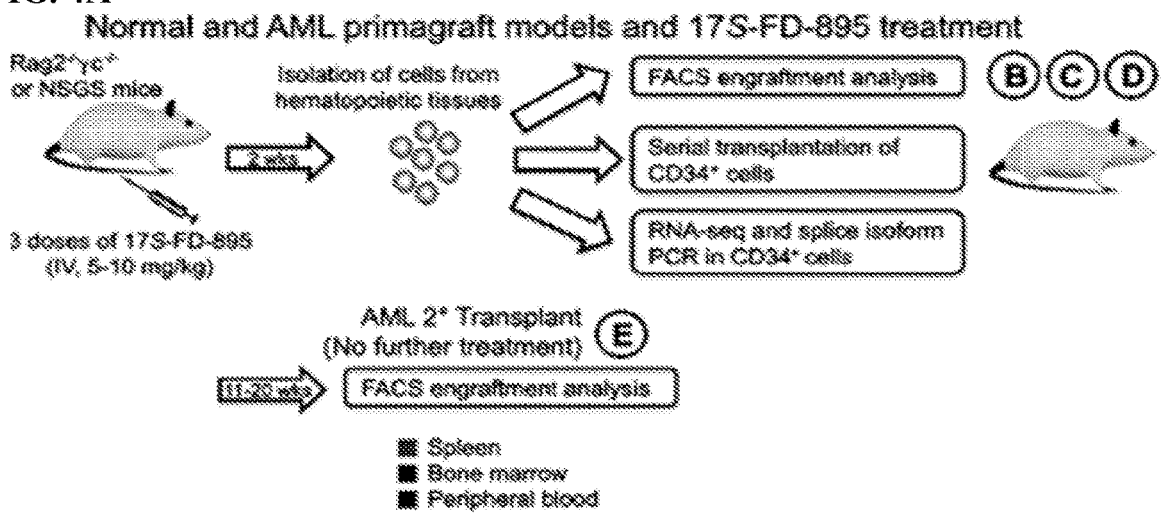
Figures 8A, 8B:
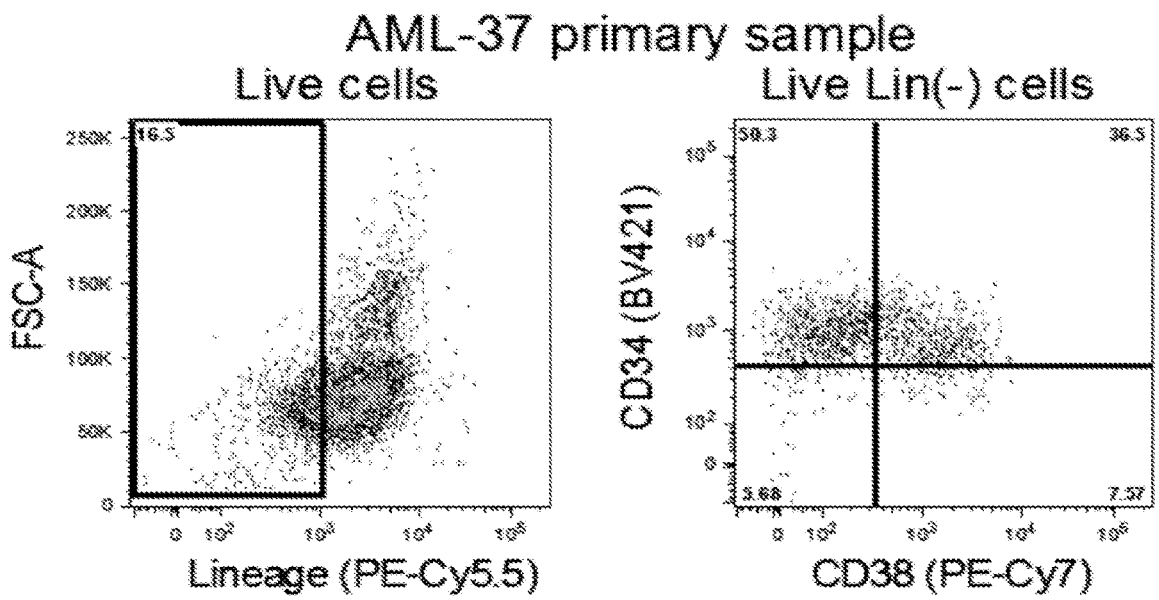
FIGS. 8A-8D. Serially transplantable AML PRIMAGRAFT™ models.
Figure 8C:
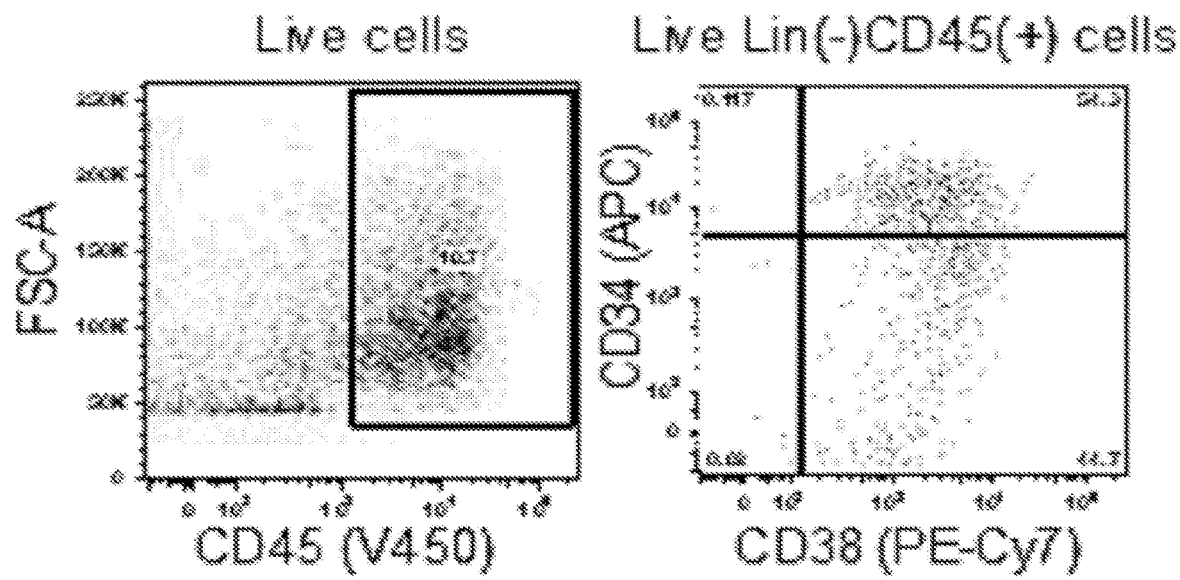
Figure 8C:
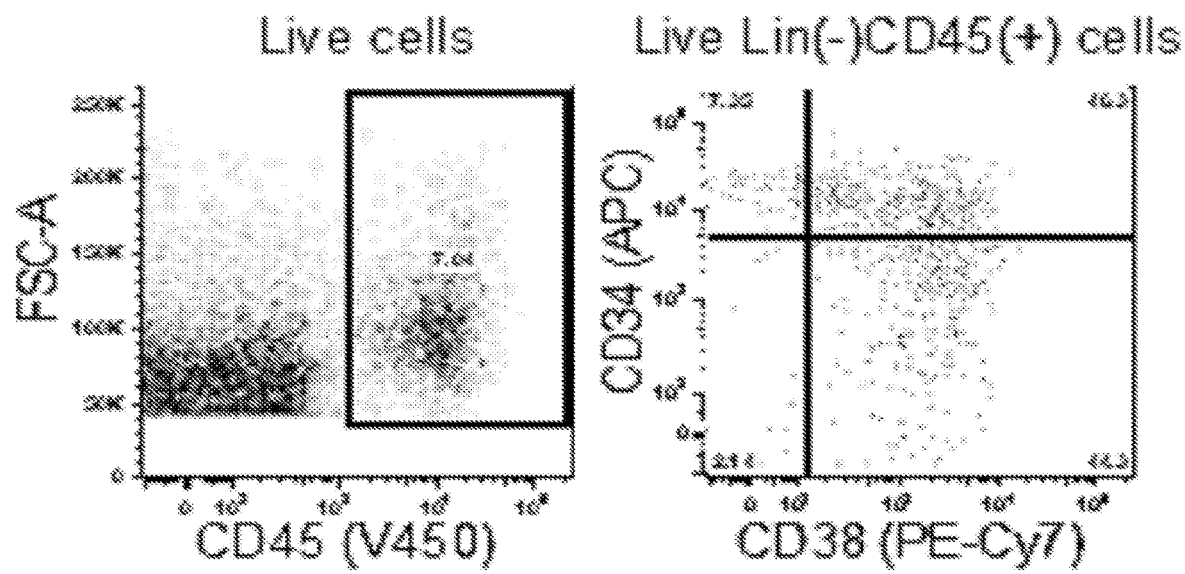
Figure 8D:
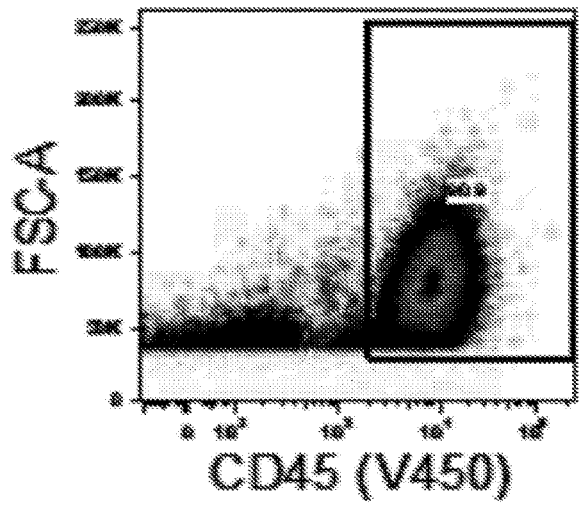
Figure 8D:
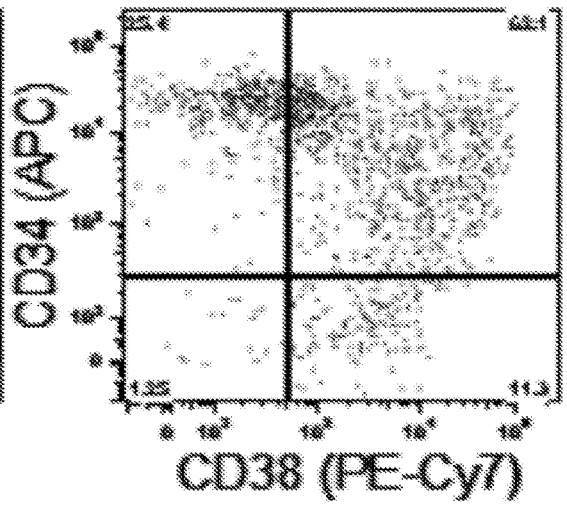
Figure 8D:
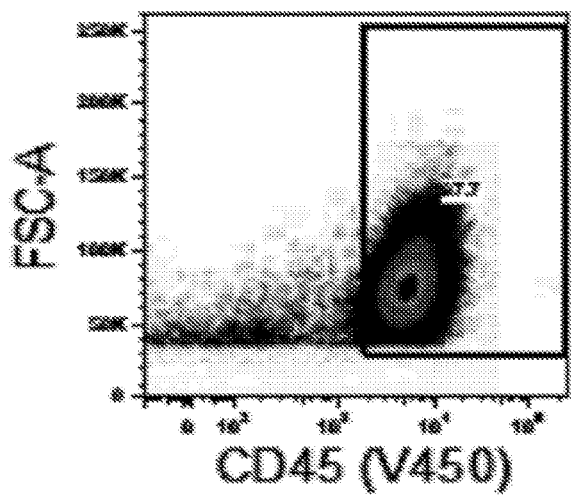
Figure 8D:
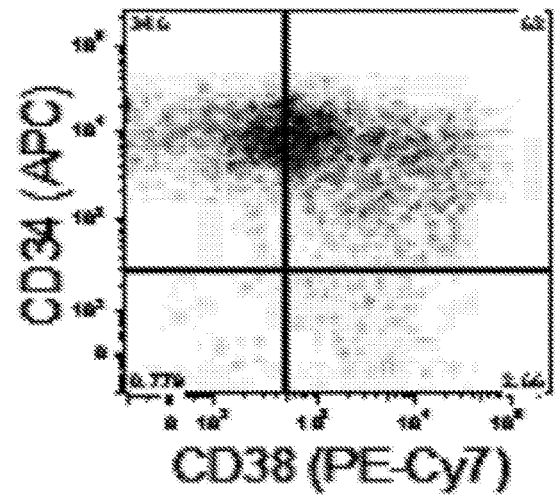
Figure 9A:
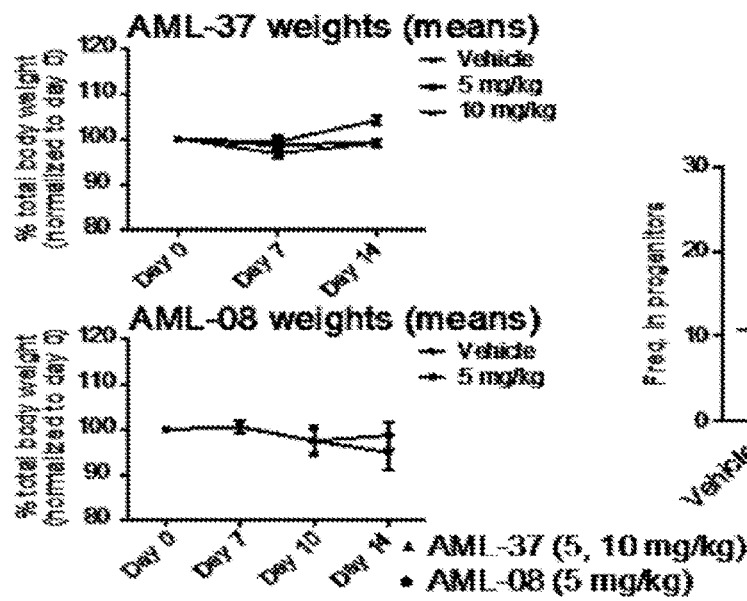
FIGS. 9A-9H. Engraftment analysis in AML PRIMAGRAFT™ mouse models after splicing modulation and serial transplantation.
Figure 9B:
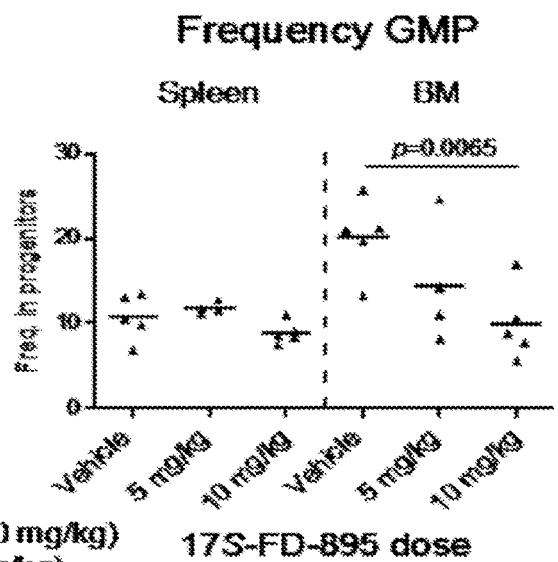
Figure 9C:
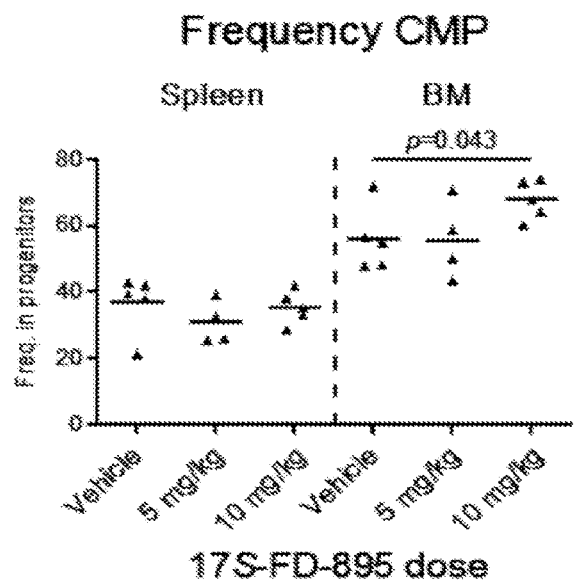
Figure 9D:
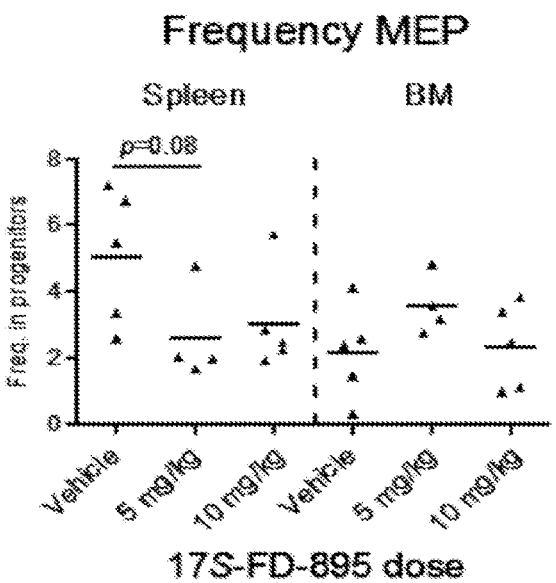

Since 17S-FD-895 showed a favorable therapeutic index and greater functional potency than FD-895 in LSC assays, we performed pre-clinical 17S-FD-895 studies in AML PRIMAGRAFT™ assays. Transplantation of CD34+ LSC-enriched fractions from three patient samples (Table 1, FIGS. 8A-8B) resulted in engraftment (n=136 mice) of serially transplantable human LSC after 7-28 weeks (FIGS. 8C-8D). Two sets of engrafted mice were further treated with 17S-FD-895 (n=13) or vehicle control (n=9), followed by FACS and splice isoform analyses in CD34' LSC-enriched fractions (FIG. 4A). The treatment was well tolerated, with no significant weight changes detected (FIG. 9A).

Figure 4B:
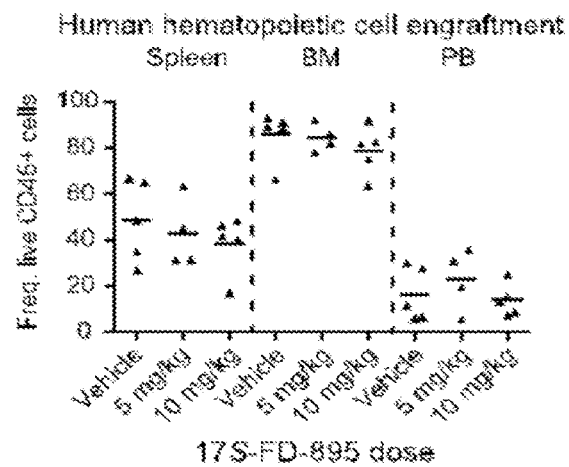
Figure 4C:
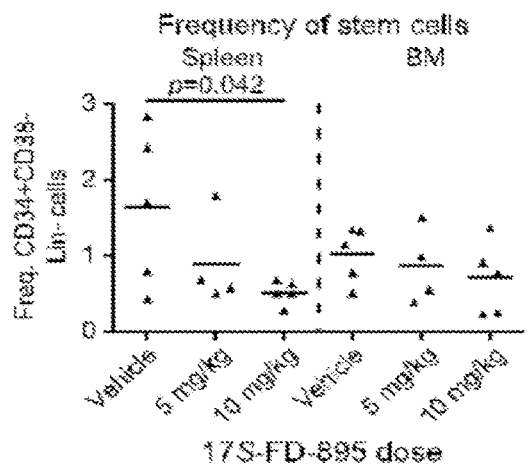
Figure 4D:
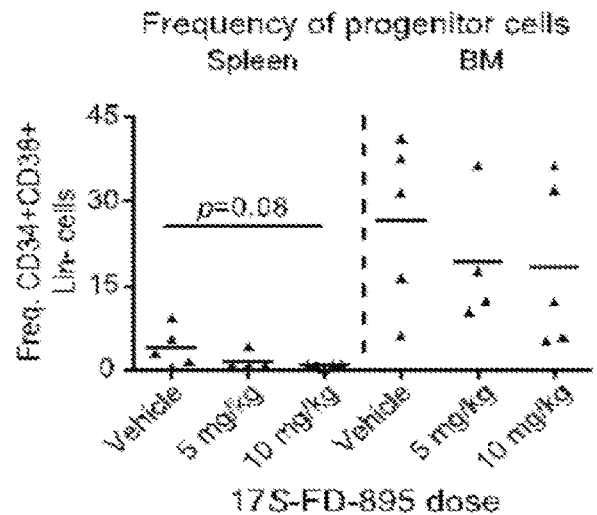
Figure 4E:
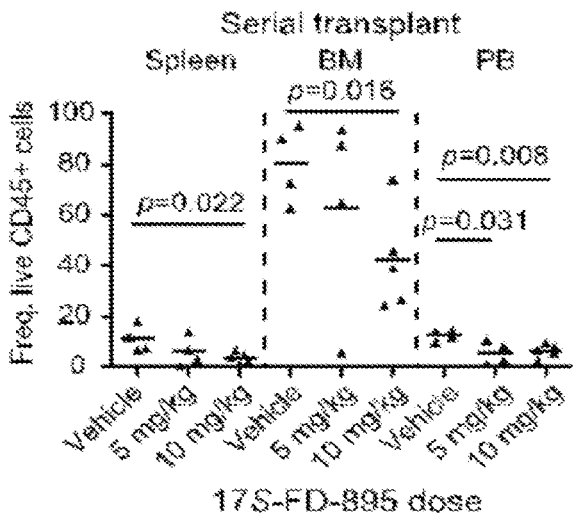
Figure 9E:
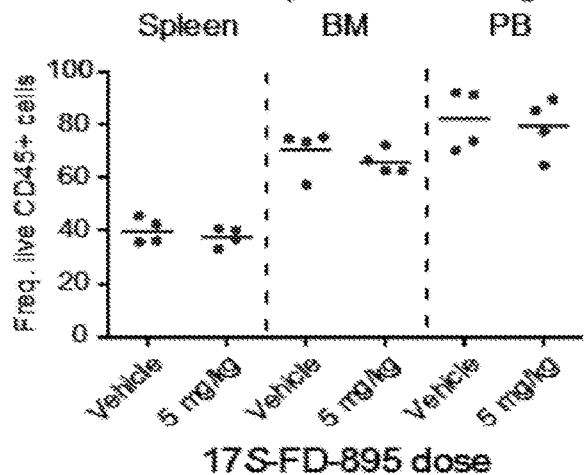
Figure 9F:
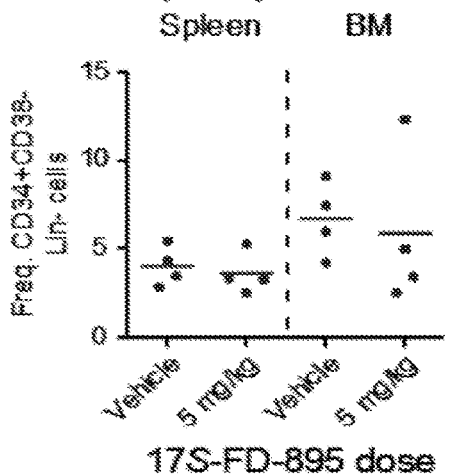
Figure 9G:
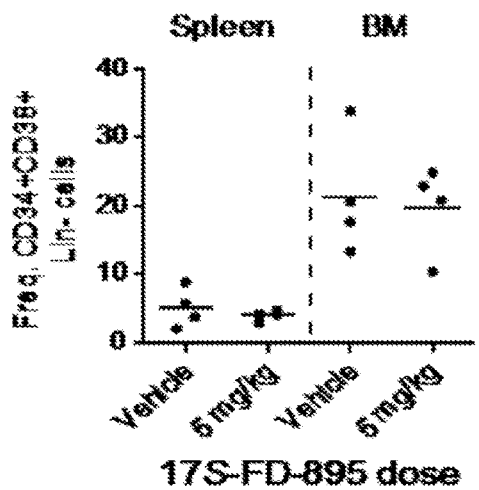
Figure 9H:
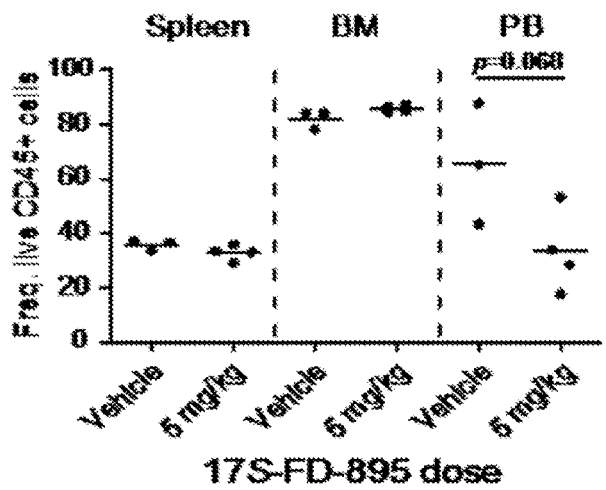
Figure 22A:
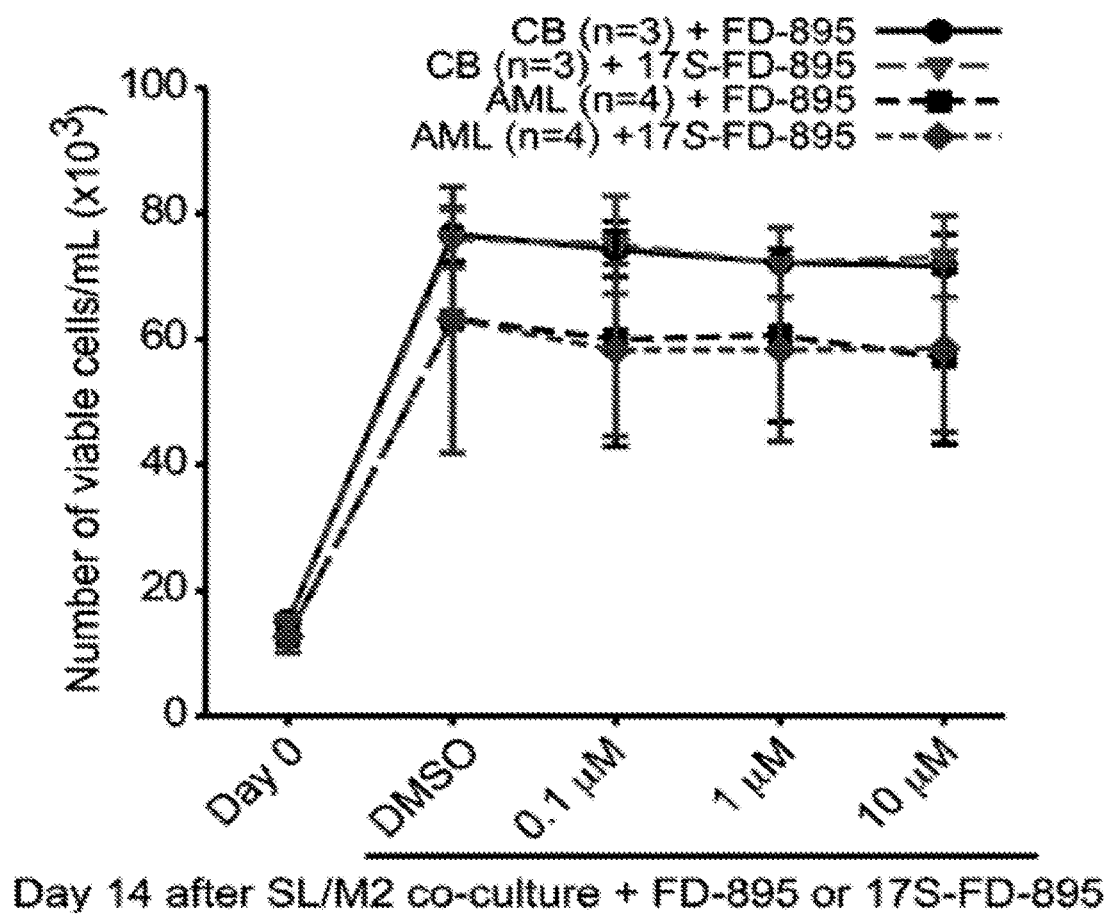
FIGS. 22A-22G. Time Course and Hematopoietic Progenitor Cell Fate Studies in Bone Marrow Stromal Co-Cultures Treated with 17S-FD-895.
Figure 22B:
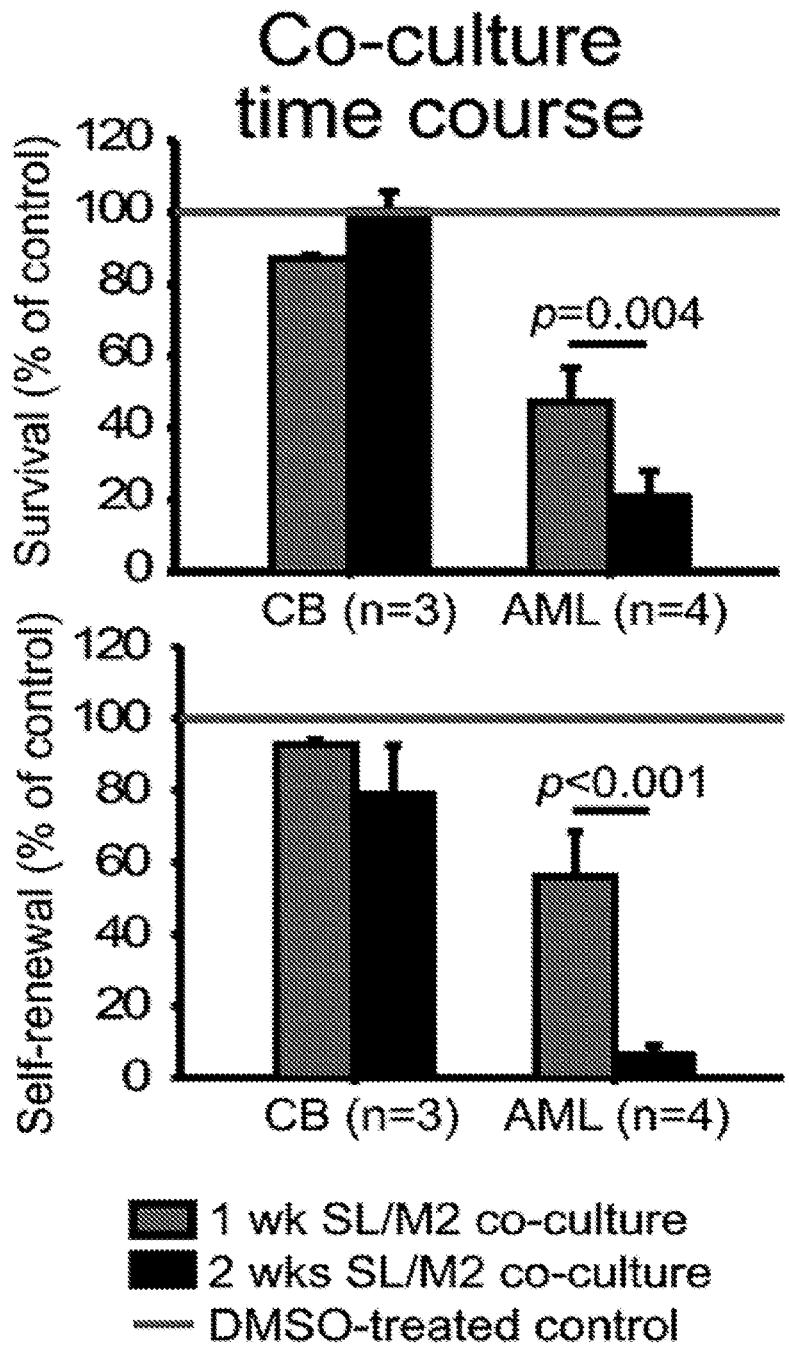
Figure 22C:
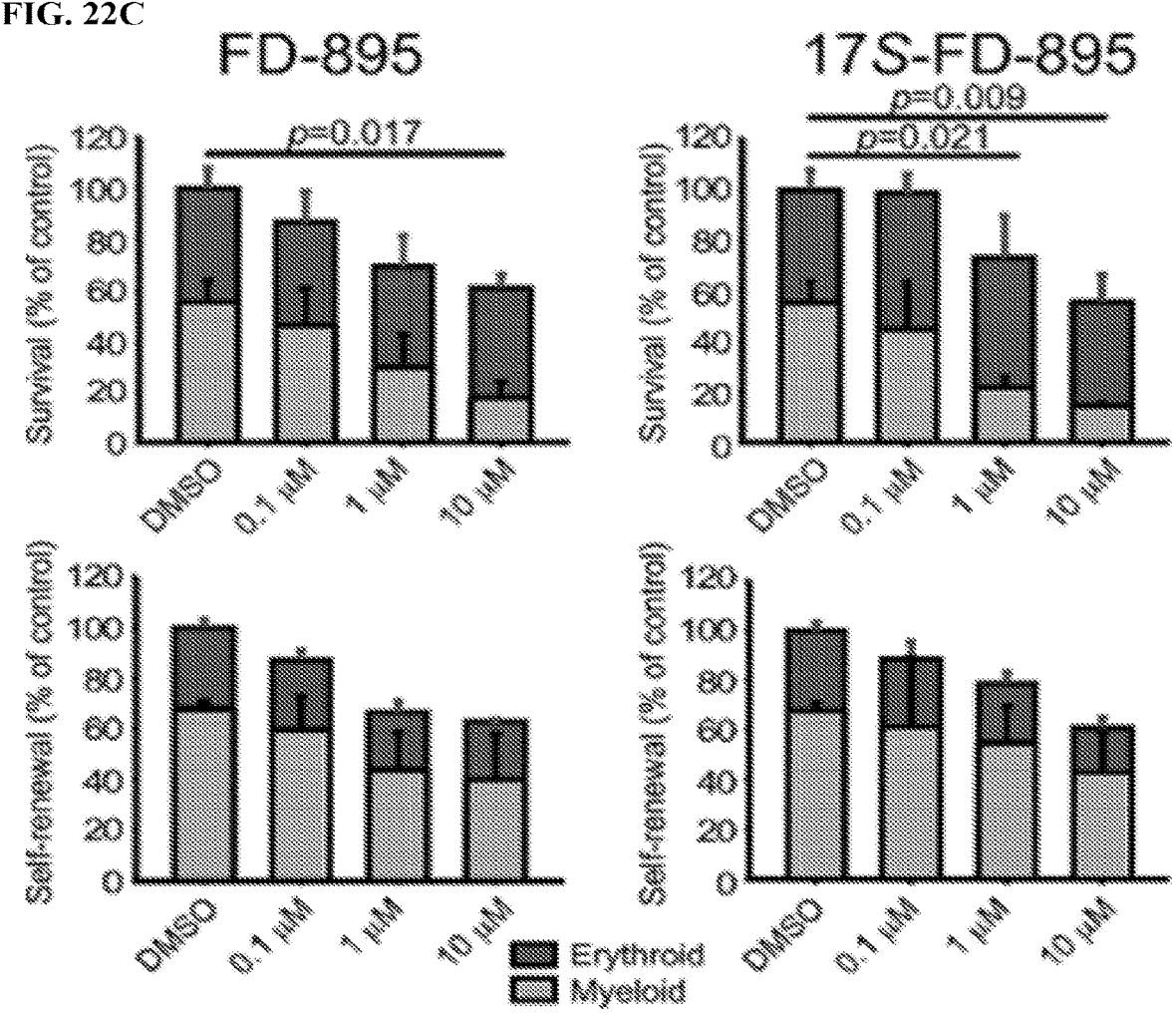
Figure 22D:
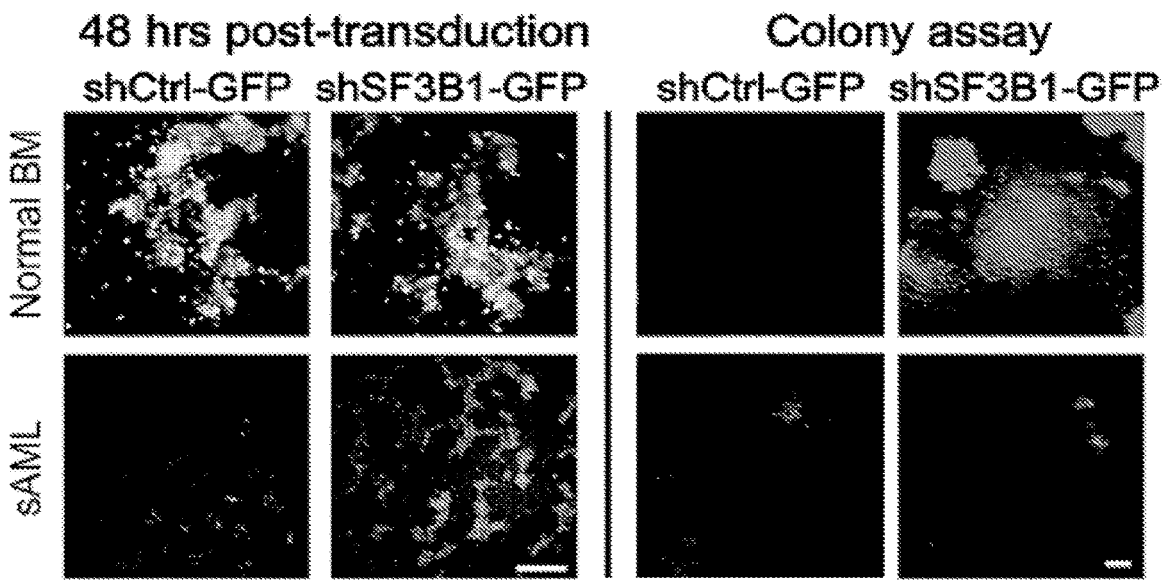
Figure 22E:
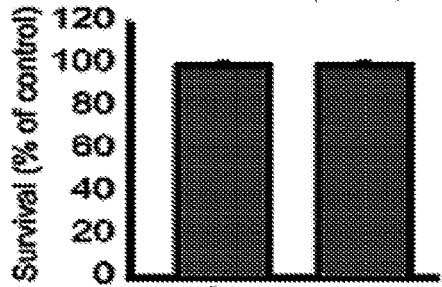
Figure 22E:
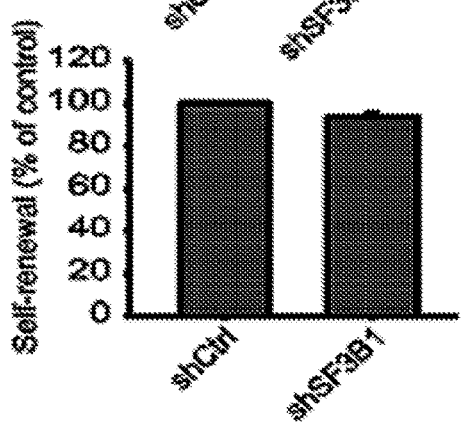
Figure 22F:
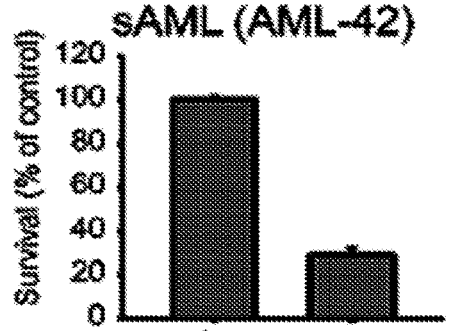
Figure 22F:
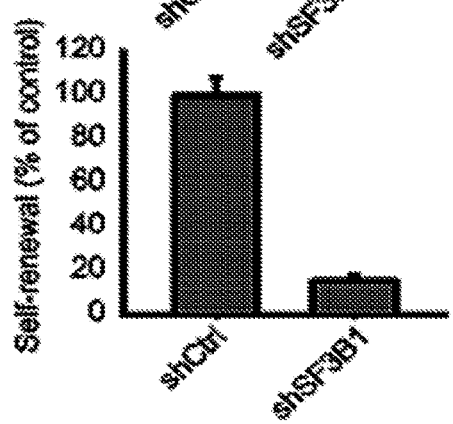
Figure 22G:
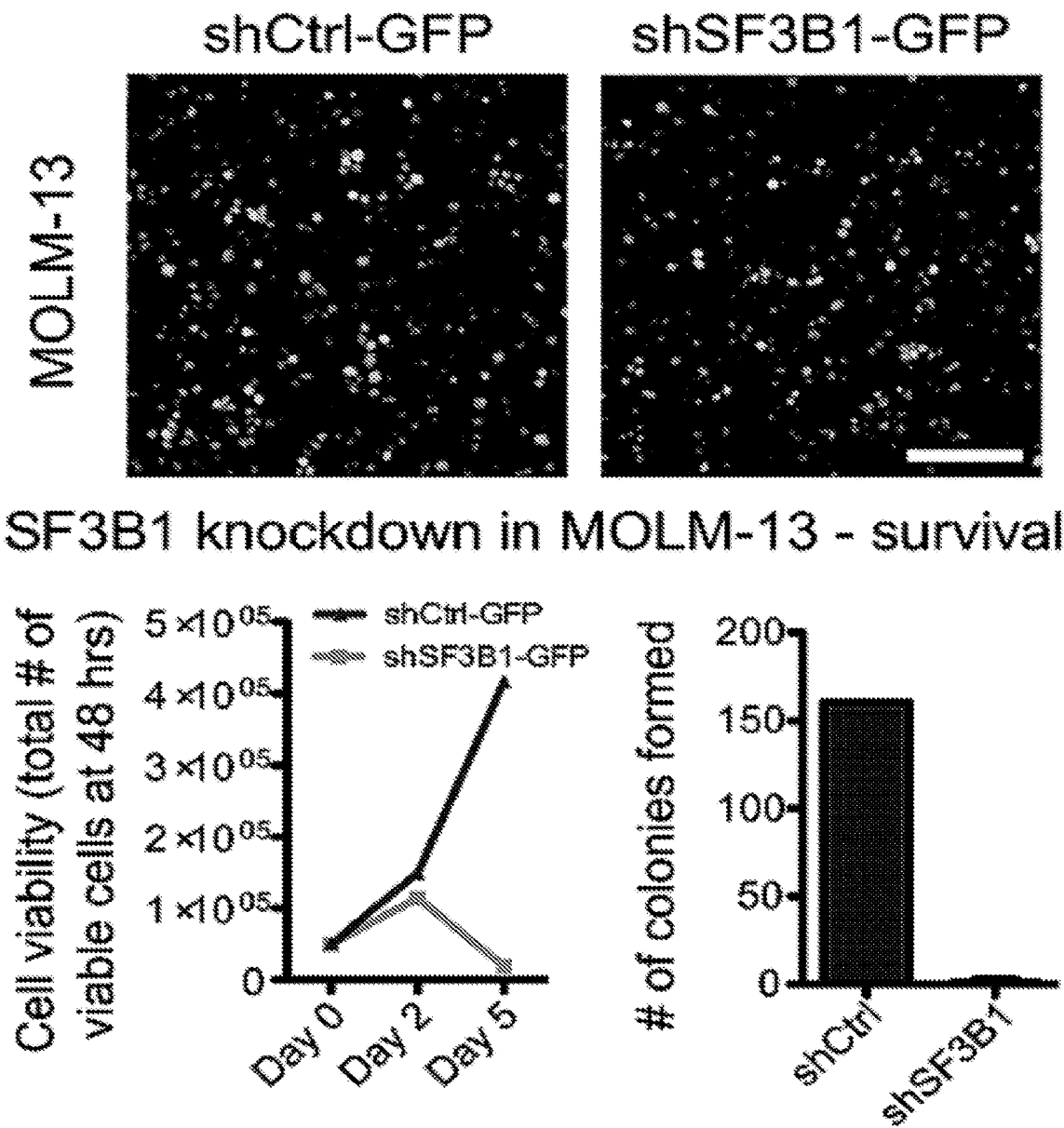

Self-renewing AML LSC reside in the hematopoietic stem (CD34+CD38−) or progenitor (CD34+CD38+) compartments [10], which are comprised of expanded granulocyte-macrophage progenitor (GMP) populations [9]. Therefore, we analyzed the hematopoietic stem and progenitor cell frequencies in a sAML PRIMAGRAFT™ model treated with 5 or 10 mg/kg of 17S-FD-895. Flow cytometry analyses revealed a decrease in human stem and progenitor cells (80% reduction to nearly zero in the 10 mg/kg group versus vehicle controls) in the spleens of treated mice (FIGS. 4B-4D). Among progenitor cell subpopulations, there was reduced GMP frequency and a slight increase in common myeloid progenitor (CMP) frequency in 17S-FD-895-treated mice (FIGS. 22B-22D). Notably, these effects occurred after only three doses of 17S-FD-895. Consistent with a reduction in functional LSC burden after 17S-FD-895 treatment, subsequent serial transplantation studies revealed a marked reduction in human leukemic burden in the hematopoietic tissues of recipients of CD34+ cells from mice in the 10 mg/kg treatment group versus vehicle controls (FIG. 4E). In a de novo AML PRIMAGRAFT™ model with high disease burden (FIGS. 9E-9G), there was a similar trend towards decreased circulating leukemic cells in secondary recipients of CD34+ cells from mice treated with a lower dose of 17S-FD-895 (FIG. 9H). Together, these data demonstrate that short-term treatment with a pharmacological splicing modulator compound reduces LSC survival and self-renewal in AML PRIMAGRAFT™ models. These data provide a strong rationale for expanding pre-clinical studies of 17S-FD-895 to investigate longer dosing regimens and establish a therapeutic index compared with normal hematopoietic stem and progenitor cells (HSPC) in validated in vivo models [19].

In Vivo Splicing Modulation Disrupts AML LSC Pro-Survival Splice Isoform Expression.

Figure 4F:
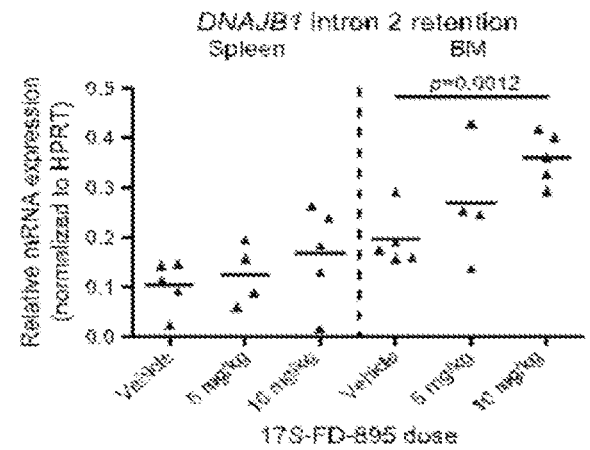
Figure 4F:
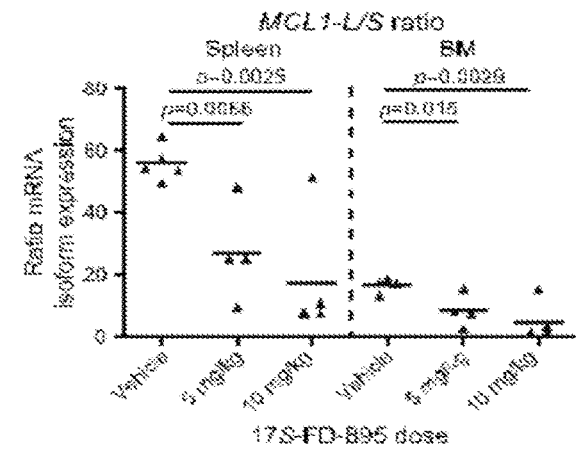
Figure 4H:
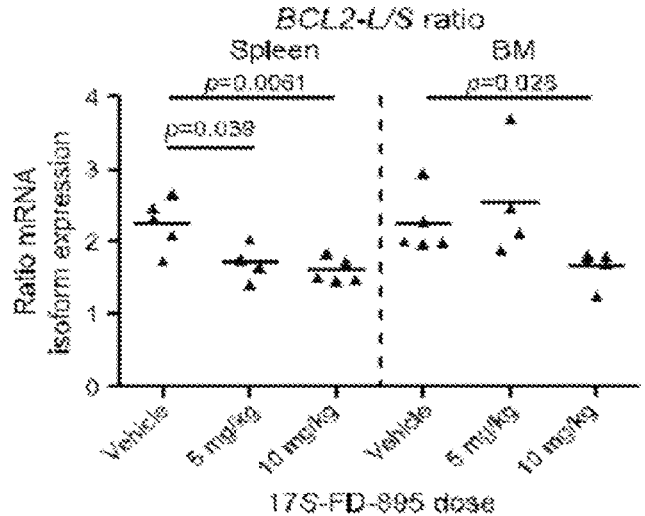
Figure 10A:
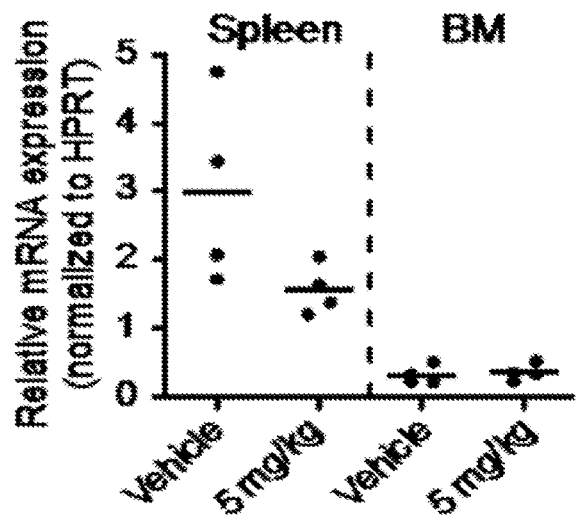
FIGS. 10A-10H. Quantitative RT-PCR analysis and RT-PCR in AML PRIMAGRAFT™ mouse models after splicing modulation.
Figure 10B:
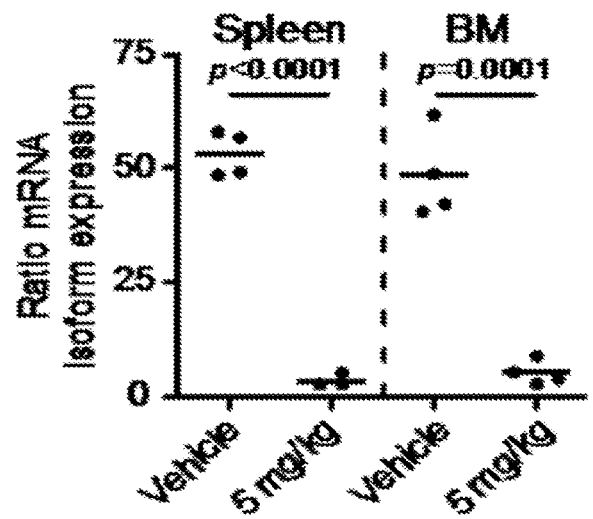
Figure 10C:
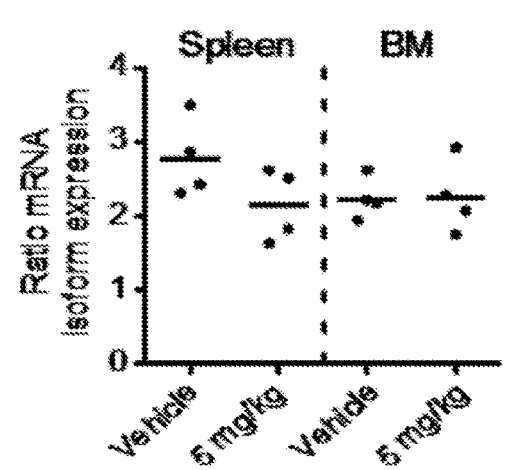
Figure 10D:
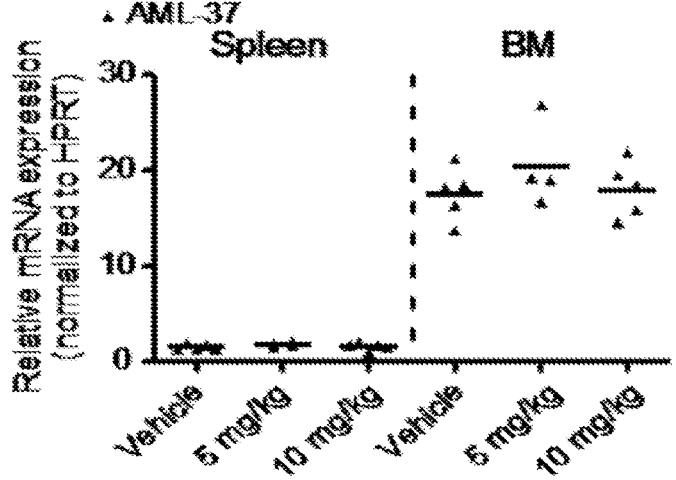
Figure 10E:
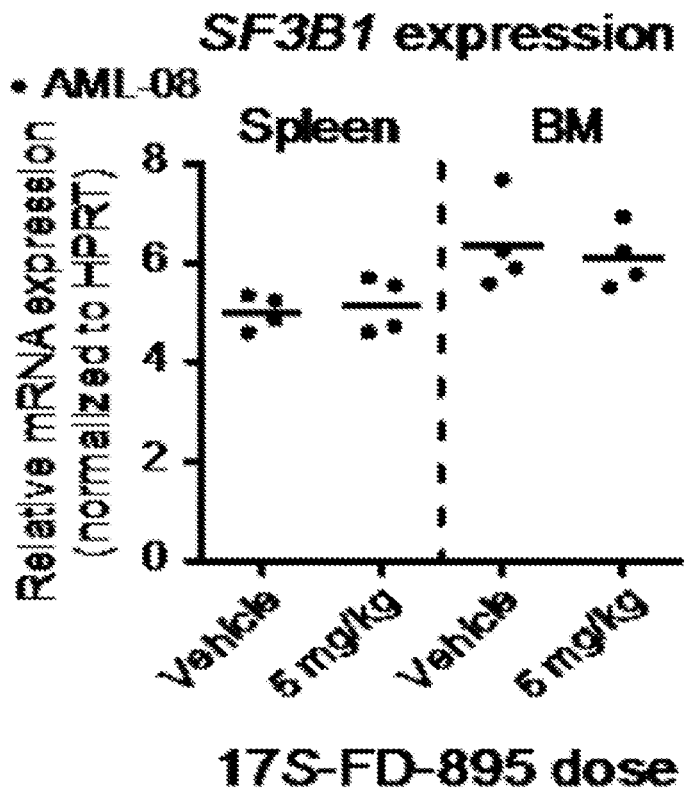
Figure 10F:
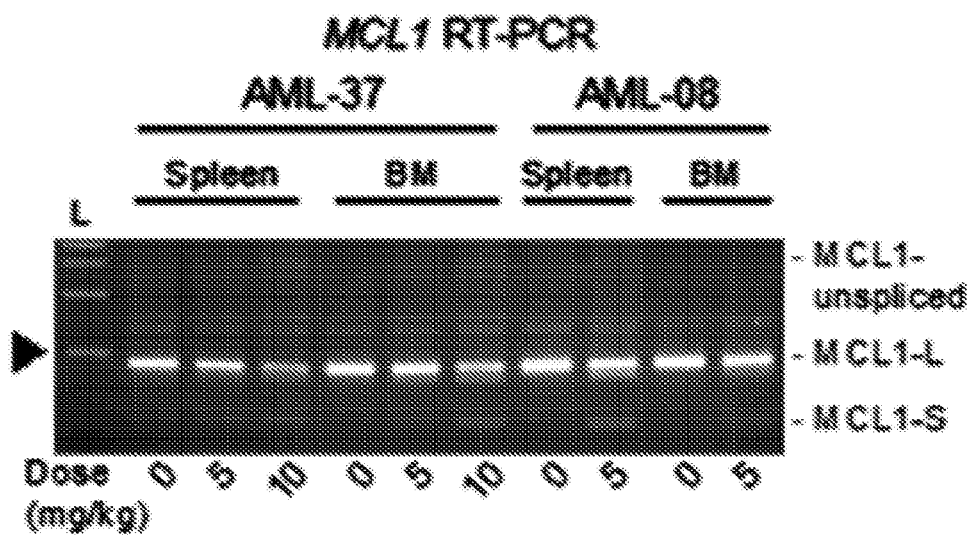
Figure 10G:
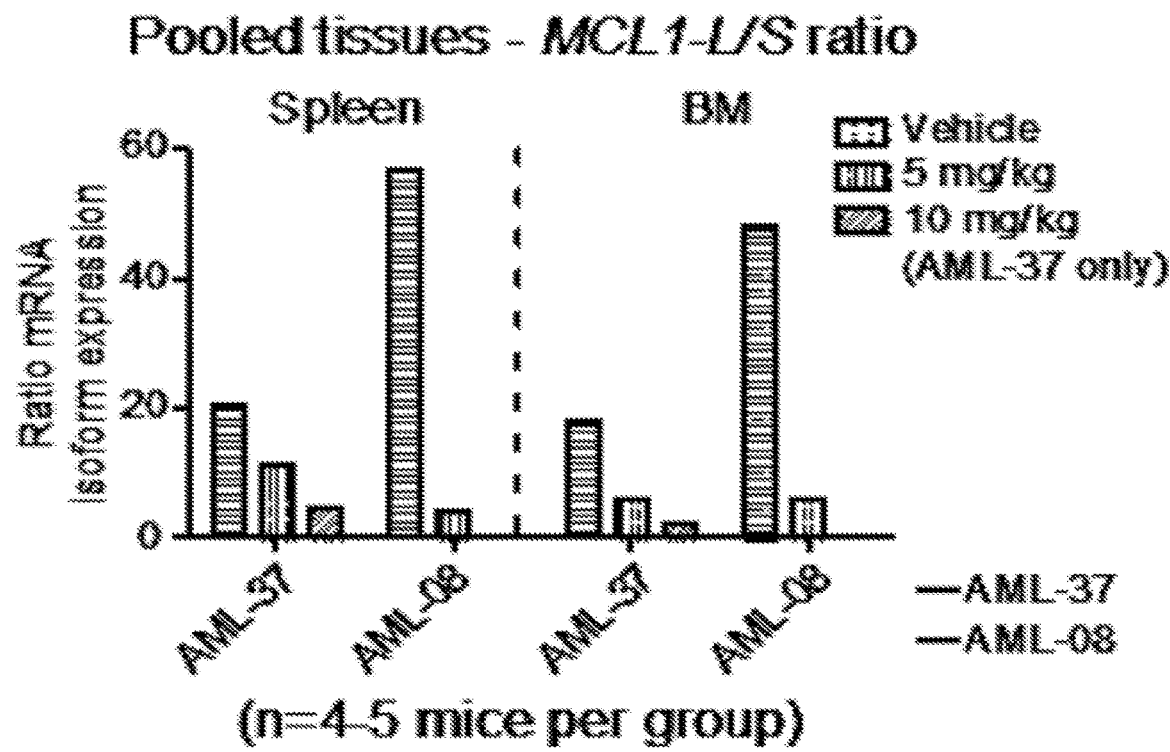
Figure 10H:
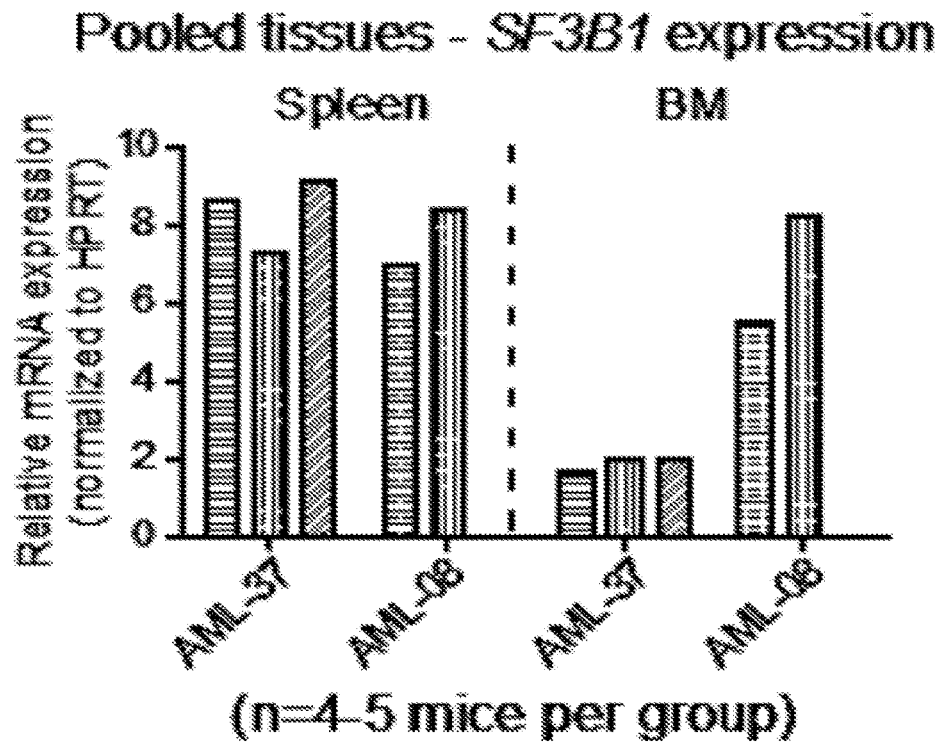

AML LSC functional capacity to propagate leukemia is dictated by stem cell gene expression [10]. Therefore, we hypothesized that stem cell isoform-specific expression profiles could be reprogrammed through splicing modulation. To assess in vivo splice isoform-targeted activity of 17S-FD-895, CD34-selected human cells from treated mice were analyzed by PCR. Consistent with our in vitro studies, there was increased DNAJB1 intron 2 expression in human CD34' cells from 17S-FD-895-treated mice (FIG. 4F, FIG. 10A). Notably, splice isoform-specific qRT-PCR showed a significant reduction in MCL1-L/S and BCL2-L/S expression ratios compared to vehicle-treated controls (FIGS. 4G-4H; FIGS. 10B-10C). Consistent with a functional reduction in activity of SF3B1, the putative target of FD-895, SF3B1 mRNA expression was unchanged after 17S-FD-895 treatment (FIGS. 10D-10E). Pooled CD34+ cells from 17S-FD-895-treated mice displayed MCL1 exon skipping and intron inclusion (FIG. 10F), along with dramatically reduced MCL1-L/S expression ratios, and as expected, SF3B1 expression was unaffected (FIGS. 10G-10H). Together, pharmacological splicing modulation with 17S-FD-895 restored normal ratios of MCL1-L'S and BCL2-L'S expression, suggesting that reprogramming stem cell pro-survival gene splicing may contribute to this agent's functional impact on AML LSC maintenance.

Discussion

The heterogeneity of molecular abnormalities in sAML, along with a lack of effective treatment options for this predominantly older patient population, has hampered improvement in clinical outcomes. In addition to clinical therapies such as the DNA-modifying agents 5-azacytidine and decitabine, many experimental agents including clofarabine and vorinostat tested in recent clinical trials for sAML also target epigenetic pathways that regulate gene expression [46]. However, several of these agents failed to improve patient survival [47], suggesting that epigenetic modifier therapies may be sufficient to reduce leukemic burden but may not effectively target a subpopulation of drug-resistant LSC that contribute to disease progression and relapse. Hence, there is a need for clinical candidates that operate through different modes of action. Here, we demonstrate that splicing modulation impairs AML LSC maintenance and promotes pro-apoptotic splice isoform expression and intron inclusion. Our RNA-Seq analyses suggest that widespread changes in spliceosome components sensitize self-renewing AML LSC to pharmacological splicing modulation. The potent and stable FD-895 analogue, 17S-FD-895, reverted sAML-specific splice isoform (PTK2B-202) expression patterns and MCL1-L/S and BLC2-L'S ratios, and reduced AML LSC survival and self-renewal in a dose-dependent manner in in vitro and in vivo pre-clinical models. Moreover, 17S-FD-895 exhibited a favorable therapeutic index, impairing LSC maintenance while sparing cord blood or normal bone marrow-derived HSPC survival and self-renewal in humanized bone marrow stromal co-culture assays.

Notably, drug resistance in AML has been attributed, in part, to high levels of MCL1 [48]. Genetic and epigenetic alterations typical of AML can induce dependence on BCL2 pro-survival activity [49]. Splicing modulation effectively reduced pro-survival splice isoform expression and impaired LSC maintenance while sparing normal stem and progenitor cells. Thus, it may represent a key component of combination therapeutic strategies aimed at eradicating therapy-resistant AML LSC. While the results of the present study suggest that splicing modulation impairs in vivo LSC maintenance primarily through reducing LSC self-renewal, we predict that more frequent dosing over longer periods of time in these pre-clinical models may reveal more robust effects on LSC survival and tumor burden after treatment. The small molecule treatment conditions used in the PRIMAGRAFT™ models were limited to few doses due to current availability of the compound, but are consistent with weekly intravenous dosing regimens used in clinical trials of less stable spliceosome inhibitory agents in patients with solid tumors [41]. Future expansion of these studies using longer treatment regimens and other pre-clinical models will be relevant to the treatment of a variety of advanced stage hematopoietic malignancies and solid tumors [18,35,50,51] typified by tissue-specific and cancer stem cell-associated aberrant RNA splicing. Notably, increased total pre-mRNA synthesis associated with oncogenic MYC activation has been recently linked to spliceosome stress in MYC-driven cancers, and these malignant cells can be therapeutically targeted by spliceosome inhibition [52]. Prior to the initiation of clinical trials with splicing modulators including 17S-FD-895 and future application of these findings to cancer treatment in the clinic, pharmacokinetic studies including in vivo monitoring of the compound and potential generation of breakdown products will provide important information on the stability and distribution of this compound compared with previous less stable spliceosome-targeted small molecules [41]. It will also be important to perform pre-clinical combination treatment studies in AML PRIMAGRAFT™ models to assess the efficacy of 17S-FD-895 in comparison to, and in combination with, current standard of care epigenetic modifier therapies.

In addition to establishing the LSC inhibitory efficacy of splicing modulatory agents, identification and validation of tumor-specific isoforms is a subject of great interest for cancer diagnosis and therapy [35]. Our results revealed select transcripts of genes that have been previously implicated in AML pathogenesis, such as TP53, NPM1, CD82 and PTK2B, that were differentially expressed in leukemic versus normal progenitors, suggesting that putative translated protein products of these transcripts may play a greater functional role in AML initiation or progression than other alternative isoforms, and could provide unique antigens for translational development. Moreover, overexpressed transcripts such as CD82-004 and PTK2B-202 may represent important LSC-specific biomarkers of disease initiation or progression, functionally relevant therapeutic targets for small molecule or antibody-mediated inhibition strategies, and potential companion diagnostics for splicing modulator therapies or other AML LSC-targeted agents. Moreover, tumor-specific isoform-targeted therapies might synergize with splicing modulator treatments and other current standards of care for therapy-resistant AML patients. Together, these results suggest that development of splicing-targeted monotherapy and new combination strategies hold great potential for reducing LSC burden. Furthermore, rapid clinical development of LSC-targeted strategies will be an important step forward in preventing disease relapse in AML and other recalcitrant malignancies, with relevance to a variety of other age-related diseases associated with changes in alternative splicing [29].

Materials and Methods
Study Design.
The overall research objectives of this study were to both discover new splice isoform biomarkers specific to sAML LSC, and evaluate the potent and stable spliceosome-targeted small molecule compound 17S-FD-895 in AML LSC survival and self-renewal assays in pre-clinical models. In controlled laboratory experiments, research samples included primary peripheral blood or bone marrow samples from consenting AML patients (n=22) and age-matched normal control bone marrow samples (n=12) obtained from healthy volunteer individuals undergoing hip replacement therapy for reasons other than leukemia, or normal cord blood (n=6) controls obtained from a commercial source (AllCells, Alameda, Calif.). For experiments using primary samples, the sample size of each experiment is limited by the availability of rare and valuable samples specific for disease and stage from patients. To discover new splice isoform biomarkers specific to sAML LSC, primary AML and normal control samples were FACS-purified and analyzed by RNA-Seq, and whole transcriptome analyses and hierarchical clustering analyses were utilized to establish a splice isoform expression signature. We use a definition of significance as a two-sided alpha level of 0.05 and aim to have power of 0.80. Based on an expected effect size that is twice the standard deviation we can achieve 0.79 power with five samples per arm based on a normal distribution. The goal of each experiment is to get close to five or more samples per arm depending on clinical sample availability and viability. The effect size we are able to detect with this power is variable based on intra-arm sample variability via standard deviation. Consistent with AML genetic heterogeneity, there was some variability in primary patient sample analyses by RNA-Seq and qRT-PCR. Therefore, more than five samples per group were included for these analyses. When considering sequencing of multiple genes it is assumed that a much larger effect size will be required due to appropriate adjustment for multiple comparisons.

In hypothesis-driven experiments, the splicing modulatory compound 17S-FD-895 was tested to determine efficacy in altering splicing activity in cell lines, and to evaluate effects on AML LSC survival and self-renewal capacity in humanized bone marrow stromal co-cultures and in PRIMAGRAFT™ AML LSC models. Cell culture experiments were performed using 293T and sAML (MOLM-13) cell lines, and SL and M2 bone marrow stromal cell lines. Animal studies were performed using immunocompromised Rag2$-/-\gamma_c-/-$[20] or NOD/SCID-IL2RG mice (Jackson Laboratory, Bar Harbor, Me.) [53]. Primary AML and normal control samples were used in in vitro hematopoietic stem and progenitor assays after bone marrow stromal co-culture and treatment with splicing modulatory compounds (FD-895 or 17S-FD-895) or vehicle control (DMSO). Colony formation potential and self-renewal capacity were assessed by counting colony numbers (survival) after two weeks of growth in semi-solid (methylcellulose) media, and subsequent replating capacity (self-renewal) was assessed after transfer to fresh methylcellulose for an additional two weeks of culture. Three primary AML samples were utilized to establish PRIMAGRAFT™ models in immunocompromised mice, and mice engrafted with cells from two of these models (AML-37 and AML-08) were treated with 17S-FD-895 or vehicle (DMSO) to evaluate changes in AML LSC survival and self-renewal capacity in vivo. Data were collected by flow cytometry and qRT-PCR analysis of CD34-selected human LSC-enriched cells from engrafted mice.

In in vivo experiments, before initiation of treatment, AML-engrafted mice were randomized according to human cell engraftment rates (CD45[+] cell frequency) in peripheral blood, and total body weights. Inclusion/exclusion criteria were pre-established based on minimum CD45$^+$ cell engraftment rates of 1% in peripheral blood, and endpoints included human stem and progenitor engraftment analyses as establish by previous P$_{RIMA}$G$_{RAFT}$™ experiments [20,54]. For AML-37 treatment, one additional transplanted mouse was treated with vehicle control (total n=6), however leukemic burden was 0.2% before treatment, and because this value was >2 standard deviations lower in spleen and bone marrow than all other vehicle-treated controls (n=5) at the end of the experiment, this animal was excluded from FACS and PCR analyses. All reported n represent individual experimental replicates (either individual patient samples for primary sample analyses or in vitro studies, or individual animals for in vivo studies). All qRT-PCR analyses were performed using two technical replicates for each sample, with the average of the two replicates shown in all graphs. For in vitro experiments, the same investigator performed treatments and all analyses. For in vivo experiments, investigators performing FACS and qRT-PCR analyses were blinded to each animal's treatment status until after all data were collected.

Patient Samples.

A collection of leukemia patient samples from peripheral blood or bone marrow (Table 1) and normal age-matched control bone marrow samples were obtained from patients who gave their informed consent in accordance with Institutional Review Board-approved protocols at UCSD (Human Research Protections Program) and the Fred Hutchinson Cancer Research Center's Leukemia Repository.

Whole Transcriptome Sequencing and Determination of Gene and Splice Isoform Expression Values.

Gene and isoform expression data in FPKM was obtained for seven sAML and six normal bone marrow samples by aligning paired end unstranded 100 bp poly-A reads to the human reference genome (GRCh37/hg19) using STAR [55] and quantifying transcripts using Cufflinks [56] (FIGS. 18D, 18E, 19A). Datasets from RNA-Seq analyses are available through the NIH Sequence Read Archive (SRA), Biosample ID # SUB985785, BioProject ID # PRJNA287527.

Chemical Synthesis and Preparation of Splicing Modulatory Compounds.

Synthesis of FD-895 and 17S-FD-895 compounds was performed essentially as previously described [34]. For in vivo studies, 10 mg of 17S-FD-895 was prepared in DMSO at a concentration of 10 mg/mL.

In Vitro Stromal Co-Culture and Splicing Modulation.

Bone marrow SL/M2 monolayers were established from freshly inactivated (irradiated) cells and then human CD34$^+$ cells selected from AML primary samples (n=8) and normal controls (CD34$^+$ cells from cord blood, CB, n=6; or aged bone marrow, n=6) were added. Survival and self-renewal of the CD34+ cells were investigated by methylcellulose-based colony and replating assays. Two SF3B1-targeted splicing modulators, FD-895 or 17S-FD-895, were added at the initiation of co-culture at concentrations ranging from 0.1 to 10 μM.

AML LSC P$_{RIMA}$G$_{RAFT}$™ Assays and In Vivo 17S-FD-895 Treatment.

All animal studies were performed in accordance with UCSD and NIH-equivalent ethical guidelines and were approved by the Institutional Animal Care and Use Committee (IACUC protocol # S06015). For all in vivo experiments, animals of both genders were utilized. Three AML P$_{RIMA}$G$_{RAFT}$™ models were established by transplanting AML LSC-enriched cell fractions (either CD34-selected or FACS-purified stem or progenitor cell fractions from primary patient samples) into immunocompromised Rag2$^{-/-}$γ$_c^{-/-}$[20] or NOD/SCID-IL2RG mice (Jackson Laboratory) constitutively expressing human SCF, GM-CSF and IL-3 (NSGS) [53] (FIGS. 8A-8D). For all transplantations into Rag2$^{-/-}$γ$_c^{-/-}$ animals, neonatal mice were transplanted with human cells intrahepatically as previously described [21], and for all transplantations into NSGS animals, sublethally irradiated (300 Rad) adult (6-8 weeks old) mice were transplanted intravenously with 1-2×10$^5$ CD34$^+$ human cells.

For in vivo treatments, a 10 mg/mL stock solution of 17S-FD-895 solubilized in DMSO was used. After randomization, AML-engrafted mice were dosed intravenously with 17S-FD-895 (5-10 mg/kg) or vehicle (for AML-08, vehicle control=15% DMSO in PBS; for AML-37, vehicle control=20% DMSO in PBS) three times over a two-week period, with the first dose given on day 1, the second on day 7, and the third on day 14. For preparation of RNA from human LSC-enriched populations, single cell suspensions from spleen and bone marrow were CD34 double-selected (over two LS selection columns, Miltenyi) and 1-2×10$^5$ cells were collected in lysis buffer or pooled according to treatment group for serial transplantation assays.

Statistical Analyses.

For AML LSC survival and self-renewal assays, differences among groups were assessed using one-way ANOVA with values expressed as means±SD (for in vitro hematopoietic progenitor assays where comparisons were made among multiple sample types and treatment groups), or Student's t-test with values expressed as means±SEM (for in vitro splicing reporter assays) or as means of individual data points representing biological replicates (for in vivo engraftment and qRT-PCR analyses). Quantitative RT-PCR data were measured as a continuous outcome and each group was assessed for distribution and variance. For normally distributed data, unpaired two-tailed Student's t-tests were applied to determine differences in mRNA expression, and values were expressed as individual data points or means (±SEM) from a minimum of two independent experiments. All experiments were performed on blind-coded samples, with the experimental group allocation identified after data collection. All statistical analyses were performed using Microsoft Excel, SigmaPlot, or GraphPad Prism (San Diego, Calif.).

Additional reagent information and detailed procedures for sample processing, PCR, gene set enrichment and pathway analyses, spliceosome component mutational analyses, splicing reporter assays, bone marrow stromal cell co-culture methods, and in vivo study design and analyses are described following.

Reagents

Antibodies—

For primary sample FACS purification of hematopoietic stem and progenitor cell populations, CD34-selected (Miltenyi) primary samples were stained with a panel of well-validated human-specific antibodies [19-21,54] was utilized. Antibodies included human CD34-APC and CD38-PECy7 (BD Biosciences, San Diego, Calif.) and lineage markers (cocktail, all antibodies from Life Technologies, Carlsbad, Calif.). For flow cytometric analyses of P$_{RIMA}$G$_{RAFT}$™ models, the same panel of antibodies was used for analysis of spleen and bone marrow-derived cells, with the addition of CD45-V450, CD123-PE (both from BD Biosciences), and CD45RA-FITC (Life Technologies) for further visualization of progenitor cell subpopulations. Due to background autofluorescence in blood, for flow cytometric analysis of peripheral blood from treated mice, the CD34 and CD45 antibodies were replaced with alternative antibodies to exclude FITC labeled reagents (CD34-PE, BD Biosciences and CD45-APC, Life Technologies).

RNA and PCR Reagents—

All RNA samples were prepared after lysis of live cells in RLT buffer (Qiagen, Germantown, Md.) followed by RNA extraction using RNEASY® kits according to the manufacturer's instructions (Qiagen). cDNA was synthesized using the First-Strand SUPERSCRIPT™ III Reverse Transcriptase Supermix (Life Technologies) and qRT-PCR was performed using SYBR® GREENER™ Super Mix (Life Technologies). All primers (Table 2) were synthesized by ValueGene (San Diego, Calif.).

Sample Processing and Primary HSC and AML LSC Purification.

Peripheral blood or bone marrow samples were processed by Ficoll density centrifugation and viable cells stored in liquid nitrogen. Mononuclear cells from AML patients or normal controls were then further purified by magnetic bead separation of CD34$^+$ cells (MACS; Miltenyi, Bergisch Gladbach, Germany) essentially as previously described [21] for subsequent FACS-purification of hematopoietic stem (CD34$^+$CD38$^-$ Lin$^-$) and progenitor (CD34$^+$CD38$^+$ Lin$^-$) cell fractions. For the majority of AML patient samples utilized, only very few purified viable HSC were obtained

TABLE 2

Primers used for qRT-PCR, RT-PCR, and direct sequencing analyses.

| Gene | Primer set | Forward (5'-3') | Reverse (5'-3') | Ref. |
|---|---|---|---|---|
| Human HPRT | Total (qRT-PCR) | TCAGGGATTTGAATCATGTTTGTG (SEQ ID NO: 1) | CGATGTCAATAGGACTCCAGATG (SEQ ID NO: 2) | Crews et al., 2015 |
| SF3B1 (ex14) | Total (qRT-PCR) | AGCTTTTGCTGTTGTAGCCTCTG (SEQ ID NO: 3) | GCTTGCCAGGACTTCTTGCT (SEQ ID NO: 4) | Jeromin et al., 2013 |
| BCL2-L | Isoform-specific (qRT-PCR) | ATGTGTGTGGAGAGCGTCAA (SEQ ID NO: 5) | TTCAGAGACAGCCAGGAGAAA (SEQ ID NO: 6) | Goff et al., 2013 |
| BCL2-S | Isoform-specific (qRT-PCR) | ATGTGTGTGGAGAGCGTCAA (SEQ ID NO: 7) | CTCAGCCCAGACTCACATCA (SEQ ID NO: 8) | Goff et al., 2013 |
| MCL1-L | Isoform-specific (qRT-PCR) | AGACCTTACGACGGGTTGG (SEQ ID NO: 9) | AATCCTGCCCCAGTTTGTTA (SEQ ID NO: 10) | Goff et al., 2013 |
| MCL1-S | Isoform-specific (qRT-PCR) | GAGGAGGACGAGTTGTACCG (SEQ ID NO: 11) | ACTCCACAAACCCATCCTTG (SEQ ID NO: 12) | Goff et al., 2013 |
| BCLX-L | Isoform-specific (qRT-PCR) | CATGGCAGCAGTAAAGCAAG (SEQ ID NO: 13) | GAAGGAGAAAAAGGCCACAA (SEQ ID NO: 14) | Goff et al., 2013 |
| PTK2B-202 | Isoform-specific (qRT-PCR) | CTGCAGTTCCAGGAGGAG (SEQ ID NO: 15) | CTGTGAACTCCAGGTAGCC (SEQ ID NO: 16) | New |
| DNAJB1 (in2) | Intronic (qRT-PCR) | GGCCTGATGGGTCTTATCTATGG (SEQ ID NO: 17) | TTAGATGGAAGCTGGCTCAAGAG (SEQ ID NO: 18) | Kotake et al., 2007 |
| SF3B1 (ex10-17) | Sequencing (PCR) | TGACCAGCCATCTGGAAATC (SEQ ID NO: 19) | CACCATCTGTCCCACAACAC (SEQ ID NO: 20) | Jeromin et al., 2013 |
| DNAJB1 | RT-PCR | GAACCAAAATCACTTTCCCCAAGGAAGG (SEQ ID NO: 21) | AATGAGGTCCCCACGTTTCTCGGGTGT (SEQ ID NO: 22) | Kotake et al., 2007 |
| MCL1 | RT-PCR | CTCGGTACCTTCGGGAGCAGGC (SEQ ID NO: 23) | CCAGCAGCACATTCCTGATGCC (SEQ ID NO: 24) | Kashyap et al., 2015 |

Cell Culture Reagents—

All media (DMEM, RPMI) and supplements (GLUTAMAX™, penicillin-streptomycin) used in cell culture were from Corning (Manassas, Va.) or Life Technologies. Fetal bovine serum (FBS) was from Gemini Bio-Products (Sacramento, Calif.). For experiments involving transfection of reporter vector plasmids [42], HEK293 cells were transiently transfected using Lipofectamine (Life Technologies).

(<5,000 cells on average). Therefore the progenitor fractions were utilized for subsequent RNA-Seq and qRT-PCR analyses as these represent the majority of cells present in LSC-enriched fractions prepared for functional in vitro and in vivo assays using CD34 selection.

For primary hematopoietic progenitor cell purification, CD34-selected cells were stained with fluorescent antibodies against human CD34 and CD38 (BD Biosciences) and lineage markers (cocktail, all antibodies from Life Technologies) and propidium iodide as previously described [20,21,54]. Following staining, cells were analyzed and sorted using a FACS Aria II (Sanford Consortium Stem Cell Core Facility), and hematopoietic stem (CD34$^+$CD38$^-$ Lin$^-$) and progenitor (CD34$^+$CD38$^+$ Lin$^-$) populations were isolated. Freshly-sorted cells were collected in lysis buffer (Qiagen) for RNA extraction followed by RNA-Seq (The Scripps Research Institute Next Generation Sequencing Core) or qRT-PCR analyses as previously described [21].

Nucleic Acid Isolation and PCR (qRT-PCR and RT-PCR).

Primary CD34$^+$CD38$^+$ Lin$^-$ cells or enriched human CD34$^+$ cells from mouse tissues were isolated using FACS purification or CD34 microbead-selection, and 2-10×10$^4$ cells were harvested in lysis buffer (Qiagen). RNA was purified using RNEASY® micro RNA purification kits with a DNase (Qiagen) incubation step to digest any trace genomic DNA present. RNA was stored at −80° C. Immediately prior to reverse transcription of RNA samples, nucleic acid concentrations were quantified on a NANODROP™ 2000 spectrophotometer (Thermo Scientific), and purity was considered acceptable if A260/A280 values were >1.8. Samples submitted for RNA-Seq were further subjected to quality control assessment on an Agilent Bioanalyzer (The Scripps Research Institute Next Generation Sequencing Core). Samples with RNA integrity (RIN) values >7 were used for RNA-Seq.

For qRT-PCR analysis of relative total mRNA expression levels or splice isoform-specific expression analyses, cDNA was synthesized using 50 ng-1 pg of template RNA in 20 μL reaction volumes using the First-Strand SUPERSCRIPT™ III Reverse Transcriptase Supermix (Life Technologies) followed by incubation with RNase H according to the manufacturer's protocol and as described previously [20,22]. All cDNA products were stored at −20° C. Splice isoform-specific primers for PTK2B-202 were designed to bind to unique exon junctions for this transcript, which lacks exon 24. All primers (Table 2) were diluted to 10 μM working dilutions in DNase/RNase-free water. qRT-PCR was performed in duplicate using cDNA (1 μL reverse transcription product per reaction) on an iCycler (Bio-Rad, Hercules, Calif.) using SYBR® GREENER™ Super Mix (Life Technologies) in 25-μL volume reactions containing 0.2 μM of each forward and reverse primer. Cycling conditions were as follows: 50° C. for 2 minutes, then 95° C. for 8 minutes and 30 seconds, followed by 40 cycles of 95° C. for 15 seconds and 60° C. for 60 seconds. Melting curve analysis was performed on each plate according to the manufacturer's instructions. For standard qRT-PCR, human HPRT mRNA transcript levels were used to normalize Ct values obtained for each gene, and relative expression levels were calculated using the $2^{-ddCt}$ method. To ensure validity of results, only Ct values <35 were used in gene expression analyses. All primer sets were tested in a no-template control (NTC) reaction containing only water instead of cDNA, and all gave Ct values >35 in NTC reactions.

Gene Set Enrichment and Pathway Analyses.

Gene expression data in FPKM was submitted to GSEA to determine significant KEGG pathways, and enrichment plots describing ranked gene expression in those pathways. We acknowledge our use of the gene set enrichment analysis, GSEA software, and Molecular Signature Database (see website: broad.mit.edu).

Log 2 fold change (L2FC) and p values for comparison between sAML and normal bone marrow were computed from this gene and isoform expression data. Heat maps were generated using GENE-E default settings and gene expression data for the intersection of genes with L2FC>0.5 and genes in the KEGG Spliceosome gene set. A volcano plot was made using isoform L2FC and p values for all transcripts with a minimum median FPKM of 1 in one condition, highlighting genes with absolute L2FC>1 and p value >0.05. A heat map was made using GENE-E default settings and expression data for moderate to highly expressed transcripts with a median FPKM of at least 10 in one condition, p value <0.01, and absolute L2FC>1, displaying the top 50 isoforms ranked by absolute L2FC.

Mutational Analysis of SF3B1 and Other Spliceosome Genes.

RNA-Seq reads were aligned with the genomic coordinates of known mutations in SF3B1, U2AF1, SRSF2 and ZRSF2 to assess potential somatic mutations in these splicing factor genes that are highly specific for diagnosis of sAML [6]. For RNA-Seq reads from sAML and normal bone marrow progenitors, 100 bp reads were obtained. These were cleaned of adapters and primers using cutadapt, then aligned using STAR. REDItools [57] was used to identify putative somatic mutations at loci previously described in MDS or AML samples [6,17]. One out of seven sAML patient samples in the RNA-Seq dataset harbored a single G>C mutation in exon 14 of SF3B1 (538 G reads versus 520 C reads), corresponding to an aa change of K666N in SF3B1. For validation by PCR and targeted Sanger sequencing analysis of SF3B1, 1 μL of first-strand cDNA templates was prepared for PCR in 25-μL reaction volumes using the high-fidelity KOD Hot Start DNA Polymerase kit according to the manufacturer's instructions (EMD Millipore, Temecula, Calif.). PCR primers for sequencing SF3B1 in cDNA were located in exon 10 (forward, FW) and exon 17 (reverse, REV, Table 2) [40]. PCR cycling conditions were as follows: 95° C. for 2 minutes, followed by 35 cycles of 95° C. for 20 seconds, 62° C. for 10 seconds and 70° C. for 10 seconds, with a final extension step of 70° C. for 30 seconds. Amplicons of the predicted size were verified for each outer primer set by DNA gel electrophoresis using 10-20 μL of the completed reaction mixture separated on 2% agarose gels containing ethidium bromide and visualized under UV light. Then, 15 μL of each reaction was processed within 24 hrs for PCR purification, and sequencing was performed on ABI 3730xl DNA Sequencers (Eton Bioscience, San Diego, Calif.). Sanger sequencing was carried out using two primers, a FW and REV primer each localized to exon 14 (Table 2). Sequence chromatograms were analyzed using 4Peaks.

Splicing Reporter Assay and In Vitro Splicing Analyses.

For evaluation of in vitro splicing activity using a two-color fluorescent splicing reporter system [42], HEK293T cells (*mycoplasma*-free authenticated cell lines obtained from ATCC) were grown in complete media (DMEM+10% FBS) and transfected with a series of fluorescent protein-expressing plasmids. Vector controls include pFlare5A, which expresses solely GFP, and pFlare5G, which expresses maximal RFP. The pFlare reporter contains microtubule-associated protein tau (MAPT) exon 10 as an indicator of alternative splicing. Under physiological conditions, the pFlare conditional reporter vector allows in-frame expression of GFP but not RFP. In the presence of splicing inhibitors, exon skipping favors production of RFP over GFP. Twenty-four hours after transfection with the three plasmids in separate wells of a 24-well plate, 17S-FD-895 or equivalently diluted DMSO vehicle controls (<1%) were added to the media for an additional 24 hrs, to allow sufficient time for translation of the alternatively spliced transcripts driving expression of RFP or GFP protein products. Fluorescence was evaluated on a Leica fluorescent microscope (Sanford Consortium Stem Cell Core facility) and then analyzed by flow cytometry on a Miltenyi MAC-SQuant® to assess transfection efficiency (ranging from over 70% at 24 hrs after transfection to approximately 20% at 48 hrs after transfection) and mean fluorescence intensity (MFI) of RFP and GFP in positive cells. In HEK293 cells transiently transfected with control GFP or RFP vectors, or the pFlare splicing reporter vector, the dynamic range of the assay as measured by MFI of GFP and RFP 48 hours after transfection ranged from 0.41-1.69 for RFP/GFP ratios (FIG. 6A). For time-lapse imaging, splicing reporter-transfected cells were transferred to glass-bottom 35-mm dishes and treated with 1-10 μM of 17S-FD-895, followed by sequential imaging on an Olympus FV10i confocal microscope equipped with a 5% $CO_2$ cell culture incubation chamber (Tokai Hit, Japan) for up to 24 hrs.

For evaluation of in vitro splicing activity of endogenous transcripts in HEK293 or a sAML cell line, MOLM-13 (*mycoplasma*-free and cytogenetically-authenticated cell lines obtained from DMSZ), cells were plated in complete media (DMEM containing 10% FBS for HEK293 and RPMI containing 20% FBS for MOLM-13). The next day, FD-895, 17S-FD-895 or DMSO vehicle controls were added at doses ranging from 0.01-10 μM for 4 hrs of treatment. Cells were lysed in RLT buffer (Qiagen) and processed for RNA extraction and subsequent PCR analyses using primers specific for DNAJB1 or MCL1 (Table 2). For all experiments in cell line, cells obtained from the vendors were frozen down in bulk at low passage numbers and used within 20 passages to minimize risk of cell line misidentification or acquisition of additional chromosomal abnormalities.

Bone Marrow Stromal Cell Culture.

Mouse bone marrow stromal cell lines (SL and M2 *mycoplasma*-free authenticated cells obtained from ATCC) expressing human interleukin-3 (IL-3), stem cell factor (SCF) and granulocyte-colony stimulating factor (G-CSF), which support erythroid and myeloid cell expansion and differentiation, were maintained under standard culture conditions, as previously described [19]. Briefly, SL cells were grown in complete medium containing DMEM (Corning), 10% FBS, 1% Glutamax, and 1% penicillin-streptomycin (Life Technologies), while M2 cells were grown in complete medium containing RPMI, 10% FBS, 1% Glutamax, and 1% penicillin-streptomycin (all from Life Technologies). Every four passages, cells were selected by addition of G418 and hygromycin to the culture media for one passage (3-4 days), to maintain human cytokine expression. All cell lines were maintained in T-25 or T-75 culture flasks and were passaged at dilutions of 1:5-1:10 every 2-4 days. Low passage aliquots of cells were thawed every two months to ensure consistency of experiments.

PRIMAGRAFT™ Models and Analyses.

Mice transplanted with 1-2×10$^5$ CD34$^+$ AML LSC-enriched fractions or no-transplant controls were screened for human hematopoietic cell engraftment (CD45$^+$ cells) in peripheral blood by FACS starting at 7-10 weeks post transplant. At 7-28 weeks post-transplant (7-36 weeks old), mice were euthanized, and peripheral blood and single cell suspensions of hematopoietic organs were analyzed for human cell engraftment by FACS. Total cell suspensions from bone marrow and spleen were either transplanted immediately or CD34-selected for transplant into secondary recipient mice (1-2×10$^5$ cells per animal) to expand the cells in vivo. Both mouse strains were found to support serial transplantation of all three patient samples, however for subsequent experiments, AML-37 was maintained in Rag2$^{-/-}$γ$_c^{-/-}$ mice and AML-08 was maintained in NSGS mice. Secondary recipient mice were euthanized after 8-23 weeks, and cell suspensions from bone marrow and spleen were CD34-selected for transplant into tertiary recipients for 17S-FD-895 treatment.

In Vivo 17S-FD-895 Treatment, Tissue Analysis and Serial Transplantation.

The 17S-FD-895 dosing regimen was selected as the maximum number of doses possible for the treatment of three experimental groups with the amount of synthesized compound that was available, and is consistent with weekly IV dosing regimens used in clinical trials of spliceosome inhibitory compounds in patients with solid tumors [41]. Animals were euthanized within two hours after delivery of the final dose of 17S-FD-895, and peripheral blood, spleens and bone marrows were collected for analysis of total human cell and stem and progenitor cell engraftment, and for RNA extraction for splice isoform-specific qRT-PCR.

Flow cytometric analysis was performed on single cell suspensions from each hematopoietic tissue essentially as for primary patient samples, and frequencies of total live human CD45$^+$ cells, and CD45$^+$CD34$^+$CD38$^-$ Lin$^-$ (stem) and CD45$^+$CD34$^+$CD38$^+$ Lin$^-$ (progenitor) cells were determined in each tissue. Analysis of progenitor cell subpopulations was performed for AML-37, with GMP identified as CD123$^+$CD45RA$^+$, CMP as CD123$^+$CD45RA$^-$ and megakaryocyte-erythroid progenitors (MEP) as CD123$^+$CD45RA$^-$. Inclusion/exclusion criteria were pre-established based on minimum CD45$^+$ cell engraftment rates of 1% in peripheral blood, as determined by previous PRIMAGRAFT™ experiments [20,54]. For AML-37 treatment, one additional transplanted mouse was treated with vehicle control (total n=6), however leukemic burden was 0.2% before treatment, and because this value >2 standard deviations lower in spleen and bone marrow than all other vehicle-treated controls (n=5) at the end of the experiment, this animal was excluded from FACS and PCR analyses.

For serial transplantation of LSC-enriched fractions from treated mice (AML-37), cells from individual mice were pooled according to treatment group for each hematopoietic tissue. For AML-08, after 17S-FD-895 treatment, fresh spleen and bone marrow-derived CD34$^+$ cells were pooled (1:1 ratio per tissue and equivalent numbers of cells from each treated mouse). For both models, 2×10$^5$ cells were transplanted intravenously into adult (6-8 weeks old) NSGS mice.

REFERENCES (EXAMPLE 1)

[1] A. L. Paguirigan, J. Smith, S. Meshinchi, M. Carroll, C. Maley, J. P. Radich, Single-cell genotyping demonstrates complex clonal diversity in acute myeloid leukemia. Sci Transl Med 7, 281re282 (2015); [2] L. Ding, T. J. Ley, D. E. Larson, C. A. Miller, D. C. Koboldt, J. S. Welch, J. K. Ritchey, M. A. Young, T. Lamprecht, M. D. McLellan, J. F. McMichael, J. W. Wallis, C. Lu, D. Shen, C. C. Harris, D. J. Dooling, R. S. Fulton, L. L. Fulton, K. Chen, H. Schmidt, J. Kalicki-Veizer, V. J. Magrini, L. Cook, S. D. McGrath, T. L. Vickery, M. C. Wendl, S. Heath, M. A. Watson, D. C. Link, M. H. Tomasson, W. D. Shannon, J. E. Payton, S. Kulkarni, P. Westervelt, M. J. Walter, T. A. Graubert, E. R. Mardis, R. K. Wilson, J. F. DiPersio, Clonal evolution in relapsed acute myeloid leukaemia revealed by whole-genome sequencing. Nature 481, 506-510 (2012); [3] B. Bartholdy, M. Christopeit, B. Will, Y. Mo, L. Barreyro, Y. Yu, T. D. Bhagat, U. C. Okoye-Okafor, T. I. Todorova, J. M. Greally, R. L. Levine, A. Melnick, A. Verma, U. Steidl, HSC commitment-associated epigenetic signature is prognostic in acute myeloid leukemia. J Clin Invest 124, 1158-1167 (2014); [4] A. Raza, M. Mehdi, M. Mumtaz, F. Ali, S. Lascher, N. Galili, Combination of 5-azacytidine and thalidomide for the treatment of myelodysplastic syndromes and acute myeloid leukemia. Cancer 113, 1596-1604 (2008); [5] M. J. Walter, D. Shen, L. Ding, J. Shao, D. C. Koboldt, K. Chen, D. E. Larson, M. D. McLellan, D. Dooling, R. Abbott, R. Fulton, V. Magrini, H. Schmidt, J. Kalicki-Veizer, M. O'Laughlin, X. Fan, M. Grillot, S. Witowski, S. Heath, J. L. Frater, W. Eades, M. Tomasson, P. Westervelt, J. F. DiPersio, D. C. Link, E. R. Mardis, T. J. Ley, R. K. Wilson, T. A. Graubert, Clonal architecture of secondary acute myeloid leukemia. N Engl J Med 366, 1090-1098 (2012); [6] R. C. Lindsley, B. G. Mar, E. Mazzola, P. V. Grauman, S. Shareef, S. L. Allen, A. Pigneux, M. Wetzler, R. K. Stuart, H. P. Erba, L. E. Damon, B. L. Powell, N. Lindeman, D. P. Steensma, M. Wadleigh, D. J. DeAngelo, D. Neuberg, R. M. Stone, B. L. Ebert, Acute myeloid leukemia ontogeny is defined by distinct somatic mutations. Blood 125, 1367-1376 (2015); [7] A. Quintas-Cardama, F. Ravandi, T. Liu-Dumlao, M. Brandt, S. Faderl, S. Pierce, G. Borthakur, G. Garcia-Manero, J. Cortes, H. Kantarjian, Epigenetic therapy is associated with similar survival compared with intensive chemotherapy in older patients with newly diagnosed acute myeloid leukemia. Blood 120, 4840-4845 (2012); [8] P. L. Greenberg, R. M. Stone, R. Bejar, J. M. Bennett, C. D. Bloomfield, U. Borate, C. M. De Castro, H. J. Deeg, A. E. DeZern, A. T. Fathi, O. Frankfurt, K. Gaensler, G. Garcia-Manero, E. A. Griffiths, D. Head, V. Klimek, R. Komrokji, L. A. Kujawski, L. J. Maness, M. R. O'Donnell, D. A. Pollyea, B. Scott, P. J. Shami, B. L. Stein, P. Westervelt, B. Wheeler, D. A. Shead, C. Smith, Myelodysplastic syndromes, version 2.2015. J Natl Compr Canc Netw: JNCCN 13, 261-272 (2015); [9] N. Goardon, E. Marchi, A. Atzberger, L. Quek, A. Schuh, S. Soneji, P. Woll, A. Mead, K. A. Alford, R. Rout, S. Chaudhury, A. Gilkes, S. Knapper, K. Beldjord, S. Begum, S. Rose, N. Geddes, M. Griffiths, G. Standen, A. Sternberg, J. Cavenagh, H. Hunter, D. Bowen, S. Killick, L. Robinson, A. Price, E. Macintyre, P. Virgo, A. Burnett, C. Craddock, T. Enver, S. E. Jacobsen, C. Porcher, P. Vyas, Coexistence of LMPP-like and GMP-like leukemia stem cells in acute myeloid leukemia. Cancer Cell 19, 138-152 (2011); [10] K. Eppert, K. Takenaka, E. R. Lechman, L. Waldron, B. Nilsson, P. van Galen, K. H. Metzeler, A. Poeppl, V. Ling, J. Beyene, A. J. Canty, J. S. Danska, S. K. Bohlander, C. Buske, M. D. Minden, T. R. Golub, I. Jurisica, B. L. Ebert, J. E. Dick, Stem cell gene expression programs influence clinical outcome in human leukemia. Nat Med 17, 1086-1093 (2011); [11]L. A. Crews, C. H. Jamieson, Selective elimination of leukemia stem cells: Hitting a moving target. Cancer Lett 338, 15-22 (2012); [12] S. Jaiswal, C. H. Jamieson, W. W. Pang, C. Y. Park, M. P. Chao, R. Majeti, D. Traver, N. van Rooijen, I. L. Weissman, CD47 is upregulated on circulating hematopoietic stem cells and leukemia cells to avoid phagocytosis. Cell 138, 271-285 (2009); [13] W. W. Pang, E. A. Price, D. Sahoo, I. Beerman, W. J. Maloney, D. J. Rossi, S. L. Schrier, I. L. Weissman, Human bone marrow hematopoietic stem cells are increased in frequency and myeloid-biased with age. Proc Natl Acad Sci USA 108, 20012-20017 (2011); [14] D. Bonnet, J. E. Dick, Human acute myeloid leukemia is organized as a hierarchy that originates from a primitive hematopoietic cell. Nat Med 3, 730-737 (1997); [15] C. N. Hahn, H. S. Scott, Spliceosome mutations in hematopoietic malignancies. Nat Genet 44, 9-10 (2012); [16]L. I. Shlush, S. Zandi, A. Mitchell, W. C. Chen, J. M. Brandwein, V. Gupta, J. A. Kennedy, A. D. Schimmer, A. C. Schuh, K. W. Yee, J. L. McLeod, M. Doedens, J. J. Medeiros, R. Marke, H. J. Kim, K. Lee, J. D. McPherson, T. J. Hudson, A. M. Brown, F. Yousif, Q. M. Trinh, L. D. Stein, M. D. Minden, J. C. Wang, J. E. Dick, Identification of pre-leukaemic haematopoietic stem cells in acute leukaemia. Nature 506, 328-333 (2014); [17] K. Yoshida, M. Sanada, Y. Shiraishi, D. Nowak, Y. Nagata, R. Yamamoto, Y. Sato, A. Sato-Otsubo, A. Kon, M. Nagasaki, G. Chalkidis, Y. Suzuki, M. Shiosaka, R. Kawahata, T. Yamaguchi, M. Otsu, N. Obara, M. Sakata-Yanagimoto, K. Ishiyama, H. Mori, F. Nolte, W. K. Hofmann, S. Miyawaki, S. Sugano, C. Haferlach, H. P. Koeffler, L. Y. Shih, T. Haferlach, S. Chiba, H. Nakauchi, S. Miyano, S. Ogawa, Frequent pathway mutations of splicing machinery in myelodysplasia. Nature 478, 64-69 (2011); [18] C. DeBoever, E. M. Ghia, P. J. Shepard, L. Rassenti, C. L. Barrett, K. Jepsen, C. H. Jamieson, D. Carson, T. J. Kipps, K. A. Frazer, Transcriptome sequencing reveals potential mechanism of cryptic 3' splice site selection in SF3B1-mutated cancers. PLoS Comp Biol 11, e1004105 (2015); [19] D. J. Goff, A. C. Recart, A. Sadarangani, H. J. Chun, C. L. Barrett, M. Krajewska, H. Leu, J. Low-Marchelli, W. Ma, A. Y. Shih, J. Wei, D. Zhai, I. Geron, M. Pu, L. Bao, R. Chuang, L. Balaian, J. Gotlib, M. Minden, G. Martinelli, J. Rusert, K. H. Dao, K. Shazand, P. Wentworth, K. M. Smith, C. A. Jamieson, S. R. Morris, K. Messer, L. S. Goldstein, T. J. Hudson, M. Marra, K. A. Frazer, M. Pellecchia, J. C. Reed, C. H. Jamieson, A Pan-BCL2 inhibitor renders bone-marrow-resident human leukemia stem cells sensitive to tyrosine kinase inhibition. Cell Stem Cell 12, 316-328 (2013); [20] A. E. Abrahamsson, I. Geron, J. Gotlib, K. H. Dao, C. F. Barroga, I. G. Newton, F. J. Giles, J. Durocher, R. S. Creusot, M. Karimi, C. Jones, J. L. Zehnder, A. Keating, R. S. Negrin, I. L. Weissman, C. H. Jamieson, Glycogen synthase kinase 3 missplicing contributes to leukemia stem cell generation. Proc Natl Acad Sci USA 106, 3925-3929 (2009); [21] Q. Jiang, L. A. Crews, C. L. Barrett, H. J. Chun, A. C. Court, J. M. Isquith, M. A. Zipeto, D. J. Goff, M. Minden, A. Sadarangani, J. M. Rusert, K. H. Dao, S. R. Morris, L. S. Goldstein, M. A. Marra, K. A. Frazer, C. H. Jamieson, ADAR1 promotes malignant progenitor reprogramming in chronic myeloid leukemia. Proc Natl Acad Sci USA 110, 1041-1046 (2013); [22] L. A. Crews, Q. Jiang, M. A. Zipeto, E. Lazzari, A. C. Court, S. Ali, C. L. Barrett, K. A. Frazer, C. H. M. Jamieson, An RNA editing fingerprint of cancer stem cell reprogramming. J Transl Med 13, (2015); [23] C. Lobry, P. Oh, M. R. Mansour, A. T. Look, I. Aifantis, Notch signaling: switching an oncogene to a tumor suppressor. Blood 123, 2451-2459 (2014); [24] T. Trimarchi, E. Bilal, P. Ntziachristos, G. Fabbri, R. Dalla-Favera, A. Tsirigos, I. Aifantis, Genome-wide mapping and characterization of Notch-regulated long noncoding RNAs in acute leukemia. Cell 158, 593-606 (2014); [25] H. Dolatshad, A. Pellagatti, M. Fernandez-Mercado, B. H. Yip, L. Malcovati, M. Attwood, B. Przychodzen, N. Sahgal, A. A. Kanapin, H. Lockstone, L. Scifo, P. Vandenberghe, E. Papaemmanuil, C. W. Smith, P. J. Campbell, S. Ogawa, J. P. Maciejewski, M. Cazzola, K. I. Savage, J. Boultwood, Disruption of SF3B1 results in deregulated expression and splicing of key genes and pathways in myelodysplastic syndrome hematopoietic stem and progenitor cells. Leukemia 29, 1092-1103 (2015); [26] S. Adamia, B. Haibe-Kains, P. M. Pilarski, M. Bar-Natan, S. Pevzner, H. Avet-Loiseau, L. Lode, S. Verselis, E. A. Fox, J. Burke, I. Galinsky, I. Dagogo-Jack, M. Wadleigh, D. P. Steensma, G. Motyckova, D. J. Deangelo, J. Quackenbush, R. Stone, J. D. Griffin, A genome-wide aberrant RNA splicing in patients with acute myeloid leukemia identifies novel potential disease markers and therapeutic targets. Clin Cancer Res 20, 1135-1145 (2014); [27] J. M. Johnson, J. Castle, P. Garrett-Engele, Z. Kan, P. M. Loerch, C. D. Armour, R. Santos, E. E. Schadt, R. Stoughton, D. D. Shoemaker, Genome-wide survey of human alternative pre-mRNA splicing with exon junction microarrays. Science 302, 2141-2144 (2003); [28] Q. Pan, M. A. Bakowski, Q. Morris, W. Zhang, B. J. Frey, T. R. Hughes, B. J. Blencowe, Alternative splicing of conserved exons is frequently species-specific in human and mouse. Trends Genet 21, 73-77 (2005); [29] P. Mazin, J. Xiong, X. Liu, Z. Yan, X. Zhang, M. Li, L. He, M. Somel, Y. Yuan, Y. P. Phoebe Chen, N. Li, Y. Hu, N. Fu, Z. Ning, R. Zeng, H. Yang, W. Chen, M. Gelfand, P. Khaitovich, Widespread splicing changes in human brain development and aging. Mol Sys Biol 9, 633 (2013); [30] L. Li, M. Li, C. Sun, L. Francisco, S. Chakraborty, M. Sabado, T. McDonald, J. Gyorffy, K. Chang, S. Wang, W. Fan, J. Li, L. P. Zhao, J. Radich, S. Forman, S. Bhatia, R. Bhatia, Altered hematopoietic cell gene expression precedes development of therapy-related myelodysplasia/acute myeloid leukemia and identifies patients at risk. Cancer Cell 20, 591-605 (2011); [31] T. Graubert, M. J. Walter, Genetics of myelodysplastic syndromes: new insights. Hematology Am Soc Hematol Educ Program 2011, 543-549 (2011); [32] S. Bonnal, L. Vigevani, J. Valcarcel, The spliceosome as a target of novel antitumour drugs. Nat Rev Drug Discov 11, 847-859 (2012); [33] C. Lagisetti, G. Palacios, T. Goronga, B. Freeman, W. Caufield, T. R. Webb, Optimization of antitumor modulators of pre-mRNA splicing. J Med Chem 56, 10033-10044 (2013); [34] R. Villa, A. L. Mandel, B. D. Jones, J. J. La Clair, M. D. Burkart, Structure of FD-895 revealed through total synthesis. Org Lett 14, 5396-5399 (2012); [35] C. L. Barrett, C. DeBoever, K. Jepsen, C. C. Saenz, D. A. Carson, K. A. Frazer, Systematic transcriptome analysis reveals tumor-specific isoforms for ovarian cancer diagnosis and therapy. Proc Natl Acad Sci USA 112, E3050-3057 (2015); [36] A. Burchert, M. Notter, H. Dietrich Menssen, S. Schwartz, W. Knauf, A. Neubauer, E. Thiel, CD82 (KAI1), a member of the tetraspan family, is expressed on early haemopoietic progenitor cells and up-regulated in distinct human leukaemias. Br J Haematol 107, 494-504 (1999); [37] P. G. Miller, F. Al-Shahrour, K. A. Hartwell, L. P. Chu, M. Jaras, R. V. Puram, A. Puissant, K. P. Callahan, J. Ashton, M. E. McConkey, L. P. Poveromo, G. S. Cowley, M. G. Kharas, K. Labelle, S. Shterental, J. Fujisaki, L. Silberstein, G. Alexe, M. A. Al-Hajj, C. A. Shelton, S. A. Armstrong, D. E. Root, D. T. Scadden, R. O. Hynes, S. Mukherjee, K. Stegmaier, C. T. Jordan, B. L. Ebert, In Vivo RNAi screening identifies a leukemia-specific dependence on integrin beta 3 signaling. Cancer Cell 24, 45-58 (2013); [38] J. H. Lee, Y. W. Seo, S. R. Park, Y. J. Kim, K. K. Kim, Expression of a splice variant of KAI1, a tumor metastasis suppressor gene, influences tumor invasion and progression. Cancer Res 63, 7247-7255 (2003); [39] S. M. Weis, S. T. Lim, K. M. Lutu-Fuga, L. A. Barnes, X. L. Chen, J. R. Gothert, T. L. Shen, J. L. Guan, D. D. Schlaepfer, D. A. Cheresh, Compensatory role for Pyk2 during angiogenesis in adult mice lacking endothelial cell FAK. J Cell Biol 181, 43-50 (2008); [40] Y. Kotake, K. Sagane, T. Owa, Y. Mimori-Kiyosue, H. Shimizu, M. Uesugi, Y. Ishihama, M. Iwata, Y. Mizui, Splicing factor SF3b as a target of the antitumor natural product pladienolide. Nat Chem Biol 3, 570-575 (2007); [41] D. S. Hong, R. Kurzrock, A. Naing, J. J. Wheler, G. S. Falchook, J. S. Schiffman, N. Faulkner, M. J. Pilat, J. O'Brien, P. LoRusso, A phase I, open-label, single-arm, dose-escalation study of E7107, a precursor messenger ribonucleic acid (pre-mRNA) splicesome inhibitor administered intravenously on days 1 and 8 every 21 days to patients with solid tumors. Invest New Drugs 32, 436-444 (2014); [42] P. Stoilov, C. H. Lin, R. Damoiseaux, J. Nikolic, D. L. Black, A high-throughput screening strategy identifies cardiotonic steroids as alternative splicing modulators. Proc Natl Acad Sci USA 105, 11218-11223 (2008); [43] D. Kaida, H. Motoyoshi, E. Tashiro, T. Nojima, M. Hagiwara, K. Ishigami, H. Watanabe, T. Kitahara, T. Yoshida, H. Nakajima, T. Tani, S. Horinouchi, M. Yoshida, Spliceostatin A targets SF3b and inhibits both splicing and nuclear retention of pre-mRNA. Nat Chem Biol 3, 576-583 (2007); [44] L. Wang, M. S. Lawrence, Y. Wan, P. Stojanov, C. Sougnez, K. Stevenson, L. Werner, A. Sivachenko, D. S. DeLuca, L. Zhang, W. Zhang, A. R. Vartanov, S. M. Fernandes, N. R. Goldstein, E. G. Folco, K. Cibulskis, B. Tesar, Q. L. Sievers, E. Shefler, S. Gabriel, N. Hacohen, R. Reed, M. Meyerson, T. R. Golub, E. S. Lander, D. Neuberg, J. R. Brown, G. Getz, C. J. Wu, SF3B1 and other novel cancer genes in chronic lymphocytic leukemia. N Engl J Med 365, 2497-2506 (2011); [45] M. K. Kashyap, D. Kumar, R. Villa, J. J. La Clair, C. Benner, R. Sasik, H. Jones, E. M. Ghia, L. Z. Rassenti, T. J. Kipps, M. D. Burkart, J. E. Castro, Targeting the spliceosome in chronic lymphocytic leukemia with the macrolides FD-895 and pladienolide-B. Haematologica 100, 945-954 (2015); [46] H. M. Kantarjian, H. P. Erba, D. Claxton, M. Arellano, R. M. Lyons, T. Kovascovics, J. Gabrilove, M. Craig, D. Douer, M. Maris, S. Petersdorf, P. J. Shami, A. M. Yeager, S. Eckert, R. Abichandani, S. Faderl, Phase II study of clofarabine monotherapy in previously untreated older adults with acute myeloid leukemia and unfavorable prognostic factors. J Clin Oncol 28, 549-555 (2010); [47] A. K. Burnett, N. H. Russell, A. E. Hunter, D. Milligan, S. Knapper, K. Wheatley, J. Yin, M. F. McMullin, S. Ali, D. Bowen, R. K. Hills, U. K. N. C. R. I. A. W. Group, Clofarabine doubles the response rate in older patients with acute myeloid leukemia but does not improve survival. Blood 122, 1384-1394 (2013); [48] S. P. Glaser, E. F. Lee, E. Trounson, P. Bouillet, A. Wei, W. D. Fairlie, D. J. Izon, J. Zuber, A. R. Rappaport, M. J. Herold, W. S. Alexander, S. W. Lowe, L. Robb, A. Strasser, Anti-apoptotic Mcl-1 is essential for the development and sustained growth of acute myeloid leukemia. Genes Dev 26, 120-125 (2012); [49] S. M. Chan, D. Thomas, M. R. Corces-Zimmerman, S. Xavy, S. Rastogi, W. J. Hong, F. Zhao, B. C. Medeiros, D. A. Tyvoll, R. Majeti, Isocitrate dehydrogenase 1 and 2 mutations induce BCL-2 dependence in acute myeloid leukemia. Nat Med 21, 178-184 (2015); [50] M. Salton, W. K. Kasprzak, T. Voss, B. A. Shapiro, P. I. Poulikakos, T. Misteli, Inhibition of vemurafenib-resistant melanoma by interference with pre-mRNA splicing. Nat Commun 6, 7103 (2015); [51] R. Ferrarese, G. R. t. Harsh, A. K. Yadav, E. Bug, D. Maticzka, W. Reichardt, S. M. Dombrowski, T. E. Miller, A. P. Masilamani, F. Dai, H. Kim, M. Hadler, D. M. Scholtens, I. L. Yu, J. Beck, V. Srinivasa-sainagendra, F. Costa, N. Baxan, D. Pfeifer, D. von Elverfeldt, R. Backofen, A. Weyerbrock, C. W. Duarte, X. He, M. Prinz, J. P. Chandler, H. Vogel, A. Chakravarti, J. N. Rich, M. S. Carro, M. Bredel, Lineage-specific splicing of a brain-enriched alternative exon promotes glioblastoma progression. J Clin Invest 124, 2861-2876 (2014); [52] T. Y. Hsu, L. M. Simon, N. J. Neill, R. Marcotte, A. Sayad, C. S. Bland, G. V. Echeverria, T. Sun, S. J. Kurley, S. Tyagi, K. L. Karlin, R. Dominguez-Vidana, J. D. Hartman, A. Renwick, K. Scorsone, R. J. Bernardi, S. O. Skinner, A. Jain, M. Orellana, C. Lagisetti, I. Golding, S. Y. Jung, J. R. Neilson, X. H. Zhang, T. A. Cooper, T. R. Webb, B. G. Neel, C. A. Shaw, T. F. Westbrook, The spliceosome is a therapeutic vulnerability in MYC-driven cancer. Nature Epub 2 September (2015); [53] M. Wunderlich, F. S. Chou, K. A. Link, B. Mizukawa, R. L. Perry, M. Carroll, J. C. Mulloy, AML xenograft efficiency is significantly improved in NOD/SCID-IL2RG mice constitutively expressing human SCF, GM-CSF and IL-3. Leukemia 24, 1785-1788 (2010); [54] C. H. Jamieson, L. E. Ailles, S. J. Dylla, M. Muijtjens, C. Jones, J. L. Zehnder, J. Gotlib, K. Li, M. G. Manz, A. Keating, C. L. Sawyers, I. L. Weissman, Granulocyte-macrophage progenitors as candidate leukemic stem cells in blast-crisis CML. N Engl J Med 351, 657-667 (2004); [55] A. Dobin, C. A. Davis, F. Schlesinger, J. Drenkow, C. Zaleski, S. Jha, P. Batut, M. Chaisson, T. R. Gingeras, STAR: ultrafast universal RNA-seq aligner. Bioinformatics 29, 15-21 (2013); [56] C. Trapnell, B. A. Williams, G. Pertea, A. Mortazavi, G. Kwan, M. J. van Baren, S. L. Salzberg, B. J. Wold, L. Pachter, Transcript assembly and quantification by RNA-Seq reveals unannotated transcripts and isoform switching during cell differentiation. Nat Biotechnol 28, 511-515 (2010); [57] E. Picardi, G. Pesole, REDItools: high-throughput RNA editing detection made easy. Bioinformatics 29, 1813-1814 (2013); [58] S. Jeromin, T. Haferlach, V. Grossmann, T. Alpermann, A. Kowarsch, C. Haferlach, W. Kern, S. Schnittger, High frequencies of SF3B1 and JAK2 mutations in refractory anemia with ring sideroblasts associated with marked thrombocytosis strengthen the assignment to the category of myelodysplastic/myeloproliferative neoplasms. Haematologica 98, e15-17 (2013).

Example 2. RNA Splicing Modulation Selectively Impairs Leukemia Stem Cell Maintenance in Secondary Human AML Abstract.

Age-related human hematopoietic stem cell (HSC) exhaustion and myeloid-lineage skewing promote oncogenic transformation of hematopoietic progenitor cells into therapy-resistant leukemia stem cells (LSC) in secondary acute myeloid leukemia (sAML). While acquisition of clonal DNA mutations have been linked to increased rates of sAML for individuals over 60, the contribution of RNA processing alterations to human hematopoietic stem and progenitor aging and LSC generation remains unclear. Comprehensive RNA-sequencing and splice isoform-specific PCR uncovered characteristic RNA splice isoform expression patterns that distinguished normal young and aged HSPCs, compared with malignant MDS and AML progenitors. In splicing reporter assays and in pre-clinical patient-derived AML models, treatment with a pharmacologic splicing modulator, 17S-FD-895, reversed pro-survival splice isoform switching and significantly impaired LSC maintenance. By comparing splice isoform biomarkers of normal HSPC aging with those of LSC generation, splicing modulation may be employed safely and effectively to prevent relapse—the leading cause of leukemia-related mortality.

Introduction

Age-related defects in hematopoietic stem cell (HSC) function (Essers et al., 2009) are typified by myeloid lineage bias (Pang et al., 2011), altered survival, dormancy and regenerative capacity. Microenvironmental alterations (Rossi et al., 2008) and clonal DNA mutations in HSCs are acquired during aging and may set the stage for hematopoietic malignancy development (Corces-Zimmerman et al., 2014; Genovese et al., 2015; Jaiswal et al., 2014; Shlush et al., 2014). Notably, myelodysplastic syndromes (MDS), myeloproliferative neoplasms (MPNs) and therapy-resistant secondary AML (sAML) harbor characteristic splicing factor mutations suggesting that the accumulation of DNA mutations over time is a major determinant of lifetime leukemia risk (McKerrell et al., 2015). However, these observations do not completely explain the exponential increase in leukemia incidence with advanced age (Adams et al., 2015), in part because they do not take into account microenvironment-responsive RNA processing events that promote leukemic transformation.

Recent RNA-sequencing (RNA-Seq) studies comparing aged versus young mouse HSC identified changes in TGF-β signaling, epigenetic regulator expression and alternative splicing (Sun et al., 2014). Although disruption of cell cycle and differentiation programs were identified by RNA-seq at the single cell level during mouse HSC aging (Kowalczyk et al., 2015), fundamental differences in mouse and human stem and progenitor cell (HSPC) pre-mRNA splicing regulation (Abrahamsson et al., 2009; Crews et al., 2015; Goff et al., 2013; Han et al., 2013; Holm et al., 2015; Jiang et al., 2013; Pan et al., 2005) preclude a direct extrapolation of these data to human HSPC. Thus, a comparative RNA-seq analysis of RNA processing alterations governing human HSPC aging and LSC generation will be required to identify mechanisms of therapeutic resistance in sAML.

Seminal studies have shown that subversion of stem cell regulatory pathways (Bonnet and Dick, 1997; Eppert et al., 2011), combined with epigenetic alterations and mutations in splicing regulatory genes (Bartholdy et al., 2014; Eppert et al., 2011; Lindsley et al., 2015; Shlush et al., 2014; Yoshida et al., 2011), portends a poor prognosis in sAML. Recently, pre-mRNA splicing alterations (Abrahamsson et al., 2009; Adamia et al., 2014; DeBoever et al., 2015; Goff et al., 2013; Holm et al., 2015), together with RNA editing and lncRNA deregulation, were associated with therapeutic resistance in leukemia (Crews et al., 2015; Jiang et al., 2013; Trimarchi et al., 2014). With regard to the functional impact of RNA processing alterations on therapeutic resistance, we discovered that malignant reprogramming of human preleukemic progenitors into self-renewing LSC was enhanced by missplicing of a stem cell regulatory transcript, GSK3β (Abrahamsson et al., 2009), through RNA editing (Crews et al., 2015; Jiang et al., 2013; Zipeto et al., 2016) and pro-survival BCL2 family splice isoform switching in CML (Goff et al., 2013). Moreover, reversion to an embryonic splicing program by MBNL3 downregulation also promoted acute leukemic transformation (Holm et al., 2015) and underscored the importance of splicing deregulation in human LSC generation.

Recent MDS (Dolatshad et al., 2015) and de novo AML (Adamia et al., 2014) studies demonstrate that differential exon usage in epigenetic modifier and tumor suppressor transcripts contribute to myeloid malignancy pathogenesis. However, whether differences exist in alternative splicing regulation between aged human HSPC and LSC, and whether RNA splicing alterations selectively sensitize LSC to splicing modulator therapy had not been determined (Bonnal et al., 2012). Thus, we sought to identify RNA processing signatures of malignant versus benign HSPC aging and to evaluate the LSC-selective efficacy of a pharmacological splicing modulator, 17S-FD-895.

Results

Splice Isoform Signatures of Human Hematopoietic Stem and Progenitor Cell Aging.

Figure 11B:
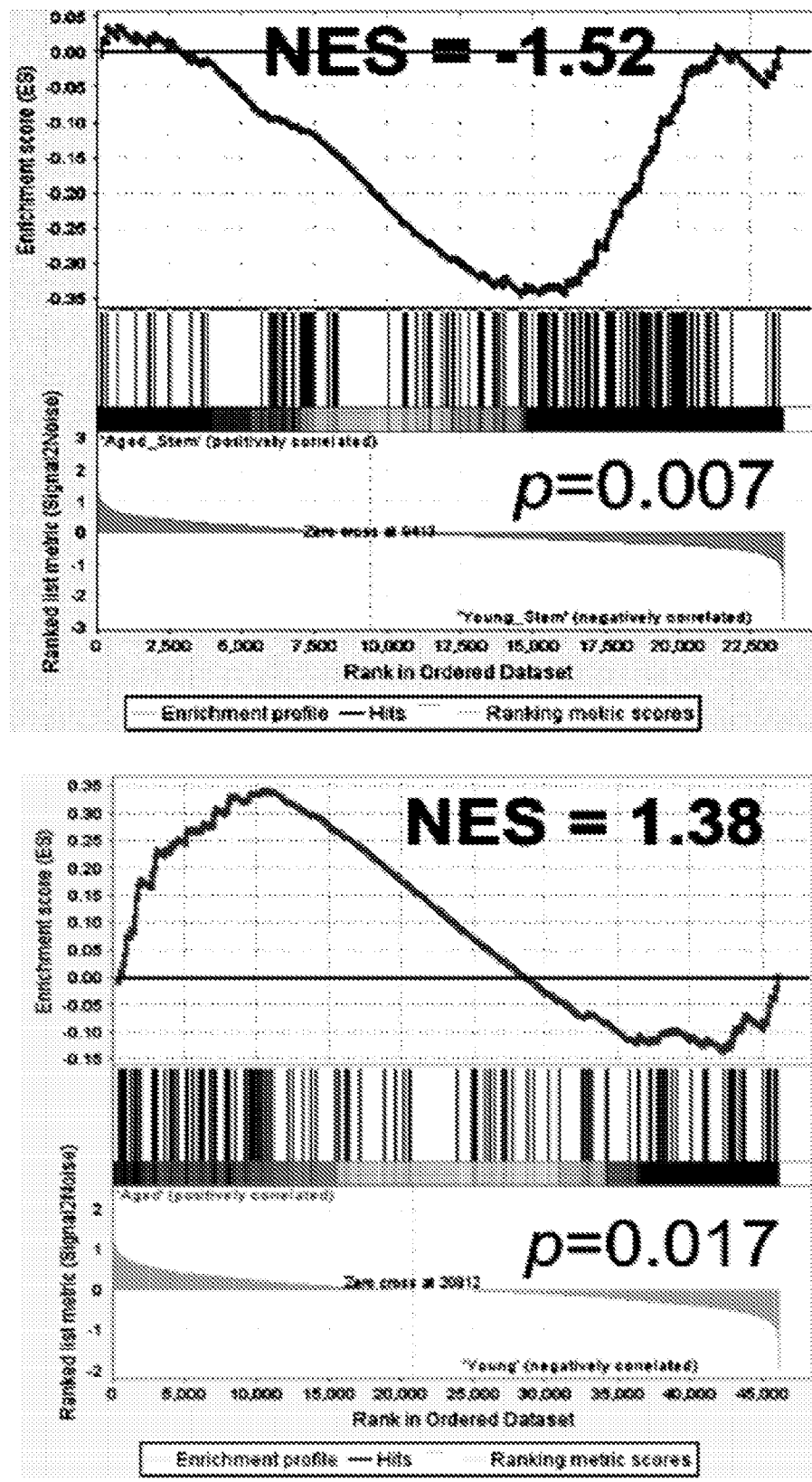

Mutations in various components of the human RNA splicing machinery (FIG. 11A) have been associated with age-related hematopoietic malignancies. However, whether normal aging sets the stage for RNA processing deregulation in cancer, and whether non-mutation-based splicing alterations are associated with human stem cell aging or malignant stem cell generation has not been established. To generate a comprehensive transcriptome expression map of human HSPC aging, we performed RNA-Seq of highly purified normal young and aged HSC (CD34$^+$CD38$^-$Lin$^-$) and hematopoietic progenitor cells (CD34$^+$CD38$^+$Lin$^-$ HPC) from human bone marrow (FIG. 18A) followed by whole gene, splice isoform, transcription factor and lncRNA analyses. In FACS-purified HSC from aged versus young adults, gene set enrichment analyses (GSEA) revealed disruption of vital stem cell regulatory pathways such as oxidative phosphorylation, DNA replication, and proteostasis (Signer et al., 2014) (FIG. 18B, Table 3). In aged versus young HPC, deregulation of DNA mismatch repair and recombination and inflammation-associated pathways was observed (FIG. 18C). Genes encoding signal transduction molecules such as protein phosphatases (DUSP1) were commonly upregulated during human HSC and HPC aging. Additionally, in aging human HPC, expression of DNA damage (GADD45A, GADD45B) and pro-inflammatory genes (CXCL2) was increased (FIG. 18D-18E). Notably, KEGG spliceosome pathway genes revealed distinctive expression changes between HSC compared with HPC suggestive of differential splicing regulation during aging (FIG. 11B; Table 3).

Figure 11C:
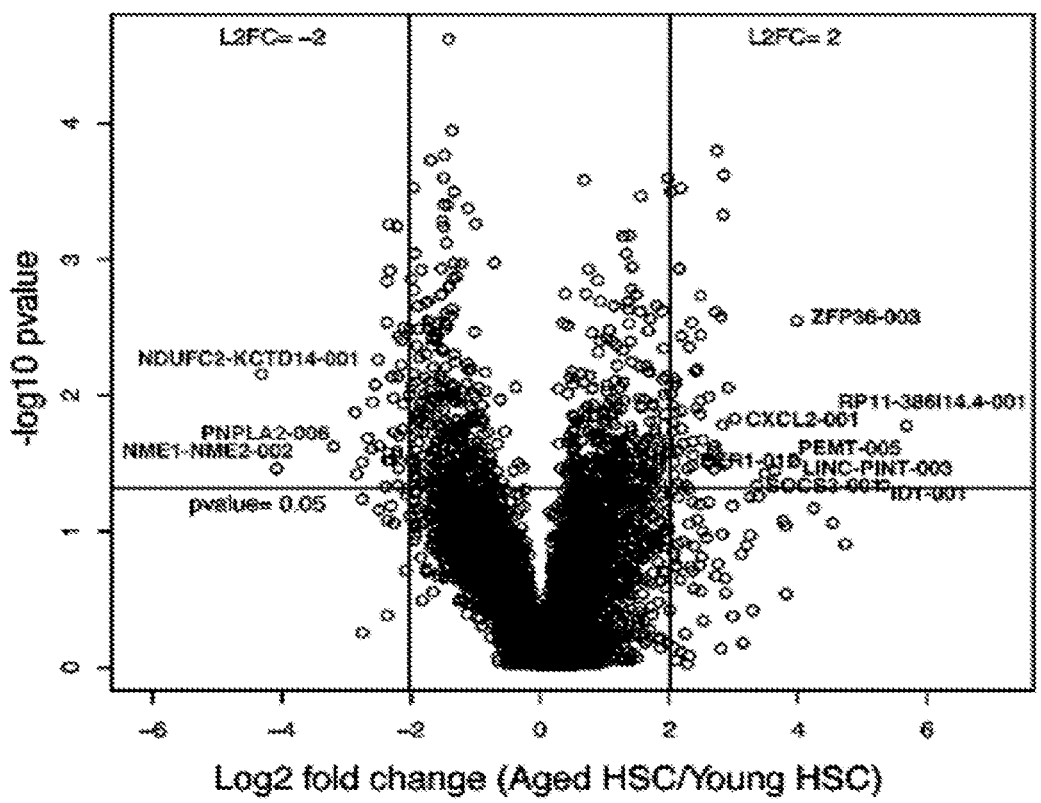
Figure 11C:
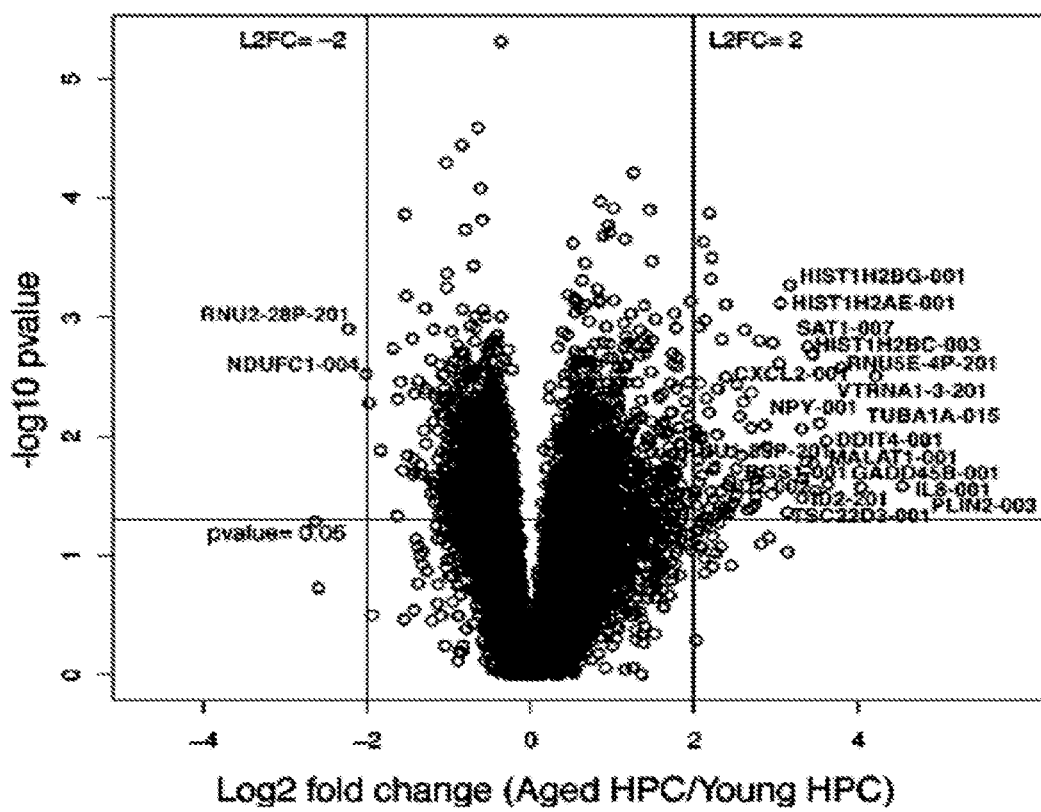
Figure 18F:
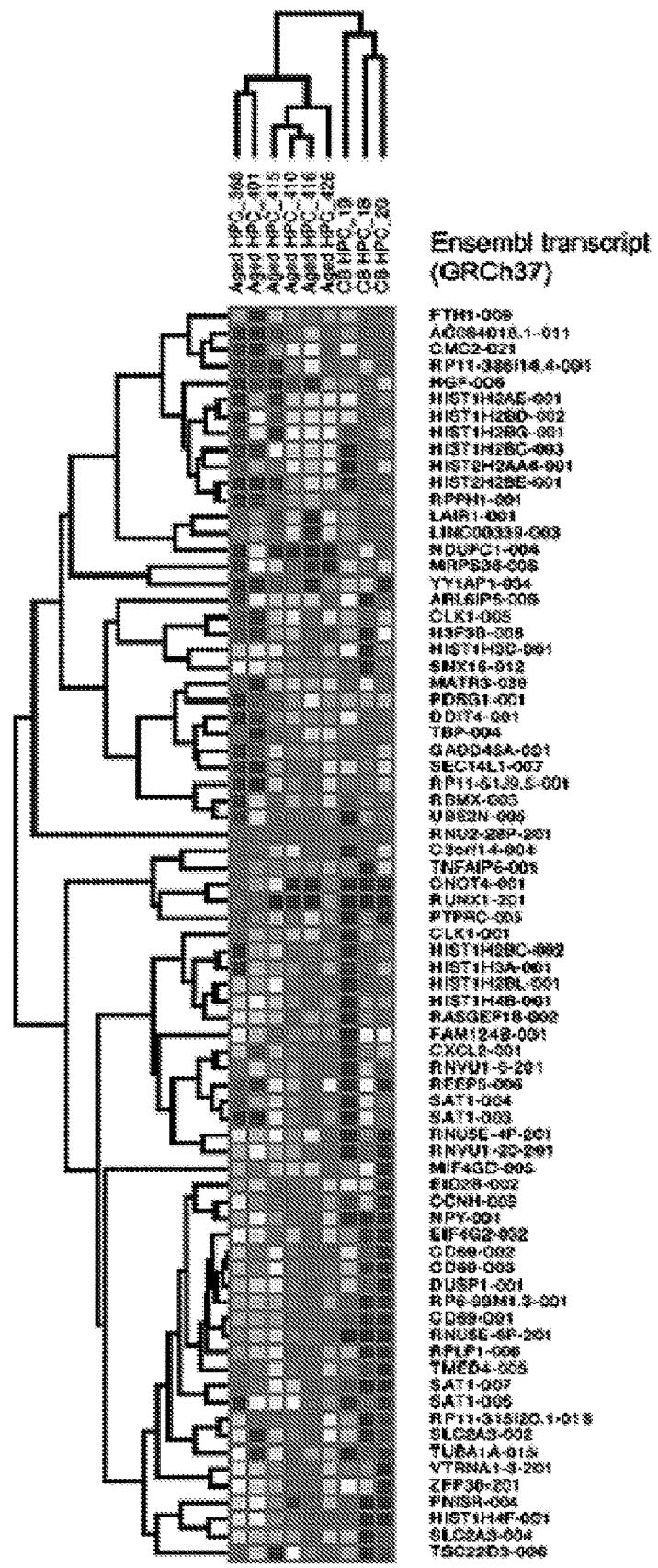
Figure 18G:
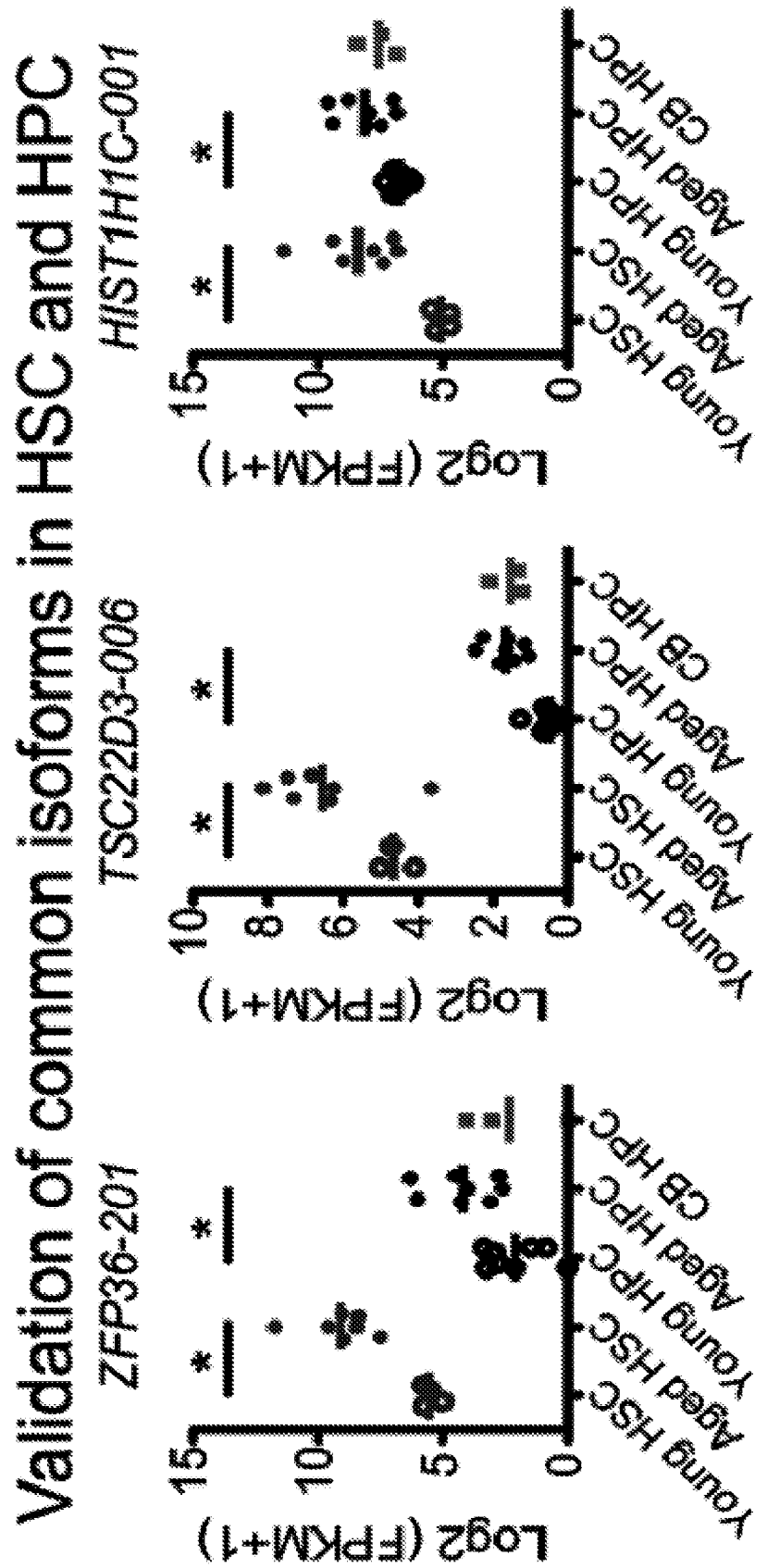
Figure 19B:
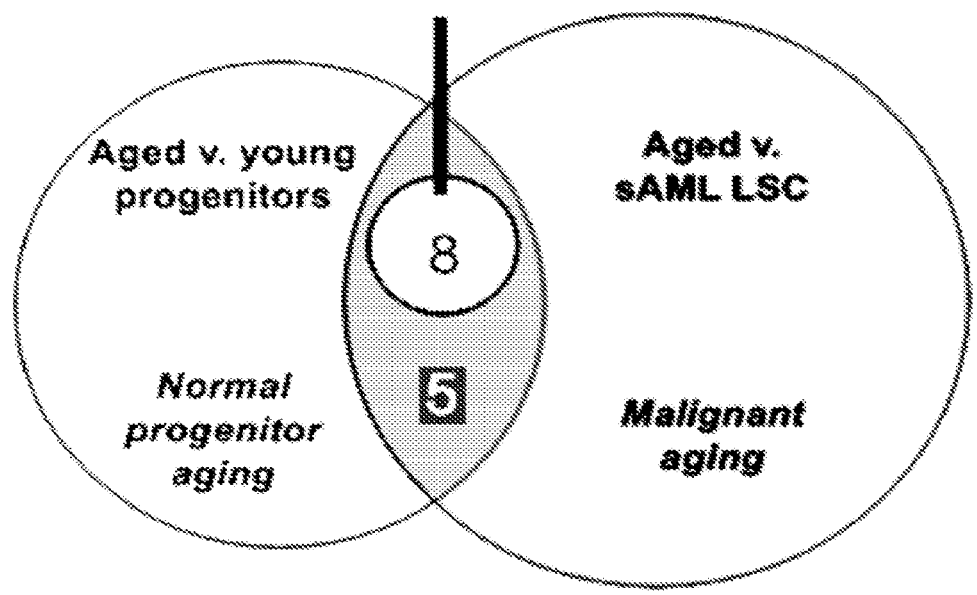

Next, we evaluated splice isoform profiles of aged versus young human HSC and HPC. Utilizing an isoform-specific alignment algorithm that incorporates all known transcript sequences from Ensembl (GRCh37) (Barrett et al., 2015; Jiang et al., 2013) and a false discovery rate (FDR) of <5% (FIGS. 11D, 11E, 1D), we identified splice isoform signatures of human HSC and HPC aging (FIGS. 11C-11E) that were distinct from normal young and cord blood (CB) progenitors (FIGS. 11E, 18F). Commonly upregulated transcripts during HSC and HPC aging included isoforms of transcription factors and histone regulatory gene products (FIG. 11F), indicative of a prominent epigenetic contribution to HSPC aging. These transcripts were abundant in both aged HSC and HPC, as confirmed in validation cohorts of additional young and aged HSC and HPC (FIG. 18G).

Figure 11G:
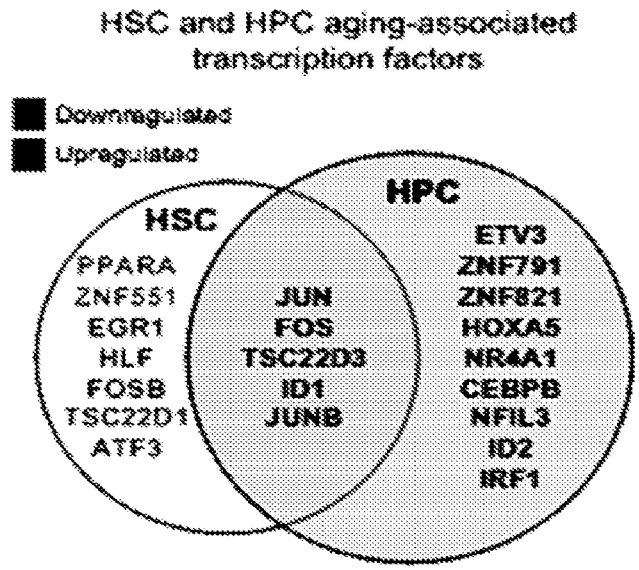

To investigate the mechanisms governing cell fate commitment during human HSC and HPC aging, we utilized a human transcription factor database (Supplemental Experimental Procedures) to analyze RNA-seq data. Significantly upregulated transcription factors distinguished both aged HSC and aged HPC from their younger counterparts (FIG. 11G; FIGS. 18D, 18E, 19A). Consistent with a role for inflammation in human aging and myeloid lineage skewing of hematopoiesis, we found increased expression of inflammation-responsive (NFIL3, IRF1) and myeloid lineage-directing (ETV3, CEBPB) transcription factors in the HPC compartment.

Figure 11H:
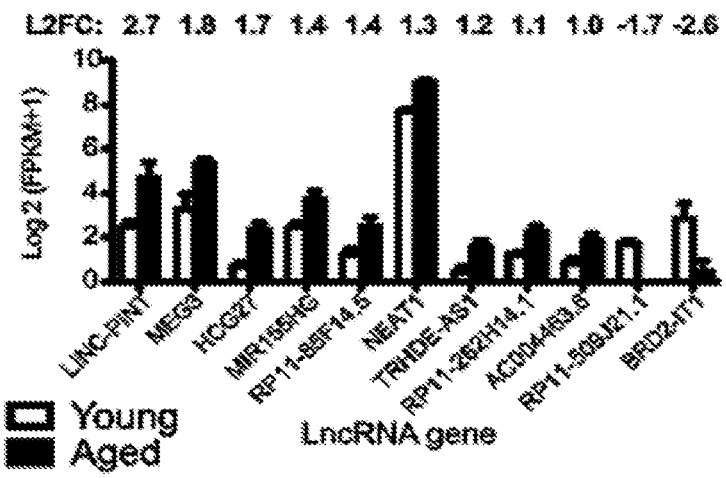
Figure 11H:
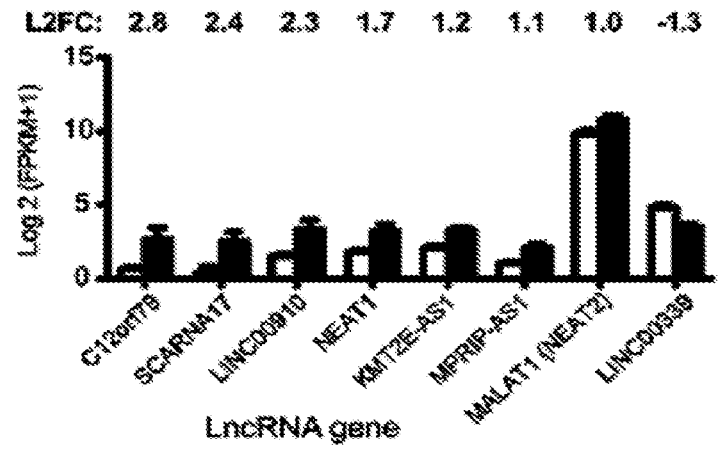

Long non-coding RNAs (lncRNAs) have emerged as key determinants of mouse HSC cell fate commitment (Luo et al., 2015) and alternative splicing. LncRNA profiling revealed upregulation of the nuclear transcriptional regulator NEAT1 in HSC and HPC, along with HPC-specific upregulation of MALAT1 (also known as NEAT2, FIG. 11H), which influences alternative splicing through regulation of serine/arginine (SR) splicing factors (Tripathi et al., 2010). Together, these whole gene and splice isoform expression signatures of human HSC and HPC aging identify pathways that are deregulated during stem cell aging.

TABLE 3

Gene set enrichment analyses (GSEA) showing top differentially regulated pathways in sAML LSC and aging human HSC and HPC (FDR<10%).

| COMPARED GROUPS | NAME | SIZE | NES | NOM p-val | FDR q-val |
|---|---|---|---|---|---|
| sAML LSC versus Aged HPC | SAML_VS_AGED_SPLICE_ISOFORM_SIGNATURE_GENES_SAML_UP | 36 | 2.71 | 0.00 | 0.00 |
| sAML LSC versus Aged HPC | SAML_VS_AGED_SPLICE_ISOFORM_SIGNATURE_GENES_AGED_UP | 34 | −3.01 | 0.00 | 0.00 |
| sAML LSC versus Aged HPC | AGED_VS_YOUNG_SPLICE_ISOFORM_SIGNATURE_GENES_AGED_UP | 55 | −2.59 | 0.00 | 0.00 |
| sAML LSC versus Aged HPC | KEGG_SPLICEOSOME | 125 | −2.15 | 0.00 | 0.00 |
| sAML LSC versus Aged HPC | KEGG_PROTEIN_EXPORT | 24 | −2.09 | 0.00 | 0.00 |
| sAML LSC versus Aged HPC | KEGG_CELL_CYCLE | 124 | −1.97 | 0.00 | 0.00 |
| sAML LSC versus Aged HPC | KEGG_GLYCOSPHINGOLIPID_BIOSYNTHESIS_GANGLIO_SERIES | 15 | 1.99 | 0.00 | 0.00 |
| sAML LSC versus Aged HPC | KEGG_DNA_REPLICATION | 36 | −1.87 | 0.00 | 0.01 |
| sAML LSC versus Aged HPC | KEGG_RIBOSOME | 88 | −1.85 | 0.00 | 0.01 |
| sAML LSC versus Aged HPC | KEGG_PROTEASOME | 46 | −1.83 | 0.00 | 0.01 |
| sAML LSC versus Aged HPC | KEGG_NATURAL_KILLER_CELL_MEDIATED_CYTOTOXICITY | 127 | 1.86 | 0.00 | 0.01 |
| sAML LSC versus Aged HPC | KEGG_FC_GAMMA_R_MEDIATED_PHAGOCYTOSIS | 96 | 1.83 | 0.00 | 0.01 |
| sAML LSC versus Aged HPC | KEGG_PHOSPHATIDYLINOSITOL_SIGNALING_SYSTEM | 76 | 1.81 | 0.00 | 0.01 |
| sAML LSC versus Aged HPC | KEGG_APOPTOSIS | 86 | 1.76 | 0.00 | 0.02 |
| sAML LSC versus Aged HPC | KEGG_LEUKOCYTE_TRANSENDOTHELIAL_MIGRATION | 115 | 1.72 | 0.00 | 0.03 |
| sAML LSC versus Aged HPC | KEGG_LYSOSOME | 119 | 1.69 | 0.00 | 0.04 |
| sAML LSC versus Aged HPC | KEGG_OXIDATIVE_PHOSPHORYLATION | 116 | −1.66 | 0.00 | 0.04 |
| sAML LSC versus Aged HPC | KEGG_CHEMOKINE_SIGNALING_PATHWAY | 189 | 1.68 | 0.00 | 0.04 |
| sAML LSC versus Aged HPC | KEGG_VEGF_SIGNALING_PATHWAY | 75 | 1.69 | 0.00 | 0.04 |
| sAML LSC versus Aged HPC | KEGG_RNA_DEGRADATION | 59 | −1.66 | 0.00 | 0.04 |
| sAML LSC versus Aged HPC | KEGG_PARKINSONS_DISEASE | 113 | −1.64 | 0.00 | 0.04 |
| sAML LSC versus Aged HPC | KEGG_GLYCEROPHOSPHOLIPID_METABOLISM | 76 | 1.65 | 0.00 | 0.05 |
| sAML LSC versus Aged HPC | KEGG_GLYCOSAMINOGLYCAN_DEGRADATION | 21 | 1.63 | 0.01 | 0.06 |
| sAML LSC versus Aged HPC | KEGG_RIG_I_LIKE_RECEPTOR_SIGNALING_PATHWAY | 66 | 1.62 | 0.00 | 0.06 |
| sAML LSC versus Aged HPC | KEGG_VIRAL_MYOCARDITIS | 68 | 1.61 | 0.00 | 0.06 |
| sAML LSC versus Aged HPC | KEGG_GLYCEROLIPID_METABOLISM | 49 | 1.62 | 0.00 | 0.06 |
| sAML LSC versus Aged HPC | KEGG_MISMATCH_REPAIR | 23 | −1.58 | 0.02 | 0.06 |
| sAML LSC versus Aged HPC | KEGG_GNRH_SIGNALING_PATHWAY | 101 | 1.55 | 0.00 | 0.07 |
| sAML LSC versus Aged HPC | KEGG_FOCAL_ADHESION | 199 | 1.59 | 0.00 | 0.07 |
| sAML LSC versus Aged HPC | KEGG_ONE_CARBON_POOL_BY_FOLATE | 17 | −1.55 | 0.02 | 0.07 |
| sAML LSC versus Aged HPC | KEGG_LEISHMANIA_INFECTION | 70 | 1.56 | 0.00 | 0.07 |
| sAML LSC versus Aged HPC | KEGG_PROGESTERONE_MEDIATED_OOCYTE_MATURATION | 85 | 1.54 | 0.01 | 0.07 |
| sAML LSC versus Aged HPC | KEGG_REGULATION_OF_ACTIN_CYTOSKELETON | 211 | 1.56 | 0.00 | 0.07 |
| sAML LSC versus Aged HPC | KEGG_FC_EPSILON_RI_SIGNALING_PATHWAY | 79 | 1.56 | 0.00 | 0.07 |
| sAML LSC versus Aged HPC | KEGG_ENDOCYTOSIS | 179 | 1.54 | 0.00 | 0.07 |

TABLE 3-continued

Gene set enrichment analyses (GSEA) showing top differentially regulated pathways in sAML LSC and aging human HSC and HPC (FDR<10%).

| COMPARED GROUPS | NAME | SIZE | NES | NOM p-val | FDR q-val |
|---|---|---|---|---|---|
| sAML LSC versus Aged HPC | KEGG_CELL_ADHESION_MOLECULES_CAMS | 130 | 1.56 | 0.00 | 0.07 |
| sAML LSC versus Aged HPC | KEGG_TOLL_LIKE_RECEPTOR_SIGNALING_PATHWAY | 97 | 1.57 | 0.00 | 0.08 |
| sAML LSC versus Aged HPC | KEGG_ALLOGRAFT_REJECTION | 35 | 1.52 | 0.02 | 0.08 |
| sAML LSC versus Aged HPC | KEGG_ERBB_SIGNALING_PATHWAY | 87 | 1.51 | 0.00 | 0.08 |
| Aged versus Young HSC | KEGG_OXIDATIVE_PHOSPHORYLATION | 106 | −2.18 | 0.00 | 0.00 |
| Aged versus Young HSC | KEGG_HUNTINGTONS_DISEASE | 161 | −2.08 | 0.00 | 0.00 |
| Aged versus Young HSC | KEGG_RIBOSOME | 86 | −1.96 | 0.00 | 0.01 |
| Aged versus Young HSC | KEGG_DNA_REPLICATION | 36 | −1.94 | 0.00 | 0.01 |
| Aged versus Young HSC | KEGG_PROTEASOME | 43 | −1.90 | 0.00 | 0.01 |
| Aged versus Young HSC | KEGG_PARKINSONS_DISEASE | 102 | −1.87 | 0.00 | 0.01 |
| Aged versus Young HSC | KEGG_RNA_POLYMERASE | 29 | −1.72 | 0.00 | 0.04 |
| Aged versus Young HSC | KEGG_N_GLYCAN_BIOSYNTHESIS | 46 | −1.70 | 0.00 | 0.05 |
| Aged versus Young HSC | KEGG_ALZHEIMERS_DISEASE | 144 | −1.73 | 0.00 | 0.05 |
| Aged versus Young HSC | KEGG_PYRIMIDINE_METABOLISM | 91 | −1.70 | 0.00 | 0.05 |
| Aged versus Young HSC | KEGG_VALINE_LEUCINE_AND_ISOLEUCINE_DEGRADATION | 43 | −1.66 | 0.00 | 0.06 |
| Aged versus Young HSC | KEGG_PRIMARY_IMMUNODEFICIENCY | 32 | −1.64 | 0.01 | 0.07 |
| Aged versus Young HSC | KEGG_BASE_EXCISION_REPAIR | 34 | −1.61 | 0.01 | 0.08 |
| Aged versus Young HSC | KEGG_PURINE_METABOLISM | 140 | −1.60 | 0.00 | 0.09 |
| Aged versus Young HPC | KEGG_SYSTEMIC_LUPUS_ERYTHEMATOSUS | 132 | 2.98 | 0.00 | 0.00 |
| Aged versus Young HPC | KEGG_MISMATCH_REPAIR | 23 | −2.14 | 0.00 | 0.00 |
| Aged versus Young HPC | KEGG_HOMOLOGOUS_RECOMBINATION | 28 | −2.10 | 0.00 | 0.00 |
| Aged versus Young HPC | KEGG_GLYCOSAMINOGLYCAN_BIOSYNTHESIS_HEPARAN_SULFATE | 26 | −2.01 | 0.00 | 0.00 |
| Aged versus Young HPC | KEGG_AMINOACYL_TRNA_BIOSYNTHESIS | 41 | −1.87 | 0.00 | 0.01 |
| Aged versus Young HPC | KEGG_GLYCOSAMINOGLYCAN_BIOSYNTHESIS_CHONDROITIN_SULFATE | 22 | −1.83 | 0.00 | 0.01 |
| Aged versus Young HPC | KEGG_DNA_REPLICATION | 36 | −1.80 | 0.00 | 0.02 |
| Aged versus Young HPC | KEGG_RNA_POLYMERASE | 29 | −1.75 | 0.01 | 0.03 |
| Aged versus Young HPC | KEGG_ADIPOCYTOKINE_SIGNALING_PATHWAY | 67 | 1.86 | 0.00 | 0.03 |
| Aged versus Young HPC | KEGG_VALINE_LEUCINE_AND_ISOLEUCINE_BIOSYNTHESIS | 11 | −1.66 | 0.01 | 0.05 |
| Aged versus Young HPC | KEGG_NON_HOMOLOGOUS_END_JOINING | 13 | −1.67 | 0.02 | 0.05 |
| Aged versus Young HPC | KEGG_SELENOAMINO_ACID_METABOLISM | 26 | −1.63 | 0.02 | 0.06 |
| Aged versus Young HPC | KEGG_VALINE_LEUCINE_AND_ISOLEUCINE_DEGRADATION | 44 | −1.61 | 0.01 | 0.06 |
| Aged versus Young HPC | KEGG_AMINO_SUGAR_AND_NUCLEOTIDE_SUGAR_METABOLISM | 44 | −1.60 | 0.01 | 0.07 |
| Aged versus Young HPC | KEGG_ACUTE_MYELOID_LEUKEMIA | 57 | 1.74 | 0.00 | 0.07 |
| Aged versus Young HPC | KEGG_PYRIMIDINE_METABOLISM | 96 | −1.57 | 0.00 | 0.08 |

Splicing Deregulation Distinguishes sAML, MDS and Normal Aging Progenitors.

Figure 12A:
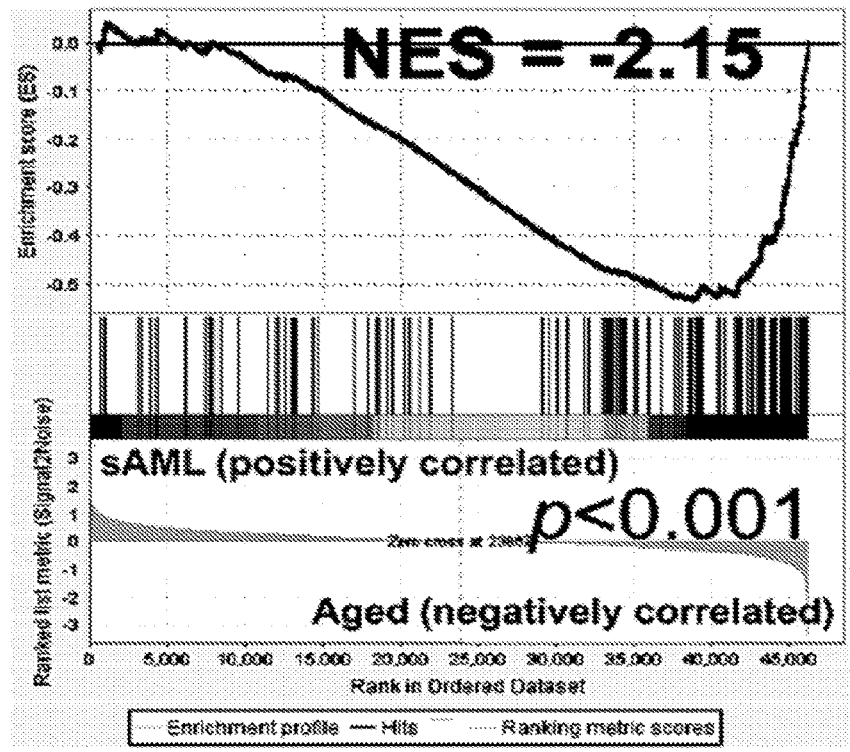

To determine if sAML evolves as a result of splicing deregulation in aged and MDS progenitors, we performed whole transcriptome analyses of FACS-purified progenitors (CD34$^+$CD38$^+$Lin$^-$) isolated from sAML samples along with de novo AML and MDS samples (Table 1). Comparative RNA-Seq and GSEA of purified sAML progenitors revealed that the spliceosome was the top disrupted KEGG gene set compared with age-matched progenitors (FIG. 12A; Table 3). Additionally, in sAML there was enrichment of genes involved in hematopoiesis, cell adhesion, and signal transduction (FIGS. 18D, 18E, 19A-19B; Table 3). Similar to our previous findings of inflammatory mediator upregulation in CML LSC (Jiang et al., 2013), GSEA (FDR<25%) of sAML LSC showed upregulation of pro-inflammatory signaling and anti-viral response pathways (FIG. 19B; Table 3). Together, these results suggest that deregulation of pro-inflammatory cytokine signal transduction mechanisms represents a common feature of HSPC aging and LSC generation.

Figure 1B:
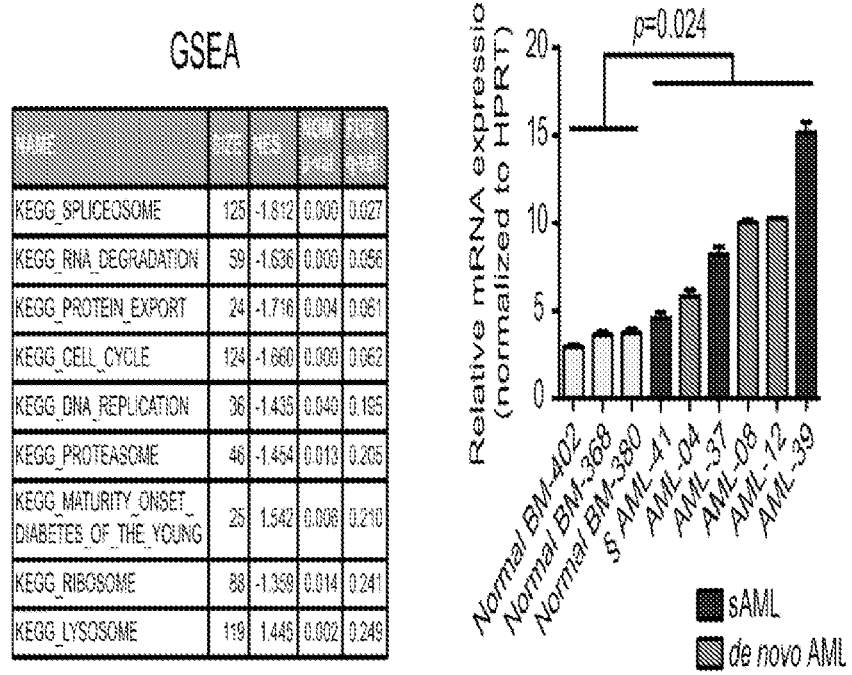
Figure 5B:
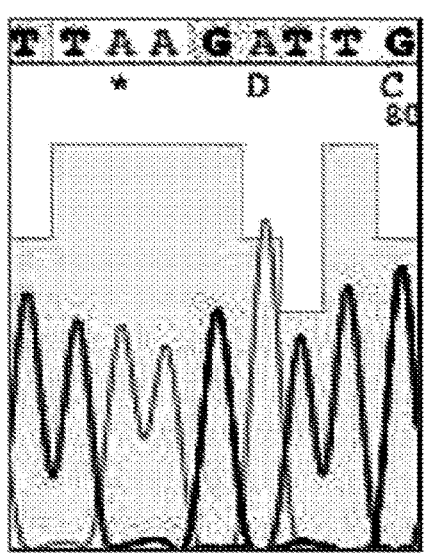
Figure 5B:
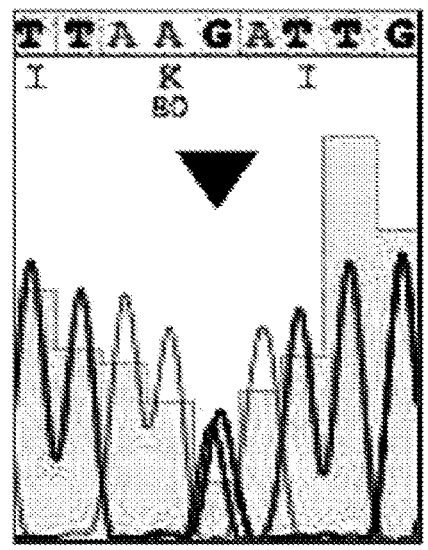
Figure 5C:
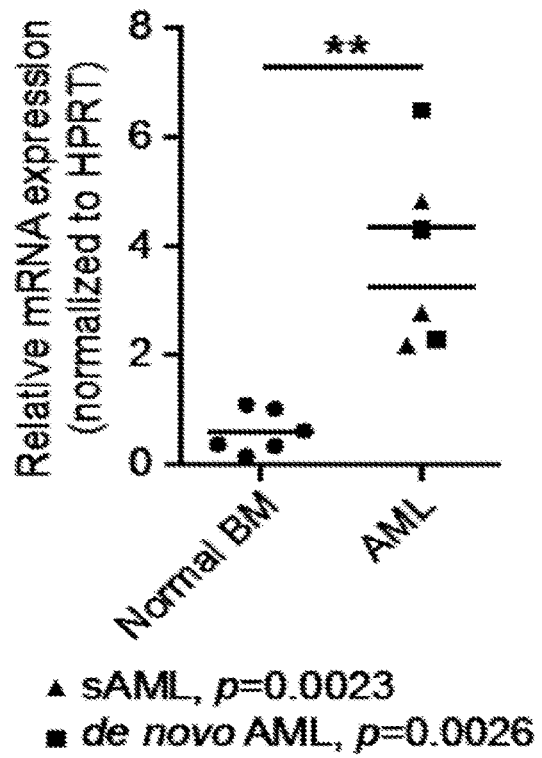
Figure 12B:
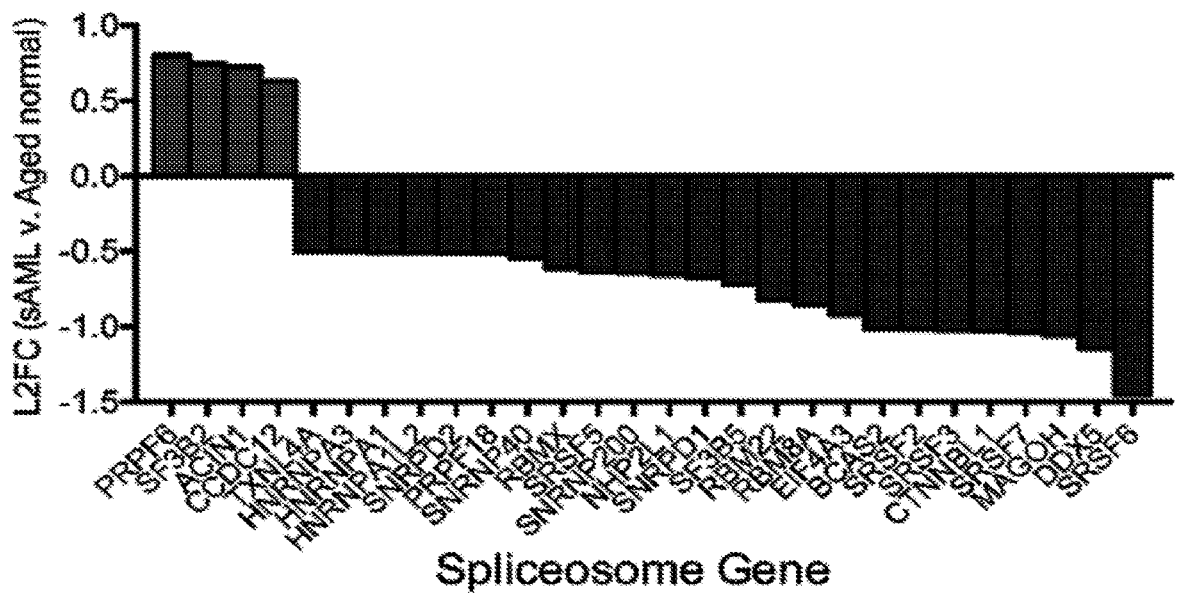
Figure 13A:
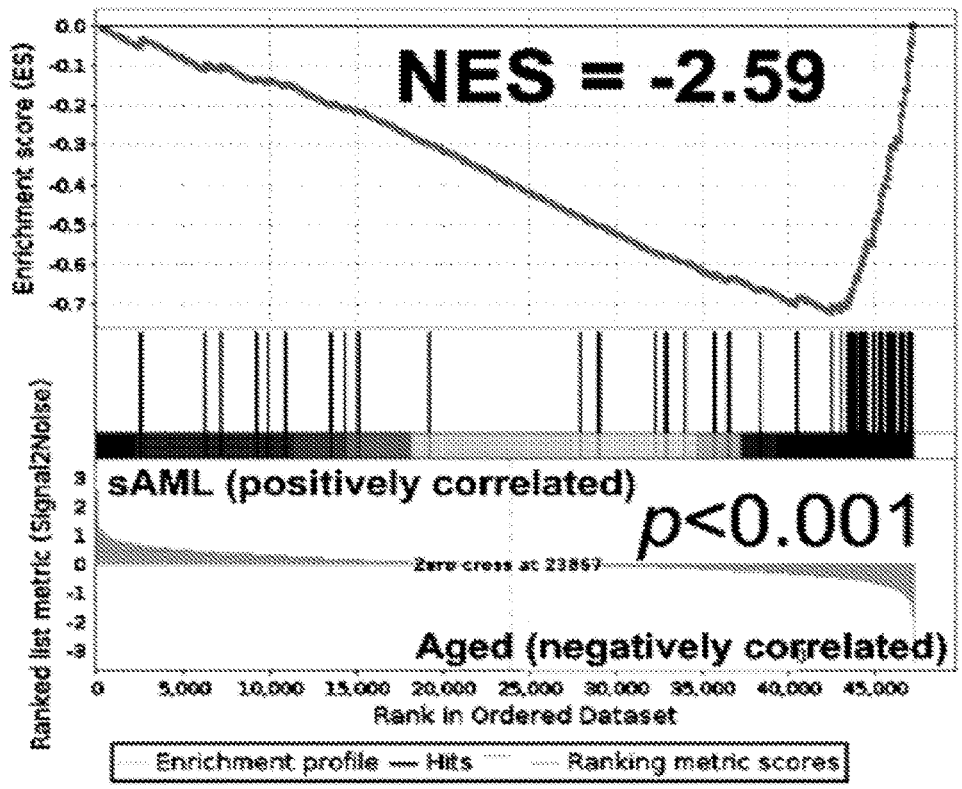
FIGS. 13A-13F. Splice Isoform Switching Distinguishes Malignant from Normal Progenitor Aging. Gene and isoform expression data in FPKM were obtained from sAML LSC, MDS progenitors, and normal aged and young HPC RNA-Seq datasets using Cufflinks. GSEA was performed using all KEGG pathways plus custom gene sets including genes associated with the top differentially expressed transcript signatures in aged versus young HPC, and sAML versus aged HPC. Specifically, the sets of genes associated with isoforms that were enriched (AGED_VS_YOUNG_SPLICE_ISOFORM_SIGNATURE_GENES_AGED_UP) or depleted (AGED_VS_YOUNG_SPLICE_ISOFORM_SIGNATURE_GENES_YOUNG_UP) in HPC aging were used to query the sAML versus aged normal progenitor datasets for GSEA. Similarly, the sAML signature was used to generate a custom gene set representing genes associated with isoforms enriched (SAML_VS_AGED_SPLICE_ISOFORM_SIGNATURE_GENES_SAML_UP) or depleted (SAML_VS_AGED_SPLICE_ISOFORM_SIGNATURE_GENES_AGED_UP) in sAML.

While mutations in splicing factor genes have been associated with transformation to sAML, the role of non-mutation driven splicing alterations has been less extensively studied. Thus, we further examined spliceosome components in sAML LSC. Single nucleotide resolution analysis of our RNA-Seq datasets for known mutations in MDS/sAML associated loci in splicing regulatory genes (Lindsley et al., 2015; Yoshida et al., 2011) revealed only one sAML sample harboring a heterozygous mutation in the U2 splicing factor SF3B1, as validated by PCR and Sanger sequencing (FIGS. 1B, 5B). Quantitative real-time (qRT)-PCR analysis of a subset of wild-type SF3B1 samples showed increased SF3B1 expression in AML LSC (FIGS. 1B, 5B), suggesting that splicing factor gene expression alterations in MDS/sAML may occur in a mutation-independent manner. Interestingly, GSEA of purified progenitors from MDS samples revealed similar disruption of the spliceosome compared with normal age-matched controls (FIG. 13A). Pathway-specific analyses of RNA-Seq data revealed significant alterations in gene expression of many splicing factors in sAML, including upregulation of PRPF6, SF3B2, and ACIN1, and downregulation of the SRSF family of splicing regulatory gene products (FIG. 12B). Among the upregulated transcripts, SF3B2 is a component of the U2 complex that promotes splicing, and ACIN1 participates in the exon junction complex (EJC) where it regulates production of the pro-survival splice isoform of the BCL2 family member BCL2L1 (BCL-XL) (Michelle et al., 2012), which contributes to LSC generation (Goff et al., 2013). Together, these data suggest that spliceosome disruption is prevalent in sAML and may drive splicing alterations of stem cell regulatory genes contributing to LSC generation.

Figure 12C:
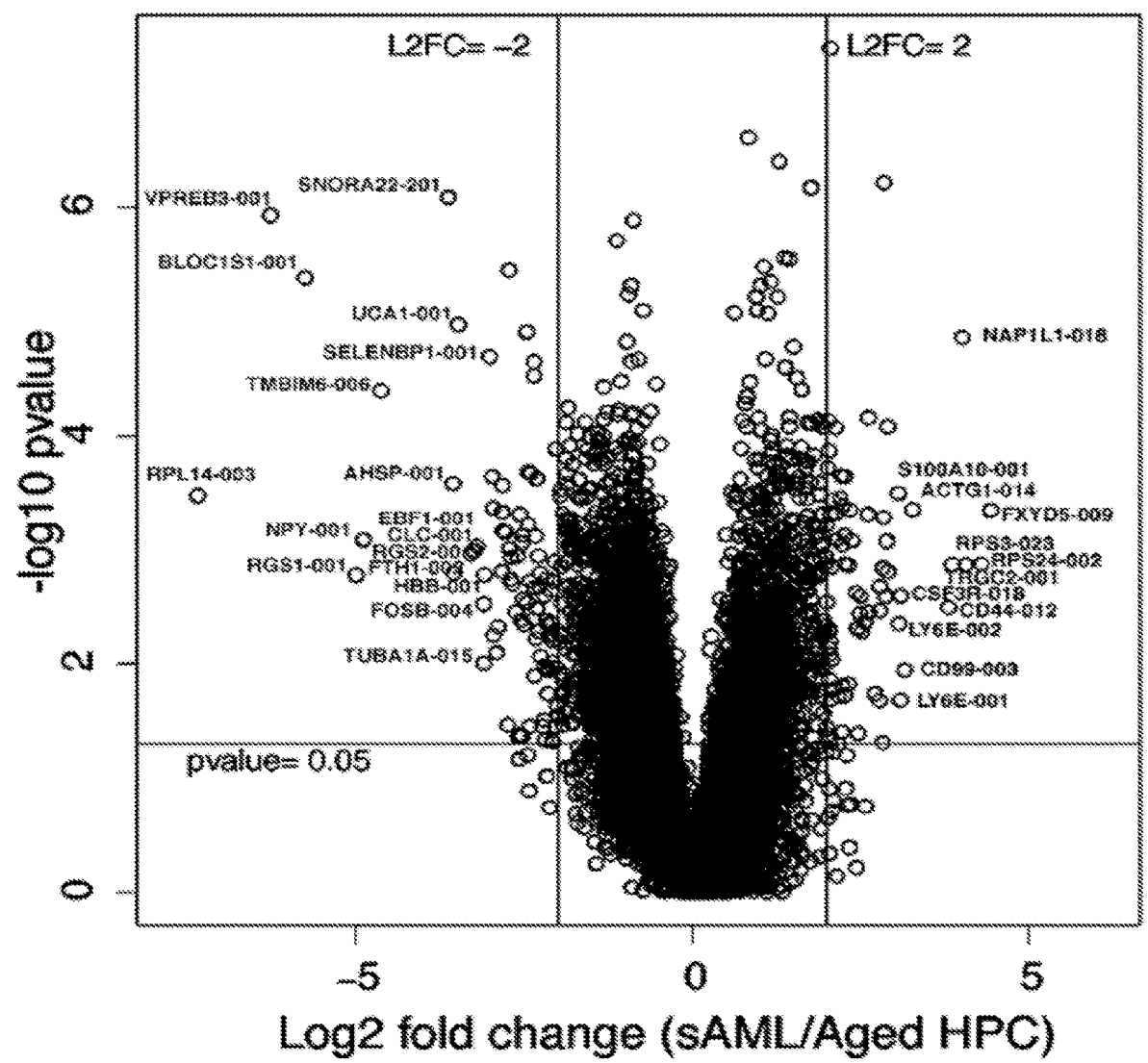
Figure 12E:
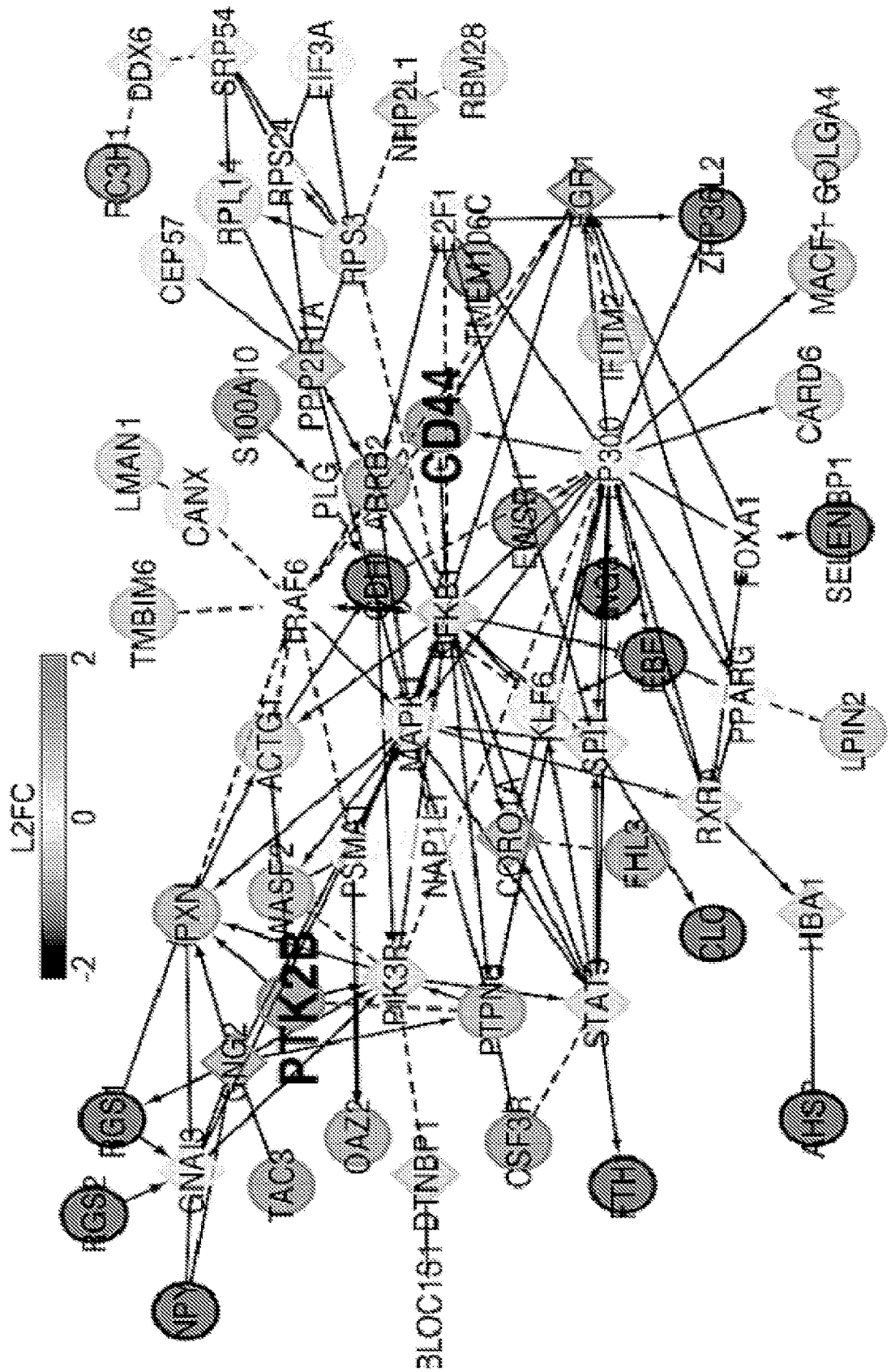
Figure 12F:
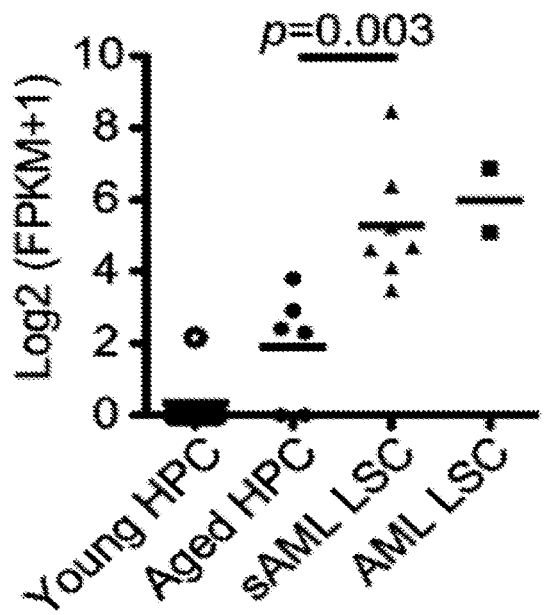
Figure 12G:
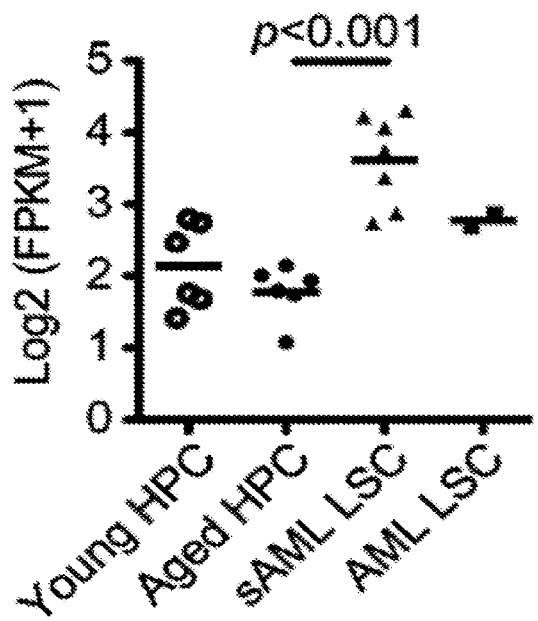
Figure 12H:
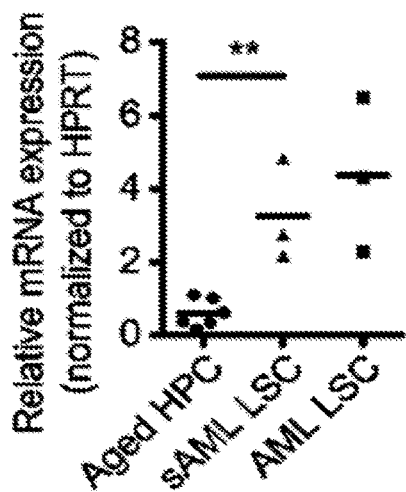

A splice isoform signature of sAML LSC was identified by ranking all significantly differentially expressed transcripts (L2FC>1, FDR<5%) from greatest to least distance from the origin on a volcano plot (FIG. 12C). A complete list of all significantly differentially expressed transcripts is provided in FIGS. 11D, 11E, 12D. The top 75 splice isoform signature of sAML LSC was typified by several alternatively spliced signal transduction (PTPN6, PTK2B) and cell adhesion gene products (e.g. CD44 and ITGB2; FIGS. 11D, 11E, 12C, 12D). Notably, misspliced gene products of the non-receptor protein tyrosine phosphatase PTPN6 (also known as SHP-1) and the focal adhesion kinase (FAK)-related tyrosine kinase PTK2B (PYK2) have been associated with AML (Beghini et al., 2000; Despeaux et al., 2012; Weis et al., 2008) or other hematological malignancies (Salesse et al., 2004). Cytoscape analysis of the gene networks associated with the top differentially expressed splice isoforms revealed inflammatory signaling genes including hubs at PTK2B and the stem cell regulatory factor and adhesion molecule CD44, linked by transcription factors such as STAT3 and NFKB1 (FIGS. 12E-12F). Consistent with the hypothesis that global spliceosome disruption alters pre-mRNA processing in sAML LSC, enriched splice isoforms in sAML included transcripts with retained introns (non protein-coding PTPN6-003) and protein-coding transcripts with exon skipping (PTK2B-202; FIGS. 12G-12H). In a validation cohort of additional young, aged, and cord blood HPC, the sAML LSC splice isoform signature also distinguished between normal and cord blood HPC, and MDS progenitors clustered with sAML LSC when compared with age-matched HPC (FIG. 12D).

Figure 12I:
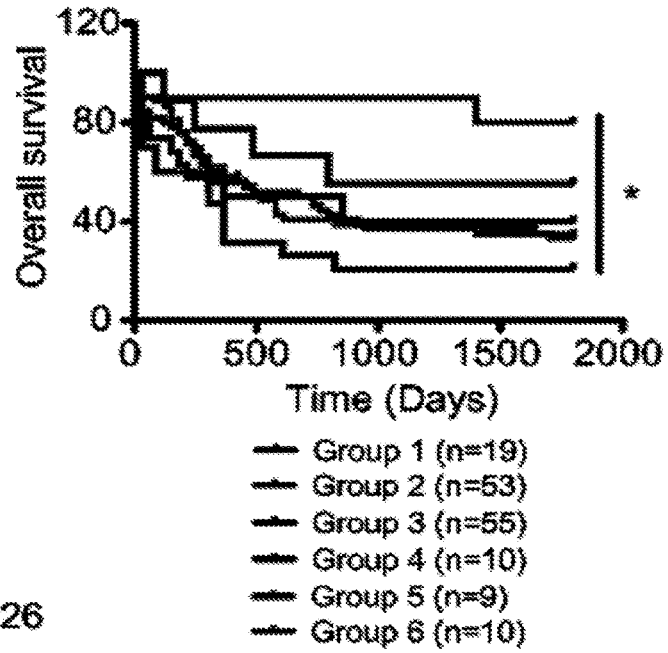

To explore the potential clinical relevance of this splice isoform signature, sAML-associated transcripts were quantified in TCGA isoform datasets from RNA-Seq studies performed on unsorted leukemic cells from 164 AML samples. Unsupervised clustering using the sAML LSC splice isoform expression signature revealed six distinct subgroups. One group, consisting of 19 samples (12%), displayed significantly reduced overall survival compared with a favorable expression profile observed in a separate group of 10 samples (6%), with an overall hazard ratio of 4.26 between these two groups (FIG. 12I). These TCGA RNA-seq data highlight the potential clinical relevance of LSC splice isoform patterns and suggest that they may have utility as prognostic biomarkers.

Figure 12J:
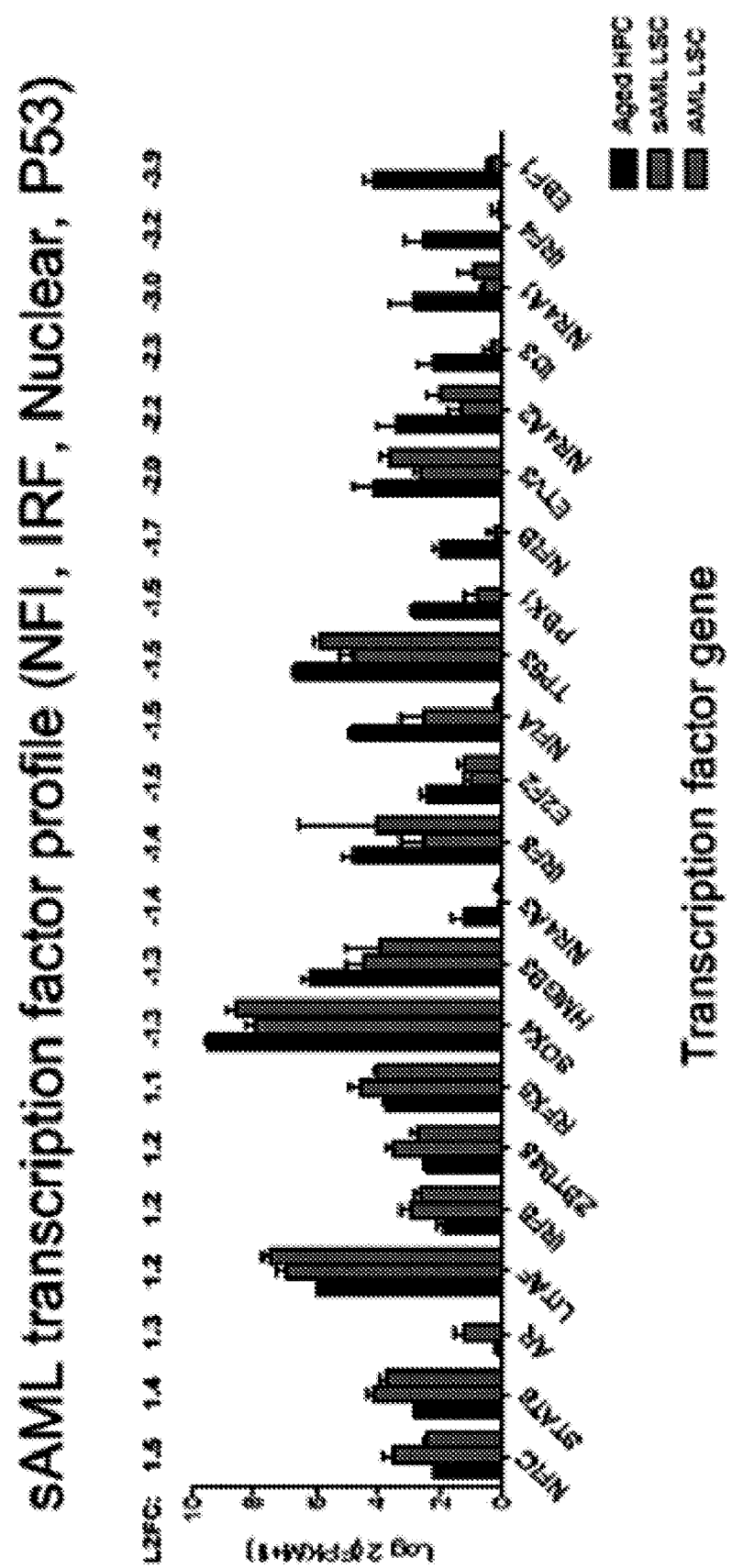
Figure 12K:
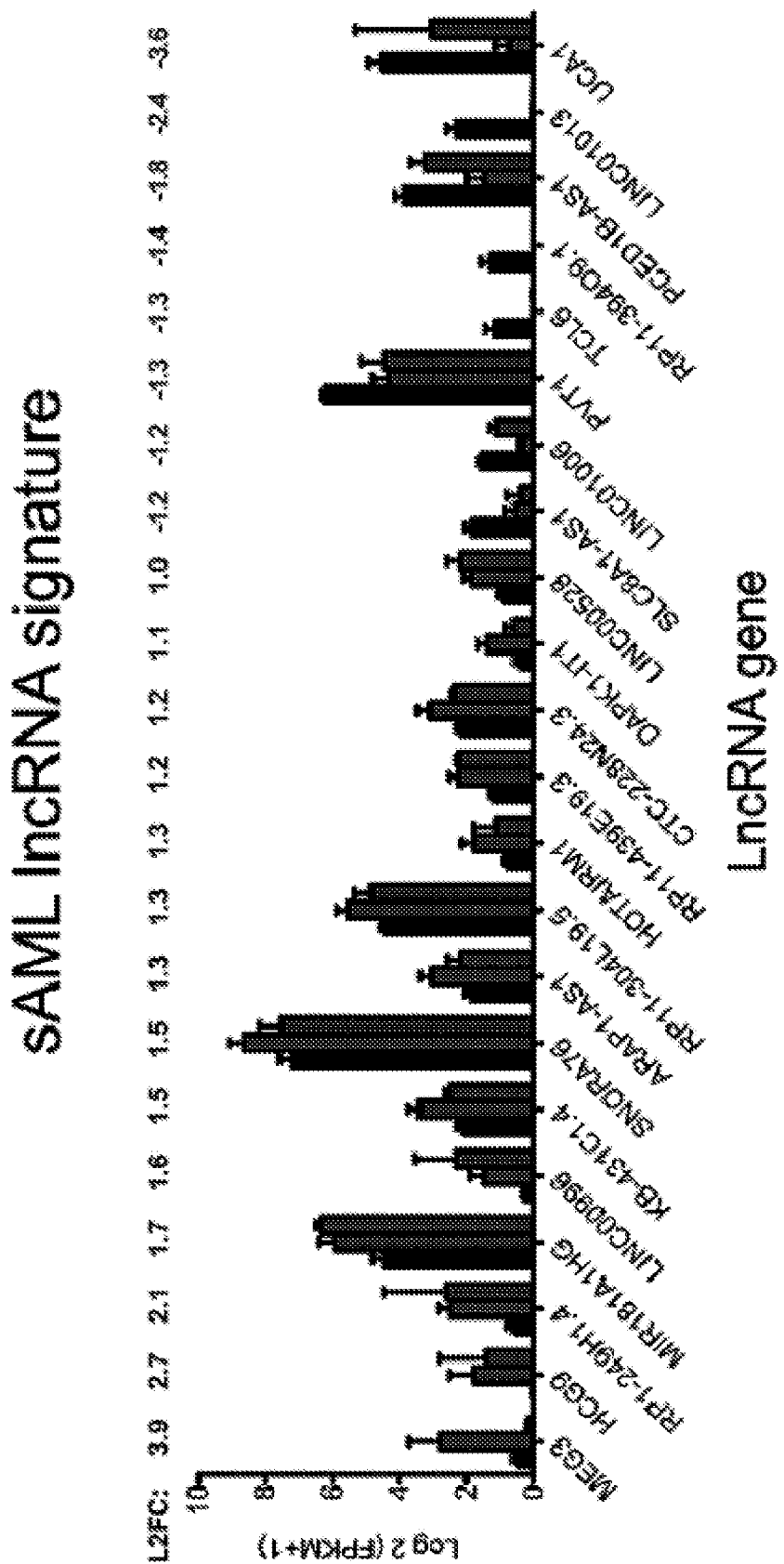

Recently, MYC-driven cancers were reported to exhibit a high degree of splicing due to global upregulation of transcription (Hsu et al., 2015). We hypothesized that a similar mechanism may disrupt spliceosome function and promote transcriptome instability in sAML. Thus, we established a transcription factor signature of sAML LSC compared with normal young and aged progenitors (FIG. 12J). Differential gene expression of inflammation-responsive transcription factors including STAT6, IRF4, IRF5, and IRF8 typified sAML progenitors, along with deregulation of several zinc-finger transcription factors (FIGS. 18D, 18E, 19A). Notably, decreased expression of tumor suppressor genes, such as TP53 and IRF8 (Will et al., 2015), could lead to widespread upregulation of transcription, thus increasing pre-mRNA burden on the spliceosome. Moreover, lncRNA profiling revealed an sAML LSC-specific lncRNA, MEG3 (FIG. 12K), which interacts with p53 and regulates p53 target gene expression.

Pro-Survival Splice Isoform Switching Distinguishes Malignant from Normal Progenitor Aging.

Figure 13B:
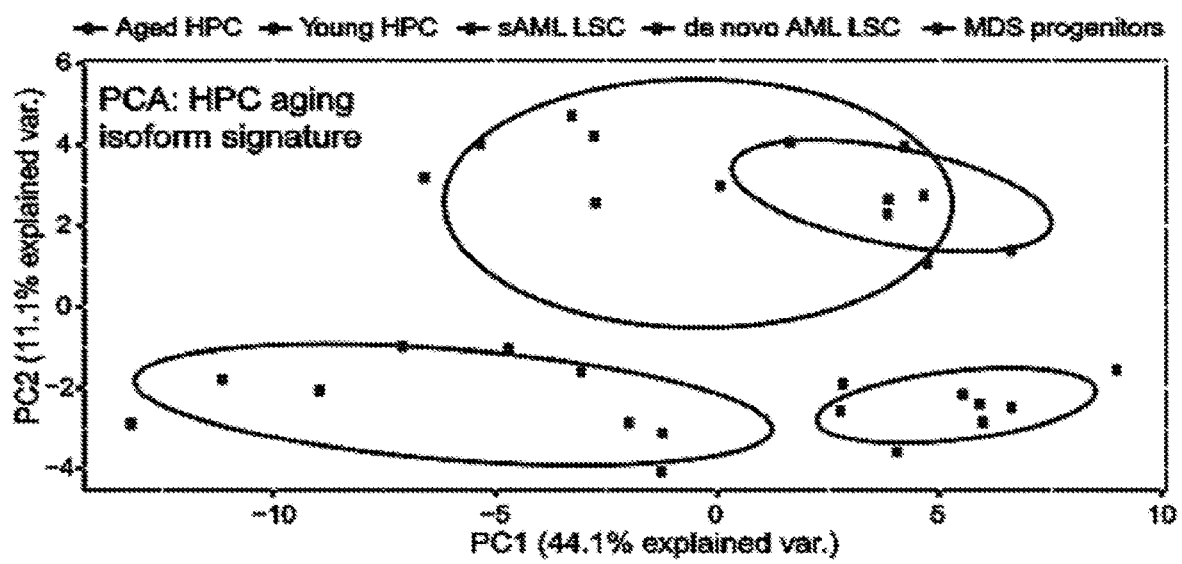
Figure 13C:
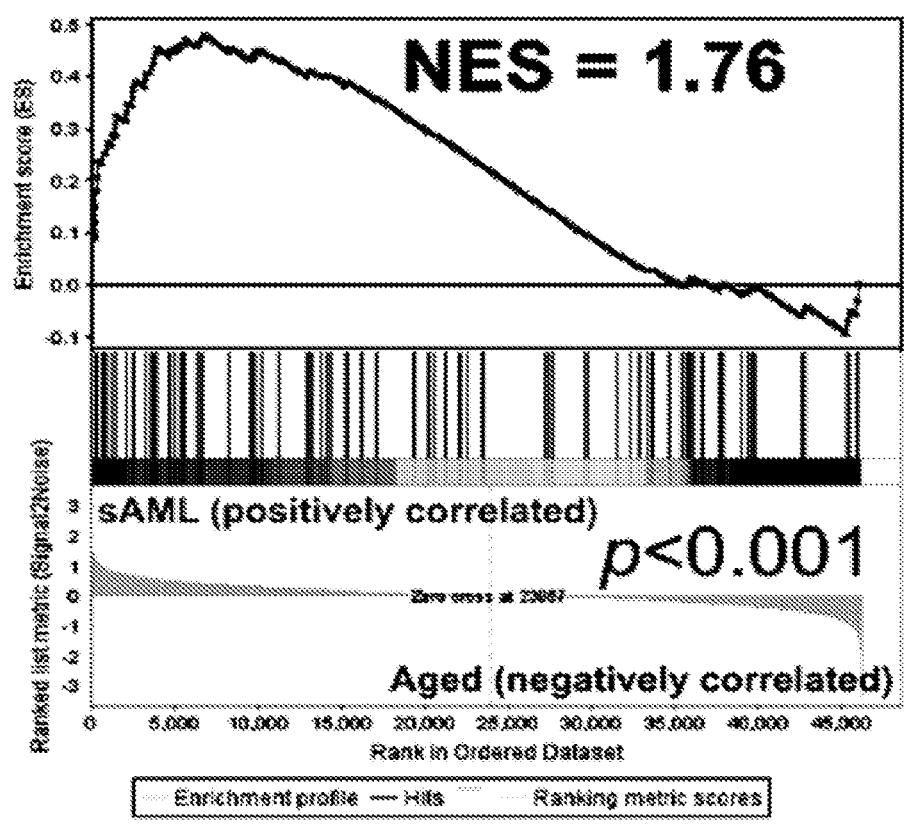

To further explore the relationship between malignant and normal HPC aging, we utilized custom gene sets developed from the splice isoform signatures of HPC aging and sAML. Notably, GSEA revealed a negative enrichment score (NES −2.59) of aged HPC-associated transcripts in sAML progenitors (FIG. 13A). In contrast, select young HPC-associated transcripts, such as LAIR1-001, were among the increased transcripts in sAML progenitors (FIGS. 11D, 11E, 12D). In keeping with our previous findings of a reversion to a more embryonic transcriptome signature in advanced stage leukemias (Goff et al., 2013; Holm et al., 2015), LAIR1-001 was also highly expressed in cord blood progenitors (FIG. 18F). Moreover, a principal components analysis (PCA) demonstrated that expression of HPC aging-associated isoforms distinguished young and aged HPC from sAML and MDS progenitors (FIG. 13B). Additionally, genes associated with sAML-enriched isoforms were highly enriched in MDS progenitors (FIG. 13B). Other enriched genes sets in sAML versus MDS progenitors included several inflammation-associated pathways, along with HPC aging-associated genes (FIG. 13C).

Figure 13D:
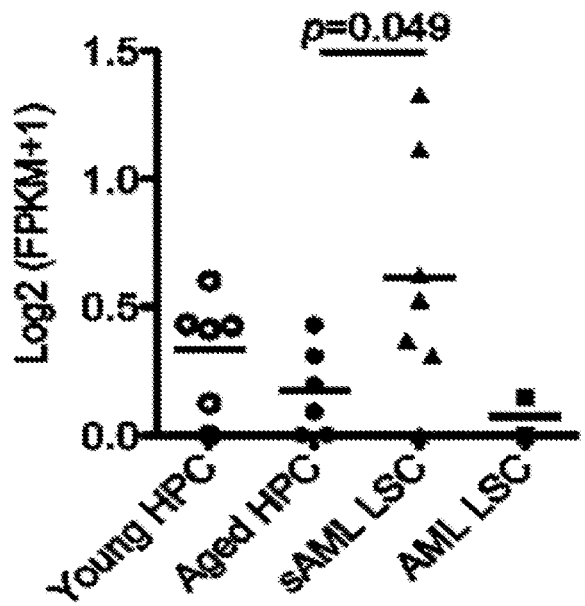
Figure 13E:
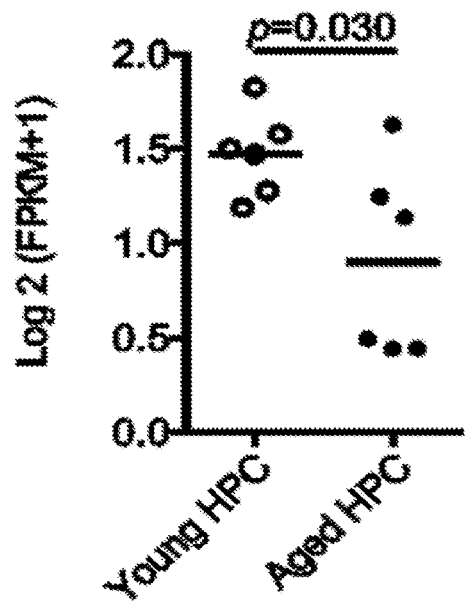
Figure 13F:
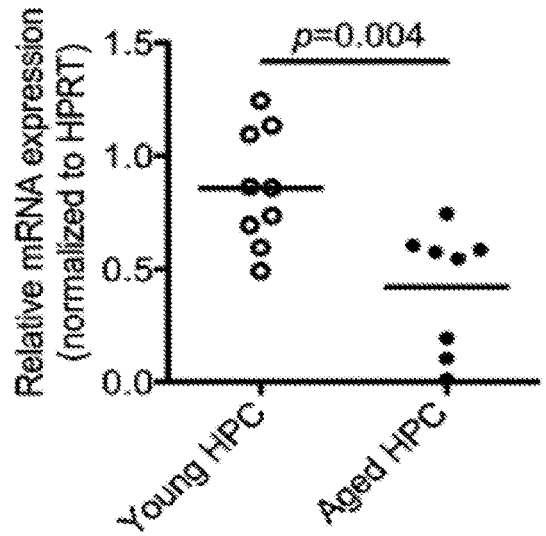

Alternative splicing has been implicated as a crucial mechanism regulating cell survival and LSC generation (Goff et al., 2013; Schwerk and Schulze-Osthoff, 2005). Long isoforms of the Bcl2 family of apoptosis regulatory genes, including BCL2, BCL2L1 (BCLXL), BCL2A1 (BFL1), and MCL1, promote cell survival, while short isoforms are pro-apoptotic (Goff et al., 2013). Notably, GSEA revealed that apoptosis regulators were among the most enriched gene sets in sAML compared with normal age-matched controls (FIG. 13C). In particular, expression of a pro-survival isoform, BCL2L1-001 (BCL-XL), was increased in sAML (FIG. 13D). In contrast, aged HPC had decreased pro-survival BCL2 isoform expression (FDR<10%; FIGS. 13E-13F). Hence, pro-survival splice isoform switching may have clinical utility in predicting malignant HPC aging.

Selective Spliceosome Modulation Reverses sAML Splicing Deregulation In Vitro.

Based on spliceosome deregulation patterns in sAML LSC and a recent report showing that aberrant splicing represents a therapeutic vulnerability in MYC driven solid tumors (Hsu et al., 2015), we hypothesized that pharmacological spliceosome modulation might have potent LSC inhibitory effects. Several natural products with anti-tumor properties, including the macrolide pladienolide B, target the SF3B subunit of the spliceosome (Kotake et al., 2007). Until recently, structural complexity constrained development. The natural product pladienolide B and derivatives, including FD-895 (Villa et al., 2012), demonstrate poor stability in aqueous and biological media. The short half lives ($t_{1/2} \leq 15$ min) of these compounds and toxicity (Hong et al., 2014) arising from hydrolyzed seco-acids highlight the need for development of stabilized and selective spliceosome-targeted compounds. We previously described a series of synthetic analogues of FD-895 that demonstrate enhanced activity and metabolic stability, including a stereoisomer (17S-FD-895) with 25-fold higher activity (Villa et al., 2012). Thus, we evaluated FD-895 and 17S-FD-895 (FIG. 3A) in splicing reporter activity, PCR, and functional hematopoietic progenitor assays.

Figure 14A:
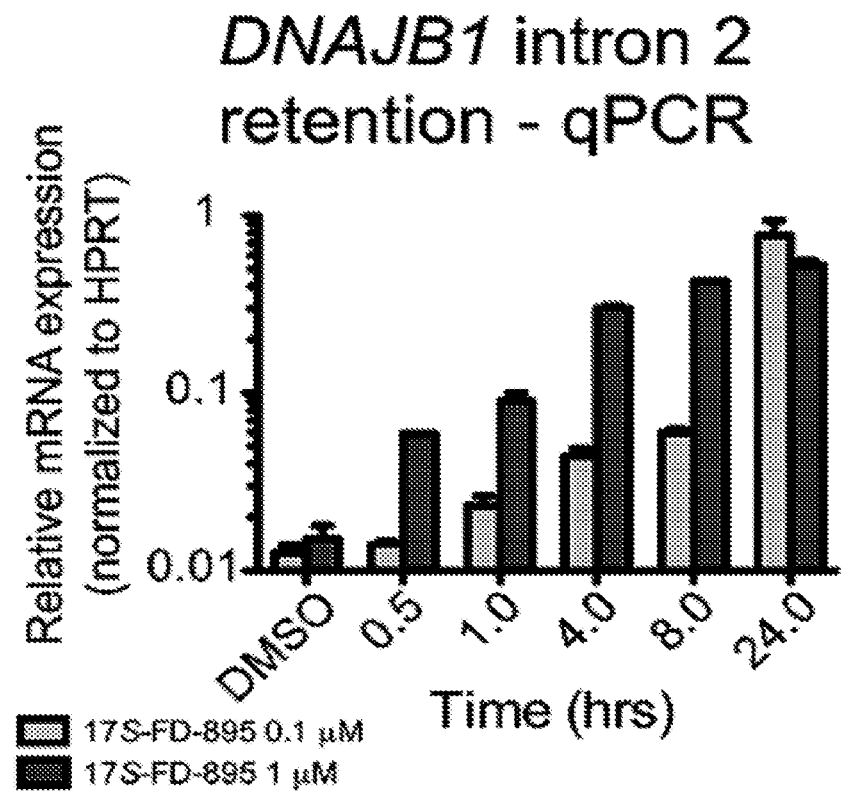
FIGS. 14A-14E. Selective Spliceosome Modulation Reverses sAML Splicing Deregulation In Vitro.
Figure 14B:
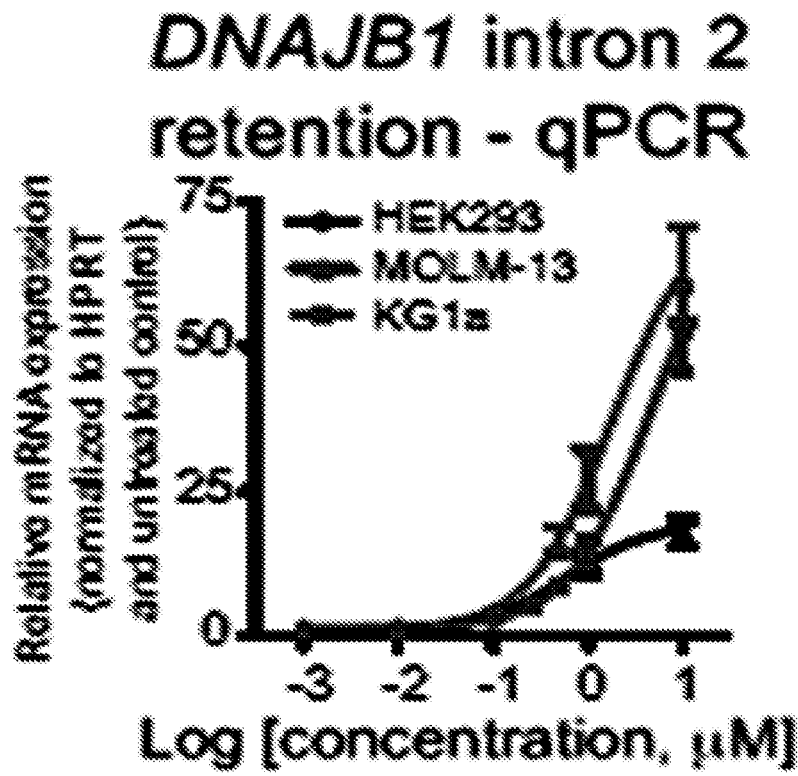
Figure 14C:
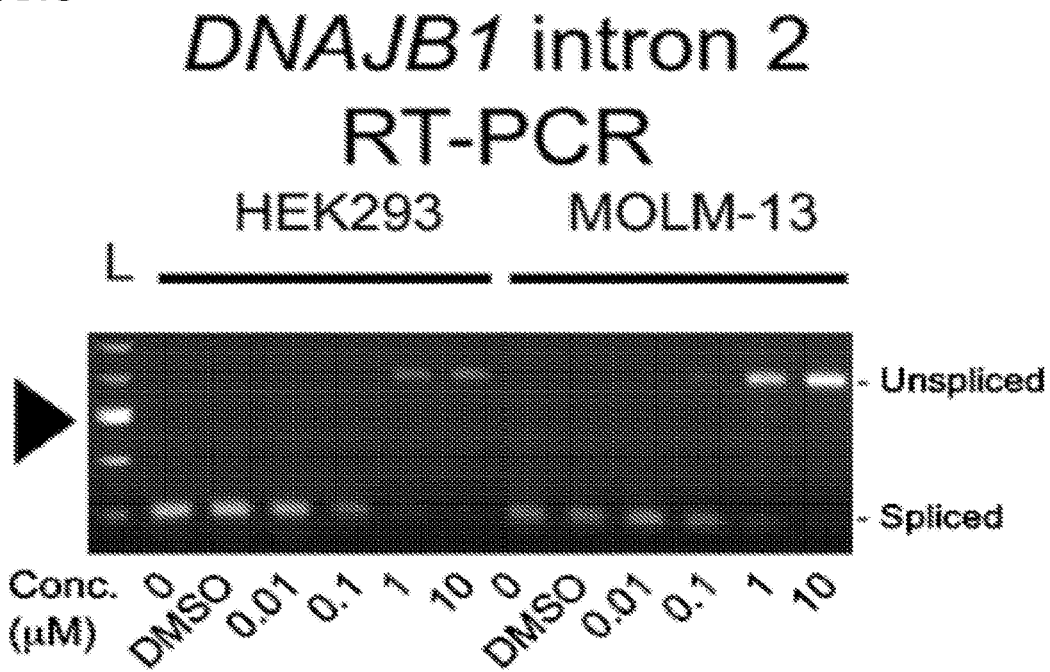
Figure 14D:
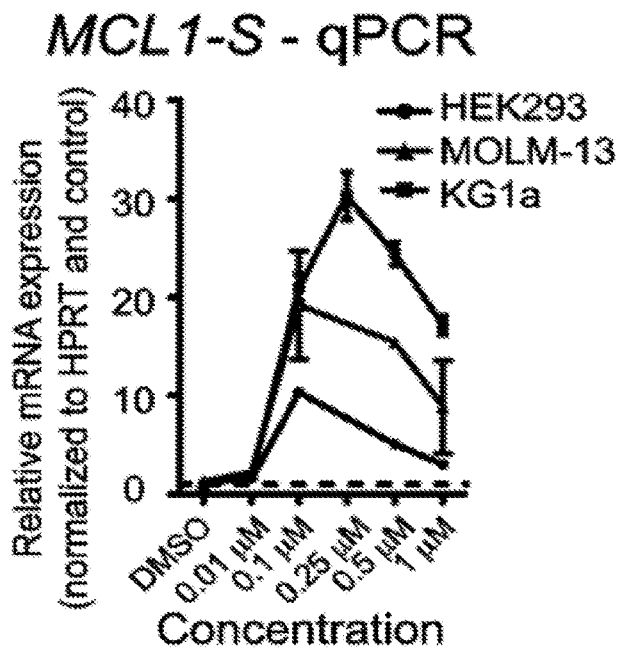
Figure 14E:
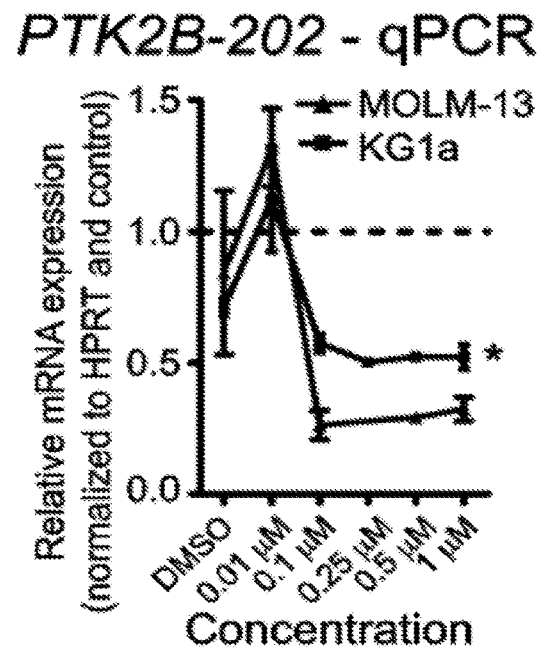
Figure 21A:
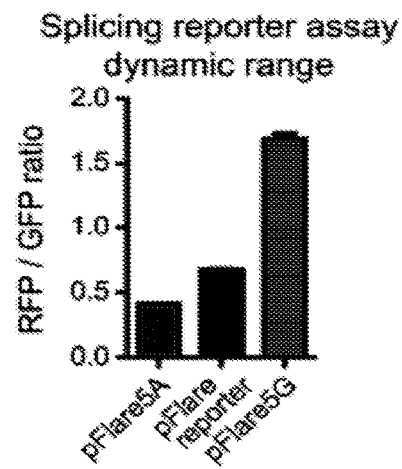
FIGS. 21A-21C. Splicing Reporter Assays in HEK293 Treated with 17S-FD-895.
Figure 21B:
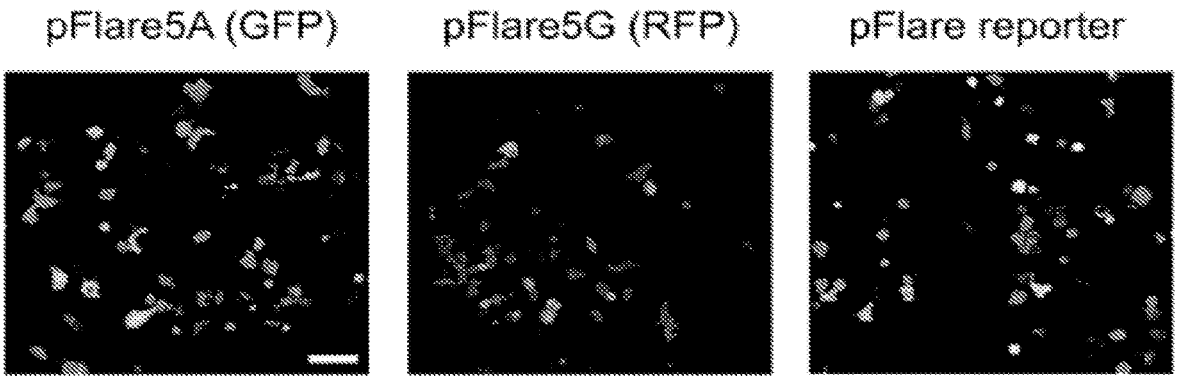
Figure 21C:
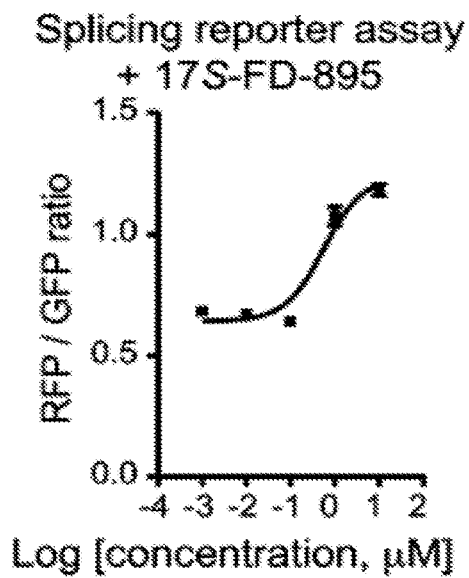

In a dual fluorescence splicing (pFlare) reporter assay (Stoilov et al., 2008) (FIGS. 3B, 21A, 21B), there was a dose-dependent increase in RFP/GFP ratios in HEK293 cells (FIGS. 3B and 21C) indicative of potent spliceosome disruption. Time-lapse confocal fluorescence microscopy confirmed increased RFP fluorescence following 17S-FD-895 treatment. In keeping with previous research showing pladienolide derivatives alter intron retention of DNAJB1 (Kotake et al., 2007), PCR demonstrated a time- and dose-dependent increase in DNAJB1 intron 2 levels following 17S-FD-895 treatment of MOLM-13 sAML cells, which occurred as rapidly as 30 minutes after the initiation of treatment (FIG. 14A) and to a lesser extent in KG1a AML cells and HEK293 cells (FIGS. 14B-14C). Because previous studies involving genetic and pharmacologic modulation show SF3B1 inhibition alters splicing and pre-mRNA nuclear retention (Kaida et al., 2007) of vital cancer-related and cell survival transcripts (Wang et al., 2011), such as MCL1 (Kashyap et al., 2015), we analyzed MCL1 isoform expression. Quantitative RT-PCR analyses revealed that pharmacologic splicing modulation triggered MCL1 exon 2 skipping, producing MCL1-S. At high concentrations, 17S-FD-895 treatment induced an array of other intron-retained and unspliced products specific to sAML cells (FIGS. 3G, 14D), suggesting that sAML cells harbor marked sensitivity to splicing modulation. In addition, 17S-FD-895 reduced expression of the sAML-associated transcript PTK2B-202 (FIG. 14E), indicating splicing modulation could suppress sAML splice isoform expression patterns, or favor survival of cells with less-perturbed spliceosome function.

Splicing Modulation Impairs LSC Maintenance in Stromal Co-Cultures.

Figure 15A:
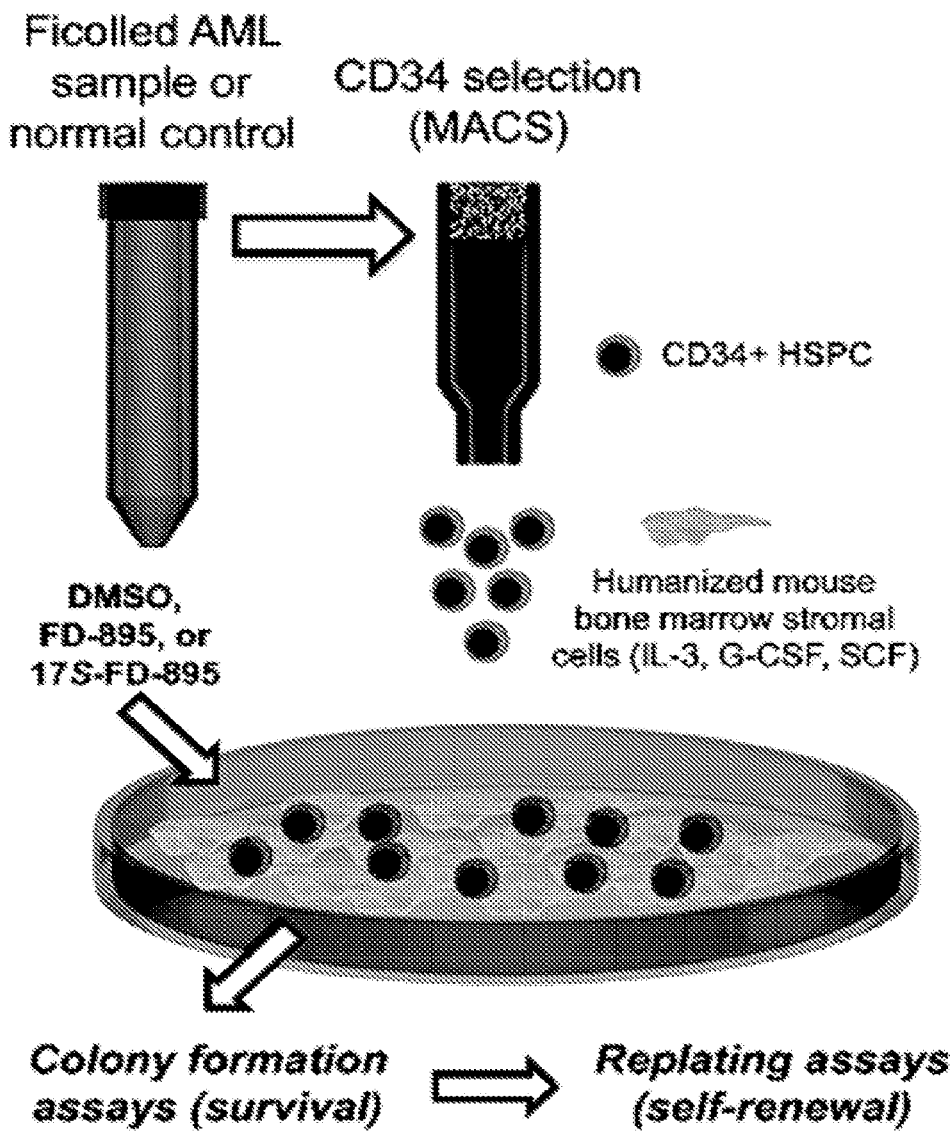
FIGS. 15A-15B. Splicing Modulation Impairs LSC Maintenance in Stromal Co-cultures.
Figure 15B:
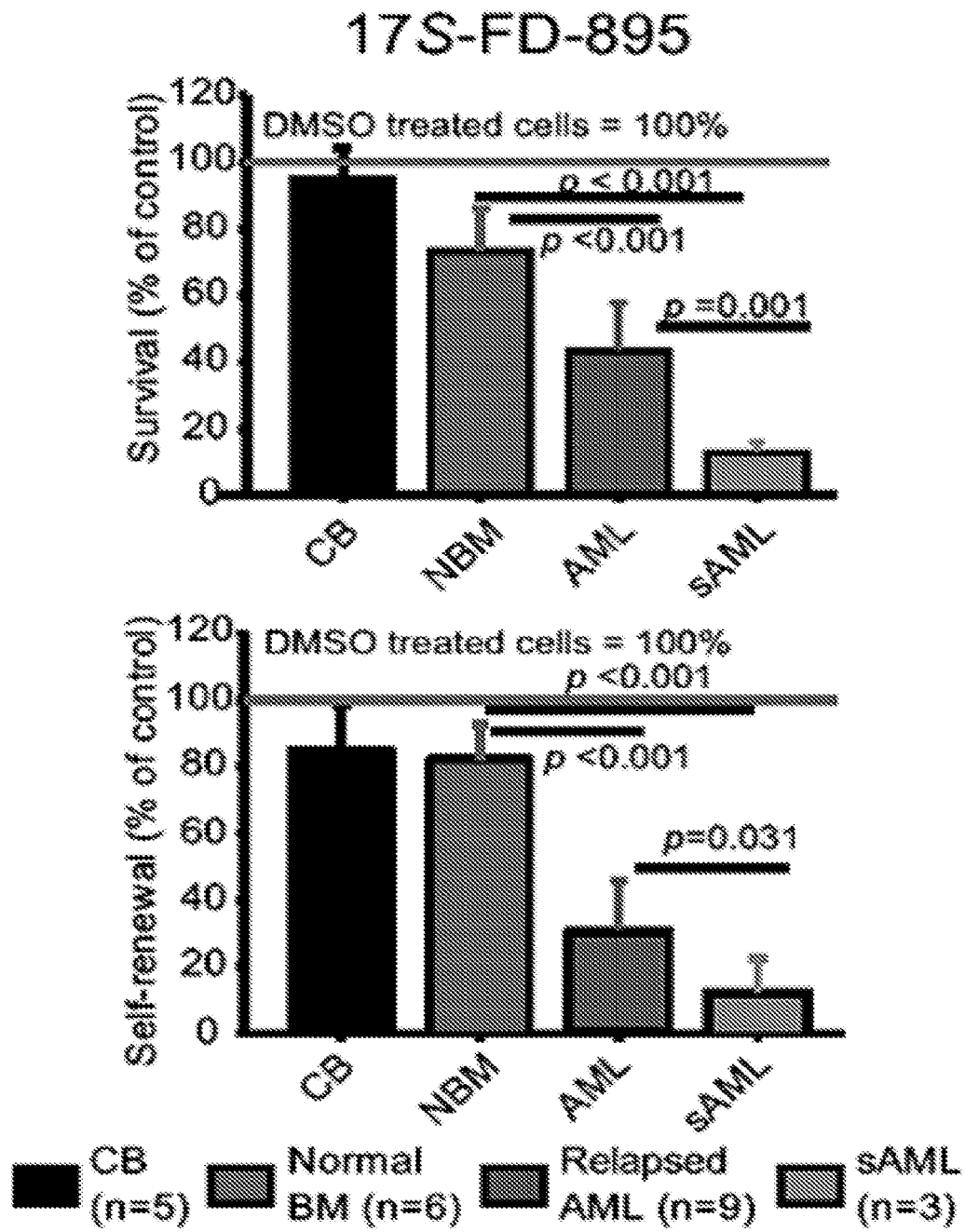

Previous studies identified an in vitro therapeutic index for FD-895 (the parent compound for 17S-FD-895), in CLL cells compared with normal B cells (Kashyap et al., 2015). However, the LSC inhibitory efficacy of FD-895 was not established. Moreover, decreased in vivo stability limited potential clinical utility. Thus, we compared FD-895 with the more stable analogue, 17S-FD-895, in LSC-supportive stromal co-culture assays (FIG. 15A) (Crews et al., 2015; Goff et al., 2013). Hematopoietic progenitor assays demonstrated a dose-dependent reduction in AML LSC clonogenicity and self-renewal (FIGS. 3D-3G, 22A) with a favorable therapeutic index after two weeks of stromal co-culture (FIG. 22B) with 17S-FD-895 (FIGS. 3E, 3G) compared with vehicle-treated and normal controls. Notably, sAML samples were more sensitive to splicing modulation than relapsed de novo AML (FIG. 15B). In normal bone marrow HSPC, minimal changes were observed in myeloid colony survival, with no significant effects on erythroid colony maintenance (FIG. 22C). Normal CB samples were unaffected by splicing modulator treatment even at high doses, possibly due to differences in their splice isoform expression profiles compared with aged normal controls (FIGS. 15B, 18F).

Because SF3B1 has been implicated as a target of 17S-FD-895, we performed lentiviral shRNA SF3B1 knockdown studies in MOLM-13 cells, primary CD34' HSPC and AML samples. Colony formation and serial replating assays revealed that aged HSPC survived lentiviral-shRNA SF3B1 knockdown while AML samples and MOLM-13 cells were exceptionally sensitive (FIGS. 22D-22G), indicating that the spliceosome represents a therapeutic vulnerability in AML.

Splicing Modulation Impairs LSC Maintenance while Sparing Normal Hematopoietic Cells In Vivo.

Figure 16A:
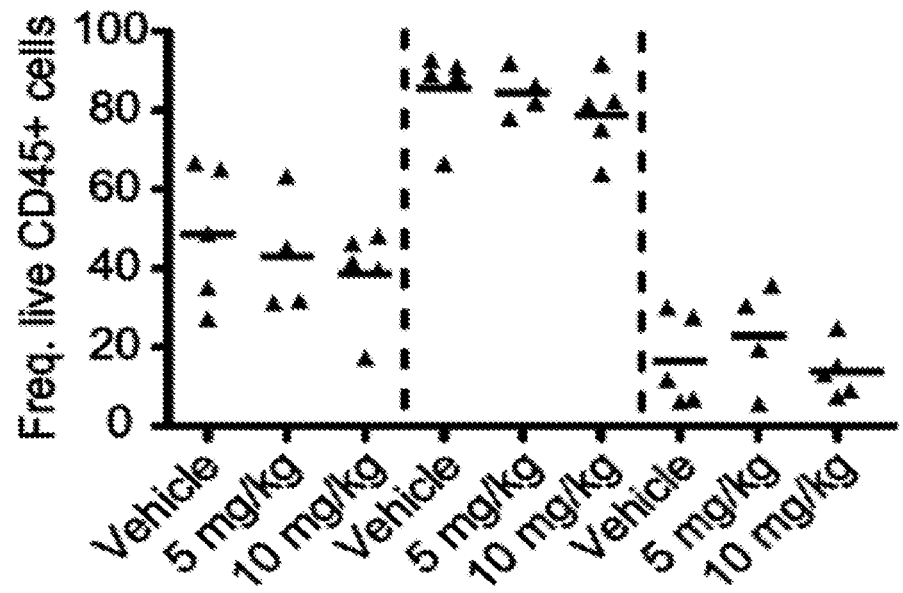
FIGS. 16A-16D. Splicing Modulation Impairs LSC Maintenance in AML P$_{\text{RIMAGRAFT}}$™ Models. Histograms depict FACS analysis of human hematopoietic cell (CD45$^+$, FIG. 16A), progenitor (CD34$^+$CD38$^+$ Lin$^-$, FIG. 16B), and granulocyte macrophage progenitor (GMP, FIG. 16C) cell engraftment in hematopoietic tissues from mice transplanted with AML-37 and treated with vehicle (DMSO, n=5) or 17S-FD-895 (5 mg/kg, n=4; 10 mg/kg, n=5).
Figure 16B:
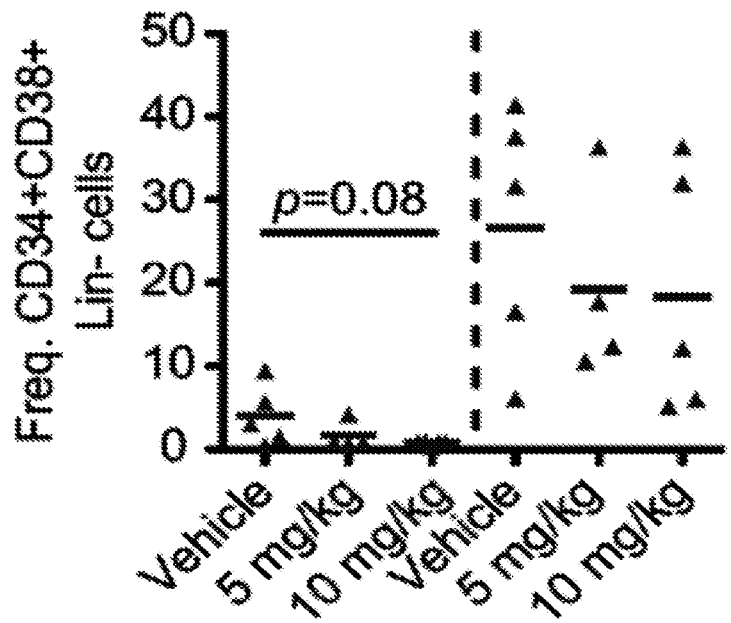
Figure 16C:
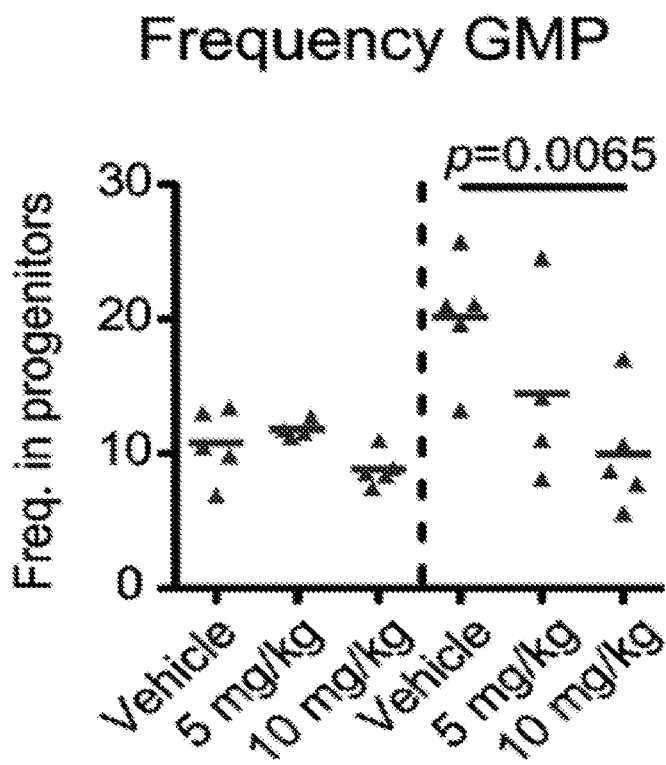
Figure 16D:
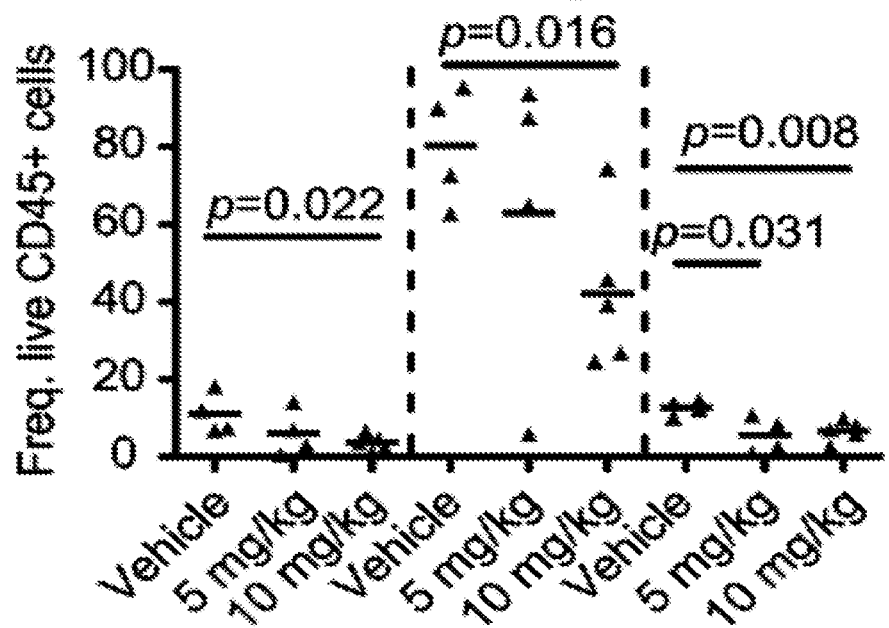
Figure 23A:
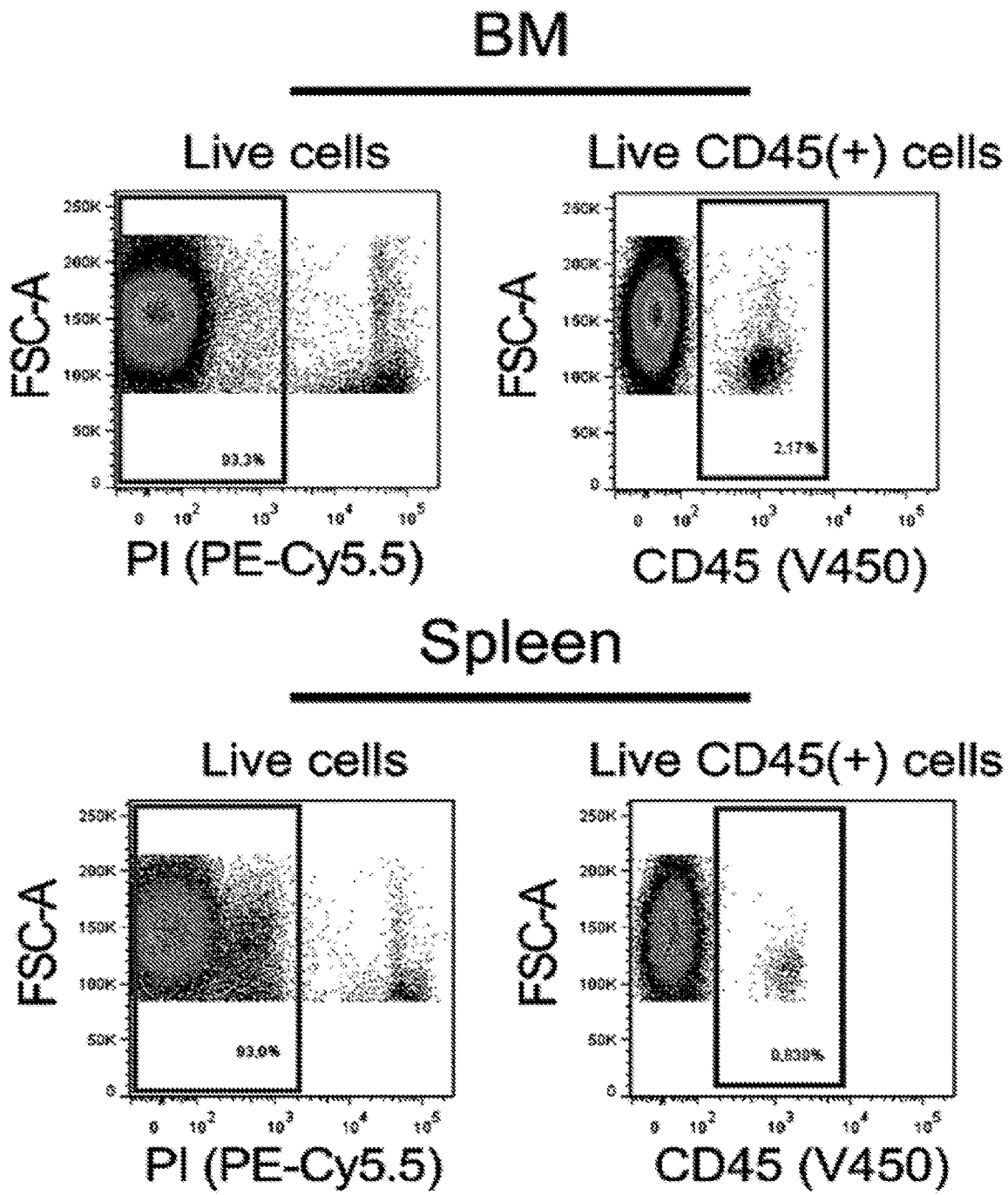
Figure 23B:
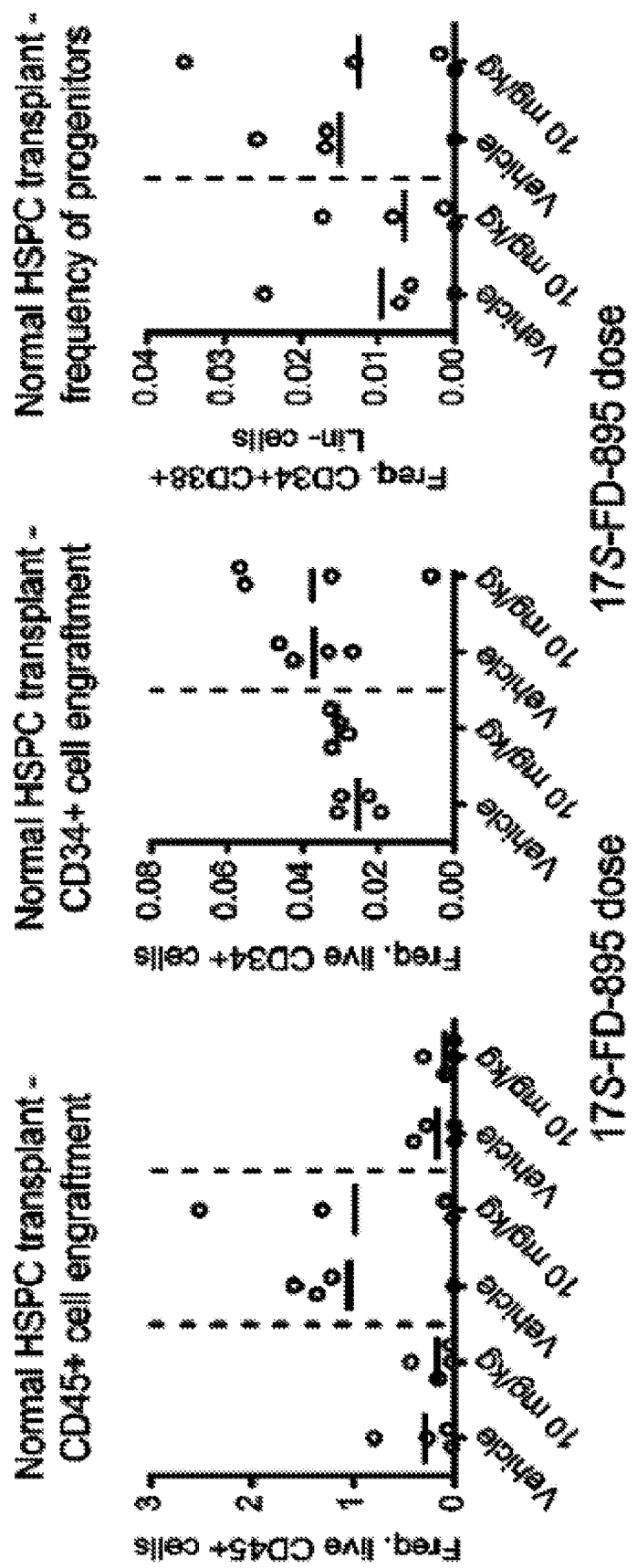
Figure 23D:
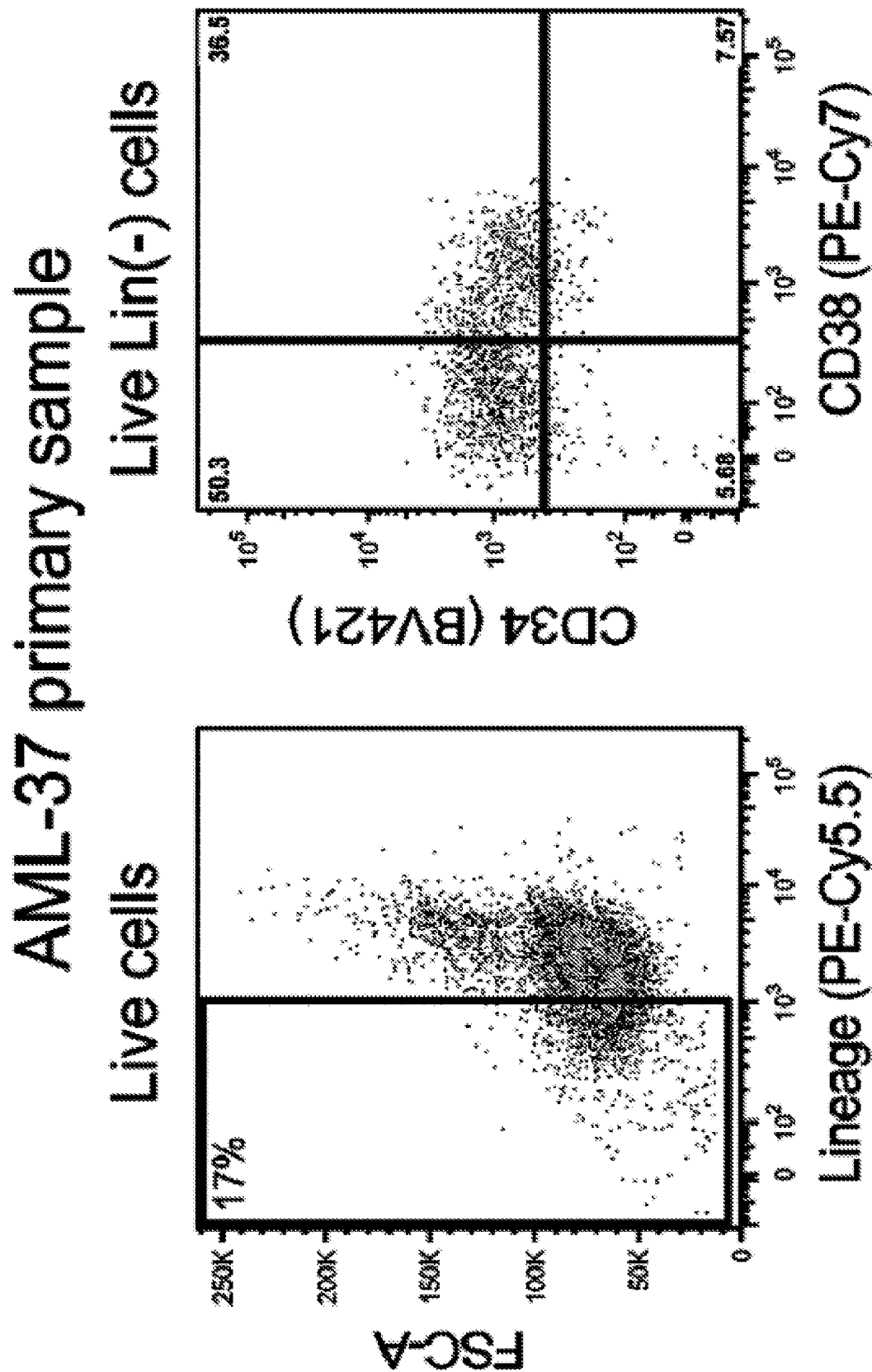
Figure 23E:
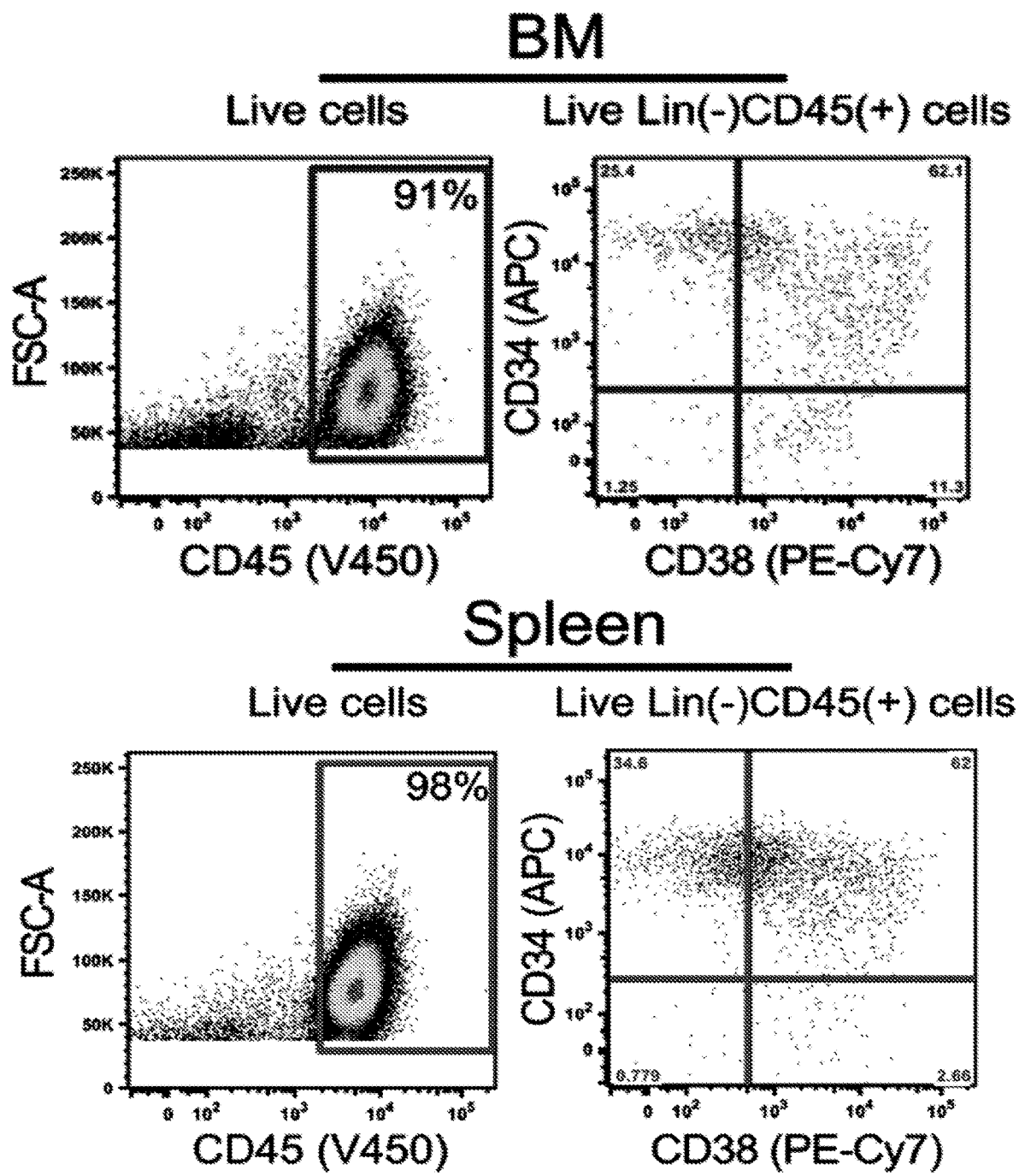
Figure 23F:
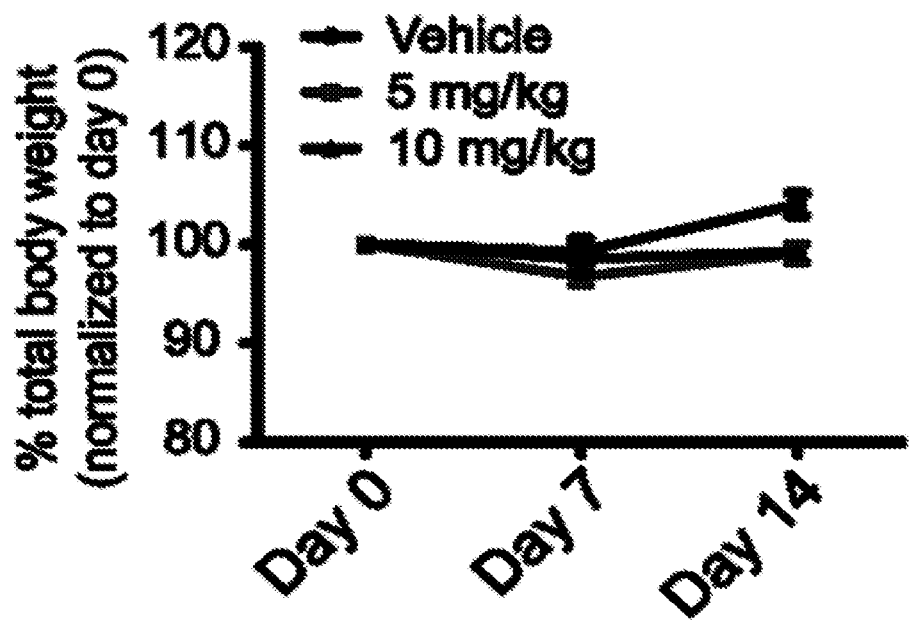
Figure 23F:
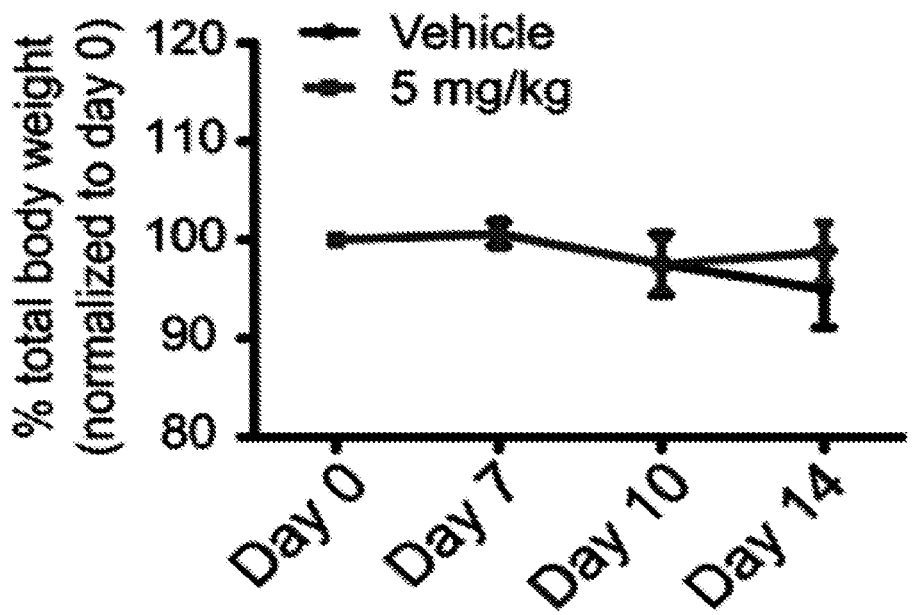
Figure 23G:
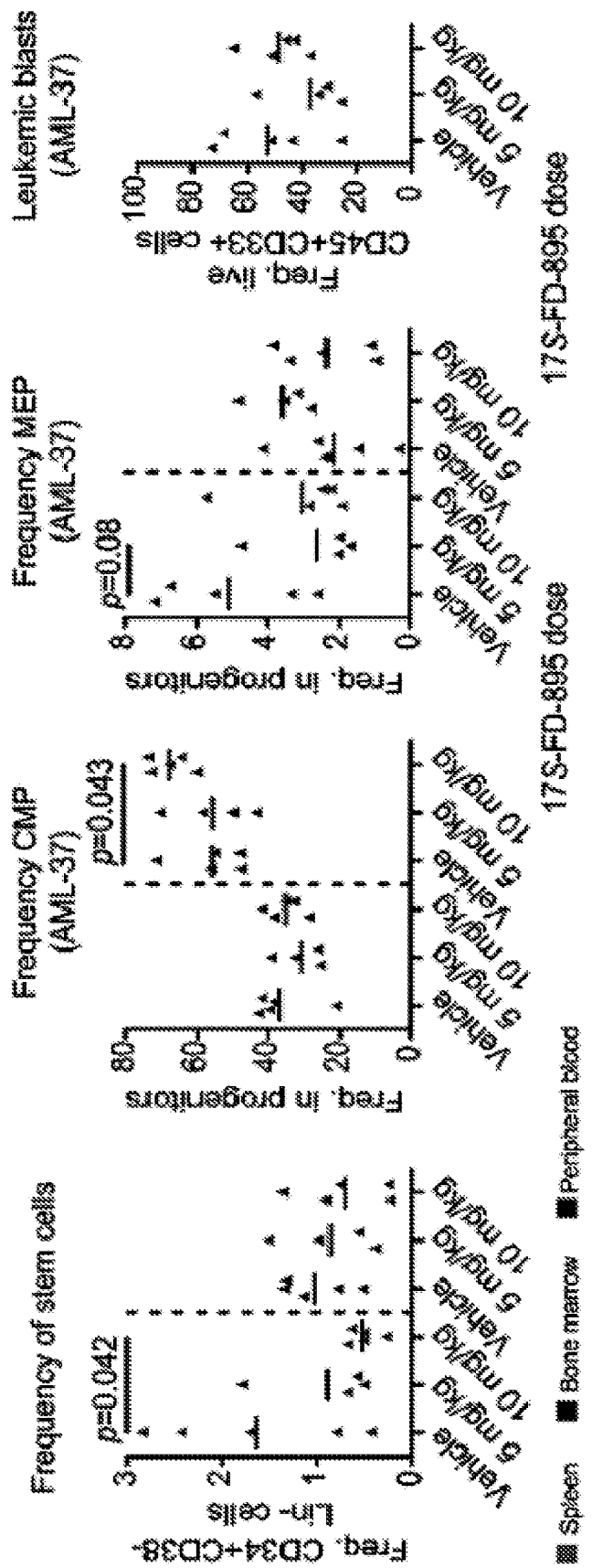
Figure 23H:
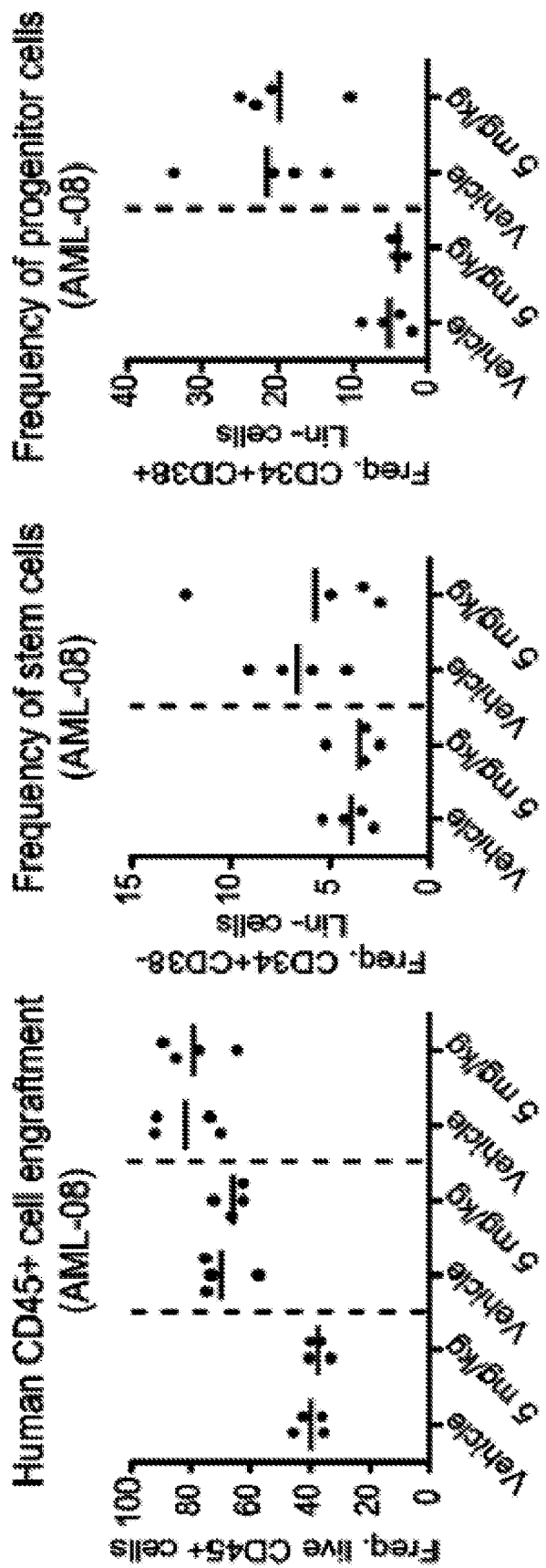
Figure 23I:
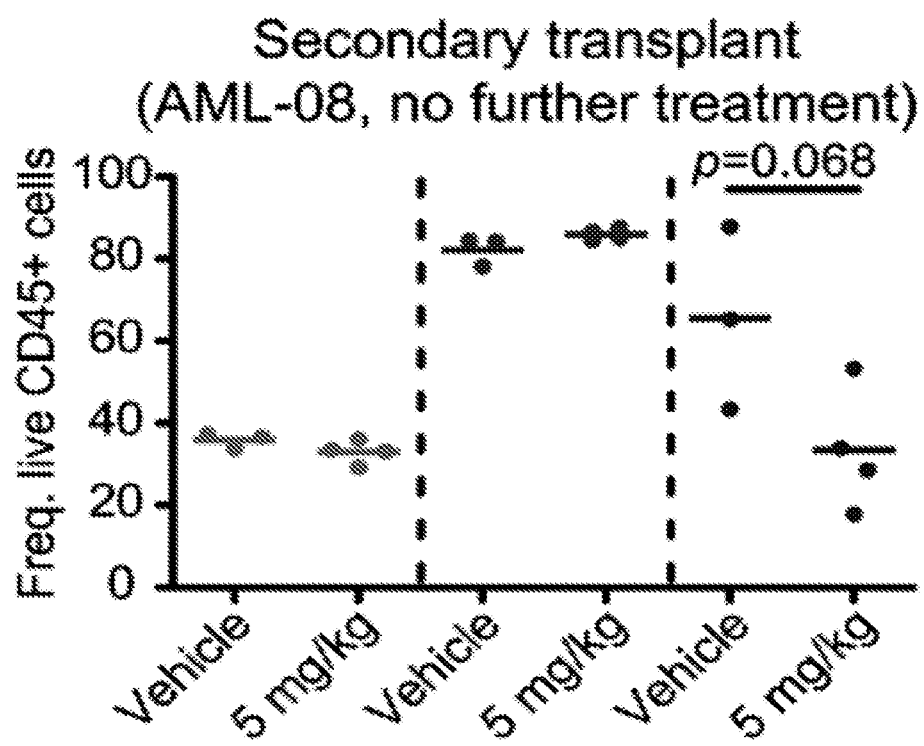

Since the 17S-FD-895 analogue showed a favorable therapeutic index and greater functional potency than FD-895 in LSC assays, we performed pre-clinical 17S-FD-895 efficacy studies in normal HSPC and AML PRIMAGRAFT™ models (FIG. 4A). Consistent with in vitro normal HSPC assays, 17S-FD-895 treatment of normal cord blood CD34$^+$ cell engrafted mice showed no effect on total human hematopoietic cell or HSPC survival (FIGS. 23A-23B). Transplantation of CD34$^+$ LSC-enriched fractions from three AML patient samples (Table 1; FIGS. 23C-23D; n=25 mice transplanted with primary human cells) serially engrafted human LSC (n=111 mice) after 7-28 weeks (FIG. 23E). Because of relatively high human engraftment, two sets of engrafted mice were deemed to be amenable to statistically quantifiable treatment with 17S-FD-895 (n=13) or vehicle control (n=9), followed by FACS, RNA-Seq, and splice isoform PCR analyses. The treatment was well tolerated, with no significant weight changes detected (FIG. 23F). In contrast to the in vivo normal HSPC model (FIG. 23B), FACS analysis revealed a decrease in human HSPC frequency in the spleens of AML PRIMAGRAFT™ treated mice treated with 10 mg/kg of 17S-FD-895 compared with vehicle (FIGS. 16A-16B, 23G). Because LSC have been detected in CD34$^+$CD38$^+$ or CD34$^+$CD38$^+$ compartments (Eppert et al., 2011), which are comprised of an expanded granulocyte-macrophage progenitor (GMP) population (Goardon et al., 2011; Jamieson et al., 2004), we analyzed these subpopulations in hematopoietic tissues of treated mice. In 17S-FD-895 treated mouse bone marrow, leukemic GMP frequency was significantly reduced resulting in reversion to normal progenitor frequencies (FIGS. 16E, 23G). Consistent with the impaired LSC replating potential observed after 17S-FD-895 treatment, serial transplantation studies revealed a marked decrease in human leukemic cells in recipients of CD34$^+$ cells from mice in the 10 mg/kg treatment group versus vehicle controls (FIG. 16D) in all hematopoietic tissues analyzed. In a de novo AML PRIMAGRAFT™ model with high disease burden (FIG. 23H), there was a similar trend towards decreased circulating leukemic cells in secondary recipients of CD34$^+$ cells from mice treated with a lower dose of 17S-FD-895 (FIG. 23I). Taken together, these data demonstrate that short-term treatment with a pharmacological splicing modulatory compound reduced AML LSC burden and self-renewal potential in serial transplantation assays.

Figure 17A:
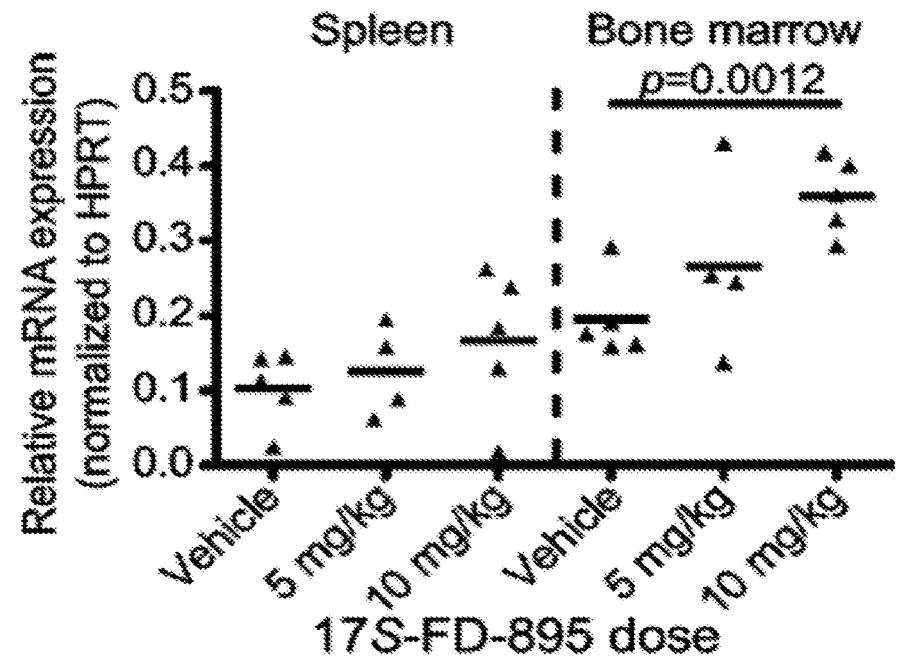
FIGS. 17A-17H. Splicing Modulation Reverses sAML Splicing Deregulation in P$_{\text{RIMAGRAFT}}$™ Models.
Figure 17B:
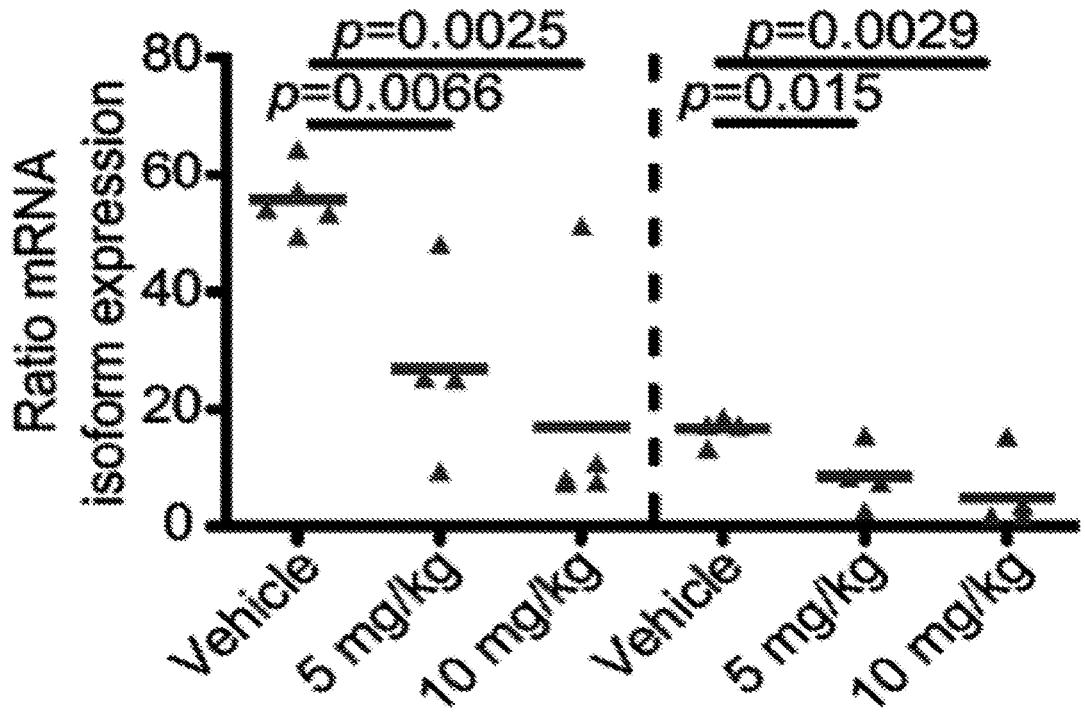
Figure 17C:
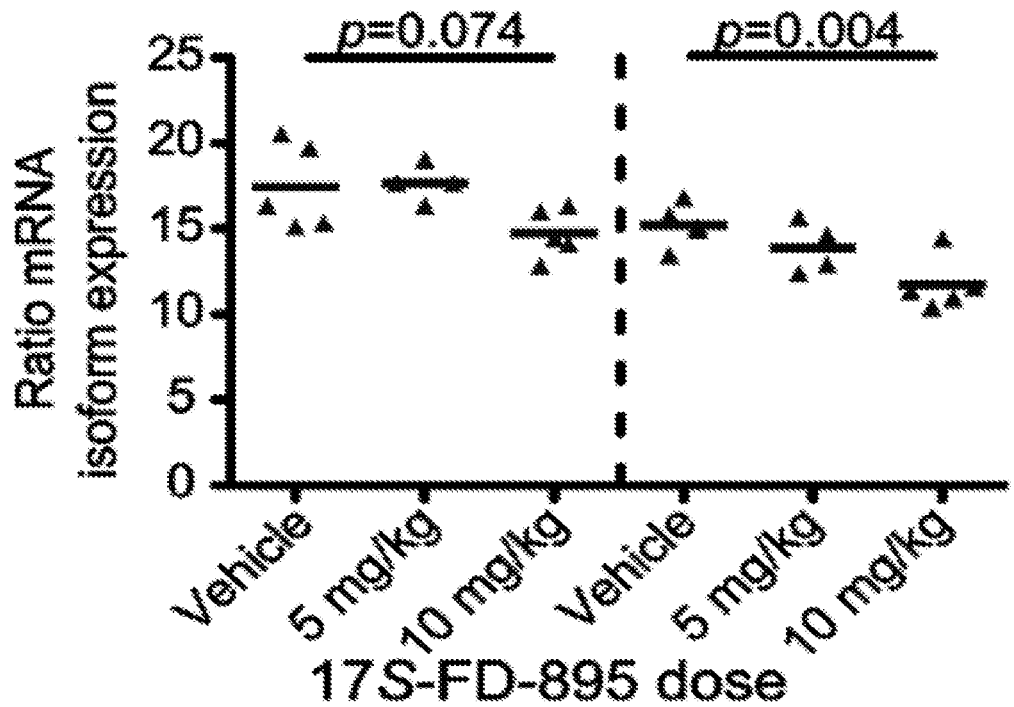
Figure 17D:
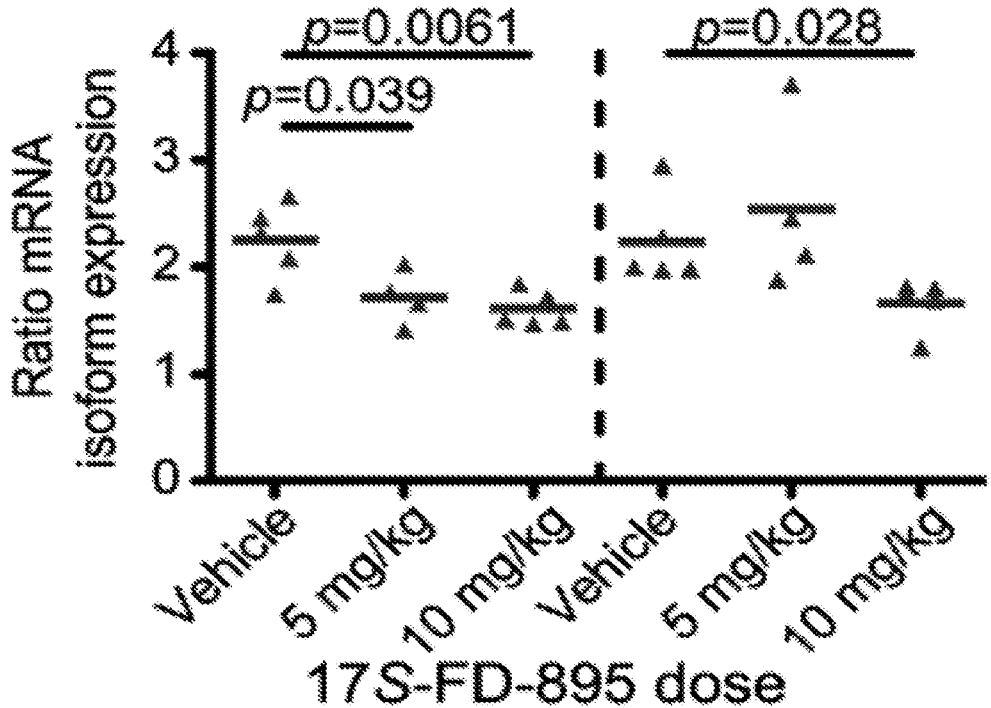
Figure 17E:
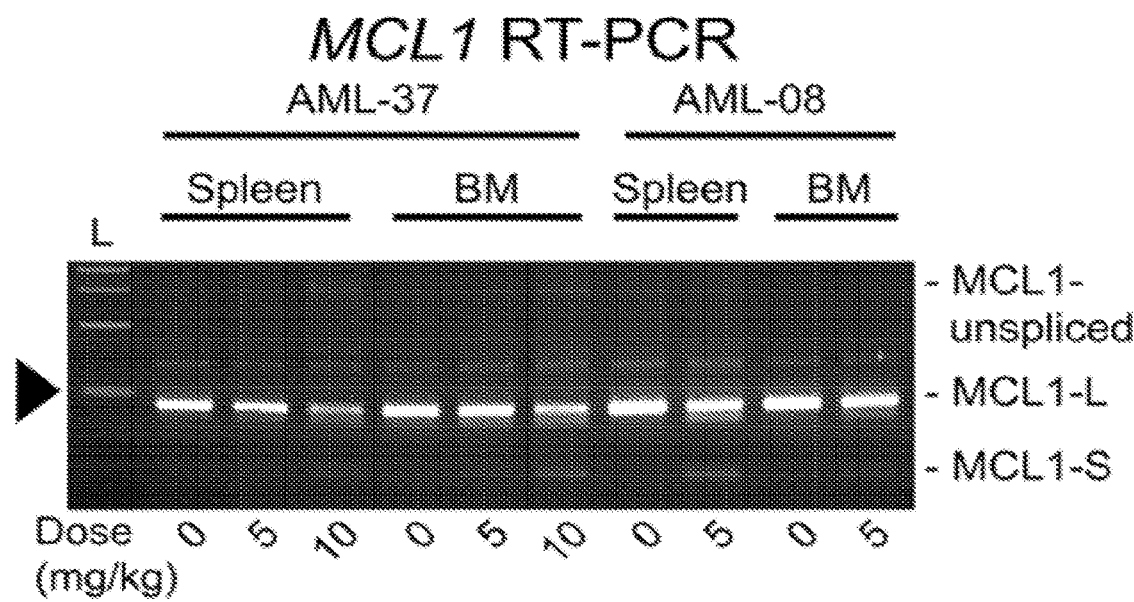
Figure 17F:
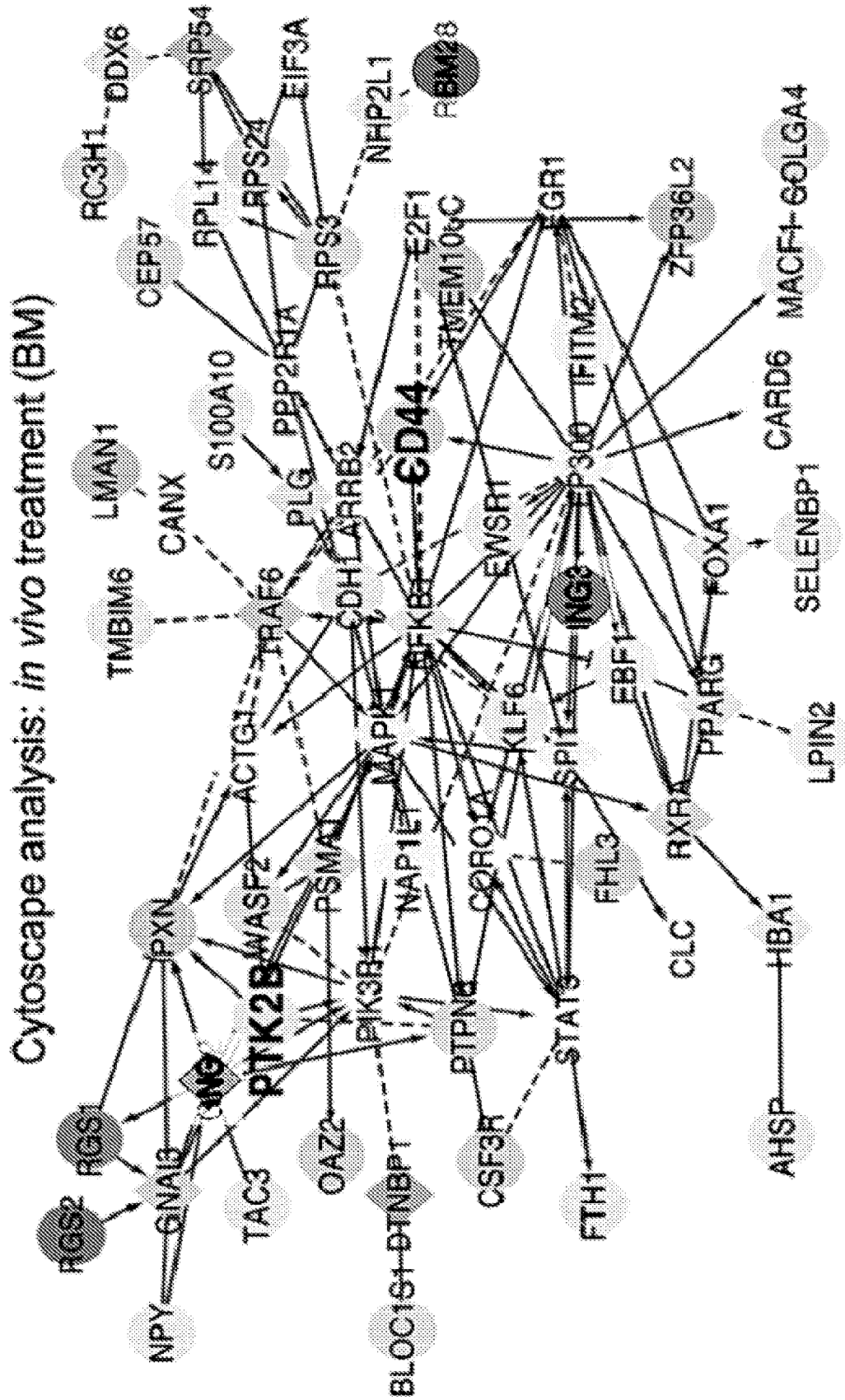
Figure 24A:
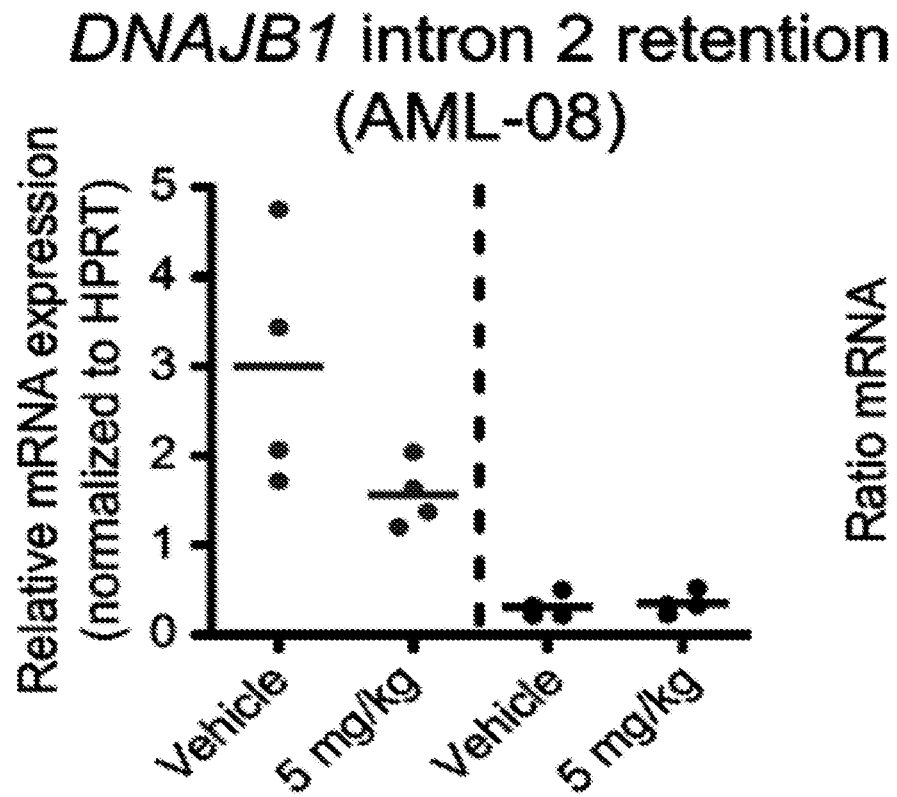
FIGS. 24A-24I. Quantitative RT-PCR Analysis and RT-PCR in AML PRIMAGRAFT™ Models After Splicing Modulator Treatment. For qRT-PCR analysis of in vivo splicing alterations, single cell suspensions from hematopoietic tissues of 17S-FD-895-treated mice were CD34-selected and processed for RNA extraction and cDNA preparation or RNA-Seq analysis.
Figure 24B:
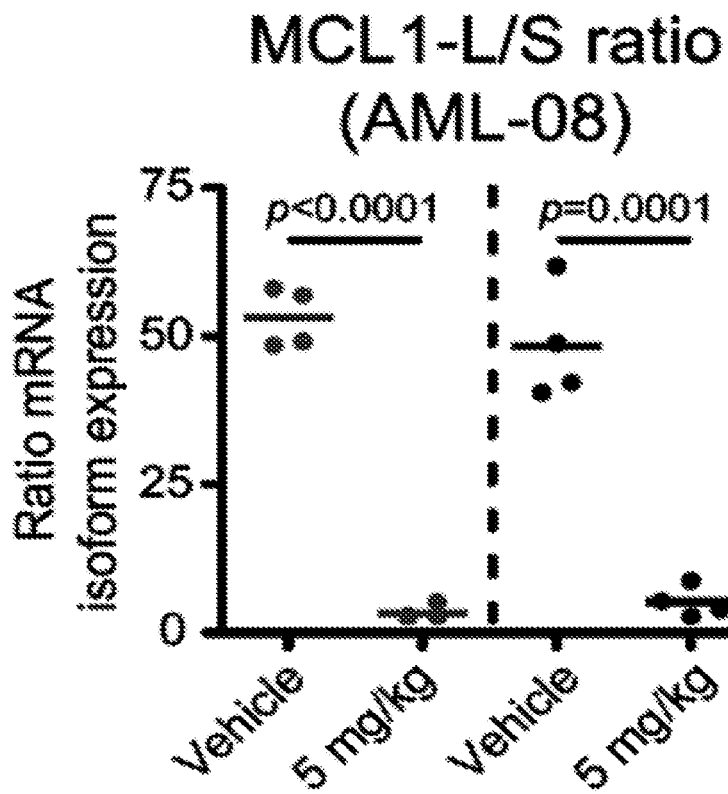
Figure 24C:
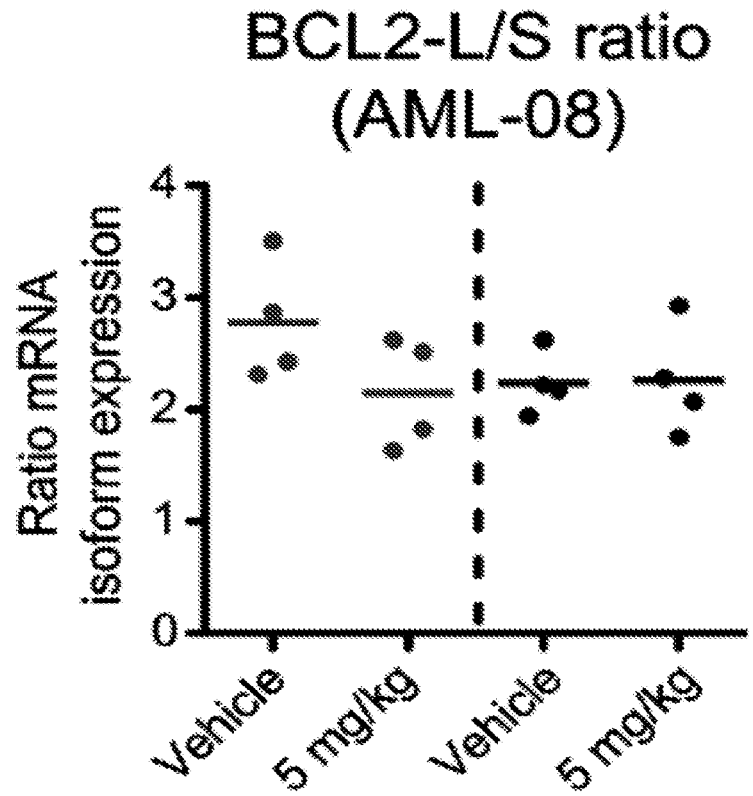
Figure 24D:
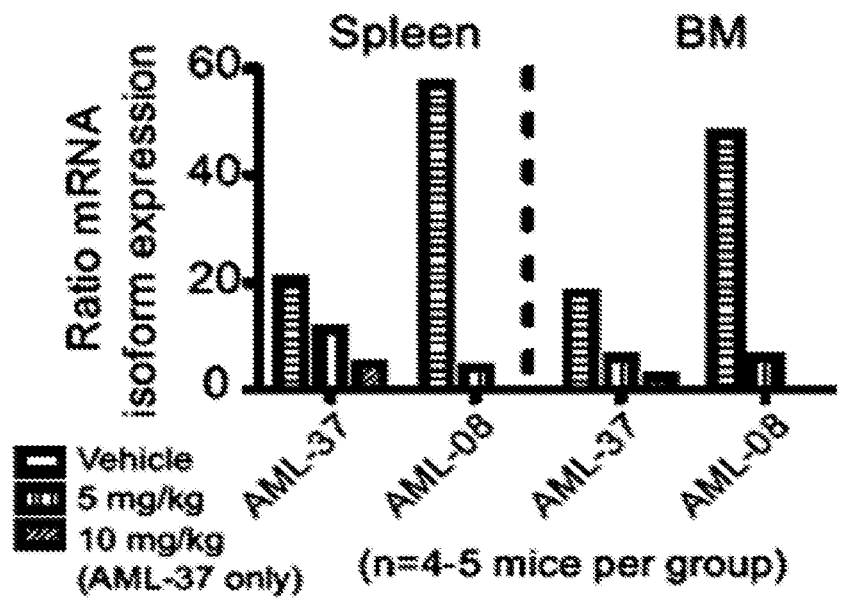
Figure 24E:
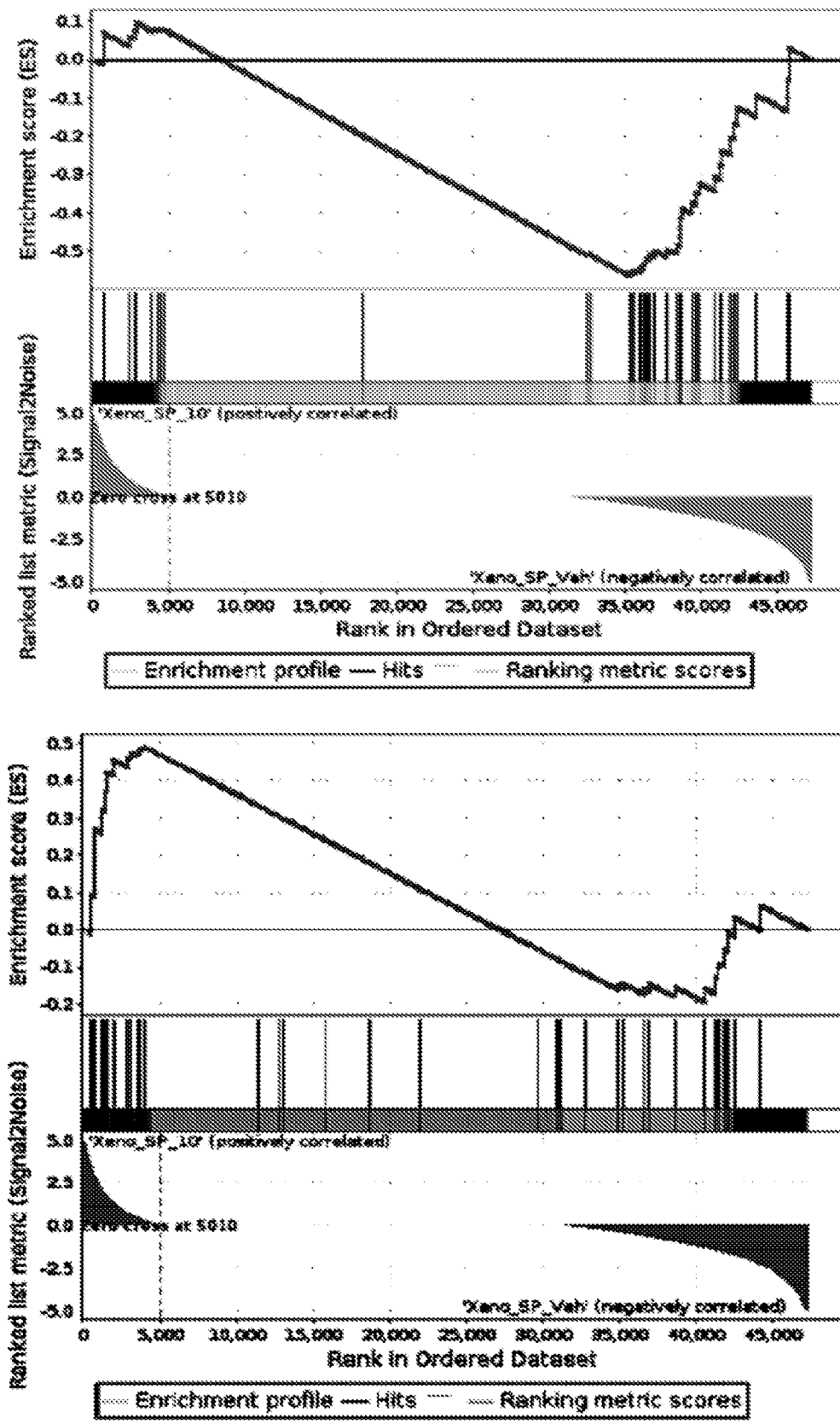

To quantify splice isoform modulation by 17S-FD-895 in the PRIMAGRAFT™ setting, human CD34-selected cells from treated mice were analyzed by RNA-seq, PCR and splice isoform-specific qRT-PCR. Consistent with in vitro 17S-FD-895 mechanism of action studies, PCR analyses demonstrated increased DNAJB1 intron 2 retention and a significant reduction in BCL2L1-L/S or BCL2-L/S and MCL1-L/S expression ratios in CD34$^+$ cells from 17S-FD-895-treated compared with control mice (FIGS. 17A-17D, 24A-24C). Pooled CD34$^+$ cells from 17S-FD-895-treated mice used for serial transplantation assays displayed MCL1 exon skipping and intron inclusion, along with significantly reduced MCL1-LS expression ratios (FIGS. 17E; 24D). Comparative RNA-Seq analysis was performed on CD34$^+$ cells pooled from the spleens and bone marrow of each group of treated AML PRIMAGRAFT™ assays. GSEA included all KEGG pathways and custom gene sets comprising genes related to overexpressed splice isoforms in sAML versus normal progenitors ("sAML up"), and the genes associated with decreased isoforms in sAML vs normal age-matched progenitors ("aged up"). As expected, the "sAML up" signature was enriched in cells isolated from vehicle-treated mice (FIG. 24E). Conversely, the "aged up" signature was enriched in the 10 mg/kg 17S-FD-895 treated mice (FIG. 24E), suggesting that reversion to an aged splice isoform signature is a biomarker of LSC eradication. Moreover, expression profiles of genes associated with differentially expressed transcripts identified in the sAML versus normal bone marrow HPC signature (FIG. 12E) showed opposite trends in bone marrow from treated mice (FIG. 17F), supporting a trend towards reversion to a normal bone marrow transcriptome profile.

To further investigate specific molecular signatures of in vivo response to 17S-FD-895, sAML-associated transcripts (e.g., FIGS. 11D, 11E, 12D) were assessed to identify those that changed (absolute L2FC>0.5) in response to the higher treatment doses in both bone marrow and spleen. Notably, sAML-specific transcripts, such as STAT6-016 and ITGB2-201, reverted to a normal expression pattern (FIG. 17G).

Figure 17G:
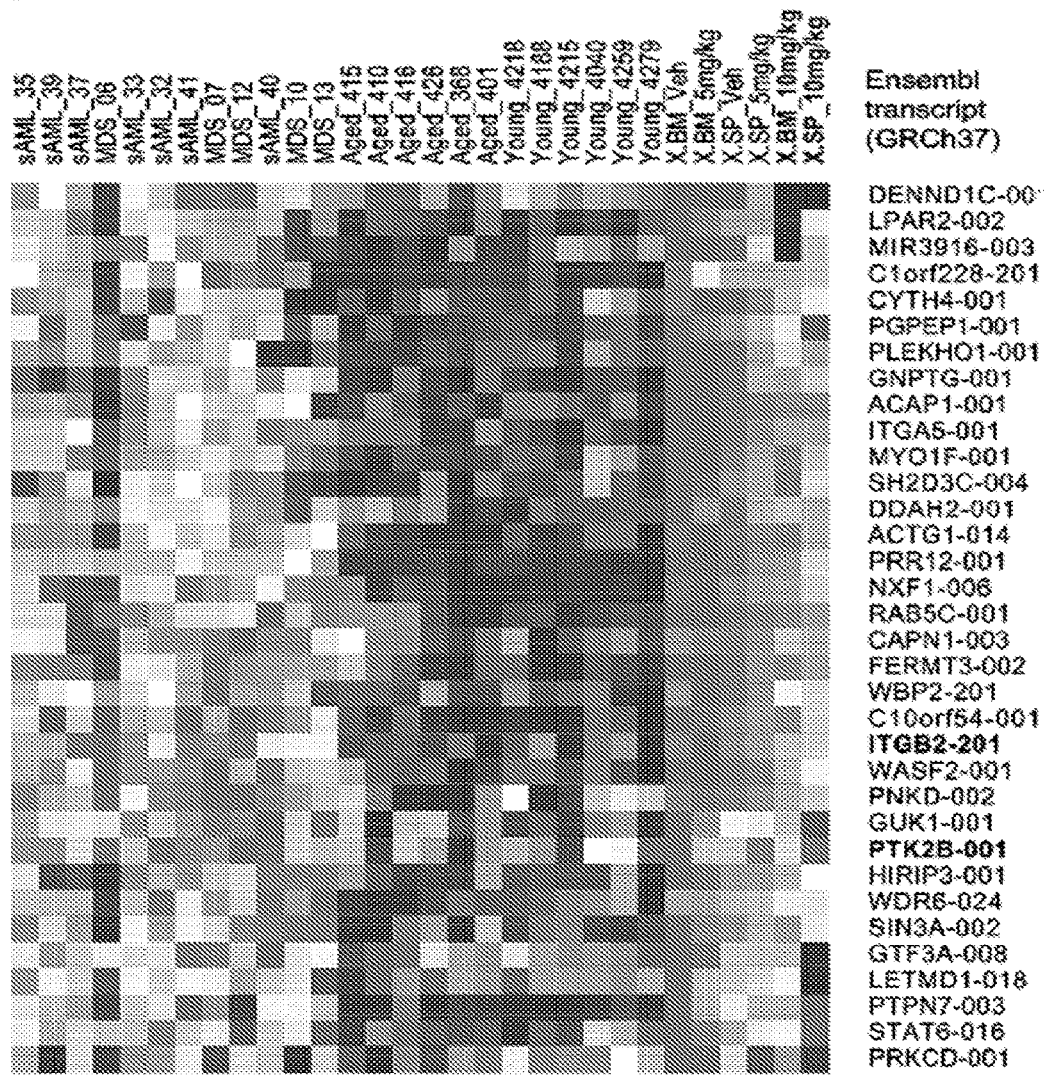
Figure 17H:
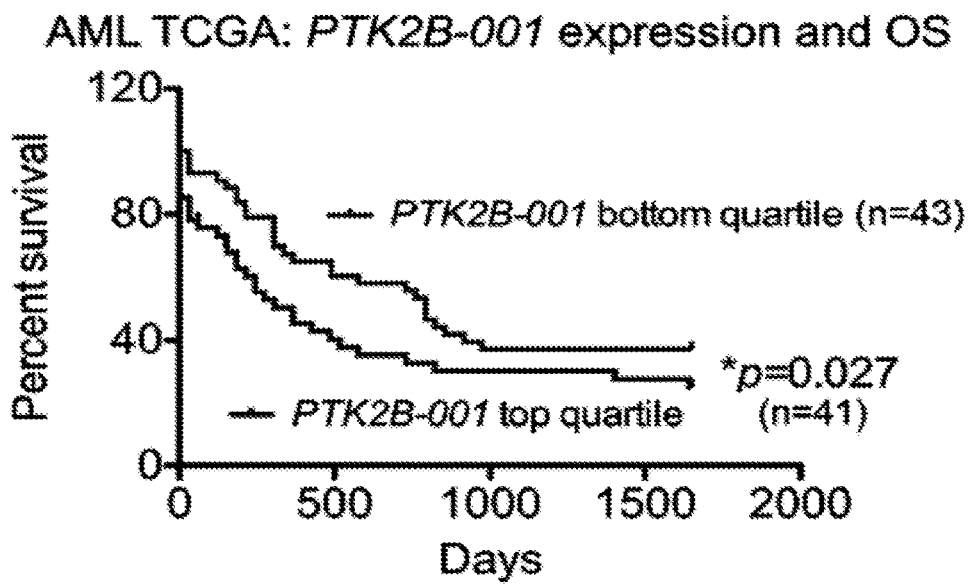
Figure 24F:
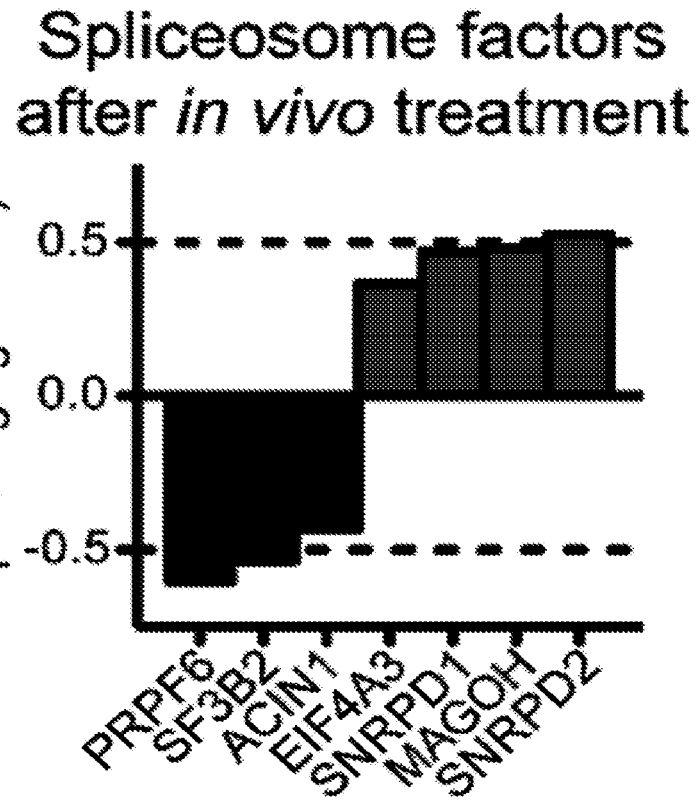
Figure 24G:
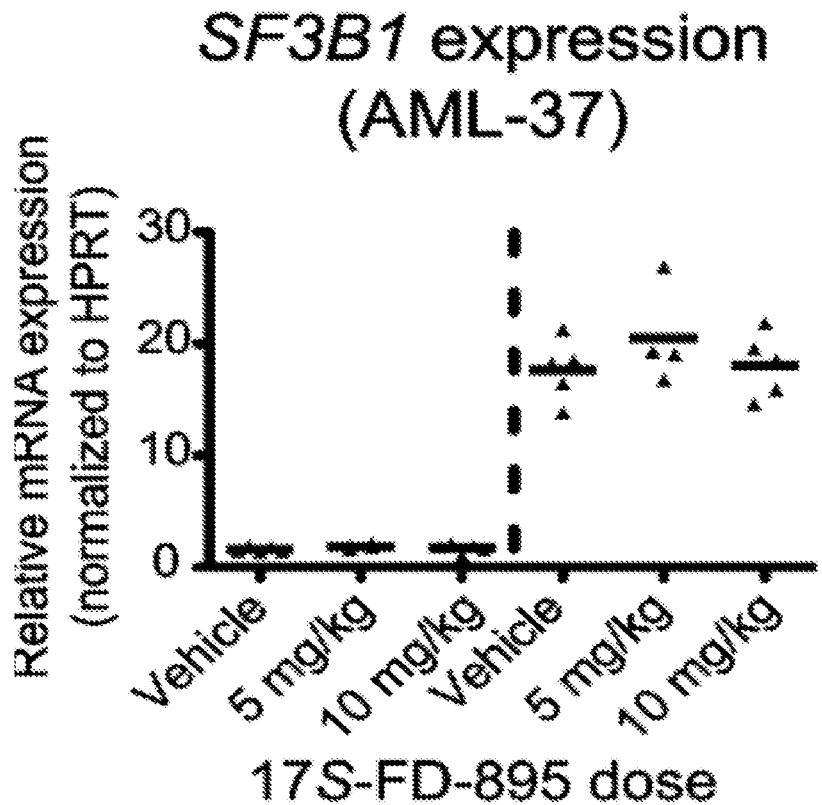
Figure 24H:
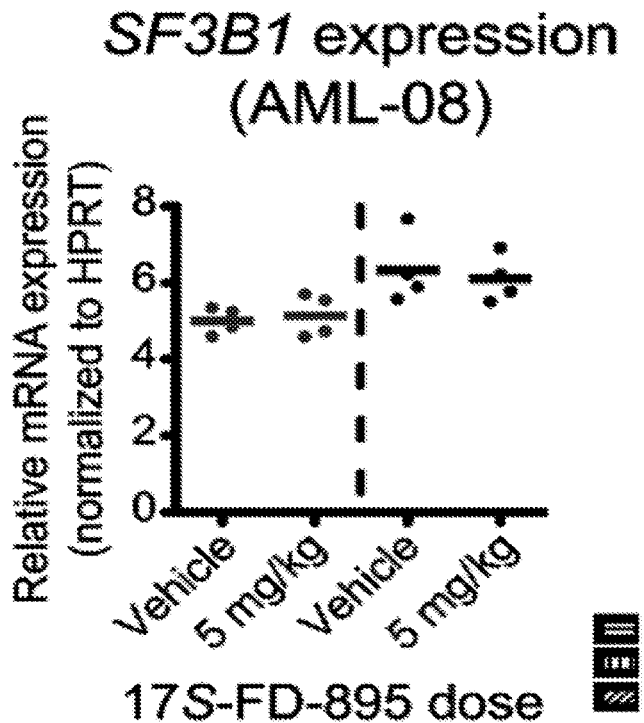
Figure 24I:
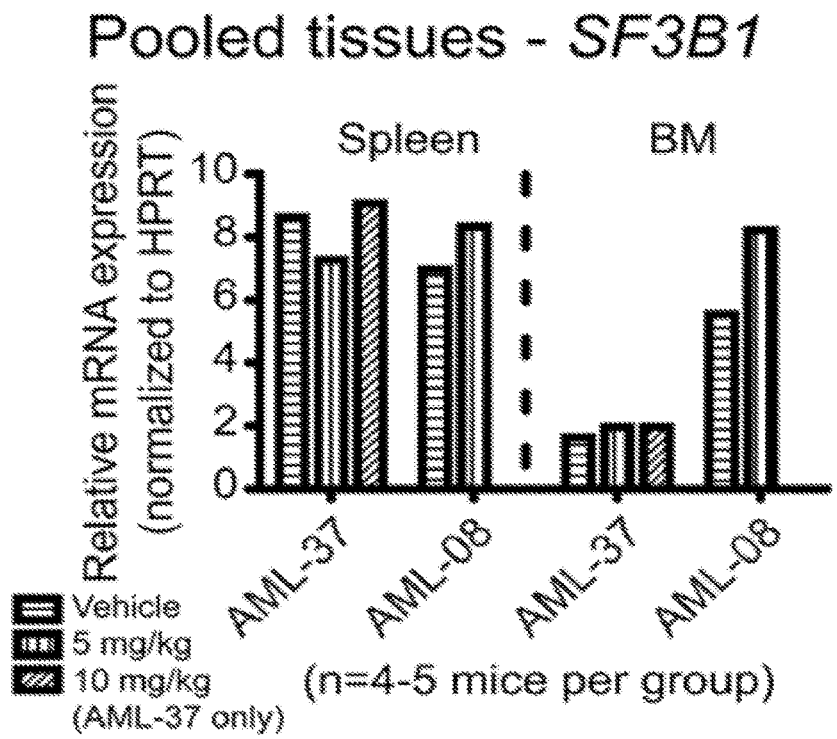

Notably, PTK2B transcripts were decreased after treatment in both spleen and bone marrow (FIG. 17G). Notably, TCGA splice isoform analyses revealed that low AML LSC splice isoform levels were associated with improved overall survival (FIG. 17H). Moreover, RNA-Seq data from PRIMAGRAFT™ analyzed mice showed normalization of expression levels of several splicing factor genes that were disrupted in sAML (FIG. 24F), further supporting the possibility that splicing modulation can restore HSPC splicing patterns by favoring survival of cells with more normal spliceosome function and splice isoform expression profiles. SF3B1 expression levels were unchanged after treatment in individual mice and in pooled samples utilized for serial transplantation studies (FIGS. 24G-24I). Thus, pharmacological splicing modulation with 17S-FD-895 promoted reversion to a normal splicing pattern typified by a reduction in sAML-specific transcripts and pro-apoptotic BCLX-L, BCL2 and MCL1 splice isoform switching. Cumulatively, these data suggest that inhibition of pro-survival gene splicing may contribute to the impairment of AML LSC maintenance by 17S-FD-895.

In vivo molecular response to therapeutic splicing modulation. RNA-seq analysis was performed in human CD34+ cell fractions isolated from spleens and bone marrow of 17S-FD-895-treated sAML-engrafted mice. Among splice isoforms that showed significant changes in expression in sAML versus normal aged HPC, the isoforms shown were restored to more normal aged HPC-like expression patterns in spleens and bone marrow in 17S-treated mice compared with vehicle controls. The data are set forth in Table 4 following, which formed the basis for calculation of FIG. 17G.

TABLE 4

In vivo molecular response to therapeutic splicing modulation.

| transcript_id (Ensembl GRCh37) | transcript_name | L2FC BM 10 | L2FC sp 10 | Average L2FC |
|---|---|---|---|---|
| ENST00000426951 | RBM39-039 | 2.701 | 3.541 | 3.121 |
| ENST00000596102 | AL353354.2-201 | 3.801 | 1.976 | 2.888 |
| ENST00000360385 | ZNF317-002 | 3.274 | 2.127 | 2.700 |
| ENST00000461326 | CLK1-013 | 3.722 | 0.840 | 2.281 |
| ENST00000428863 | MDM2-204 | 2.293 | 1.906 | 2.100 |
| ENST00000495394 | RPSA-004 | 2.430 | 1.656 | 2.043 |
| ENST00000579996 | DDX5-007 | 2.553 | 1.451 | 2.002 |
| ENST00000577787 | DDX5-019 | 2.845 | 1.136 | 1.991 |
| ENST00000533161 | RPS2-002 | 2.826 | 1.136 | 1.981 |
| ENST00000548363 | TUBA1A-015 | 1.877 | 2.062 | 1.970 |
| ENST00000409817 | CXCR4-003 | 2.913 | 0.999 | 1.956 |
| ENST00000489149 | DTL-003 | 1.698 | 2.082 | 1.890 |
| ENST00000583894 | DDX5-017 | 2.895 | 0.853 | 1.874 |
| ENST00000510864 | PRIMPOL-010 | 1.100 | 2.343 | 1.722 |
| ENST00000576274 | NDC80-013 | 0.851 | 2.280 | 1.566 |
| ENST00000514518 | CAMLG-002 | 0.540 | 2.424 | 1.482 |
| ENST00000557134 | MNAT1-008 | 1.739 | 1.212 | 1.475 |
| ENST00000402105 | HPS4-008 | 1.915 | 0.932 | 1.423 |
| ENST00000492674 | STAG3-018 | 1.407 | 1.428 | 1.418 |
| ENST00000327898 | AFMID-001 | 1.761 | 1.055 | 1.408 |
| ENST00000590308 | LDLRAD4-005 | 1.233 | 1.090 | 1.162 |
| ENST00000553494 | PRC1-011 | 0.974 | 1.298 | 1.136 |
| ENST00000222597 | CBLL1-014 | 0.696 | 1.140 | 0.918 |
| ENST00000435634 | EXOSC6-001 | 0.653 | 0.545 | 0.599 |
| ENST00000416501 | AC015987.2-201 | 0.646 | 0.544 | 0.595 |
| ENST00000279247 | CAPN1-003 | −0.661 | −0.567 | −0.614 |
| ENST00000314830 | SH2D3C-004 | −0.516 | −0.725 | −0.620 |
| ENST00000509198 | LRPAP1-002 | −0.566 | −0.731 | −0.648 |
| ENST00000158762 | ACAP1-001 | −0.803 | −0.505 | −0.654 |
| ENST00000556363 | MCTP2-005 | −0.645 | −0.663 | −0.654 |
| ENST00000380870 | ZNF738-002 | −0.708 | −0.618 | −0.663 |
| ENST00000258412 | TMBIM1-001 | −0.553 | −0.780 | −0.667 |
| ENST00000394957 | C10orf54-001 | −0.620 | −0.737 | −0.678 |
| ENST00000608424 | WDR6-024 | −0.657 | −0.713 | −0.685 |
| ENST00000338257 | MYO1F-001 | −0.626 | −0.753 | −0.689 |
| ENST00000532402 | GANAB-004 | −0.784 | −0.599 | −0.691 |
| ENST00000258362 | PNKD-002 | −0.519 | −0.871 | −0.695 |
| ENST00000345728 | FERMT3-002 | −0.758 | −0.694 | −0.726 |
| ENST00000406520 | COMT-001 | −0.681 | −0.771 | −0.726 |
| ENST00000548410 | RP11-571M6.8-001 | −0.568 | −0.891 | −0.729 |
| ENST00000430629 | WASF2-001 | −0.593 | −0.923 | −0.758 |
| ENST00000308436 | TUT1-201 | −0.949 | −0.597 | −0.773 |
| ENST00000307768 | JAGN1-001 | −0.879 | −0.759 | −0.819 |
| ENST00000293379 | ITGA5-001 | −0.988 | −0.669 | −0.828 |
| ENST00000492819 | CCDC12-005 | −0.831 | −0.829 | −0.830 |
| ENST00000346213 | RAB5C-001 | −0.911 | −0.783 | −0.847 |
| ENST00000457928 | TBL1XR1-002 | −1.066 | −0.641 | −0.854 |
| ENST00000374296 | PAQR7-001 | −0.682 | −1.047 | −0.864 |
| ENST00000548273 | NAP1L1-016 | −0.890 | −0.843 | −0.867 |
| ENST00000254806 | WBP2-201 | −0.785 | −0.972 | −0.879 |
| ENST00000279392 | HIRIP3-001 | −0.992 | −0.790 | −0.891 |
| ENST00000570382 | ACTG1-014 | −0.529 | −1.269 | −0.899 |
| ENST00000373166 | TRAPPC3-001 | −0.863 | −0.945 | −0.904 |
| ENST00000418929 | PRR12-001 | −0.589 | −1.242 | −0.916 |

TABLE 4-continued

In vivo molecular response to therapeutic splicing modulation.

| transcript_id (Ensembl GRCh37) | transcript_name | L2FC BM 10 | L2FC sp 10 | Average L2FC |
|---|---|---|---|---|
| ENST00000429426 | MLLT3-202 | −1.097 | −0.762 | −0.930 |
| ENST00000227155 | CD82-001 | −0.733 | −1.170 | −0.952 |
| ENST00000599461 | ZNF493-007 | −0.592 | −1.332 | −0.962 |
| ENST00000325207 | RIC8A-001 | −0.805 | −1.123 | −0.964 |
| ENST00000299299 | PCBD1-001 | −0.599 | −1.338 | −0.968 |
| ENST00000258947 | CALCOCO2-001 | −0.776 | −1.203 | −0.990 |
| ENST00000382280 | ZG16B-001 | −1.221 | −0.761 | −0.991 |
| ENST00000483519 | USP40-006 | −1.153 | −0.831 | −0.992 |
| ENST00000360439 | SIN3A-002 | −0.892 | −1.105 | −0.999 |
| ENST00000375464 | C9orf89-001 | −0.867 | −1.176 | −1.022 |
| ENST00000269919 | PGPEP1-001 | −0.884 | −1.172 | −1.028 |
| ENST00000204679 | GNPTG-001 | −1.457 | −0.651 | −1.054 |
| ENST00000394729 | PRKCD-001 | −0.746 | −1.375 | −1.061 |
| ENST00000341183 | MKNK1-201 | −0.531 | −1.603 | −1.067 |
| ENST00000531709 | NXF1-006 | −0.705 | −1.432 | −1.069 |
| ENST00000215838 | TCN2-001 | −1.199 | −0.953 | −1.076 |
| ENST00000535358 | C1orf228-201 | −1.353 | −0.867 | −1.110 |
| ENST00000275635 | LAT2-009 | −0.920 | −1.319 | −1.119 |
| ENST00000302347 | ITGB2-201 | −1.140 | −1.175 | −1.157 |
| ENST00000248901 | CYTH4-001 | −0.798 | −1.536 | −1.167 |
| ENST00000354434 | ZYX-006 | −1.819 | −0.536 | −1.178 |
| ENST00000367279 | PTPN7-003 | −1.342 | −1.042 | −1.192 |
| ENST00000322354 | SERTAD3-001 | −0.858 | −1.587 | −1.222 |
| ENST00000508045 | LUC7L3-003 | −1.043 | −1.531 | −1.287 |
| ENST00000356151 | PXK-001 | −1.478 | −1.102 | −1.290 |
| ENST00000346049 | PTK2B-001 | −1.296 | −1.303 | −1.300 |
| ENST00000485708 | RPS24-002 | −0.741 | −1.867 | −1.304 |
| ENST00000493903 | GTF3A-008 | −0.931 | −1.723 | −1.327 |
| ENST00000440963 | APOPT1-005 | −0.553 | −2.110 | −1.331 |
| ENST00000337130 | UGP2-001 | −0.733 | −1.984 | −1.358 |
| ENST00000557781 | STAT6-016 | −1.456 | −1.327 | −1.391 |
| ENST00000312726 | GUK1-001 | −1.456 | −1.334 | −1.395 |
| ENST00000471726 | IQCB1-007 | −1.074 | −1.741 | −1.407 |
| ENST00000586476 | U2AF1L4-001 | −1.791 | −1.049 | −1.420 |
| ENST00000311337 | GNPDA1-001 | −2.115 | −0.776 | −1.445 |
| ENST00000381125 | PFKP-003 | −0.763 | −2.237 | −1.500 |
| ENST00000330188 | TPM3-009 | −0.574 | −2.459 | −1.516 |
| ENST00000574024 | PDE6G-003 | −0.965 | −2.105 | −1.535 |
| ENST00000268099 | SCAMP2-001 | −1.250 | −1.865 | −1.558 |
| ENST00000375792 | DDAH2-001 | −1.257 | −1.881 | −1.569 |
| ENST00000455895 | BSDC1-001 | −1.445 | −1.847 | −1.646 |
| ENST00000369124 | PLEKHO1-001 | −1.399 | −1.938 | −1.669 |
| ENST00000322310 | SSNA1-001 | −1.291 | −2.091 | −1.691 |
| ENST00000569495 | C1orf63-016 | −2.297 | −1.091 | −1.694 |
| ENST00000548390 | LETMD1-018 | −1.841 | −1.576 | −1.709 |
| ENST00000512234 | SQSTM1-011 | −2.830 | −0.600 | −1.715 |
| ENST00000372115 | MUTYH-001 | −2.213 | −1.265 | −1.739 |
| ENST00000530003 | RPS6KA1-003 | −0.558 | −2.996 | −1.777 |
| ENST00000590720 | PSME3-001 | −0.701 | −2.932 | −1.817 |
| ENST00000216155 | SYNGR1-006 | −1.260 | −2.525 | −1.893 |
| ENST00000519882 | ZNF706-003 | −2.177 | −1.626 | −1.902 |
| ENST00000409240 | DCTN1-006 | −0.826 | −2.995 | −1.911 |
| ENST00000371514 | SCP2-001 | −1.218 | −2.609 | −1.914 |
| ENST00000466877 | NAA10-003 | −2.033 | −2.136 | −2.084 |
| ENST00000238823 | FAM98A-001 | −1.203 | −3.017 | −2.110 |
| ENST00000504689 | PLXND1-018 | −3.107 | −1.345 | −2.226 |
| ENST00000248450 | AAMP-001 | −3.757 | −0.903 | −2.330 |
| ENST00000606454 | MIR3916-003 | −3.866 | −0.988 | −2.427 |
| ENST00000407877 | LPAR2-002 | −4.170 | −0.740 | −2.455 |
| ENST00000467943 | COMT-009 | −1.054 | −4.152 | −2.603 |
| ENST00000429586 | ABCF3-001 | −2.377 | −2.990 | −2.683 |
| ENST00000491935 | ADRM1-002 | −4.924 | −0.750 | −2.837 |
| ENST00000264080 | GPR108-001 | −2.672 | −3.020 | −2.846 |
| ENST00000344995 | LAT2-001 | −2.304 | −3.573 | −2.938 |
| ENST00000381480 | DENND1C-001 | −2.977 | −2.926 | −2.951 |
| ENST00000542902 | TAOK3-010 | −3.604 | −2.377 | −2.990 |
| ENST00000393710 | NAA10-017 | −4.818 | −1.179 | −2.999 |
| ENST00000357355 | CD97-002 | −3.353 | −2.743 | −3.048 |
| ENST00000429120 | LY6E-002 | −5.018 | −1.187 | −3.102 |
| ENST00000262629 | TYROBP-001 | −3.955 | −2.933 | −3.444 |

Discussion

The heterogeneity of molecular abnormalities in sAML combined with a paucity of effective treatment options has resulted in high relapse-related mortality rates. In addition to approved therapies, such as the DNA-modifying agents 5-azacytidine and decitabine, many experimental agents also target epigenetic regulators of gene expression in clinical trials for sAML (Kantarjian et al., 2010). However, most of these agents fail to improve patient survival (Burnett et al., 2013), suggesting that epigenetic modifier therapies may reduce leukemic burden but may not effectively target a subpopulation of therapy resistant LSC that drive relapse. Hence, there is a critical need for developing clinical candidates with different modes of action.

Here, we demonstrate that selective splicing modulation impairs AML LSC maintenance and promotes splicing patterns more typical of normal aged HPC expression profiles. Comparative RNA-Seq analyses demonstrate that aging human progenitors display pro-apoptotic BCL2 splice isoform switching, while sAML LSC favor pro-survival expression of BCL2L1 (Bcl-xL). Notably, global spliceosome deregulation sensitizes therapy-resistant AML LSC to pharmacological splicing modulation. In particular, a potent and stable FD-895 analogue, 17S-FD-895, reverted sAML isoform expression and pro-survival BCL2 family splicing patterns, and reduced AML LSC survival and self-renewal in a dose-dependent manner in pre-clinical models. Moreover, 17S-FD-895 exhibited a favorable therapeutic index, impairing LSC maintenance while sparing normal HSPC in humanized hematopoietic progenitor assays.

Alternative splicing occurs in up to 95% of human multi-exon genes during human development and aging (Johnson et al., 2003; Pan et al., 2005), and widespread changes in pre-mRNA splicing have been implicated in various age-related disorders (Mazin et al., 2013). Seminal DNA sequencing and microarray gene expression studies suggest that the risk for transformation to AML is governed by mutations in splicing-related genes (Graubert and Walter, 2011; Li et al., 2011) and epigenetic modifiers of gene expression (Graubert and Walter, 2011; Yoshida et al., 2011). However, the contribution of mutation-dependent or independent spliceosome alterations and other primate-specific RNA processing alterations to LSC generation has not been elucidated.

Here, we provide RNA-Seq based whole transcript, lncRNA and splice isoform expression signatures of human HSC and progenitor aging. Together, these whole gene and splice isoform expression signatures of identify key pathways that are deregulated during human stem cell aging. Unlike HSC, HPC harbor select alterations in inflammatory pathways and alternative splicing of pro-survival genes during aging that may be utilized as biomarkers of premature aging and to identify the therapeutic index provided by splicing modulator therapy.

In contrast to normal aging, widespread disruption of splicing factor gene expression and alternative splicing was observed in sAML LSC and MDS progenitors. Recent studies implicate the spliceosome as a therapeutic vulnerability in solid tumors (Hsu et al., 2015), and here we show that pharmacological splicing modulation with a potent and stable SF3B1-targeted agent selectively eradicated sAML LSC and promoted BCL2 family splice isoform switching, while sparing normal stem and progenitor cells. Notably, genetic and epigenetic alterations typical of AML can induce dependence on BCL2 pro-survival activity (Chan et al., 2015). Moreover, a recent study demonstrated that BCL2-targeted small molecules have the capacity to rejuvenate aged HSC in mice, and may represent a new class of anti-aging molecules (Chang et al., 2016). Thus, splicing modulation leading to BCL2 family splice isoform reprogramming may represent a key component of therapeutic strategies aimed at inducing selective clearance of senescent HSC during normal aging, and eradicating therapy-resistant AML LSC. The results of the present study indicate splicing modulation impairs LSC maintenance primarily through reducing LSC self-renewal, which has direct relevance to the treatment of a variety of advanced stage hematopoietic malignancies and cancer stem cell-driven solid tumors (Barrett et al., 2015; DeBoever et al., 2015; Ferrarese et al., 2014; Salton et al., 2015). Additionally, these studies provide the necessary rationale for carrying out pharmacokinetic analyses including in vivo monitoring of 17S-FD-895 and potential generation of breakdown products, to provide important information on the stability and distribution of this compound compared with less stable spliceosome-targeted small molecules (Hong et al., 2014).

In addition to establishing the in vitro and in vivo LSC inhibitory efficacy of a potent splicing modulatory agent, 17S-FD-895, at doses that spare normal hematopoietic cells, RNA-seq analyses distinguished sAML LSC-specific splice isoforms that may represent predictive biomarkers of disease progression that would enable early intervention. Furthermore, normal versus malignant aging splice isoform switching profiles could be exploited in companion diagnostics to evaluate the efficacy of splicing modulators or other LSC-targeted agents. Together, these results support further development of splicing-targeted LSC eradication strategies, representing an important step forward in preventing disease relapse in AML and other recalcitrant malignancies typified by splicing deregulation (Mazin et al., 2013).

Experimental Procedures

Patient Samples and HSPC Purification.

A collection of AML and MDS patient samples from peripheral blood or bone marrow (Table 1) and normal age-matched controls (FIG. 18A) were obtained from patients who gave informed consent in accordance with Institutional Review Board-approved protocols at UCSD (Human Research Protections Program) and the Fred Hutchinson Cancer Research Center's Leukemia Repository. Bone marrow samples from young donors (FIG. 18A) and CB were obtained from AllCells (Alameda, Calif.). Purified human HSPC and LSC were isolated by FACS and processed for RNA extraction as previously described (Jiang et al., 2013).

Whole Transcriptome Sequencing Analyses.

Gene and isoform expression values in FPKM were obtained from RNA-Seq data essentially as previously described (Jiang et al., 2013) and as detailed in the Supplemental Experimental Procedures. Similar to previous reports (Kirschner et al., 2015), for each comparison, positives for differentially expressed transcripts were identified by the L2FC of the per-group average FPKM+1, then a Benjamini-Hochberg FDR correction was applied using the p.adjust method in the R statistical package.

Chemical Synthesis and Preparation of Splicing Modulatory Compounds.

Synthesis of FD-895 and 17S-FD-895 compounds was performed as previously described (Villa et al., 2012). For in vive studies, 17S-FD-895 was prepared in DMSO at a concentration of 10 mg/mL.

In Vitro Stromal Co-Culture and Splicing Modulation.

As previously described (Goff et al., 2013), humanized bone marrow SL/M2 monolayers were inactivated (irradiated) and then human CD34+ cells selected from AML primary samples and normal controls were added for two weeks of co-culture, followed by methylcellulose-based colony and replating assays. FD-895 or 17S-FD-895 were added at the initiation of co-culture, with DMSO as a vehicle control.

The top 50 significantly differentially expressed isoforms ranked from most increased to most decreased expression in aged (n=4) versus young (n=4) human normal bone marrow stromal cells grown in stromal monolayers, are set forth in Table 5 following. Log 2 fold change (L2FC) values are calculated from FPKM values for all isoforms with average FPKM>1 in aged or young bone marrow stromal cells, absolute L2FC>1, p<0.05.

TABLE 5

Top significantly differentially expressed isoforms ranked from most increased to most decreased expression in aged (n = 4) versus young (n = 4) human normal bone marrow stromal cells grown in stromal monolayers.

| transcript_id (Ensembl GRCh37) | transcript_name | L2FC | PVAL |
|---|---|---|---|
| ENST00000492229 | SON-011 | 3.878 | 0.034 |
| ENST00000459155 | SCARNA12-201 | 3.798 | 0.028 |
| ENST00000518678 | TRAM1-004 | 2.940 | 0.043 |
| ENST00000497055 | SGIP1-008 | 2.709 | 0.000 |
| ENST00000537041 | QKI-016 | 2.707 | 0.049 |
| ENST00000534733 | ST3GAL4-015 | 2.664 | 0.003 |
| ENST00000506409 | MED28-003 | 2.534 | 0.009 |
| ENST00000515114 | CCDC109B-005 | 2.496 | 0.023 |
| ENST00000490253 | PLCG1-006 | 2.481 | 0.002 |
| ENST00000368961 | CD164-201 | 2.424 | 0.004 |
| ENST00000260702 | LOXL4-001 | 2.300 | 0.042 |
| ENST00000533234 | OSBPL5-014 | 2.270 | 0.047 |
| ENST00000394353 | GSN-203 | 2.235 | 0.049 |
| ENST00000574151 | HCFC1R1-004 | 1.829 | 0.010 |
| ENST00000511186 | HSD17B4-015 | 1.568 | 0.006 |
| ENST00000419703 | FNDC1-IT1-001 | 1.489 | 0.002 |
| ENST00000473202 | SERPINE2-004 | 1.265 | 0.001 |
| ENST00000578991 | ELAC2-019 | 1.051 | 0.001 |
| ENST00000589416 | ILF3-019 | 1.045 | 0.004 |
| ENST00000354503 | MFF-022 | 1.023 | 0.001 |
| ENST00000335327 | WASF3-001 | 1.022 | 0.004 |
| ENST00000567999 | DEF8-009 | −1.170 | 0.001 |
| ENST00000393108 | STEAP3-202 | −1.184 | 0.004 |
| ENST00000297620 | FAM219A-008 | −1.399 | 0.006 |
| ENST00000379772 | C20orf27-001 | −1.452 | 0.003 |
| ENST00000451354 | PLEKHG2-006 | −1.478 | 0.006 |
| ENST00000428228 | EMD-007 | −1.681 | 0.009 |
| ENST00000332298 | RGS19-001 | −1.701 | 0.002 |
| ENST00000362068 | ADM2-201 | −1.712 | 0.010 |
| ENST00000552775 | C17orf49-005 | −1.846 | 0.011 |
| ENST00000536752 | AACS-007 | −1.850 | 0.001 |
| ENST00000356488 | SPATA20-004 | −1.874 | 0.015 |
| ENST00000216780 | PCK2-002 | −1.907 | 0.014 |
| ENST00000434436 | MBD3-001 | −1.913 | 0.003 |
| ENST00000400890 | AC011043.1-201 | −1.933 | 0.014 |
| ENST00000413016 | AK1-011 | −1.942 | 0.003 |
| ENST00000592528 | PLIN3-007 | −2.064 | 0.014 |
| ENST00000590869 | ILF3-023 | −2.081 | 0.013 |
| ENST00000549775 | RNASEK-C17orf49-001 | −2.095 | 0.005 |
| ENST00000548577 | RNASEK-001 | −2.121 | 0.012 |
| ENST00000395648 | TP53I11-006 | −2.140 | 0.024 |
| ENST00000498491 | FLNA-008 | −2.164 | 0.004 |
| ENST00000541435 | FXYD5-013 | −2.193 | 0.043 |
| ENST00000565223 | ATP6V0C-004 | −2.241 | 0.003 |
| ENST00000526395 | SIGIRR-023 | −2.338 | 0.008 |
| ENST00000485803 | FHL3-002 | −2.339 | 0.035 |
| ENST00000495313 | SWI5-004 | −2.392 | 0.013 |
| ENST00000550925 | SH2B3-003 | −2.630 | 0.030 |
| ENST00000594568 | TRPM4-010 | −3.189 | 0.020 |
| ENST00000345517 | ACTG2-001 | −3.291 | 0.018 |

AML LSC Primagraft™ Assays and In Vivo 17S-FD-895 Treatment.

All animal studies were performed in accordance with UCSD and NIH-equivalent ethical guidelines and were approved by the Institutional Animal Care and Use Committee. Three AML Primagraft™ models were established from AML LSC-enriched cell fractions (1-2×10$^5$ CD34+ cells) transplanted intrahepatically into neonatal Rag2$^{-/-}$ γ$_c^{-/-}$ as previously described (Abrahamsson et al., 2009), or intravenously into sublethally irradiated adult (6-8 weeks old) NOD/SCID-IL2RG mice (NSGS, Jackson Laboratory). AML-engrafted mice were dosed intravenously with 17S-FD-895 (5-10 mg/kg) or vehicle (15-20% DMSO in PBS) three times over a two-week period (day 1, day 7, and day 14). After treatment, hematopoietic tissues were analyzed as described following.

Reagent and Data Summary

Table 6 following tabulates transcription factors useful in the methods disclosed herein by Ensembl GRCh37 gene_ID and gene-name.

TABLE 6

| Transcription factors | |
|---|---|
| gene_ID (Ensembl GRCh37) | gene_name |
| ENSG00000186951 | PPARA |
| ENSG00000204519 | ZNF551 |
| ENSG00000120738 | EGR1 |
| ENSG00000120738 | HLF |
| ENSG00000125740 | FOSB |
| ENSG00000102804 | TSC22D1 |
| ENSG00000162772 | ATF3 |
| ENSG00000177606 | JUN |
| ENSG00000170345 | FOS |
| ENSG00000157514 | TSC22D3 |
| ENSG00000125968 | ID1 |
| ENSG00000171223 | JUNB |
| ENSG00000117036 | ETV3 |
| ENSG00000173875 | ZNF791 |
| ENSG00000102984 | ZNF821 |
| ENSG00000106004 | HOXA5 |
| ENSG00000123358 | NR4A1 |
| ENSG00000172216 | CEBPB |
| ENSG00000165030 | NFIL3 |
| ENSG00000115738 | ID2 |
| ENSG00000125347 | IRF1 |

Tables 7A-7B tabulate lncRNAs useful for the methods disclosed herein by Ensembl GRCh37 gene_ID and gene-name, for HSC (Table 7A) and HPC (Table 7B). Also tabulated are the L2FC values for each lncRNA.

TABLE 7A

| HSC lncRNAs | | |
|---|---|---|
| gene_ID (Ensembl GRCh37) | gene_name | L2FC |
| ENSG00000231721 | LINC-PINT | 2.7 |
| ENSG00000214548 | MEG3 | 1.8 |
| ENSG00000206344 | HCG27 | 1.7 |
| ENSG00000234883 | MIR155HG | 1.4 |
| ENSG00000239213 | RP11-85F14.5 | 1.4 |
| ENSG00000245532 | NEAT1 | 1.3 |
| ENSG00000236333 | TRHDE-AS1 | 1.2 |
| ENSG00000238113 | RP11-262H14.1 | 1.1 |
| ENSG00000260924 | AC004463.6 | 1 |
| ENSG00000232104 | RP11-509J21.1 | −1.7 |
| ENSG00000223837 | BRD2-IT1 | −2.6 |

TABLE 7B

HPC lncRNAs

| gene_ID (Ensembl GRCh37) | gene_name | L2FC |
|---|---|---|
| ENSG00000257242 | C12orf79 | 2.8 |
| ENSG00000251992 | SCARNA17 | 2.4 |
| ENSG00000188825 | LINC00910 | 2.3 |
| ENSG00000245532 | NEAT1 | 1.7 |
| ENSG00000239569 | KMT2E-AS1 | 1.2 |
| ENSG00000225442 | MPRIP-AS1 | 1.1 |
| ENSG00000251562 | MALAT1 (NEAT2) | 1 |
| ENSG00000218510 | LINC00339 | -1.3 |

Table 8 tabulates spliceosome genes useful in the methods disclosed herein by Ensembl GRCh37 gene_ID and gene-name.

TABLE 8

Spliceosome genes

| gene_ID (Ensembl GRCh37) | gene_name | L2FC | PVAL | QVAL |
|---|---|---|---|---|
| ENSG00000101161 | PRPF6 | 0.80310461 | 0.01135946 | 0.02408806 |
| ENSG00000087365 | SF3B2 | 0.74775823 | 0.0121265 | 0.02419781 |
| ENSG00000100813 | ACIN1 | 0.72369451 | 0.01344323 | 0.02419781 |
| ENSG00000147144 | CCDC12 | 0.63074694 | 0.00925191 | 0.02408806 |
| ENSG00000141759 | TXNL4A | -0.5043694 | 0.03814817 | 0.04928551 |
| ENSG00000170144 | HNRNPA3 | -0.5047599 | 0.03384472 | 0.04887085 |
| ENSG00000135486 | HNRNPA1 | -0.5083236 | 0.00020676 | 0.00372166 |
| ENSG00000139675 | HNRNPA1L2 | -0.5091854 | 0.01583795 | 0.02715076 |
| ENSG00000125743 | SNRPD2 | -0.5162715 | 0.03833318 | 0.04928551 |
| ENSG00000165630 | PRPF18 | -0.5165423 | 0.03402466 | 0.04887085 |
| ENSG00000060688 | SNRNP40 | -0.5488529 | 0.03529562 | 0.04887085 |
| ENSG00000147274 | RBMX | -0.6109845 | 0.00650762 | 0.02342745 |
| ENSG00000100650 | SRSF5 | -0.6375131 | 0.01339621 | 0.02419781 |
| ENSG00000144028 | SNRNP200 | -0.6423808 | 0.00085565 | 0.00694006 |
| ENSG00000100138 | NHP2L1 | -0.655293 | 0.01137492 | 0.02408806 |
| ENSG00000167088 | SNRPD1 | -0.6746622 | 0.02440908 | 0.03994214 |
| ENSG00000169976 | SF3B5 | -0.7212635 | 0.00833504 | 0.02408806 |
| ENSG00000086589 | RBM22 | -0.8236023 | 0.0009639 | 0.00694006 |
| ENSG00000131795 | RBM8A | -0.8522745 | 0.00540306 | 0.02161224 |
| ENSG00000141543 | EIF4A3 | -0.9176155 | 0.03341139 | 0.04887085 |
| ENSG00000116752 | BCAS2 | -1.0168843 | 0.00943553 | 0.02408806 |
| ENSG00000161547 | SRSF2 | -1.0197975 | 0.00302536 | 0.01361412 |
| ENSG00000112081 | SRSF3 | -1.023265 | 0.00164531 | 0.00987185 |
| ENSG00000132792 | CTNNBL1 | -1.0273536 | 0.01047858 | 0.02408806 |
| ENSG00000115875 | SRSF7 | -1.0368379 | 0.00980652 | 0.02408806 |
| ENSG00000162385 | MAGOH | -1.0569937 | 0.00082472 | 0.00694006 |
| ENSG00000108654 | DDX5 | -1.1476375 | 0.00277436 | 0.01361412 |
| ENSG00000124193 | SRSF6 | -1.4551226 | 0.00017567 | 0.00372166 |

Table 9 tabulates additional transcription factors useful in the methods disclosed herein, by Ensembl GRCh37 gene_ID and gene-name.

TABLE 9

Additional transcription factors

| gene_ID (Ensembl GRCh37) | gene_name | L2FC |
|---|---|---|
| ENSG00000141905 | NFIC | 1.5 |
| ENSG00000166888 | STAT6 | 1.4 |
| ENSG00000169083 | AR | 1.3 |
| ENSG00000189067 | LITAF | 1.2 |
| ENSG00000128604 | IRF5 | 1.2 |
| ENSG00000204859 | ZBTB48 | 1.2 |
| ENSG00000143390 | RFX5 | 1.1 |
| ENSG00000124766 | SOX4 | -1.3 |
| ENSG00000029993 | HMGB3 | -1.3 |
| ENSG00000119508 | NR4A3 | -1.4 |
| ENSG00000140968 | IRF8 | -1.4 |
| ENSG00000007968 | E2F2 | -1.5 |

TABLE 9-continued

Additional transcription factors

| gene_ID (Ensembl GRCh37) | gene_name | L2FC |
|---|---|---|
| ENSG00000162599 | NFIA | -1.5 |
| ENSG00000141510 | TP53 | -1.5 |
| ENSG00000185630 | PBX1 | -1.5 |
| ENSG00000147862 | NFIB | -1.7 |
| ENSG00000117036 | ETV3 | -2 |
| ENSG00000153234 | NR4A2 | -2.2 |
| ENSG00000117318 | ID3 | -2.3 |
| ENSG00000123358 | NR4A1 | -3 |
| ENSG00000137265 | IRF4 | -3.2 |
| ENSG00000164330 | EBF1 | -3.9 |

Table 10 tabulated additional lncRNAs useful in the methods disclosed herein, by Ensembl GRCh37 gene_ID and gene-name.

TABLE 10

Additional lncRNAs.

| gene_ID (Ensembl GRCh37) | gene_name | L2FC |
|---|---|---|
| ENSG00000214548 | MEG3 | 3.9 |
| ENSG00000204625 | HCG9 | 2.7 |
| ENSG00000227502 | RP1-249H1.4 | 2.1 |
| ENSG00000229989 | MIR181A1HG | 1.7 |
| ENSG00000242258 | LINC00996 | 1.6 |
| ENSG00000246263 | KB-431C1.4 | 1.5 |
| ENSG00000252122 | SNORA76 | 1.5 |
| ENSG00000256007 | ARAP1-AS1 | 1.3 |
| ENSG00000260260 | RP11-304L19.5 | 1.3 |
| ENSG00000233429 | HOTAIRM1 | 1.3 |
| ENSG00000227953 | RP11-439E19.3 | 1.2 |
| ENSG00000245937 | CTC-228N24.3 | 1.2 |

TABLE 10-continued

Additional lncRNAs.

| gene_ID (Ensembl GRCh37) | gene_name | L2FC |
|---|---|---|
| ENSG00000236709 | DAPK1-IT1 | 1.1 |
| ENSG00000269220 | LINC00528 | 1 |
| ENSG00000227028 | SLC8A1-AS1 | −1.2 |
| ENSG00000182648 | LINC01006 | −1.2 |
| ENSG00000249859 | PVT1 | −1.3 |
| ENSG00000187621 | TCL6 | −1.3 |
| ENSG00000230945 | RP11-394O9.1 | −1.4 |
| ENSG00000247774 | PCED1B-AS1 | −1.8 |
| ENSG00000228495 | LTNC01013 | −2.4 |
| ENSG00000214049 | UCA1 | −3.6 |

Tables 11A-11B tabulate the results disclosed in FIG. 11D for L2FC greater than zero, and less than zero, respectively.

TABLE 11A

Tabulation of data from FIG. 11D wherein L2FC is greater than zero.

| transcript_id | transcript_name | L2FC | ABS L2FC | PVAL | QVAL | Volcano Vector |
|---|---|---|---|---|---|---|
| ENST00000486554 | TSC22D3-006 | 2.847 | 2.847 | 0.000 | 0.039 | 4.591 |
| ENST00000248673 | ZFP36-201 | 2.842 | 2.842 | 0.000 | 0.041 | 4.363 |
| ENST00000586113 | FOSB-009 | 2.744 | 2.744 | 0.000 | 0.039 | 4.672 |
| ENST00000343677 | HIST1H1C-001 | 2.183 | 2.183 | 0.000 | 0.039 | 4.129 |
| ENST00000555242 | FOS-008 | 2.031 | 2.031 | 0.000 | 0.039 | 4.029 |
| ENST00000592811 | FOSB-008 | 1.985 | 1.985 | 0.000 | 0.039 | 4.090 |
| ENST00000528443 | TOR1AIP1-001 | 1.564 | 1.564 | 0.000 | 0.039 | 3.785 |
| ENST00000554617 | FOS-005 | 1.390 | 1.390 | 0.001 | 0.044 | 3.451 |
| ENST00000499732 | NEAT1-002 | 1.297 | 1.297 | 0.001 | 0.044 | 3.411 |

TABLE 11B

Tabulation of data from FIG. 11D wherein L2FC is less than zero.

| transcript_id | transcript_name | L2FC | ABS L2FC | PVAL | QVAL | Volcano Vector |
|---|---|---|---|---|---|---|
| ENST00000379953 | LY86-001 | −1.112 | 1.112 | 0.000 | 0.039 | 3.538 |
| ENST00000495215 | TRNAU1AP-008 | −1.327 | 1.327 | 0.000 | 0.039 | 3.723 |
| ENST00000354291 | DDX55-012 | −1.363 | 1.363 | 0.000 | 0.039 | 4.158 |
| ENST00000429859 | RP4-717I23.3-011 | −1.414 | 1.414 | 0.000 | 0.036 | 4.812 |
| ENST00000375972 | YME1L1-201 | −1.423 | 1.423 | 0.000 | 0.039 | 3.671 |
| ENST00000462189 | MOGS-004 | −1.448 | 1.448 | 0.001 | 0.047 | 3.425 |
| ENST00000481007 | LYPLAL1-012 | −1.477 | 1.477 | 0.000 | 0.039 | 4.029 |
| ENST00000359301 | ZC3H14-201 | −1.489 | 1.489 | 0.000 | 0.039 | 3.698 |
| ENST00000607660 | INTS10-019 | −1.494 | 1.494 | 0.000 | 0.039 | 3.882 |
| ENST00000569770 | MBTPS1-015 | −1.495 | 1.495 | 0.001 | 0.041 | 3.554 |
| ENST00000506789 | CDK7-010 | −1.509 | 1.509 | 0.001 | 0.041 | 3.595 |
| ENST00000561855 | MAZ-012 | −1.690 | 1.690 | 0.000 | 0.039 | 4.077 |
| ENST00000447713 | ANKRD44-012 | −1.956 | 1.956 | 0.000 | 0.039 | 4.019 |
| ENST00000447740 | CARD8-204 | −2.212 | 2.212 | 0.001 | 0.041 | 3.913 |
| ENST00000552606 | CCDC59-005 | −2.341 | 2.341 | 0.001 | 0.041 | 3.995 |

Tables 12A-12B tabulate the data of FIG. 11E for L2FC greater than zero, and less than zero, respectively.

TABLE 12A

Tabulation of data from FIG. 11E wherein L2FC is greater than zero.

| transcript_id (Ensembl GRCh37) | transcript_name | L2FC | ABS L2FC | PVAL | QVAL | Volcano Vector |
|---|---|---|---|---|---|---|
| ENST00000365645 | VTRNA1-3-201 | 4.223 | 4.223 | 0.003 | 0.032 | 4.912 |
| ENST00000364931 | RNU5E-4P-201 | 3.797 | 3.797 | 0.003 | 0.030 | 4.586 |
| ENST00000307365 | DDIT4-001 | 3.615 | 3.615 | 0.011 | 0.046 | 4.112 |
| ENST00000242152 | NPY-001 | 3.535 | 3.535 | 0.008 | 0.043 | 4.115 |
| ENST00000314332 | HIST1H2BC-003 | 3.449 | 3.449 | 0.002 | 0.029 | 4.372 |
| ENST00000462639 | SAT1-007 | 3.393 | 3.393 | 0.002 | 0.028 | 4.372 |
| ENST00000548363 | TUBA1A-015 | 3.316 | 3.316 | 0.009 | 0.044 | 3.906 |
| ENST00000244601 | HIST1H2BG-001 | 3.168 | 3.168 | 0.001 | 0.028 | 4.552 |
| ENST00000303910 | HIST1H2AE-001 | 3.053 | 3.053 | 0.001 | 0.028 | 4.362 |
| ENST00000508487 | CXCL2-001 | 3.042 | 3.042 | 0.002 | 0.030 | 4.011 |

TABLE 12A-continued

Tabulation of data from FIG. 11E wherein L2FC is greater than zero.

| transcript_id (Ensembl GRCh37) | transcript_name | L2FC | ABS L2FC | PVAL | QVAL | Volcano Vector |
|---|---|---|---|---|---|---|
| ENST00000379251 | SAT1-004 | 2.957 | 2.957 | 0.002 | 0.028 | 4.062 |
| ENST00000588696 | SEC14L1-007 | 2.884 | 2.884 | 0.012 | 0.048 | 3.459 |
| ENST00000248673 | ZFP36-201 | 2.861 | 2.861 | 0.008 | 0.043 | 3.544 |
| ENST00000396984 | HIST1H2BC-002 | 2.798 | 2.798 | 0.002 | 0.028 | 3.962 |
| ENST00000474223 | SAT1-006 | 2.698 | 2.698 | 0.004 | 0.033 | 3.590 |
| ENST00000365574 | RNU5E-6P-201 | 2.696 | 2.696 | 0.008 | 0.044 | 3.400 |
| ENST00000356476 | HIST1H3D-001 | 2.616 | 2.616 | 0.001 | 0.028 | 3.899 |
| ENST00000534719 | FTH1-009 | 2.602 | 2.602 | 0.005 | 0.034 | 3.465 |
| ENST00000365626 | RNVU1-20-201 | 2.555 | 2.555 | 0.007 | 0.040 | 3.350 |
| ENST00000364688 | RNVU1-6-201 | 2.522 | 2.522 | 0.004 | 0.032 | 3.506 |
| ENST00000602277 | RP6-99M1.3-001 | 2.389 | 2.389 | 0.003 | 0.032 | 3.456 |
| ENST00000228434 | CD69-001 | 2.387 | 2.387 | 0.001 | 0.028 | 3.918 |
| ENST00000377777 | HIST1H2BD-002 | 2.341 | 2.341 | 0.002 | 0.028 | 3.661 |
| ENST00000607315 | RP11-51J9.5-001 | 2.286 | 2.286 | 0.004 | 0.033 | 3.314 |
| ENST00000379253 | SAT1-003 | 2.280 | 2.280 | 0.010 | 0.044 | 3.043 |
| ENST00000608684 | RP11-386I14.4-001 | 2.218 | 2.218 | 0.000 | 0.024 | 4.142 |
| ENST00000416624 | CD69-002 | 2.201 | 2.201 | 0.000 | 0.028 | 3.984 |
| ENST00000536709 | CD69-003 | 2.190 | 2.190 | 0.000 | 0.016 | 4.450 |
| ENST00000370986 | GADD45A-001 | 2.181 | 2.181 | 0.006 | 0.039 | 3.096 |
| ENST00000495813 | SLC2A3-002 | 2.150 | 2.150 | 0.005 | 0.034 | 3.162 |
| ENST00000369155 | HIST2H2BE-001 | 2.136 | 2.136 | 0.001 | 0.028 | 3.662 |
| ENST00000289577 | TMED4-005 | 2.115 | 2.115 | 0.000 | 0.020 | 4.203 |
| ENST00000411315 | RNU2-64P-201 | 2.096 | 2.096 | 0.010 | 0.045 | 2.896 |
| ENST00000367577 | TER5-001 | 2.092 | 2.092 | 0.011 | 0.045 | 2.879 |
| ENST00000589949 | H3F3B-008 | 2.068 | 2.068 | 0.004 | 0.032 | 3.204 |
| ENST00000239223 | DUSP1-001 | 2.064 | 2.064 | 0.001 | 0.028 | 3.579 |
| ENST00000520420 | CREBRF-004 | 2.032 | 2.032 | 0.009 | 0.044 | 2.872 |
| ENST00000601309 | HNRNPUL1-019 | 2.018 | 2.018 | 0.010 | 0.045 | 2.838 |
| ENST00000509150 | ATP2C1-023 | 2.011 | 2.011 | 0.009 | 0.044 | 2.877 |
| ENST00000357647 | HIST1H3A-001 | 1.958 | 1.958 | 0.001 | 0.028 | 3.694 |
| ENST00000343677 | HIST1H1C-001 | 1.950 | 1.950 | 0.009 | 0.044 | 2.813 |
| ENST00000482091 | IDI1-001 | 1.930 | 1.930 | 0.007 | 0.040 | 2.902 |
| ENST00000507022 | MRPS36-006 | 1.927 | 1.927 | 0.004 | 0.032 | 3.120 |
| ENST00000369163 | HIST1H3H-001 | 1.891 | 1.891 | 0.005 | 0.034 | 2.972 |
| ENST00000515833 | MATR3-036 | 1.797 | 1.797 | 0.003 | 0.030 | 3.150 |
| ENST00000511207 | CCNH-009 | 1.795 | 1.795 | 0.002 | 0.029 | 3.212 |
| ENST00000409769 | CLK1-005 | 1.780 | 1.780 | 0.004 | 0.033 | 2.990 |
| ENST00000560274 | RPLP1-006 | 1.779 | 1.779 | 0.001 | 0.028 | 3.411 |
| ENST00000377364 | HIST1H4B-001 | 1.757 | 1.757 | 0.001 | 0.028 | 3.504 |
| ENST00000534470 | EIF4G2-032 | 1.739 | 1.739 | 0.002 | 0.030 | 3.132 |
| ENST00000421512 | TBP-004 | 1.736 | 1.736 | 0.002 | 0.029 | 3.205 |
| ENST00000409685 | FAM124B-003 | 1.722 | 1.722 | 0.006 | 0.039 | 2.801 |
| ENST00000545027 | ETV6-004 | 1.713 | 1.713 | 0.004 | 0.032 | 2.986 |
| ENST00000377831 | HIST1H3D-201 | 1.616 | 1.616 | 0.004 | 0.033 | 2.857 |
| ENST00000438169 | KRR1-003 | 1.575 | 1.575 | 0.005 | 0.034 | 2.807 |
| ENST00000459299 | SNORD13-201 | 1.568 | 1.568 | 0.005 | 0.034 | 2.816 |
| ENST00000369159 | HIST2H2AA4-001 | 1.527 | 1.527 | 0.001 | 0.028 | 3.351 |
| ENST00000476634 | SLC2A3-004 | 1.484 | 1.484 | 0.002 | 0.028 | 3.173 |
| ENST00000486554 | TSC22D3-006 | 1.483 | 1.483 | 0.000 | 0.024 | 3.774 |
| ENST00000590335 | FOSB-006 | 1.473 | 1.473 | 0.003 | 0.031 | 2.936 |
| ENST00000377745 | HIST1H4F-001 | 1.457 | 1.457 | 0.000 | 0.016 | 4.163 |
| ENST00000554988 | RPPH1-001 | 1.435 | 1.435 | 0.002 | 0.028 | 3.106 |
| ENST00000243806 | FAM124B-001 | 1.421 | 1.421 | 0.001 | 0.028 | 3.179 |
| ENST00000511865 | REEP5-006 | 1.411 | 1.411 | 0.002 | 0.029 | 3.046 |
| ENST00000549490 | UBE2N-005 | 1.391 | 1.391 | 0.001 | 0.028 | 3.396 |
| ENST00000565108 | CMC2-021 | 1.377 | 1.377 | 0.002 | 0.028 | 3.137 |
| ENST00000377401 | HIST1H2BL-001 | 1.339 | 1.339 | 0.002 | 0.029 | 2.993 |
| ENST00000321356 | CLK1-001 | 1.334 | 1.334 | 0.001 | 0.028 | 3.183 |
| ENST00000484921 | ARL6IP5-006 | 1.285 | 1.285 | 0.002 | 0.028 | 3.051 |
| ENST00000520618 | SNX16-012 | 1.260 | 1.260 | 0.000 | 0.016 | 4.396 |
| ENST00000541694 | AC084018.1-011 | 1.228 | 1.228 | 0.001 | 0.028 | 3.268 |
| ENST00000601837 | EID2B-002 | 1.197 | 1.197 | 0.002 | 0.028 | 3.031 |
| ENST00000282388 | ZFP36L2-001 | 1.193 | 1.193 | 0.002 | 0.029 | 2.923 |
| ENST00000465085 | ABCD4-017 | 1.175 | 1.175 | 0.002 | 0.030 | 2.857 |
| ENST00000453677 | KMT2E-AS1-001 | 1.168 | 1.168 | 0.003 | 0.030 | 2.833 |
| ENST00000596355 | RP11-315I20.1-018 | 1.163 | 1.163 | 0.001 | 0.028 | 3.066 |
| ENST00000460600 | PNISR-004 | 1.157 | 1.157 | 0.000 | 0.020 | 3.833 |
| ENST00000243189 | C1orf63-001 | 1.148 | 1.148 | 0.003 | 0.030 | 2.825 |
| ENST00000517805 | RPL30-012 | 1.145 | 1.145 | 0.002 | 0.028 | 2.979 |
| ENST00000202017 | PDRG1-001 | 1.141 | 1.141 | 0.001 | 0.028 | 3.161 |
| ENST00000431446 | RBMX-003 | 1.019 | 1.019 | 0.001 | 0.028 | 3.301 |
| ENST00000453018 | HGF-006 | 1.013 | 1.013 | 0.000 | 0.016 | 4.043 |
| ENST00000521889 | C8orf44-005 | 1.001 | 1.001 | 0.002 | 0.029 | 2.838 |

TABLE 12B

Tabulation of data from FIG. HE wherein L2FC is less than zero.

| transcript_id (Ensembl GRCh37) | transcript_name | L2FC | ABS L2FC | PVAL | QVAL | Volcano Vector |
|---|---|---|---|---|---|---|
| ENST00000423368 | CNOT4-001 | −1.023 | 1.023 | 0.000 | 0.027 | 3.518 |
| ENST00000580571 | MIF4GD-005 | −1.025 | 1.025 | 0.001 | 0.028 | 3.407 |
| ENST00000462069 | C3orf14-004 | −1.032 | 1.032 | 0.000 | 0.016 | 4.417 |
| ENST00000574128 | MED31-004 | −1.107 | 1.107 | 0.003 | 0.030 | 2.827 |
| ENST00000391742 | LAIR1-001 | −1.184 | 1.184 | 0.001 | 0.028 | 3.129 |
| ENST00000361785 | RNF13-002 | −1.219 | 1.219 | 0.002 | 0.029 | 2.910 |
| ENST00000367367 | PTPRC-005 | −1.290 | 1.290 | 0.001 | 0.028 | 3.334 |
| ENST00000376557 | PRR3-002 | −1.374 | 1.374 | 0.003 | 0.032 | 2.822 |
| ENST00000355499 | YY1AP1-034 | −1.446 | 1.446 | 0.002 | 0.028 | 3.170 |
| ENST00000420503 | LINC00339-003 | −1.524 | 1.524 | 0.001 | 0.028 | 3.525 |
| ENST00000509081 | RASGEF1B-002 | −1.534 | 1.534 | 0.000 | 0.016 | 4.156 |
| ENST00000479041 | AOX3P-002 | −1.589 | 1.589 | 0.003 | 0.032 | 2.927 |
| ENST00000436911 | TRGC2-001 | −1.625 | 1.625 | 0.005 | 0.034 | 2.827 |
| ENST00000243347 | TNFAIP6-001 | −1.680 | 1.680 | 0.002 | 0.028 | 3.214 |
| ENST00000325074 | RUNX1-201 | −1.970 | 1.970 | 0.005 | 0.034 | 3.015 |
| ENST00000394223 | NDUFC1-004 | −2.010 | 2.010 | 0.003 | 0.032 | 3.222 |
| ENST00000410457 | RNU2-28P-201 | −2.226 | 2.226 | 0.001 | 0.028 | 3.658 |

Tables 13A-13B tabulate the data of FIG. 12D for L2FC greater than zero, and less than zero, respectively.

TABLE 13A

Tabulation of data from FIG. 12D wherein L2FC is greater than zero.

| transcript_id (Ensembl GRCh37) | transcript name | L2FC | ABS L2FC | PVAL | QVAL | Volcano Vector |
|---|---|---|---|---|---|---|
| ENST00000586925 | FXYD5-009 | 4.439 | 4.439 | 0.000 | 0.005 | 5.559 |
| ENST00000525690 | RPS3-023 | 4.299 | 4.299 | 0.001 | 0.007 | 5.170 |
| ENST00000485708 | RPS24-002 | 4.065 | 4.065 | 0.001 | 0.007 | 4.973 |
| ENST00000547479 | NAP1L1-018 | 4.018 | 4.018 | 0.000 | 0.001 | 6.303 |
| ENST00000436911 | TRGC2-001 | 3.869 | 3.869 | 0.001 | 0.007 | 4.816 |
| ENST00000528086 | CD44-012 | 3.815 | 3.815 | 0.003 | 0.011 | 4.557 |
| ENST00000570382 | ACTG1-014 | 3.278 | 3.278 | 0.000 | 0.005 | 4.688 |
| ENST00000368811 | S100A10-001 | 3.071 | 3.071 | 0.000 | 0.004 | 4.652 |
| ENST00000541549 | EIF3A-201 | 2.910 | 2.910 | 0.000 | 0.003 | 5.009 |
| ENST00000576544 | ACTG1-006 | 2.895 | 2.895 | 0.001 | 0.006 | 4.221 |
| ENST00000491410 | NRD1-005 | 2.855 | 2.855 | 0.000 | 0.000 | 6.840 |
| ENST00000302347 | ITGB2-201 | 2.848 | 2.848 | 0.001 | 0.005 | 4.347 |
| ENST00000416215 | PTPN6-003 | 2.623 | 2.623 | 0.000 | 0.003 | 4.915 |
| ENST00000589517 | TYROBP-002 | 2.616 | 2.616 | 0.000 | 0.005 | 4.219 |
| ENST00000252725 | ARPC1B-001 | 2.269 | 2.269 | 0.000 | 0.004 | 4.290 |
| ENST00000300060 | ANPEP-001 | 2.212 | 2.212 | 0.000 | 0.004 | 4.265 |
| ENST00000587561 | LMAN1-005 | 2.136 | 2.136 | 0.000 | 0.003 | 4.595 |
| ENST00000415231 | TAC3-010 | 2.052 | 2.052 | 0.000 | 0.000 | 7.670 |
| ENST00000568406 | C1orf228-020 | 2.034 | 2.034 | 0.000 | 0.004 | 4.371 |
| ENST00000541365 | CEP57-011 | 2.019 | 2.019 | 0.000 | 0.003 | 4.597 |
| ENST00000305533 | TWF2-001 | 2.013 | 2.013 | 0.000 | 0.004 | 4.226 |
| ENST00000572457 | ARRB2-003 | 1.940 | 1.940 | 0.000 | 0.003 | 4.514 |
| ENST00000420218 | PTK2B-202 | 1.912 | 1.912 | 0.000 | 0.003 | 4.536 |
| ENST00000427321 | C1orf228-011 | 1.863 | 1.863 | 0.000 | 0.003 | 4.539 |
| ENST00000502635 | DCP2-008 | 1.807 | 1.807 | 0.000 | 0.004 | 4.235 |
| ENST00000488324 | PPP1R18-003 | 1.769 | 1.769 | 0.000 | 0.003 | 4.469 |
| ENST00000472498 | RPL37P2-001 | 1.762 | 1.762 | 0.000 | 0.000 | 6.418 |
| ENST00000319511 | TMUB2-002 | 1.723 | 1.723 | 0.000 | 0.004 | 4.148 |
| ENST00000326005 | OAZ2-001 | 1.718 | 1.718 | 0.000 | 0.003 | 4.459 |
| ENST00000346049 | PTK2B-001 | 1.663 | 1.663 | 0.000 | 0.004 | 4.134 |
| ENST00000441658 | RP11-77O7.1-001 | 1.624 | 1.624 | 0.000 | 0.002 | 4.691 |
| ENST00000511155 | XPC-007 | 1.619 | 1.619 | 0.000 | 0.004 | 4.224 |
| ENST00000544691 | SDR39U1-003 | 1.551 | 1.551 | 0.000 | 0.002 | 4.764 |
| ENST00000480624 | MACF1-014 | 1.504 | 1.504 | 0.000 | 0.002 | 5.006 |
| ENST00000312423 | SWSAP1-001 | 1.443 | 1.443 | 0.000 | 0.003 | 4.404 |
| ENST00000563576 | MGA-002 | 1.443 | 1.443 | 0.000 | 0.003 | 4.327 |
| ENST00000485803 | FHL3-002 | 1.438 | 1.438 | 0.000 | 0.001 | 5.726 |
| ENST00000496289 | ZC3H15-005 | 1.404 | 1.404 | 0.000 | 0.004 | 4.157 |
| ENST00000375040 | GPSM3-001 | 1.380 | 1.380 | 0.000 | 0.002 | 4.797 |
| ENST00000459726 | RBM28-003 | 1.378 | 1.378 | 0.000 | 0.002 | 4.802 |
| ENST00000584294 | LPIN2-002 | 1.372 | 1.372 | 0.000 | 0.001 | 5.720 |
| ENST00000424649 | PXN-002 | 1.292 | 1.292 | 0.000 | 0.000 | 6.531 |
| ENST00000430629 | WASF2-001 | 1.270 | 1.270 | 0.000 | 0.001 | 5.366 |
| ENST00000293831 | EIF4A1-001 | 1.175 | 1.175 | 0.000 | 0.003 | 4.171 |

TABLE 13A-continued

Tabulation of data from FIG. 12D wherein L2FC is greater than zero.

| transcript_id (Ensembl GRCh37) | transcript name | L2FC | ABS L2FC | PVAL | QVAL | Volcano Vector |
|---|---|---|---|---|---|---|
| ENST00000496499 | RN7SL182P-201 | 1.161 | 1.161 | 0.000 | 0.001 | 5.470 |
| ENST00000600628 | SSBP4-008 | 1.120 | 1.120 | 0.000 | 0.001 | 5.192 |
| ENST00000418929 | PRR12-001 | 1.084 | 1.084 | 0.000 | 0.002 | 4.793 |
| ENST00000450863 | GOLGA4-004 | 1.063 | 1.063 | 0.000 | 0.001 | 5.577 |
| ENST00000330736 | ANKRD11-011 | 1.021 | 1.021 | 0.000 | 0.003 | 4.175 |
| ENST00000357508 | C1orf228-005 | 1.017 | 1.017 | 0.000 | 0.001 | 5.410 |

TABLE 13B

Tabulation of data from FIG. 12D wherein L2FC is less than zero.

| transcript_id (Ensembl GRCh37) | transcript_name | L2FC | ABS L2FC | PVAL | QVAL | Volcano Vector |
|---|---|---|---|---|---|---|
| ENST00000550146 | TMEM106C-007 | −1.061 | 1.061 | 0.000 | 0.002 | 4.600 |
| ENST00000498704 | RABL5-007 | −1.087 | 1.087 | 0.000 | 0.003 | 4.363 |
| ENST00000532152 | EIF4G2-022 | −1.110 | 1.110 | 0.000 | 0.003 | 4.331 |
| ENST00000521273 | HNRNPA1P7-001 | −1.119 | 1.119 | 0.000 | 0.001 | 5.815 |
| ENST00000546989 | RPLP0-008 | −1.257 | 1.257 | 0.000 | 0.003 | 4.389 |
| ENST00000452673 | CANX-005 | −1.316 | 1.316 | 0.000 | 0.002 | 4.617 |
| ENST00000548355 | TMEM106C-020 | −1.316 | 1.316 | 0.000 | 0.003 | 4.345 |
| ENST00000374594 | CTNNAL1-003 | −1.319 | 1.319 | 0.000 | 0.003 | 4.212 |
| ENST00000502784 | NPM1P27-001 | −1.366 | 1.366 | 0.000 | 0.003 | 4.175 |
| ENST00000522304 | NCAPH2-016 | −1.399 | 1.399 | 0.000 | 0.003 | 4.204 |
| ENST00000461768 | SRRM1-017 | −1.410 | 1.410 | 0.000 | 0.003 | 4.261 |
| ENST00000600519 | FAM129C-007 | −1.515 | 1.515 | 0.000 | 0.003 | 4.268 |
| ENST00000405805 | HMGB1-012 | −1.554 | 1.554 | 0.000 | 0.004 | 4.175 |
| ENST00000258349 | RC3H1-201 | −1.588 | 1.588 | 0.000 | 0.003 | 4.414 |
| ENST00000282507 | UGT3A2-001 | −1.702 | 1.702 | 0.000 | 0.003 | 4.362 |
| ENST00000409290 | WIPF3-002 | −1.777 | 1.777 | 0.000 | 0.004 | 4.147 |
| ENST00000505636 | RP11-315A17.1-001 | −1.815 | 1.815 | 0.000 | 0.004 | 4.315 |
| ENST00000431467 | ING3-006 | −1.843 | 1.843 | 0.000 | 0.003 | 4.628 |
| ENST00000427726 | ING3-005 | −1.868 | 1.868 | 0.000 | 0.003 | 4.520 |
| ENST00000520990 | CA1-009 | −1.871 | 1.871 | 0.000 | 0.004 | 4.238 |
| ENST00000450948 | IGHV5-78-001 | −2.035 | 2.035 | 0.000 | 0.004 | 4.386 |
| ENST00000503828 | CAST-038 | −2.320 | 2.320 | 0.000 | 0.004 | 4.303 |
| ENST00000261769 | CDH1-001 | −2.359 | 2.359 | 0.000 | 0.002 | 5.210 |
| ENST00000339121 | ING3-002 | −2.360 | 2.360 | 0.000 | 0.002 | 5.103 |
| ENST00000284878 | CXADR-001 | −2.412 | 2.412 | 0.000 | 0.004 | 4.390 |
| ENST00000289448 | HMHB1-001 | −2.439 | 2.439 | 0.000 | 0.004 | 4.415 |
| ENST00000416501 | AC015987.2-201 | −2.465 | 2.465 | 0.000 | 0.001 | 5.488 |
| ENST00000323224 | TYMS-002 | −2.570 | 2.570 | 0.000 | 0.005 | 4.190 |
| ENST00000282388 | ZFP36L2-001 | −2.724 | 2.724 | 0.000 | 0.001 | 6.090 |
| ENST00000509259 | CAST-039 | −2.780 | 2.780 | 0.001 | 0.006 | 4.199 |
| ENST00000302273 | VPREB1-002 | −2.817 | 2.817 | 0.001 | 0.006 | 4.235 |
| ENST00000360091 | EWSR1-019 | −2.827 | 2.827 | 0.000 | 0.004 | 4.550 |
| ENST00000420189 | FAM134A-004 | −2.830 | 2.830 | 0.000 | 0.005 | 4.369 |
| ENST00000430694 | AC096579.7-001 | −2.964 | 2.964 | 0.000 | 0.005 | 4.485 |
| ENST00000391248 | RNU1-78P-201 | −2.977 | 2.977 | 0.000 | 0.004 | 4.703 |
| ENST00000368868 | SELENBP1-001 | −3.017 | 3.017 | 0.000 | 0.002 | 5.577 |
| ENST00000335295 | HBB-001 | −3.091 | 3.091 | 0.002 | 0.008 | 4.157 |
| ENST00000313708 | EBF1-001 | −3.209 | 3.209 | 0.001 | 0.006 | 4.411 |
| ENST00000221804 | CLC-001 | −3.247 | 3.247 | 0.001 | 0.007 | 4.413 |
| ENST00000235382 | RGS2-001 | −3.298 | 3.298 | 0.001 | 0.007 | 4.430 |
| ENST00000397381 | UCA1-001 | −3.481 | 3.481 | 0.000 | 0.001 | 6.067 |
| ENST00000534180 | FTH1-002 | −3.547 | 3.547 | 0.002 | 0.008 | 4.515 |
| ENST00000302312 | AHSP-001 | −3.563 | 3.563 | 0.000 | 0.004 | 5.051 |
| ENST00000383907 | SNORA22-201 | −3.631 | 3.631 | 0.000 | 0.000 | 7.088 |
| ENST00000547798 | TMBIM6-006 | −4.629 | 4.629 | 0.000 | 0.002 | 6.381 |
| ENST00000242152 | NPY-001 | −4.888 | 4.888 | 0.001 | 0.006 | 5.780 |
| ENST00000367459 | RGS1-001 | −5.000 | 5.000 | 0.002 | 0.008 | 5.719 |
| ENST00000548925 | BLOC1S1-001 | −5.755 | 5.755 | 0.000 | 0.001 | 7.877 |
| ENST00000248948 | VPREB3-001 | −6.280 | 6.280 | 0.000 | 0.000 | 8.639 |
| ENST00000479563 | RPL14-003 | −7.357 | 7.357 | 0.000 | 0.005 | 8.135 |

Table 14A-14B tabulate the data of Table 4 for L2FC greater than zero, and less than zero, respectively.

TABLE 14A

Data of Table 4 re-tabulated wherein L2FC is greater than zero.

| transcript_id (Ensembl GRCh37) | transcript_name | L2FC BM 10 | L2FC sp 10 | Average L2FC |
|---|---|---|---|---|
| ENST00000426951 | RBM39-039 | 2.701 | 3.541 | 3.121 |
| ENST00000596102 | AL353354.2-201 | 3.801 | 1.976 | 2.888 |
| ENST00000360385 | ZNF317-002 | 3.274 | 2.127 | 2.700 |
| ENST00000461326 | CLK1-013 | 3.722 | 0.840 | 2.281 |
| ENST00000428863 | MDM2-204 | 2.293 | 1.906 | 2.100 |
| ENST00000495394 | RPSA-004 | 2.430 | 1.656 | 2.043 |
| ENST00000579996 | DDX5-007 | 2.553 | 1.451 | 2.002 |
| ENST00000577787 | DDX5-019 | 2.845 | 1.136 | 1.991 |
| ENST00000533161 | RPS2-002 | 2.826 | 1.136 | 1.981 |
| ENST00000548363 | TUBA1A-015 | 1.877 | 2.062 | 1.970 |
| ENST00000409817 | CXCR4-003 | 2.913 | 0.999 | 1.956 |
| ENST00000489149 | DTL-003 | 1.698 | 2.082 | 1.890 |
| ENST00000583894 | DDX5-017 | 2.895 | 0.853 | 1.874 |
| ENST00000510864 | PRIMPOL-010 | 1.100 | 2.343 | 1.722 |
| ENST00000576274 | NDC80-013 | 0.851 | 2.280 | 1.566 |
| ENST00000514518 | CAMLG-002 | 0.540 | 2.424 | 1.482 |
| ENST00000557134 | MNAT1-008 | 1.739 | 1.212 | 1.475 |
| ENST00000402105 | HPS4-008 | 1.915 | 0.932 | 1.423 |
| ENST00000492674 | STAG3-018 | 1.407 | 1.428 | 1.418 |
| ENST00000327898 | AFMID-001 | 1.761 | 1.055 | 1.408 |
| ENST00000590308 | LDLRAD4-005 | 1.233 | 1.090 | 1.162 |
| ENST00000553494 | PRC1-011 | 0.974 | 1.298 | 1.136 |
| ENST00000222597 | CBLL1-014 | 0.696 | 1.140 | 0.918 |
| ENST00000435634 | EXOSC6-001 | 0.653 | 0.545 | 0.599 |
| ENST00000416501 | AC015987.2-201 | 0.646 | 0.544 | 0.595 |

TABLE 14B

Data of Table 4 re-tabulated wherein L2FC is less than zero.

| transcript_id (Ensembl GRCh37) | transcript_name | L2FC BM 10 | L2FC sp 10 | Average L2FC |
|---|---|---|---|---|
| ENST00000279247 | CAPN1-003 | −0.661 | −0.567 | −0.614 |
| ENST00000314830 | SH2D3C-004 | −0.516 | −0.725 | −0.620 |
| ENST00000509198 | LRPAP1-002 | −0.566 | −0.731 | −0.648 |
| ENST00000158762 | ACAP1-001 | −0.803 | −0.505 | −0.654 |
| ENST00000556363 | MCTP2-005 | −0.645 | −0.663 | −0.654 |
| ENST00000380870 | ZNF738-002 | −0.708 | −0.618 | −0.663 |
| ENST00000258412 | TMBIM1-001 | −0.553 | −0.780 | −0.667 |
| ENST00000394957 | C10orf54-001 | −0.620 | −0.737 | −0.678 |
| ENST00000608424 | WDR6-024 | −0.657 | −0.713 | −0.685 |
| ENST00000338257 | MYO1F-001 | −0.626 | −0.753 | −0.689 |
| ENST00000532402 | GANAB-004 | −0.784 | −0.599 | −0.691 |
| ENST00000258362 | PNKD-002 | −0.519 | −0.871 | −0.695 |
| ENST00000345728 | FERMT3-002 | −0.758 | −0.694 | −0.726 |
| ENST00000406520 | COMT-001 | −0.681 | −0.771 | −0.726 |
| ENST00000548410 | RP11-571M6.8-001 | −0.568 | −0.891 | −0.729 |
| ENST00000430629 | WASF2-001 | −0.593 | −0.923 | −0.758 |
| ENST00000308436 | TUT1-201 | −0.949 | −0.597 | −0.773 |
| ENST00000307768 | JAGN1-001 | −0.879 | −0.759 | −0.819 |
| ENST00000293379 | ITGA5-001 | −0.988 | −0.669 | −0.828 |
| ENST00000492819 | CCDC12-005 | −0.831 | −0.829 | −0.830 |
| ENST00000346213 | RAB5C-001 | −0.911 | −0.783 | −0.847 |
| ENST00000457928 | TBL1XR1-002 | −1.066 | −0.641 | −0.854 |
| ENST00000374296 | PAQR7-001 | −0.682 | −1.047 | −0.864 |
| ENST00000548273 | NAP1L1-016 | −0.890 | −0.843 | −0.867 |
| ENST00000254806 | WBP2-201 | −0.785 | −0.972 | −0.879 |
| ENST00000279392 | HIRIP3-001 | −0.992 | −0.790 | −0.891 |
| ENST00000570382 | ACTG1-014 | −0.529 | −1.269 | −0.899 |
| ENST00000373166 | TRAPPC3-001 | −0.863 | −0.945 | −0.904 |
| ENST00000418929 | PRR12-001 | −0.589 | −1.242 | −0.916 |
| ENST00000429426 | MLLT3-202 | −1.097 | −0.762 | −0.930 |
| ENST00000227155 | CD82-001 | −0.733 | −1.170 | −0.952 |
| ENST00000599461 | ZNF493-007 | −0.592 | −1.332 | −0.962 |
| ENST00000325207 | RIC8A-001 | −0.805 | −1.123 | −0.964 |
| ENST00000299299 | PCBD1-001 | −0.599 | −1.338 | −0.968 |
| ENST00000258947 | CALCOCO2-001 | −0.776 | −1.203 | −0.990 |
| ENST00000382280 | ZG16B-001 | −1.221 | −0.761 | −0.991 |

TABLE 14B-continued

Data of Table 4 re-tabulated wherein L2FC is less than zero.

| transcript_id (Ensembl GRCh37) | transcript_name | L2FC BM 10 | L2FC sp 10 | Average L2FC |
|---|---|---|---|---|
| ENST00000483519 | USP40-006 | −1.153 | −0.831 | −0.992 |
| ENST00000360439 | SIN3A-002 | −0.892 | −1.105 | −0.999 |
| ENST00000375464 | C9orf89-001 | −0.867 | −1.176 | −1.022 |
| ENST00000269919 | PGPEP1-001 | −0.884 | −1.172 | −1.028 |
| ENST00000204679 | GNPTG-001 | −1.457 | −0.651 | −1.054 |
| ENST00000394729 | PRKCD-001 | −0.746 | −1.375 | −1.061 |
| ENST00000341183 | MKNK1-201 | −0.531 | −1.603 | −1.067 |
| ENST00000531709 | NXF1-006 | −0.705 | −1.432 | −1.069 |
| ENST00000215838 | TCN2-001 | −1.199 | −0.953 | −1.076 |
| ENST00000535358 | C1or228-201 | −1.353 | −0.867 | −1.110 |
| ENST00000275635 | LAT2-009 | −0.920 | −1.319 | −1.119 |
| ENST00000302347 | ITGB2-201 | −1.140 | −1.175 | −1.157 |
| ENST00000248901 | CYTH4-001 | −0.798 | −1.536 | −1.167 |
| ENST00000354434 | ZYX-006 | −1.819 | −0.536 | −1.178 |
| ENST00000367279 | PTPN7-003 | −1.342 | −1.042 | −1.192 |
| ENST00000322354 | SERTAD3-001 | −0.858 | −1.587 | −1.222 |
| ENST00000508045 | LUC7L3-003 | −1.043 | −1.531 | −1.287 |
| ENST00000356151 | PXK-001 | −1.478 | −1.102 | −1.290 |
| ENST00000346049 | PTK2B-001 | −1.296 | −1.303 | −1.300 |
| ENST00000485708 | RPS24-002 | −0.741 | −1.867 | −1.304 |
| ENST00000493903 | GTF3A-008 | −0.931 | −1.723 | −1.327 |
| ENST00000440963 | APOPT1-005 | −0.553 | −2.110 | −1.331 |
| ENST00000337130 | UGP2-001 | −0.733 | −1.984 | −1.358 |
| ENST00000557781 | STAT6-016 | −1.456 | −1.327 | −1.391 |
| ENST00000312726 | GUK1-001 | −1.456 | −1.334 | −1.395 |
| ENST00000471726 | IQCB1-007 | −1.074 | −1.741 | −1.407 |
| ENST00000586476 | U2AF1L4-001 | −1.791 | −1.049 | −1.420 |
| ENST00000311337 | GNPDA1-001 | −2.115 | −0.776 | −1.445 |
| ENST00000381125 | PFKP-003 | −0.763 | −2.237 | −1.500 |
| ENST00000330188 | TPM3-009 | −0.574 | −2.459 | −1.516 |
| ENST00000574024 | PDE6G-003 | −0.965 | −2.105 | −1.535 |
| ENST00000268099 | SCAMP2-001 | −1.250 | −1.865 | −1.558 |
| ENST00000375792 | DDAH2-001 | −1.257 | −1.881 | −1.569 |
| ENST00000455895 | BSDC1-001 | −1.445 | −1.847 | −1.646 |
| ENST00000369124 | PLEKHO1-001 | −1.399 | −1.938 | −1.669 |
| ENST00000322310 | SSNA1-001 | −1.291 | −2.091 | −1.691 |
| ENST00000569495 | C1orf63-016 | −2.297 | −1.091 | −1.694 |
| ENST00000548390 | LETMD1-018 | −1.841 | −1.576 | −1.709 |
| ENST00000512234 | SQSTM1-011 | −2.830 | −0.600 | −1.715 |
| ENST00000372115 | MUTYH-001 | −2.213 | −1.265 | −1.739 |
| ENST00000530003 | RPS6KA1-003 | −0.558 | −2.996 | −1.777 |
| ENST00000590720 | PSME3-001 | −0.701 | −2.932 | −1.817 |
| ENST00000216155 | SYNGR1-006 | −1.260 | −2.525 | −1.893 |
| ENST00000519882 | ZNF706-003 | −2.177 | −1.626 | −1.902 |
| ENST00000409240 | DCTN1-006 | −0.826 | −2.995 | −1.911 |
| ENST00000371514 | SCP2-001 | −1.218 | −2.609 | −1.914 |
| ENST00000466877 | NAA10-003 | −2.033 | −2.136 | −2.084 |
| ENST00000238823 | FAM98A-001 | −1.203 | −3.017 | −2.110 |
| ENST00000504689 | PLXND1-018 | −3.107 | −1.345 | −2.226 |
| ENST00000248450 | AAMP-001 | −3.757 | −0.903 | −2.330 |
| ENST00000606454 | MIR3916-003 | −3.866 | −0.988 | −2.427 |
| ENST00000407877 | LPAR2-002 | −4.170 | −0.740 | −2.455 |
| ENST00000467943 | COMT-009 | −1.054 | −4.152 | −2.603 |
| ENST00000429586 | ABCF3-001 | −2.377 | −2.990 | −2.683 |
| ENST00000491935 | ADRM1-002 | −4.924 | −0.750 | −2.837 |
| ENST00000264080 | GPR108-001 | −2.672 | −3.020 | −2.846 |
| ENST00000344995 | LAT2-001 | −2.304 | −3.573 | −2.938 |
| ENST00000381480 | DENND1C-001 | −2.977 | −2.926 | −2.951 |
| ENST00000542902 | TAOK3-010 | −3.604 | −2.377 | −2.990 |
| ENST00000393710 | NAA10-017 | −4.818 | −1.179 | −2.999 |
| ENST00000357355 | CD97-002 | −3.353 | −2.743 | −3.048 |
| ENST00000429120 | LY6E-002 | −5.018 | −1.187 | −3.102 |
| ENST00000262629 | TYROBP-001 | −3.955 | −2.933 | −3.444 |

Table 15A-15B re-tabulate the data of Table 5 for L2FC greater than zero, and less than zero, respectively.

TABLE 15A

Data of Table 5 re-tabulated wherein L2FC is greater than zero.

| transcript_id (Ensembl GRCh37) | transcript_name | L2FC | PVAL |
|---|---|---|---|
| ENST00000492229 | SON-011 | 3.878 | 0.034 |
| ENST00000459155 | SCARNA12-201 | 3.798 | 0.028 |
| ENST00000518678 | TRAM 1-004 | 2.940 | 0.043 |
| ENST00000497055 | SGIP1-008 | 2.709 | 0.000 |
| ENST00000537041 | QKI-016 | 2.707 | 0.049 |
| ENST00000534733 | ST3GAL4-015 | 2.664 | 0.003 |
| ENST00000506409 | MED28-003 | 2.534 | 0.009 |
| ENST00000515114 | CCDC109B-005 | 2.496 | 0.023 |
| ENST00000490253 | PLCG1-006 | 2.481 | 0.002 |
| ENST00000368961 | CD164-201 | 2.424 | 0.004 |
| ENST00000260702 | LOXL4-001 | 2.300 | 0.042 |
| ENST00000533234 | OSBPL5-014 | 2.270 | 0.047 |
| ENST00000394353 | GSN-203 | 2.235 | 0.049 |
| ENST00000574151 | HCFC1R1-004 | 1.829 | 0.010 |
| ENST00000511186 | HSD17B4-015 | 1.568 | 0.006 |
| ENST00000419703 | FNDC1-IT1-001 | 1.489 | 0.002 |
| ENST00000473202 | SERPINE2-004 | 1.265 | 0.001 |
| ENST00000578991 | ELAC2-019 | 1.051 | 0.001 |
| ENST00000589416 | ILF3-019 | 1.045 | 0.004 |
| ENST00000354503 | MFF-022 | 1.023 | 0.001 |
| ENST00000335327 | WASF3-001 | 1.022 | 0.004 |

TABLE 15B

Data of Table 5 re-tabulated wherein L2FC is less than zero.

| transcript_id (Ensembl GRCh37) | transcript_name | L2FC | PVAL |
|---|---|---|---|
| ENST00000567999 | DEF8-009 | −1.170 | 0.001 |
| ENST00000393108 | STEAP3-202 | −1.184 | 0.004 |
| ENST00000297620 | FAM219A-008 | −1.399 | 0.006 |
| ENST00000379772 | C20orf27-001 | −1.452 | 0.003 |
| ENST00000451354 | PLEKHG2-006 | −1.478 | 0.006 |
| ENST00000428228 | EMD-007 | −1.681 | 0.009 |
| ENST00000332298 | RGS19-001 | −1.701 | 0.002 |
| ENST00000362068 | ADM2-201 | −1.712 | 0.010 |
| ENST00000552775 | C17orf49-005 | −1.846 | 0.011 |
| ENST00000536752 | AACS-007 | −1.850 | 0.001 |
| ENST00000356488 | SPATA20-004 | −1.874 | 0.015 |
| ENST00000216780 | PCK2-002 | −1.907 | 0.014 |
| ENST00000434436 | MBD3-001 | −1.913 | 0.003 |
| ENST00000400890 | AC011043.1-201 | −1.933 | 0.014 |
| ENST00000413016 | AK1-011 | −1.942 | 0.003 |
| ENST00000592528 | PLIN3-007 | −2.064 | 0.014 |
| ENST00000590869 | ILF3-023 | −2.081 | 0.013 |
| ENST00000549775 | RNASEK-C17orf49-001 | −2.095 | 0.005 |
| ENST00000548577 | RNASEK-001 | −2.121 | 0.012 |
| ENST00000395648 | TP53I11-006 | −2.140 | 0.024 |
| ENST00000498491 | FLNA-008 | −2.164 | 0.004 |
| ENST00000541435 | FXYD5-013 | −2.193 | 0.043 |
| ENST00000565223 | ATP6V0C-004 | −2.241 | 0.003 |
| ENST00000526395 | SIGIRR-023 | −2.338 | 0.008 |
| ENST00000485803 | FHL3-002 | −2.339 | 0.035 |
| ENST00000495313 | SWI5-004 | −2.392 | 0.013 |
| ENST00000550925 | SH2B3-003 | −2.630 | 0.030 |
| ENST00000594568 | TRPM4-010 | −3.189 | 0.020 |
| ENST00000345517 | ACTG2-001 | −3.291 | 0.018 |

Tables 16A-16B re-tabulate the data of Table 7A for L2FC greater than zero, and less than zero, respectively.

TABLE 16A

HSC lncRNAs of Table 7A re-tabulated wherein L2FC is greater than zero.

| gene_ID (Ensembl GRCh37) | gene_name | L2FC |
|---|---|---|
| ENSG00000231721 | LINC-PINT | 2.7 |
| ENSG00000214548 | MEG3 | 1.8 |
| ENSG00000206344 | HCG27 | 1.7 |
| ENSG00000234883 | MIR155HG | 1.4 |
| ENSG00000239213 | RP11-85F14.5 | 1.4 |
| ENSG00000245532 | NEAT1 | 1.3 |
| ENSG00000236333 | TRHDE-AS1 | 1.2 |
| ENSG00000238113 | RP11-262H14.1 | 1.1 |
| ENSG00000260924 | AC004463.6 | 1 |

TABLE 16B

HSC lncRNAs of Table 7A re-tabulated wherein L2FC is greater than zero.

| gene_ID (Ensembl GRCh37) | gene_name | L2FC |
|---|---|---|
| ENSG00000232104 | RP11-509J21.1 | −1.7 |
| ENSG00000223837 | BRD2-IT1 | −2.6 |

Tables 17A-17B re-tabulate the data of Table 7B for L2FC greater than zero, and less than zero, respectively.

TABLE 17A

HPC lncRNAs of Table 7B re-tabulated wherein L2FC is greater than zero.

| gene_ID (Ensembl GRCh37) | gene_name | L2FC |
|---|---|---|
| ENSG00000257242 | C12orf79 | 2.8 |
| ENSG00000251992 | SCARNA17 | 2.4 |
| ENSG00000188825 | LINC00910 | 2.3 |
| ENSG00000245532 | NEAT1 | 1.7 |
| ENSG00000239569 | KMT2E-AS1 | 1.2 |
| ENSG00000225442 | MPRIP-AS1 | 1.1 |
| ENSG00000251562 | MALAT1 (NEAT2) | 1 |

TABLE 17B

HPC lncRNAs of Table 7B re-tabulated wherein L2FC is less than zero.

| gene_ID (Ensembl GRCh37) | gene_name | L2FC |
|---|---|---|
| ENSG00000218510 | LINC00339 | −1.3 |

Tables 18A-18B re-tabulate the data of Table 8 for L2FC greater than zero, and less than zero, respectively.

TABLE 18A

Spliceosome genes of Table 8 re-tabulated for L2FC greater than zero.

| gene_ID (Ensembl GRCh37) | gene_name | L2FC | PVAL | QVAL |
|---|---|---|---|---|
| ENSG00000101161 | PRPF6 | 0.80310461 | 0.01135946 | 0.02408806 |
| ENSG00000087365 | SF3B2 | 0.74775823 | 0.0121265 | 0.02419781 |
| ENSG00000100813 | ACIN1 | 0.72369451 | 0.01344323 | 0.02419781 |
| ENSG00000147144 | CCDC12 | 0.63074694 | 0.00925191 | 0.02408806 |

TABLE 18B

Spliceosome genes of Table 8 re-tabulated for L2FC less than zero.

| gene_ID (Ensembl GRCh37) | gene_name | L2FC | PVAL | QVAL |
|---|---|---|---|---|
| ENSG00000141759 | TXNL4A | −0.5043694 | 0.03814817 | 0.04928551 |
| ENSG00000170144 | HNRNPA3 | −0.5047599 | 0.03384457 | 0.04887085 |
| ENSG00000135486 | HNRNPA1 | −0.5083236 | 0.00020676 | 0.00372166 |
| ENSG00000139675 | HNRNPA1L2 | −0.5091854 | 0.01583795 | 0.02715076 |
| ENSG00000125743 | SNRPD2 | −0.5162715 | 0.03833318 | 0.04928551 |
| ENSG00000165630 | PRPF18 | −0.5165423 | 0.03402466 | 0.04887085 |
| ENSG00000060688 | SNRNP40 | −0.5488529 | 0.03529562 | 0.04887085 |
| ENSG00000147274 | RBMX | −0.6109845 | 0.00650762 | 0.02342745 |
| ENSG00000100650 | SRSF5 | −0.6375131 | 0.01339621 | 0.02419781 |
| ENSG00000144028 | SNRNP200 | −0.6423808 | 0.00085565 | 0.00694006 |
| ENSG00000100138 | NHP2L1 | −0.655293 | 0.01137492 | 0.02408806 |
| ENSG00000167088 | SNRPD1 | −0.6746622 | 0.02440908 | 0.03994214 |
| ENSG00000169976 | SF3B5 | −0.7212635 | 0.00833504 | 0.02408806 |
| ENSG00000086589 | RBM22 | −0.8236023 | 0.0009639 | 0.00694006 |
| ENSG00000131795 | RBM8A | −0.8522745 | 0.00540306 | 0.02161224 |
| ENSG00000141543 | EIF4A3 | −0.9176155 | 0.03341139 | 0.04887085 |
| ENSG00000116752 | BCAS2 | −1.0168843 | 0.00943553 | 0.02408806 |
| ENSG00000161547 | SRSF2 | −1.0197975 | 0.00302536 | 0.01361412 |
| ENSG00000112081 | SRSF3 | −1.023265 | 0.00164531 | 0.00987185 |
| ENSG00000132792 | CTNNBL1 | −1.0273536 | 0.01047858 | 0.02408806 |
| ENSG00000115875 | SRSF7 | −1.0368379 | 0.00980652 | 0.02408806 |
| ENSG00000162385 | MAGOH | −1.0569937 | 0.00082472 | 0.00694006 |
| ENSG00000108654 | DDX5 | −1.1476375 | 0.00277436 | 0.01361412 |
| ENSG00000124193 | SRSF6 | −1.4551226 | 0.00017567 | 0.00372166 |

Tables 19A-19B re-tabulate the data of Table 9 for L2FC greater than zero, and less than zero, respectively.

TABLE 19A

Transcription factors of Table 9 re-tabulated for L2FC greater than zero.

| gene_ID (Ensembl GRCh37) | gene_name | L2FC |
|---|---|---|
| ENSG00000141905 | NF1C | 1.5 |
| ENSG00000166888 | STAT6 | 1.4 |
| ENSG00000169083 | AR | 1.3 |
| ENSG00000189067 | LITAF | 1.2 |
| ENSG00000128604 | IRF5 | 1.2 |
| ENSG00000204859 | ZBTB48 | 1.2 |
| ENSG00000143390 | RFX5 | 1.1 |

TABLE 19B

Transcription factors of Table 9 re-tabulated for L2FC less than zero.

| gene_ID (Ensembl GRCh37) | gene_name | L2FC |
|---|---|---|
| ENSG00000124766 | SOX4 | −1.3 |
| ENSG00000029993 | HMGB3 | −1.3 |
| ENSG00000119508 | NR4A3 | −1.4 |
| ENSG00000140968 | IRF8 | −1.4 |
| ENSG00000007968 | E2F2 | −1.5 |
| ENSG00000162599 | NFIA | −1.5 |
| ENSG00000141510 | TP53 | −1.5 |
| ENSG00000185630 | PBX1 | −1.5 |
| ENSG00000147862 | NFIB | −1.7 |
| ENSG00000117036 | ETV3 | −2 |
| ENSG00000153234 | NR4A2 | −2.2 |
| ENSG00000117318 | ID3 | −2.3 |
| ENSG00000123358 | NR4A1 | −3 |
| ENSG00000137265 | IRF4 | −3.2 |
| ENSG00000164330 | EBF1 | −3.9 |

Tables 20A-20B re-tabulate the data of Table 10 for L2FC greater than zero, and less than zero, respectively.

TABLE 20A lncRNAs of Table 10 re-tabulated for L2FC greater than zero.

| gene_ID (Ensembl GRCh37) | gene_name | L2FC |
|---|---|---|
| ENSG00000214548 | MEG3 | 3.9 |
| ENSG00000204625 | HCG9 | 2.7 |
| ENSG00000227502 | RP1-249H1.4 | 2.1 |
| ENSG00000229989 | MIR181A1HG | 1.7 |
| ENSG00000242258 | LINC00996 | 1.6 |

TABLE 20A-continued

IncRNAs of Table 10 re-tabulated for L2FC greater than zero.

| gene_ID (Ensembl GRCh37) | gene_name | L2FC |
| --- | --- | --- |
| ENSG00000246263 | KB-431C1.4 | 1.5 |
| ENSG00000252122 | SNORA76 | 1.5 |
| ENSG00000256007 | ARAP1-AS1 | 1.3 |
| ENSG00000260260 | RP11-304L19.5 | 1.3 |
| ENSG00000233429 | HOTAIRM1 | 1.3 |
| ENSG00000227953 | RP11-439E19.3 | 1.2 |
| ENSG00000245937 | CTC-228N24.3 | 1.2 |
| ENSG00000236709 | DAPK1-IT1 | 1.1 |
| ENSG00000269220 | LINC00528 | 1 |

TABLE 20B

IncRNAs of Table 10 re-tabulated for L2FC less than zero.

| gene_ID (Ensembl GRCh37) | gene_name | L2FC |
| --- | --- | --- |
| ENSG00000227028 | SLC8A1-AS1 | −1.2 |
| ENSG00000182648 | LINC01006 | −1.2 |
| ENSG00000249859 | PVT1 | −1.3 |
| ENSG00000187621 | TCL6 | −1.3 |
| ENSG00000230945 | RP11-394O9.1 | −1.4 |
| ENSG00000247774 | PCED1B-AS1 | −1.8 |
| ENSG00000228495 | LINC01013 | −2.4 |
| ENSG00000214049 | UCA1 | −3.6 |

Supplemental Experimental Procedures.

Study Design.

The overall research objectives of this study were to both discover new splice isoform biomarkers specific to human hematopoietic stem and progenitor cell (HSPC) aging and sAML LSC, and evaluate the potent and stable spliceosome-targeted small molecule compound 17S-FD-895 in AML LSC survival and self-renewal assays in preclinical models. In controlled laboratory experiments, research samples included primary peripheral blood or bone marrow samples from consenting AML patients (n=22) and age-matched normal control bone marrow samples (n=14) obtained from healthy volunteer individuals undergoing hip replacement therapy for reasons other than leukemia, or normal cord blood (n=6) or young bone marrow (n=8) controls obtained from a commercial source (AllCells, Alameda, Calif.). For experiments using primary samples, the sample size of each experiment is limited by the availability of rare and valuable samples specific for disease and stage from patients. To discover new splice isoform biomarkers specific to human HSPC aging compared with sAML LSC, primary AML and normal control (age-matched or young) samples were FACS-purified and analyzed by RNA-Seq, and whole transcriptome analyses and hierarchical clustering analyses were utilized to establish unique splice isoform expression signatures. We use a definition of significance as a two-sided alpha level of 0.05 and aim to have power of 0.80. Based on an expected effect size that is twice the standard deviation we can achieve 0.79 power with five samples per arm based on a normal distribution. The goal of each experiment is to get close to five or more samples per arm depending on clinical sample availability and viability. The effect size we are able to detect with this power is variable based on intra-arm sample variability via standard deviation. Consistent with AML genetic heterogeneity, there was some variability in primary patient sample analyses by RNA-Seq and qRT-PCR. When considering sequencing of multiple genes it is assumed that a much larger effect size will be required due to appropriate adjustment for multiple comparisons. For this reason, a false-discovery rate (FDR) correction was applied.

In hypothesis-driven experiments, the splicing modulatory compound 17S-FD-895 was tested to determine efficacy in altering splicing activity in cell lines, and to evaluate effects on AML LSC survival and self-renewal capacity in humanized bone marrow stromal co-cultures and in PRIMAGRAFT™ AML LSC models. Cell culture experiments were performed using 293T and sAML (MOLM-13) cell lines, and SL and M2 bone marrow stromal cell lines. Animal studies were performed using immunocompromised Rag2−/− $\gamma_c$−/− (Abrahamsson et al., 2009) or NOD/SCID-IL2RG mice (Jackson Laboratory, Bar Harbor, Me.) (Wunderlich et al., 2010). Primary AML and normal control samples were used in in vitro hematopoietic stem and progenitor assays after lentiviral-SF3B1 knockdown, or bone marrow stromal co-culture and treatment with splicing modulatory compounds (FD-895 or 17S-FD-895) or vehicle control (DMSO). Colony formation potential and self-renewal capacity were assessed by counting colony numbers (survival) after two weeks of growth in semi-solid (methylcellulose) media, and subsequent replating capacity (self-renewal) was assessed after transfer to fresh methylcellulose for an additional two weeks of culture. Three primary AML samples were utilized to establish PRIMAGRAFT™ models in immunocompromised mice, and mice engrafted with cells from two of these models (AML-37 and AML-08) were treated with 17S-FD-895 or vehicle (DMSO) to evaluate changes in AML LSC survival and self-renewal capacity in vivo. One primary normal cord blood (CB) sample was used to establish a PRIMAGRAFT™ model to evaluate 17S-FD-895 effects on normal HSPC survival and self-renewal potential. Data were collected by flow cytometry, qRT-PCR and RNA-Seq analysis of CD34-selected human LSC-enriched cells from engrafted mice.

In in vivo experiments, before initiation of treatment, CB or AML-engrafted mice were distributed among treatment groups according to human cell engraftment rates (CD45+ cell frequency) in peripheral blood, and total body weights (average engraftment and body weights for each treatment were equal at the initiation of treatment). Inclusion/exclusion criteria for AML PRIMAGRAFT™ models were pre-established based on minimum CD45+ cell engraftment rates of 1% in peripheral blood, and endpoints included human stem and progenitor engraftment analyses as established by previous PRIMAGRAFT™ experiments (Abrahamsson et al., 2009; Jamieson et al., 2004). All qRT-PCR analyses were performed using two technical replicates for each sample, with the average of the two replicates shown in all graphs. For in vitro experiments, the same investigator performed treatments and analyses. For in vivo experiments, investigators performing FACS and qRT-PCR analyses were blinded to each animal's treatment status until after all data were collected.

Reagents

Antibodies.

For primary sample FACS purification of hematopoietic stem and progenitor cell populations, CD34-selected (Miltenyi) primary samples were stained with a panel of well-validated human-specific antibodies (Abrahamsson et al., 2009; Goff et al., 2013; Jamieson et al., 2004; Jiang et al., 2013) was utilized. Antibodies included human CD34-APC and CD38-PECy7 (BD Biosciences, San Diego, Calif.) and lineage markers (CD2, CD3, CD4, CD8, CD14, CD19, CD20 and CD56 cocktail, all antibodies PECy5.5 conjugated, from Life Technologies, Carlsbad, Calif.). For flow cytometric analyses of PRIMAGRAFT™ models, the same panel of antibodies was used for analysis of spleen and bone marrow-derived cells, with the addition of CD45-V450, CD123-PE (both from BD Biosciences), and CD45RA-FITC (Life Technologies) for further visualization of progenitor cell subpopulations, or CD45-APC (Life Technologies) and CD33-PE (BD Biosciences), for leukemic blast populations. Due to background autofluorescence in blood, for flow cytometric analysis of peripheral blood from treated mice, the CD34 and CD45 antibodies were replaced with alternative antibodies to exclude FITC labeled reagents (CD34-PE, BD Biosciences and CD45-APC, Life Technologies).

RNA and PCR Reagents.

All RNA samples were prepared after lysis of live cells in RLT buffer (Qiagen, Germantown, Md.) followed by RNA extraction using RNEASY® kits according to the manufacturer's instructions (Qiagen). cDNA was synthesized using the First-Strand SUPERSCRIPT™ III Reverse Transcriptase Supermix (Life Technologies) and qRT-PCR was performed using SYBR® GREENER™ Super Mix (Life Technologies). All primers were synthesized by ValueGene (San Diego, Calif.).

Cell Culture Reagents.

All media (DMEM, RPMI, IMDM) and supplements (Glutamax, penicillinstreptomycin) used in cell culture were from Corning (Manassas, Va.) or Life Technologies. Fetal bovine serum (FBS) was from Gemini Bio-Products (Sacramento, Calif.). For experiments involving transfection of reporter vector plasmids (Stoilov et al., 2008), HEK293 cells were transiently transfected using Lipofectamine (Life Technologies) according to the manufacturer's instructions.

Sample Processing and Primary HSPC and AML LSC Purification.

Peripheral blood or bone marrow samples were processed by Ficoll density centrifugation and viable cells stored in liquid nitrogen. Mononuclear cells from AML patients or normal controls were then further purified by magnetic bead separation of CD34+ cells (MACS; Miltenyi, Bergisch Gladbach, Germany) essentially as previously described (Jiang et al., 2013) for subsequent FACS-purification of hematopoietic stem (CD34+ CD38− Lin−) and progenitor (CD34+ CD38+ Lin−) cell fractions. For the majority of AML patient samples utilized, only very few purified viable HSC were obtained (<5,000 cells on average). Therefore the progenitor fractions were utilized for subsequent RNA-Seq and qRT-PCR analyses as these represent the majority of cells present in LSC-enriched fractions prepared for functional in vitro and in vivo assays using CD34 selection.

For primary hematopoietic progenitor cell purification, CD34-selected cells were stained with fluorescent antibodies against human CD34 and CD38 (BD Biosciences) and lineage markers (cocktail, all antibodies from Life Technologies) and propidium iodide as previously described (Abrahamsson et al., 2009; Jamieson et al., 2004; Jiang et al., 2013). Following staining, cells were analyzed and sorted using a FACS Aria II (Sanford Consortium Stem Cell Core Facility), and hematopoietic stem (CD34+ CD38− Lin−) and progenitor (CD34+ CD38+ Lin−) populations were isolated. Freshly-sorted cells were collected in lysis buffer (Qiagen) for RNA extraction followed by RNA-Seq (The Scripps Research Institute Next Generation Sequencing Core) on Illumina HiSeq (all discovery sample sets) or NextSeq (xenograft samples and some validation sample sets) platforms, or qRT-PCR analyses as previously described (Jiang et al., 2013).

Nucleic Acid Isolation and PCR (qRT-PCR and RT-PCR).

Primary CD34+CD38+ Lin− cells or enriched human CD34+ cells from mouse tissues were isolated using FACS purification or CD34 microbead-selection, and 2-10×104 cells were harvested in lysis buffer (Qiagen). RNA was purified using RNEASY® micro RNA purification kits with a DNase (Qiagen) incubation step to digest any trace genomic DNA present. RNA was stored at −80° C. Immediately prior to reverse transcription of RNA samples, nucleic acid concentrations were quantified on a NanoDrop 2000 spectrophotometer (Thermo Scientific), and purity was considered acceptable if A260/A280 values were >1.8. Samples submitted for RNA-Seq were further subjected to quality control assessment on an Agilent Bioanalyzer (The Scripps Research Institute Next Generation Sequencing Core). Samples with RNA integrity (RIN) values >7 were used for RNA-Seq.

For qRT-PCR analysis of relative total mRNA expression levels or splice isoform-specific expression analyses, cDNA was synthesized using 50 ng-1 $\propto\gamma$ of template RNA in 20 $\propto\Lambda$ reaction volumes using the First-Strand SUPERSCRIPT™ III Reverse Transcriptase Supermix (Life Technologies) followed by incubation with RNase H according to the manufacturer's protocol and as described previously (Abrahamsson et al., 2009; Crews et al., 2015). All cDNA products were stored at −20° C. Splice isoform-specific primers for PTK2B-202 were designed to bind to unique exon junctions for this transcript, which lacks exon 24. All primers (Supplemental Experimental Procedures Table) were diluted to 10 $\propto$M working dilutions in DNase/RNase-free water. qRT-PCR was performed in duplicate using cDNA (1 $\propto\Lambda$ reverse transcription product per reaction) on an iCycler (Bio-Rad, Hercules, Calif.) using SYBR® GREENER™ Super Mix (Life Technologies) in 25-$\propto$A volume reactions containing 0.2 $\propto$M of each forward and reverse primer. Cycling conditions were as follows: 50° C. for 2 minutes, then 95° C. for 8 minutes and 30 seconds, followed by 40 cycles of 95° C. for 15 seconds and 60° C. for 60 seconds. Melting curve analysis was performed on each plate according to the manufacturer's instructions. For standard qRT-PCR, human HPRT mRNA transcript levels were used to normalize Ct values obtained for each gene, and relative expression levels were calculated using the $2^{-ddCt}$ method. To ensure validity of results, only Ct values <35 were used in gene expression analyses. All primer sets were tested in a no-template control (NTC) reaction containing only water instead of cDNA, and all gave Ct values >35 in NTC reactions.

Whole Transcriptome Sequencing and Determination of Gene and Splice Isoform Expression Values.

Gene and isoform expression data in FPKM was obtained from RNA-sequencing data (sequencing performed at The Scripps Research Institute Next Generation Sequencing Core, San Diego, Calif.) for young (average 66M input reads per HPC sample) and aged (average 73M reads per HPC sample) normal samples, and sAML LSC (average 73M reads per sample) by aligning paired end unstranded 100 bp poly-A reads to the human reference genome (GRCh37/hg19) using STAR (Dobin et al., 2013). Transcripts were quantified using Cufflinks to generate FPKM values (Trapnell et al., 2010), and average log 2 fold change (L2FC) and p values for genes and isoforms were obtained as previously described (Kirschner et al., 2015; Kumar et al., 2014) (FIGS. 18D, 18E, 19A, 1D, 11E, 12D). All gene and transcript names correspond to the identifiers used in Ensembl GRCh37.

Xenograft sequencing data of 2×150 bp paired end reads were trimmed using cutadapt 1.8.1, aligned using STAR 2.5.0b against the GRCh37 reference FASTA sequence with the Ensembl GRCh37.75 GTF as a splice junction source. Strandedness was inferred using modulate "infer_experiment.py" from the RSeQC package (Wang et al., 2012). Then, transcripts were quantified using Cufflinks v2.2.1 (Trapnell et al., 2010) against the Ensembl GRCh37.75 GTF reference with bias correction against the GRCh37 reference FASTA. This yielded Cufflinks FPKM values. Isoforms sharing gene names were summed to yield gene FPKMs. FPKM values were transformed to generate log 2(FPKM+1) for all transcripts in the sAML isoform signature (FIGS. 11D, 11E, 12D), comparing vehicle versus 10 mg/kg treatment groups for spleen and bone marrow. Then, a heatmap was generated using all transcripts showing a L2FC>0.5 in both tissues, occurring in the opposite direction of the L2FC transcript expression values in sAML versus normal age-matched controls (i.e. L2FC>1 in sAML, L2FC<−0.5 in 10 mg/kg-treated spleen and bone marrow).

RNA-Seq Based Gene Set Enrichment, Gene Ontology, Network Analyses, Generation of Splice Isoform Signatures, and Principal Components Analysis.

Gene expression data in FPKM was submitted to GSEA to determine significant KEGG pathways, and enrichment plots describing ranked gene expression in those pathways. Additional analyses were performed using custom gene sets including genes associated with the top differentially expressed transcript signatures in aged ("aged up") versus young ("young up") HPC and sAML ("sAML up") versus aged ("aged up") HPC (FIGS. 11D, 11E, 12D). We acknowledge our use of the gene set enrichment analysis, GSEA software, and Molecular Signature Database (see website: broad.mit.edu). Network analyses were performed on top differentially expressed isoforms by inputting their corresponding gene identifier names into Cytoscape's Reactome FI plugin. All significantly differentially expressed genes in normal aged versus young HSC and HPC, or aged versus sAML samples, were probed for human transcription factors (Zhang et al., 2012), and commonly DE transcription factors were identified.

After FDR correction (FDR<5%, as described in main Experimental Procedures), to identify the top differentially expressed splice isoforms in aged versus young HSC, aged versus young HPC, and sAML LSC versus normal age-matched HPC, a calculation was performed to generate a composite value reflecting both the significance of the difference between groups (p value) and the magnitude of the difference (fold change). Graphical representations of p values versus fold change for large expression datasets are often visualized as volcano plots, however most selection criteria for identifying the top differentially expressed factors rely on dual cutoffs such as p<0.05 or L2FC>1, or manual selection of transcripts which relies on subjective criteria (as described for microarray data visualized by volcano plot on the NCI Genomics and Bioinformatics group website: discover.nci.nih.gov. To alleviate any manual bias of selecting "top differentially expressed transcripts", we generated volcano plots for all transcripts with an average FPKM>1 in one condition of the comparison, and applied p-value (<0.05) and L2FC (>1) cutoffs. Then, the remaining transcripts were ranked by quantifying the relative Cartesian distance from the origin on a volcano plot, where the average L2FC of each transcript is displayed on the x-axis and the −log 10(p value) on the y-axis. The formula applied for calculating the composite values was: $SQRT((L2FC^2)+(-\log 10(p\ value))^2)$. We then selected the top transcripts for the splice isoform signatures and associated heat maps using the highest-ranking (high to low values) transcripts according to this composite value, which we termed the "Volcano Vector Value". For isoform analyses, these values produced a list of transcripts that was similar to the top transcripts ranked by FDR, but included additional transcripts displaying a large magnitude of fold change. The complete sets of transcripts that passed p-value, FDR, and L2FC cutoffs are provided in FIGS. 18D, 18E, 19A, 11D, 11E and 12D, to allow for analysis of all transcripts that were differentially expressed in compared groups.

Generation of heatmaps and clustering analyses were performed using GENE-E (available at website broadinstitute.org). Gene and isoform expression heat maps were generated using GENE-E default settings and gene expression data for transcripts selected from the list of significantly differentially expressed genes/isoforms with p<0.05 absolute L2FC>1. For whole gene analyses, log 2 (FPKM+1) values for features that passed specified p value, Q-value (FDR<5%), and log 2 fold change cutoffs were clustered on heatmaps using the GENE-E default hierarchical clustering method and one minus pearson correlation distance metric.

For principal components analysis (PCA), FPKM values for the top 75 aged vs young HPC signature isoforms in aged and young HPC and sAML, AML, and MDS progenitor samples were annotated and transformed using the expression log 2 (FPKM+1). The transformed values were submitted to the R function prcomp and visualized using ggbiplot (available at github.com website).

Analysis of TCGA AML Datasets.

Survival data and RSEM gene and transcript quantifications were downloaded from TCGA for all AML (TCGA Disease Code LAML) samples for which this data was available. Top differentially expressed sAML LSC splice isoforms (FIG. 12D) were identified, then mapped from Ensembl transcript names to UCSC known transcript IDs using the MySQL interface to UCSC knownGene tables. Of the 75 transcripts in the sAML splice isoform signature, 28 corresponded to known transcripts in the UCSC database (with some of these having two UCSC identifiers that were associated with a single ensembl transcript). The UCSC-mapped sAML LSC transcript IDs were then used to retrieve the "scaled_estimate" value for that transcript and sample, multiplied by 106 to yield TPM quantifications. Transcripts with a mean TPM of at least 1 were selected. These were then transformed using log 2(TPM+1) to yield log TPM quantifications for clustering in a heatmap using GENE-E. Six Groups were identified manually from the GENE-E clustering by selecting entire dendrogram branches, and these were used to segment the survival data into different curves, visualized using Prism. For the purposes of the survival data, the days to the last known checkup were used as the study dropout date for the patient in lieu of the patient days to death, while living patients were listed as dropping out at the study's end. For PTK2B transcript analysis, expression values (TPM) of the PTK2B transcript uc003xfp.1 (mapped to ensembl transcript PTK2B-001, GRCh37) in all AML patient samples were ranked from high to low expression. The patient samples corresponding to the upper and lower quartiles of expression were compared for overall survival. The results shown here are in part based upon data from primary AML patient samples generated by the TCGA Research Network (see cancergenome.nih.gov website) (TCGA 2013).

Mutational Analysis of SF3B1 and Other Spliceosome Genes.

RNA-Seq reads were aligned with the genomic coordinates of known mutations in SF3B1, U2AF1, SRSF2 and ZRSF2 to assess potential somatic mutations in these splicing factor genes that are highly specific for diagnosis of sAML (Lindsley et al., 2015). For RNA-Seq reads from sAML and normal bone marrow progenitors, 100 bp reads were obtained. These were cleaned of adapters and primers using cutadapt, then aligned using STAR. REDItools (Picardi and Pesole, 2013) was used to identify putative somatic mutations at loci previously described in MDS or AML samples (Lindsley et al., 2015; Yoshida et al., 2011). One out of seven sAML patient samples in the RNA-Seq dataset harbored a single G>C mutation in exon 14 of SF3B1 (538 G reads versus 520 C reads), corresponding to an aa change of K666N in SF3B1. For validation by PCR and targeted Sanger sequencing analysis of SF3B1, 1 μL of first-strand cDNA templates was prepared for PCR in 25-μL reaction volumes using the high-fidelity KOD Hot Start DNA Polymerase kit according to the manufacturer's instructions (EMD Millipore, Temecula, Calif.). PCR primers for sequencing SF3B1 in cDNA were located in exon 10 (forward, FW) and exon 17 (reverse, REV, Supplemental Experimental Procedures Table) (Jeromin et al., 2013). PCR cycling conditions were as follows: 95° C. for 2 minutes, followed by 35 cycles of 95° C. for 20 seconds, 62° C. for 10 seconds and 70° C. for 10 seconds, with a final extension step of 70° C. for 30 seconds. Amplicons of the predicted size were verified for each outer primer set by DNA gel electrophoresis using 10-20 μL of the completed reaction mixture separated on 2% agarose gels containing ethidium bromide and visualized under UV light. Then, 15 μL of each reaction was processed within 24 hrs for PCR purification, and sequencing was performed on ABI 3730xl DNA Sequencers (Eton Bioscience, San Diego, Calif.). Sanger sequencing was carried out using two primers, a FW and REV primer each localized to exon 14 (Supplemental Experimental Procedures Table). Sequence chromatograms were analyzed using 4Peaks (by A. Griekspoor and Tom Groothuis, at website: nucleobytes.com).

Splicing Reporter Assay and In Vitro Splicing Analyses.

Figure 20A:
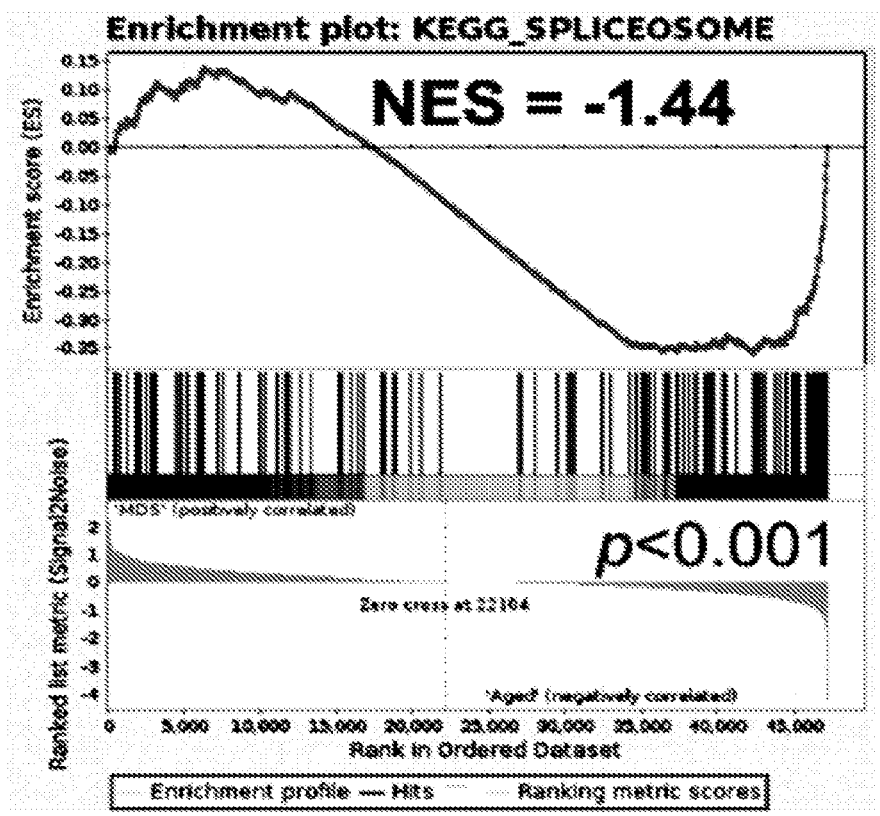

For evaluation of in vitro splicing activity using a two-color fluorescent splicing reporter system (Stoilov et al., 2008), HEK293T cells (mycoplasma-free authenticated cell lines obtained from ATCC) were grown in complete media (DMEM+10% FBS) and transfected with a series of fluorescent protein-expressing plasmids. Vector controls include pFlare5A, which expresses solely GFP, and pFlare5G, which expresses maximal RFP. The pFlare reporter contains microtubule-associated protein tau (MAPT) exon 10 as an indicator of alternative splicing. Under physiological conditions, the pFlare conditional reporter vector allows in-frame expression of GFP but not RFP. In the presence of splicing inhibitors, exon skipping favors production of RFP over GFP. Twenty-four hours after transfection with the three plasmids in separate wells of a 24-well plate, 17S-FD-895 or equivalently diluted DMSO vehicle controls (<1%) were added to the media for an additional 24 hrs, to allow sufficient time for translation of the alternatively spliced transcripts driving expression of RFP or GFP protein products. Fluorescence was evaluated on a Leica fluorescent microscope (Sanford Consortium Stem Cell Core facility) and then analyzed by flow cytometry on a Miltenyi MACSQuant® to assess transfection efficiency (ranging from over 70% at 24 hrs after transfection to approximately 20% at 48 hrs after transfection) and mean fluorescence intensity (MFI) of RFP and GFP in positive cells. In HEK293 cells transiently transfected with control GFP or RFP vectors, or the pFlare splicing reporter vector, the dynamic range of the assay as measured by MFI of GFP and RFP 48 hours after transfection ranged from 0.41-1.69 for RFP/GFP ratios (FIG. 20A). For time-lapse imaging, splicing reporter transfected cells were transferred to glass-bottom 35-mm dishes and treated with 1-10 μM of 17S-FD-895, followed by sequential imaging on an Olympus FV10i confocal microscope equipped with a 5% CO2 cell culture incubation chamber (Tokai Hit, Japan) for up to 24 hrs.

For evaluation of in vitro splicing activity of endogenous transcripts in HEK293, KG1a, or a sAML cell line, MOLM-13 (mycoplasma-free and cytogenetically-authenticated cell lines obtained from ATCC or DMSZ), cells were plated in complete media (DMEM containing 10% FBS for HEK293, IMDM containing 10-20% FBS for KG1a, and RPMI containing 20% FBS for MOLM-13). The next day, FD-895, 17S-FD-895 or DMSO vehicle controls were added at doses ranging from 0.01-10 ∝M for 4 hrs of treatment. For time course experiments in MOLM-13 sAML cells, 17S-FD-895 was added to the media at a dose of 0.1 or 1 ∝M, for 30 mins-24 hrs of culture. Cells were lysed in RLT buffer (Qiagen) and processed for RNA extraction and subsequent PCR analyses using primers specific for DNAJB1 or MCL1 (Supplemental Experimental Procedures Table). For all experiments in cell lines, cells obtained from the vendors were frozen down in bulk at low passage numbers and used within 20 passages to minimize risk of cell line misidentification or acquisition of additional chromosomal abnormalities.

For genetic SF3B1 down-modulation studies, an additional set of normal (n=4) and sAML (n=8) samples were CD34-selected and then cultured for 24 hrs in Stempro® media containing human cytokines, as previously described (Jiang et al., 2013). Cells were transduced with lentiviral vectors (multiplicity of infection=100) expressing GFP and an shRNA targeting human SF3B1 or a non-targeting control (Genecopoeia, Rockville, Md.). In parallel, MOLM-13 cells were transduced and cultured in complete media. Cell viability was assessed by trypan blue exclusion after 48 hrs of treatment, and fluorescent images were acquired immediately prior to transferring cells to methylcellulose for colony and replating assays. While the viability of the majority of AML samples (7/8) was low following lentiviral transduction with either vector control or shSF3B1, one sAML sample was sufficiently viable after lentiviral transduction to permit colony and replating assays, and showed a reduction in colony survival and self-renewal.

Bone Marrow Stromal Cell Maintenance for Co-Culture Assays.

Mouse bone marrow stromal cell lines (SL and M2 mycoplasma-free authenticated cells obtained from ATCC) expressing human interleukin-3 (IL-3), stem cell factor (SCF) and granulocyte-colony stimulating factor (G-CSF), which support erythroid and myeloid cell expansion and differentiation (Hogge et al., 1996), were maintained under standard culture conditions, as previously described (Goff et al., 2013). Briefly, SL cells were grown in complete medium containing DMEM (Corning), 10% FBS, 1% Glutamax, and 1% penicillin-streptomycin (Life Technologies), while M2 cells were grown in complete medium containing RPMI, 10% FBS, 1% Glutamax, and 1% penicillin-streptomycin (all from Life Technologies). Every four passages, cells were selected by addition of G418 and hygromycin to the culture media for one passage (3-4 days), to maintain human cytokine expression. All cell lines were maintained in T-25 or T-75 culture flasks and were passaged at dilutions of 1:5-1:10 every 2-4 days. Low passage aliquots of cells were thawed every two months to ensure consistency of experiments.

PRIMAGRAFT™ Models and Engraftment Analyses.

All animal studies were performed in accordance with UCSD and NIH-equivalent ethical guidelines and were approved by the Institutional Animal Care and Use Committee (IACUC protocol # S06015). For all in vivo experiments, animals of both genders were utilized. For all transplantations into Rag2−/− $\gamma_c$−/− animals, neonatal mice were transplanted with human cells intrahepatically as previously described (Abrahamsson et al., 2009, Jiang et al., 2013), and for all transplantations into NSGS animals, which constitutively express human stem cell supportive cytokines SCF, GM-CSF and IL-3 (Wunderlich et al., 2010), sublethally irradiated (300 Rad) adult (6-8 weeks old) mice were transplanted intravenously with 1-2×105 CD34+ human cells. Mice transplanted with 1-2×105 CD34+ AML LSC-enriched fractions or no-transplant controls were screened for human hematopoietic cell engraftment (CD45+ cells) in peripheral blood by FACS starting at 7-10 weeks post-transplant. At 7-28 weeks post-transplant (7-36 weeks old), mice were euthanized, and peripheral blood and single cell suspensions of hematopoietic organs were analyzed for human cell engraftment by FACS. Total cell suspensions from bone marrow and spleen were either transplanted immediately or CD34-selected for transplant into secondary recipient mice (1-2×105 cells per animal) to expand the cells in vivo. Both mouse strains were found to support serial transplantation of all three patient samples, however for subsequent experiments, AML-37 was maintained in Rag2−/− $\gamma_c$−/− mice and AML-08 was maintained in NSGS mice. Secondary recipient mice were euthanized after 8-23 weeks, and cell suspensions from bone marrow and spleen were CD34-selected for transplant into tertiary recipients for 17S-FD-895 treatment. For qRT-PCR analysis of in vivo splicing alterations, single cell suspensions from hematopoietic tissues of 17S-FD-895-treated mice were CD34-selected and processed for RNA extraction and cDNA preparation. As a normal HSPC in vivo control, 1×105 CD34+ cells from a mixed donor CB (AllCells, Alameda, Calif.) were injected intrahepatically into neonatal Rag2−/−$\gamma_c$−/− mice. Transplanted mice and no-transplant controls were screened for human CD45+ cells engraftment in peripheral blood by FACS starting at 5 weeks post-transplant. Treatment was initiated at 8 weeks post-transplant, and at 10 weeks post-transplant, mice were euthanized, and peripheral blood and single cell suspensions of hematopoietic organs were analyzed for human cell engraftment by FACS.

In Vivo 17S-FD-895 Treatment, Tissue Analysis and Serial Transplantation.

The 17S-FD-895 dosing regimen was selected as the maximum number of doses possible for the treatment of normal and AML PRIMAGRAFT™ experimental groups with the amount of synthesized compound that was available, and is consistent with weekly IV dosing regimens used in clinical trials of less stable spliceosome inhibitory compounds in patients with solid tumors (Hong et al., 2014). For in vivo treatments, a 10 mg/mL stock solution of 17S-FD-895 solubilized in DMSO was used. Vehicle control for AML-08 was 15% DMSO in PBS, for AML-37 and CB 20% DMSO in PBS was used. Animals were euthanized within two hours after delivery of the final dose of 17S-FD-895, and peripheral blood, spleens and bone marrows were collected for analysis of total human cell and stem and progenitor cell engraftment, and for RNA extraction for splice isoform-specific qRT-PCR.

Flow cytometric analysis was performed on single cell suspensions from each hematopoietic tissue essentially as for primary patient samples, and frequencies of total live human CD45+ cells, CD45+ CD34+ CD38− Lin− (stem) cells, CD45+ CD34+ CD38+ Lin− (progenitor) cells, and CD45+/CD33+ (leukemic blasts) were determined in each tissue. Analysis of progenitor cell subpopulations was performed for AML-37, with GMP identified as CD123+ CD45RA+, CMP as CD123+ CD45RA− and megakaryocyte-erythroid progenitors (MEP) as CD123+ CD45RA−. For AML-37 treatment, one additional transplanted mouse was treated with vehicle control (total n=6), however this animal was excluded from FACS and qRT-PCR analyses because of development of a femoral mass not typical of AML PRIMAGRAFT™ models, but suggestive of an infection occurring in the context of the immunocompromised status of the mouse.

For preparation of RNA from human LSC-enriched populations, single cell suspensions from spleen and bone marrow were CD34 double-selected (over two LS selection columns, Miltenyi) and 1-2×105 cells were collected in lysis buffer or pooled according to treatment group for serial transplantation assays. For serial transplantation of LSC-enriched fractions from treated mice, cells from individual mice were pooled according to treatment group for each hematopoietic tissue, and 2×105 cells were transplanted intravenously into adult (6-8 weeks old) NSGS mice.

Statistical Analyses.

For RNA-seq based comparisons between groups, average log 2 fold change (L2FC) and p values for genes and isoforms were obtained as previously described (Jiang et al., 2013; Kirschner et al., 2015). Because raw FPKM values are not normally distributed, p values were calculated following log 2 transformation of the FPKM values (plus 1 to allow log 2 transformation of zero values). Quantitative RT-PCR data were measured as a continuous outcome and each group was assessed for distribution and variance. For normally distributed data, unpaired two-tailed Student's t-tests were applied to determine differences in mRNA expression, and values were expressed as individual data points or means (±SEM) from a minimum of two independent experiments. For AML LSC survival and self-renewal assays, differences among groups were assessed using one-way ANOVA with values expressed as means±SD (for in vitro hematopoietic progenitor assays where comparisons were made among multiple sample types and treatment groups), or Student's t-test with values expressed as means±SEM (for in vitro splicing reporter assays) or as means of individual data points representing biological replicates (for in vivo engraftment and qRT-PCR analyses). All experiments were performed on blind-coded samples. All statistical analyses were performed using Microsoft Excel, SigmaPlot, or GraphPad Prism (San Diego, Calif.).

REFERENCES (EXAMPLE 2, SUPPLEMENTARY EXPERIMENTAL PROCEDURES)

Cancer Genome Atlas Research, N. (2013). Genomic and epigenomic landscapes of adult de novo acute myeloid leukemia. N Engl J Med 368, 2059-2074.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Hogge, D. E., Lansdorp, P. M., Reid, D., Gerhard, B., and Eaves, C. J. (1996). Enhanced detection, maintenance, and differentiation of primitive human hematopoietic cells in cultures containing murine fibroblasts engineered to produce human steel factor, interleukin-3, and granulocyte colony-stimulating factor. Blood 88, 3765-3773.

Jeromin, S., Haferlach, T., Grossmann, V., Alpermann, T., Kowarsch, A., Haferlach, C., Kern, W., and Schnittger, S. (2013). High frequencies of SF3B1 and JAK2 mutations in refractory anemia with ring sideroblasts associated with marked thrombocytosis strengthen the assignment to the category of myelodysplastic/myeloproliferative neoplasms. Haematologica 98, e15-17.

Kirschner, A. N., Wang, J., van der Meer, R., Anderson, P. D., Franco-Coronel, O. E., Kushner, M. H., Everett, J. H., Hameed, O., Keeton, E. K., Ahdesmaki, M., et al. (2015). PIM kinase inhibitor AZD1208 for treatment of MYC-driven prostate cancer. J Natl Cancer Inst 107.

Kumar, R. M., Cahan, P., Shalek, A. K., Satija, R., DaleyKeyser, A. J., Li, H., Zhang, J., Pardee, K., Gennert, D., Trombetta, J. J., et al. (2014). Deconstructing transcriptional heterogeneity in pluripotent stem cells. Nature 516, 56-61.

Picardi, E., and Pesole, G. (2013). REDItools: high-throughput RNA editing detection made easy. Bioinformatics 29, 1813-1814.

Trapnell, C., Williams, B. A., Pertea, G., Mortazavi, A., Kwan, G., van Baren, M. J., Salzberg, S. L., Wold, B. J., and Pachter, L. (2010). Transcript assembly and quantification by RNA-Seq reveals unannotated transcripts and isoform switching during cell differentiation. Nat Biotechnol 28, 511-515.

Wang, L., Wang, S., and Li, W. (2012). RSeQC: quality control of RNA-seq experiments. Bioinformatics 28, 2184-2185.

Wunderlich, M., Chou, F. S., Link, K. A., Mizukawa, B., Perry, R. L., Carroll, M., and Mulloy, J. C. (2010). AML xenograft efficiency is significantly improved in NOD/SCID-IL2RG mice constitutively expressing human SCF, GM-CSF and IL-3. Leukemia 24, 1785-1788.

Zhang, H. M., Chen, H., Liu, W., Liu, H., Gong, J., Wang, H., and Guo, A. Y. (2012). AnimalTFDB: a comprehensive animal transcription factor database. Nucleic Acids Res 40, D144-149.

REFERENCES (EXAMPLE 2)

Abrahamsson, A. E., Geron, I., Gotlib, J., Dao, K. H., Barroga, C. F., Newton, I. G., Giles, F. J., Durocher, J., Creusot, R. S., Karimi, M., et al. (2009). GSK3β missplicing contributes to leukemia stem cell generation. PNAS 106, 3925-3929.

Adamia, S., Haibe-Kains, B., Pilarski, P. M., Bar-Natan, M., Pevzner, S., Avet-Loiseau, H., Lode, L., Verselis, S., Fox, E. A., Burke, J., et al. (2014). A genome-wide aberrant RNA splicing in patients with acute myeloid leukemia identifies novel potential disease markers and therapeutic targets. Clin Cancer Res 20, 1135-1145.

Adams, P. D., Jasper, H., and Rudolph, K. L. (2015). Aging-Induced Stem Cell Mutations as Drivers for Disease and Cancer. Cell Stem Cell 16, 601-612.

Barrett, C. L., DeBoever, C., Jepsen, K., Saenz, C. C., Carson, D. A., and Frazer, K. A. (2015). Systematic transcriptome analysis reveals tumor-specific isoforms for ovarian cancer diagnosis and therapy. PNAS 112, E3050-3057.

Bartholdy, B., Christopeit, M., Will, B., Mo, Y., Barreyro, L., Yu, Y., Bhagat, T. D., Okoye-Okafor, U. C., Todorova, T. I., Greally, J. M., et al. (2014). HSC commitment-associated epigenetic signature is prognostic in acute myeloid leukemia. J Clin Invest 124, 1158-1167.

Beghini, A., Ripamonti, C. B., Peterlongo, P., Roversi, G., Cairoli, R., Morra, E., and Larizza, L. (2000). RNA hyperediting and alternative splicing of hematopoietic cell phosphatase (PTPN6) gene in acute myeloid leukemia. Hum Mol Genet 9, 2297-2304.

Bonnal, S., Vigevani, L., and Valcarcel, J. (2012). The spliceosome as a target of novel antitumour drugs. Nat Rev Drug Discov 11, 847-859.

Bonnet, D., and Dick, J. E. (1997). Human acute myeloid leukemia is organized as a hierarchy that originates from a primitive hematopoietic cell. Nat Med 3, 730-737.

Burnett, A. K., Russell, N. H., Hunter, A. E., Milligan, D., Knapper, S., Wheatley, K., Yin, J., McMullin, M. F., Ali, S., Bowen, D., et al. (2013). Clofarabine doubles the response rate in older patients with acute myeloid leukemia but does not improve survival. Blood 122, 1384-1394.

Chan, S. M., Thomas, D., Corces-Zimmerman, M. R., Xavy, S., Rastogi, S., Hong, W. J., Zhao, F., Medeiros, B. C., Tyvoll, D. A., and Majeti, R. (2015). Isocitrate dehydrogenase 1 and 2 mutations induce BCL-2 dependence in AML. Nat Med 21, 178-184.

Chang, J., Wang, Y., Shao, L., Laberge, R. M., Demaria, M., Campisi, J., Janakiraman, K., Sharpless, N. E., Ding, S., Feng, W., et al. (2016). Clearance of senescent cells by ABT263 rejuvenates aged hematopoietic stem cells in mice. Nat Med 22, 78-83.

Corces-Zimmerman, M. R., Hong, W. J., Weissman, I. L., Medeiros, B. C., and Majeti, R. (2014). Preleukemic mutations in human acute myeloid leukemia affect epigenetic regulators and persist in remission. PNAS 111, 2548-2553.

Crews, L. A., Jiang, Q., Zipeto, M. A., Lazzari, E., Court, A. C., Ali, S., Barrett, C. L., Frazer, K. A., and Jamieson, C. H. M. (2015). An RNA editing fingerprint of cancer stem cell reprogramming. J Transl Med 13.

DeBoever, C., Ghia, E. M., Shepard, P. J., Rassenti, L., Barrett, C. L., Jepsen, K., Jamieson, C. H., Carson, D., Kipps, T. J., and Frazer, K. A. (2015). Transcriptome sequencing reveals potential mechanism of cryptic 3' splice site selection in SF3B1-mutated cancers. PLoS computational biology 11, e1004105.

Despeaux, M., Chicanne, G., Rouer, E., De Toni-Costes, F., Bertrand, J., Mansat-De Mas, V., Vergnolle, N., Eaves, C., Payrastre, B., Girault, J. A., et al. (2012). Focal adhesion kinase splice variants maintain primitive acute myeloid leukemia cells through altered Wnt signaling. Stem Cells 30, 1597-1610.

Dolatshad, H., Pellagatti, A., Fernandez-Mercado, M., Yip, B. H., Malcovati, L., Attwood, M., Przychodzen, B., Sahgal, N., Kanapin, A. A., Lockstone, H., et al. (2015). Disruption of SF3B1 results in deregulated expression and splicing of key genes and pathways in myelodysplastic syndrome hematopoietic stem and progenitor cells. Leukemia 29, 1092-1103.

Eppert, K., Takenaka, K., Lechman, E. R., Waldron, L., Nilsson, B., van Galen, P., Metzeler, K. H., Poeppl, A., Ling, V., Beyene, J., et al. (2011). Stem cell gene expression programs influence clinical outcome in human leukemia. Nat Med 17, 1086-1093.

Essers, M. A., Offner, S., Blanco-Bose, W. E., Waibler, Z., Kalinke, U., Duchosal, M. A., and Trumpp, A. (2009). IFN⎕ activates dormant HSC in vivo. Nature 458, 904-908.

Ferrarese, R., Harsh, G. R. t., Yadav, A. K., Bug, E., Maticzka, D., Reichardt, W., Dombrowski, S. M., Miller, T. E., Masilamani, A. P., Dai, F., et al. (2014). Lineage-specific splicing of a brain-enriched alternative exon promotes glioblastoma progression. J Clin Invest 124, 2861-2876.

Genovese, G., Jaiswal, S., Ebert, B. L., and McCarroll, S. A. (2015). Clonal hematopoiesis and blood-cancer risk. N Engl J Med 372, 1071-1072.

Goardon, N., Marchi, E., Atzberger, A., Quek, L., Schuh, A., Soneji, S., Woll, P., Mead, A., Alford, K. A., Rout, R., et al. (2011). Coexistence of LMPP-like and GMP-like leukemia stem cells in AML. Cancer Cell 19, 138-152.

Goff, D. J., Court Recart, A., Sadarangani, A., Chun, H. J., Barrett, C. L., Krajewska, M., Leu, H., Low-Marchelli, J., Ma, W., Shih, A. Y., et al. (2013). A Pan-BCL2 inhibitor renders bone-marrow-resident human leukemia stem cells sensitive to tyrosine kinase inhibition. Cell Stem Cell 12, 316-328.

Graubert, T., and Walter, M. J. (2011). Genetics of myelodysplastic syndromes: new insights. Hematology Am Soc Hematol Educ Program 2011, 543-549.

Han, H., Irimia, M., Ross, P. J., Sung, H. K., Alipanahi, B., David, L., Golipour, A., Gabut, M., Michael, I. P., Nachman, E. N., et al. (2013). MBNL proteins repress ES-cell-specific alternative splicing and reprogramming. Nature 498, 241-245.

Holm, F., Hellqvist, E., Mason, C. N., Ali, S. A., Delos-Santos, N., Barrett, C. L., Chun, H. J., Minden, M. D., Moore, R. A., Marra, M. A., et al. (2015). Reversion to an embryonic alternative splicing program enhances leukemia stem cell self-renewal. PNAS 112, 15444-15449.

Hong, D. S., Kurzrock, R., Naing, A., Wheler, J. J., Falchook, G. S., Schiffman, J. S., Faulkner, N., Pilat, M. J., O'Brien, J., and LoRusso, P. (2014). A phase I, open-label, single-arm, dose-escalation study of E7107, a precursor messenger ribonucleic acid (pre-mRNA) spliceosome inhibitor administered intravenously on days 1 and 8 every 21 days to patients with solid tumors. Invest New Drugs 32, 436-444.

Hsu, T. Y., Simon, L. M., Neill, N. J., Marcotte, R., Sayad, A., Bland, C. S., Echeverria, G. V., Sun, T., Kurley, S. J., Tyagi, S., et al. (2015). The spliceosome is a therapeutic vulnerability in MYC-driven cancer. Nature 525, 384-388.

Jaiswal, S., Fontanillas, P., Flannick, J., Manning, A., Grauman, P. V., Mar, B. G., Lindsley, R. C., Mermel, C. H., Burtt, N., Chavez, A., et al. (2014). Age-related clonal hematopoiesis associated with adverse outcomes. N Engl J Med 371, 2488-2498.

Jamieson, C. H., Ailles, L. E., Dylla, S. J., Muijtjens, M., Jones, C., Zehnder, J. L., Gotlib, J., Li, K., Manz, M. G., Keating, A., et al. (2004). Granulocyte-macrophage progenitors as candidate leukemic stem cells in blast-crisis CML. N Engl J Med 351, 657-667.

Jiang, Q., Crews, L. A., Barrett, C. L., Chun, H. J., Court, A. C., Isquith, J. M., Zipeto, M. A., Goff, D. J., Minden, M., Sadarangani, A., et al. (2013). ADAR1 promotes malignant progenitor reprogramming in chronic myeloid leukemia. PNAS 110, 1041-1046.

Johnson, J. M., Castle, J., Garrett-Engele, P., Kan, Z., Loerch, P. M., Armour, C. D., Santos, R., Schadt, E. E., Stoughton, R., and Shoemaker, D. D. (2003). Genome-wide survey of human alternative pre-mRNA splicing with exon junction microarrays. Science 302, 2141-2144.

Kaida, D., Motoyoshi, H., Tashiro, E., Nojima, T., Hagiwara, M., Ishigami, K., Watanabe, H., Kitahara, T., Yoshida, T., Nakajima, H., et al. (2007). Spliceostatin A targets SF3b and inhibits both splicing and nuclear retention of pre-mRNA. Nat Chem Biol 3, 576-583.

Kantarjian, H. M., Erba, H. P., Claxton, D., Arellano, M., Lyons, R. M., Kovascovics, T., Gabrilove, J., Craig, M., Douer, D., Maris, M., et al. (2010). Phase II study of clofarabine monotherapy in previously untreated older adults with acute myeloid leukemia and unfavorable prognostic factors. J Clin Oncol 28, 549-555.

Kashyap, M. K., Kumar, D., Villa, R., La Clair, J. J., Benner, C., Sasik, R., Jones, H., Ghia, E. M., Rassenti, L. Z., Kipps, T. J., et al. (2015). Targeting the spliceosome in chronic lymphocytic leukemia with the macrolides FD-895 and pladienolide-B. Haematologica 100, 945-954.

Kirschner, A. N., Wang, J., van der Meer, R., Anderson, P. D., Franco-Coronel, O. E., Kushner, M. H., Everett, J. H., Hameed, O., Keeton, E. K., Ahdesmaki, M., et al. (2015). PIM kinase inhibitor AZD1208 for treatment of MYC-driven prostate cancer. J Natl Cancer Inst 107.

Kotake, Y., Sagane, K., Owa, T., Mimori-Kiyosue, Y., Shimizu, H., Uesugi, M., Ishihama, Y., Iwata, M., and Mizui, Y. (2007). Splicing factor SF3b as a target of the antitumor natural product pladienolide. Nat Chem Biol 3, 570-575.

Kowalczyk, M. S., Tirosh, I., Heckl, D., Rao, T. N., Dixit, A., Haas, B. J., Schneider, R. K., Wagers, A. J., Ebert, B. L., and Regev, A. (2015). Single-cell RNA-seq reveals changes in cell cycle and differentiation programs upon aging of HSC. Genome Res 25, 1860-1872.

Li, L., Li, M., Sun, C., Francisco, L., Chakraborty, S., Sabado, M., McDonald, T., Gyorffy, J., Chang, K., Wang, S., et al. (2011). Altered hematopoietic cell gene expression precedes development of therapy-related myelodysplasia/AML and identifies patients at risk. Cancer Cell 20, 591-605.

Lindsley, R. C., Mar, B. G., Mazzola, E., Grauman, P. V., Shareef, S., Allen, S. L., Pigneux, A., Wetzler, M., Stuart, R. K., Erba, H. P., et al. (2015). AML ontogeny is defined by distinct somatic mutations. Blood 125, 1367-1376.

Luo, M., Jeong, M., Sun, D., Park, H. J., Rodriguez, B. A., Xia, Z., Yang, L., Zhang, X., Sheng, K., Darlington, G. J., et al. (2015). Long non-coding RNAs control HSC function. Cell Stem Cell 16, 426-438.

Mazin, P., Xiong, J., Liu, X., Yan, Z., Zhang, X., Li, M., He, L., Somel, M., Yuan, Y., Phoebe Chen, Y. P., et al. (2013). Widespread splicing changes in human brain development and aging. Mol Sys Biol 9, 633.

McKerrell, T., Park, N., Moreno, T., Grove, C. S., Ponstingl, H., Stephens, J., Understanding Society Scientific, G., Crawley, C., Craig, J., Scott, M. A., et al. (2015). Leukemia-associated somatic mutations drive distinct patterns of age-related clonal haemopoiesis. Cell Rep 10, 1239-1245.

Michelle, L., Cloutier, A., Toutant, J., Shkreta, L., Thibault, P., Durand, M., Garneau, D., Gendron, D., Lapointe, E., Couture, S., et al. (2012). Proteins associated with the exon junction complex also control the alternative splicing of apoptotic regulators. Mol Cell Biol 32, 954-967.

Pan, Q., Bakowski, M. A., Morris, Q., Zhang, W., Frey, B. J., Hughes, T. R., and Blencowe, B. J. (2005). Alternative splicing of conserved exons is frequently species-specific in human and mouse. Trends Genet 21, 73-77.

Pang, W. W., Price, E. A., Sahoo, D., Beerman, I., Maloney, W. J., Rossi, D. J., Schrier, S. L., and Weissman, I. L. (2011). Human bone marrow hematopoietic stem cells are increased in frequency and myeloid-biased with age. PNAS 108, 20012-20017.

Rossi, D. J., Jamieson, C. H., and Weissman, I. L. (2008). Stem cells and the pathways to aging and cancer. Cell 132, 681-696.

Salesse, S., Dylla, S. J., and Verfaillie, C. M. (2004). p210BCR/ABL-induced alteration of pre-mRNA splicing in primary human CD34+ hematopoietic progenitor cells. Leukemia 18, 727-733.

Salton, M., Kasprzak, W. K., Voss, T., Shapiro, B. A., Poulikakos, P. I., and Misteli, T. (2015). Inhibition of vemurafenib-resistant melanoma by interference with pre-mRNA splicing. Nat Commun 6, 7103.

Schwerk, C., and Schulze-Osthoff, K. (2005). Regulation of apoptosis by alternative pre-mRNA splicing. Mol Cell 19, 1-13.

Shlush, L. I., Zandi, S., Mitchell, A., Chen, W. C., Brandwein, J. M., Gupta, V., Kennedy, J. A., Schimmer, A. D., Schuh, A. C., Yee, K. W., et al. (2014). Identification of pre-leukaemic haematopoietic stem cells in acute leukaemia. Nature 506, 328-333.

Signer, R. A., Magee, J. A., Salic, A., and Morrison, S. J. (2014). Haematopoietic stem cells require a highly regulated protein synthesis rate. Nature 509, 49-54.

Stoilov, P., Lin, C. H., Damoiseaux, R., Nikolic, J., and Black, D. L. (2008). A high-throughput screening strategy identifies cardiotonic steroids as alternative splicing modulators. PNAS 105, 11218-11223.

Sun, D., Luo, M., Jeong, M., Rodriguez, B., Xia, Z., Hannah, R., Wang, H., Le, T., Faull, K. F., Chen, R., et al. (2014). Epigenomic profiling of young and aged HSCs reveals concerted changes during aging that reinforce self-renewal. Cell Stem Cell 14, 673-688.

Trimarchi, T., Bilal, E., Ntziachristos, P., Fabbri, G., Dalla-Favera, R., Tsirigos, A., and Aifantis, I. (2014). Genome-wide mapping and characterization of Notch-regulated long noncoding RNAs in acute leukemia. Cell 158, 593-606.

Tripathi, V., Ellis, J. D., Shen, Z., Song, D. Y., Pan, Q., Watt, A. T., Freier, S. M., Bennett, C. F., Sharma, A., Bubulya, P. A., et al. (2010). The nuclear-retained noncoding RNA MALAT1 regulates alternative splicing by modulating SR splicing factor phosphorylation. Mol Cell 39, 925-938.

Villa, R., Mandel, A. L., Jones, B. D., La Clair, J. J., and Burkart, M. D. (2012). Structure of FD-895 revealed through total synthesis. Org Lett 14, 5396-5399.

Wang, L., Lawrence, M. S., Wan, Y., Stojanov, P., Sougnez, C., Stevenson, K., Werner, L., Sivachenko, A., DeLuca, D. S., Zhang, L., et al. (2011). SF3B1 and other novel cancer genes in chronic lymphocytic leukemia. N Engl J Med 365, 2497-2506.

Weis, S. M., Lim, S. T., Lutu-Fuga, K. M., Barnes, L. A., Chen, X. L., Gothert, J. R., Shen, T. L., Guan, J. L., Schlaepfer, D. D., and Cheresh, D. A. (2008). Compensatory role for Pyk2 during angiogenesis in adult mice lacking endothelial cell FAK. J Cell Biol 181, 43-50.

Will, B., Vogler, T. O., Narayanagari, S., Bartholdy, B., Todorova, T. I., da Silva Ferreira, M., Chen, J., Yu, Y., Mayer, J., Barreyro, L., et al. (2015). Minimal PU.1 reduction induces a preleukemic state and promotes development of AML. Nat Med 21, 1172-1181.

Yoshida, K., Sanada, M., Shiraishi, Y., Nowak, D., Nagata, Y., Yamamoto, R., Sato, Y., Sato-Otsubo, A., Kon, A., Nagasaki, M., et al. (2011). Frequent pathway mutations of splicing machinery in myelodysplasia. Nature 478, 64-69.

Zipeto, M. A., Court, A. C., Sadarangani, A., Delos Santos, N. P., Balaian, L., Chun, H. J., Pineda, G., Morris, S. R., Mason, C. N., Geron, I., et al. (2016). ADAR1 Activation Drives Leukemia Stem Cell Self-Renewal by Impairing Let-7 Biogenesis. Cell Stem Cell Epub 7 Jun. 2016.

EMBODIMENTS

Embodiments disclosed herein include embodiments P1 to P3 following.

Embodiment P1

A method for diagnosis of secondary acute myeloid leukemia (sAML), said method comprising obtaining a splice isoform signature from a subject, and comparing said splice isoform signature with a normal control, thereby providing diagnosis of sAML.

Embodiment P2

A method for treating secondary acute myeloid leukemia (sAML), said method comprising administering to a subject in need an effective amount of a splicing modulator, thereby treating said sAML.

Embodiment P3

The method of embodiment P2, wherein said splicing modulator is 17S-FD-895.

Further embodiments include embodiments Q1 to Q10 following.

Embodiment Q1

A method of determining physiological age of a progenitor cell, the method comprising measuring expression of one or more gene or splice isoform identified herein, wherein the progenitor cell is physiologically young if the expression of the one or more genes is more similar to the young expression level than the aged expression level shown herein, and the progenitor cell is physiologically aged if the expression of the one or more genes is more similar to the aged expression level than the young expression level shown herein.

Embodiment Q2

The method of embodiment Q1, wherein the progenitor cell is a hematopoietic progenitor cell.

Embodiment Q3

The method of embodiment Q1 or Q2, wherein the progenitor cell is from a subject that has a disease, disorder or condition that affects aging.

Embodiment Q4

The method of any one of embodiments Q1-Q3, used to diagnose a disease, disorder or condition that affects aging.

Embodiment Q5

The method of embodiment Q3, used to determine whether a treatment for the disease, disorder or condition is effective.

Embodiment Q6

The method of embodiment Q5, wherein the treatment is a pharmaceutical administration.

Embodiment Q7

The method of embodiment Q5, wherein the treatment is exercise-based.

Embodiment Q8

The method of any previous embodiment, wherein expression of one or more splice variant is determined.

Embodiment Q9

A method of determining whether a treatment of a subject for a disease, disorder or condition that affects aging is effective, the method comprising measuring expression of one or more gene or splice isoform identified herein in a progenitor cell from the subject both (a) before the treatment, and (b) during or after the treatment, and determining whether the expression of (b) is more like expression from progenitor cells from young people than the expression of (a), wherein such an expression pattern indicates that the treatment is effective.

Embodiment Q10

A method to correct human stem cell function in aged microenvironments comprising increasing protein production of the proteins identified herein that are produced in lower concentrations from aged stromal cultures compared with young bone marrow.

Further embodiments include embodiments 1 to 85 following.

Embodiment 1

A method for treating acute myeloid leukemia in a subject in need thereof, the method comprising administering to the subject an effective amount of a splicing modulator, thereby treating the acute myeloid leukemia.

Embodiment 2

A method for modulating acute myeloid leukemia stem cells, the method comprising contacting the acute myeloid leukemia stem cells with an effective amount of a splicing modulator, thereby modulating the acute myeloid leukemia stem cells.

Embodiment 3

The method of embodiment 2, wherein normal progenitor cells are not substantially modulated.

Embodiment 4

The method of embodiment 2 or 3, wherein the method is in vitro or in vivo.

Embodiment 5

A method of detecting a protein level in a subject having acute myeloid leukemia, the method comprising (i) obtaining a biological sample from the subject; (ii) contacting the biological sample with a detection agent capable of binding at least one protein encoded by at least one RNA set forth in Table 13A and/or Table 13B, thereby forming a detectable complex; (iii) detecting and quantitating the detectable complex; and (iv) comparing to a standard control, thereby detecting the protein level of the protein in the subject.

Embodiment 6

The method of embodiment 5, wherein the protein is PTK2B, CD44, or a combination thereof.

Embodiment 7

The method of embodiment 5, further comprising detecting additional protein levels for a plurality of additional proteins encoded by RNA set forth in Table 13A and/or Table 13B by further contacting the biological sample with a plurality of additional different detection agents, each additional different detection agent capable of binding to one of the plurality of additional proteins to form a plurality of additional different detectable complexes; and further detecting and quantitating the plurality of additional different detectable complexes and comparing to a standard control, thereby detecting additional protein levels the protein in the additional proteins in the subject.

Embodiment 8

The method of embodiment 5, wherein the protein and the plurality of additional proteins comprise all the proteins encoded by RNA set forth in Table 13A and/or Table 13B.

Embodiment 9

The method of embodiment 5, wherein the protein and the plurality of additional proteins comprise at least 50 of the proteins encoded by RNA set forth in Table 13A and/or Table 13B.

Embodiment 10

The method of any one of embodiment 5-9, wherein the protein levels of the proteins encoded by the RNA set forth in Table 13B are lower than in a subject that does not have acute myeloid leukemia; and the protein levels of the proteins encoded by the RNA set forth in Table 13A are higher than in a subject that does not have acute myeloid leukemia.

Embodiment 11

A method of detecting an RNA level in a subject having acute myeloid leukemia, the method comprising (i) obtaining a biological sample from the subject; (ii) contacting the biological sample with a probe capable of hybridizing to the RNA set forth in Table 13A and/or Table 13B, thereby forming a hybridized complex; (iii) detecting and quantitating the hybridized complex; and (iv) comparing to a standard control, thereby detecting the protein level of the protein in the subject.

Embodiment 12

The method of embodiment 11, further comprising detecting additional RNA levels for a plurality of additional RNAs set forth in Table 13A and/or Table 13B by further contacting the biological sample with a plurality of additional different probes, each additional different probe capable of hybridizing to one of the plurality of additional RNAs to form a plurality of additional different hybridized complexes; and further detecting and quantitating the plurality of additional different hybridized complexes and comparing to a standard control, thereby detecting additional RNA levels in the additional RNAs in the subject.

Embodiment 13

The method of embodiment 11, wherein the RNA and the plurality of additional RNAs comprise all the RNA set forth in Table 13A and Table 13B.

Embodiment 14

The method of embodiment 11, wherein the RNA and the plurality of additional RNAs comprise at least 50 of the RNA set forth in Table 13A and/or Table 13B.

Embodiment 15

The method of any one of embodiment 11-14, wherein the RNA levels of the RNAs set forth in Table 13B are lower than in a subject that does not have acute myeloid leukemia; and the RNA levels of the RNAs set forth in Table 13A are higher than in a subject that does not have acute myeloid leukemia.

Embodiment 16

The method of any one of embodiments 1-15, wherein the acute myeloid leukemia is secondary acute myeloid leukemia.

Embodiment 17

The method of any one of embodiments 1-16, wherein the acute myeloid leukemia is refractory acute myeloid leukemia.

Embodiment 18

The method of any one of embodiments 1-17, wherein the acute myeloid leukemia is relapsed acute myeloid leukemia.

Embodiment 19

The method of any one of embodiments 5-18, further comprising administering to the subject an effective amount of a splicing modulator.

Embodiment 20

A solid support comprising a plurality of detection agents that each bind to a protein encoded by the RNA set forth in Table 13A and/or 13B.

Embodiment 21

A solid support comprising one or more probes that hybridize to one or more RNA sequences selected from the group consisting of: Table 13A and/or Table 13B.

Embodiment 22

A method for modulating stem cells and progenitor cells, the method comprising contacting stem cells and progenitor cells with an effective amount of a splicing modulator, thereby modulating the stem cells and progenitor cells.

Embodiment 23

A method for treating an age-related disease in a subject in need thereof, the method comprising administering to the subject an effective amount of a splicing modulator, thereby treating the age-related disease.

Embodiment 24

A method of detecting a protein level in a subject having an age-related disorder, the method comprising (i) obtaining a biological sample from the subject; (ii) contacting the biological sample with a detection agent capable of binding a protein encoded by at least one RNA set forth in Table 12A and/or Table 12B, thereby forming a detectable complex; (iii) detecting and quantitating the detectable complex; and (iv) comparing to a standard control, thereby detecting the protein level of the protein in the subject.

Embodiment 25

The method of embodiment 24, further comprising detecting additional protein levels for a plurality of additional proteins encoded by at least one RNA set forth in Table 12A and/or Table 12B by further contacting the biological sample with a plurality of additional different detection agents, each additional different detection agent capable of binding to one of the plurality of additional proteins to form a plurality of additional different detectable complexes; and further detecting and quantitating the plurality of additional different detectable complexes and comparing to a standard control, thereby detecting additional protein levels the protein in the additional proteins in the subject.

Embodiment 26

The method of embodiment 24, wherein the protein and the plurality of additional proteins comprise all the proteins encoded by the RNA set forth in Table 12A and Table 12B.

Embodiment 27

The method of embodiment 24, wherein the protein and the plurality of additional proteins comprise at least 50 of the proteins encoded the RNA set forth in Table 12A and/or Table 12B.

Embodiment 28

The method of any one of embodiment 24-27, wherein the protein levels of the proteins encoded by at least one RNA set forth in Table 12B are lower than in a subject that does not have acute myeloid leukemia; and the protein levels of the proteins encoded by at least one RNA set forth in Table 12A are higher than in a subject that does not have acute myeloid leukemia.

Embodiment 29

A method of detecting an RNA level in a subject having an age-related disease, the method comprising (i) obtaining a biological sample from the subject; (ii) contacting the biological sample with a probe capable of hybridizing to the RNA set forth in Table 12A and Table 12B, thereby forming a hybridized complex; (iii) detecting and quantitating the hybridized complex; and (iv) comparing to a standard control, thereby detecting the protein level of the protein in the subject.

Embodiment 30

The method of embodiment 29, further comprising detecting additional RNA levels for a plurality of additional RNAs set forth in Table 12A and Table 12B by further contacting the biological sample with a plurality of additional different probes, each additional different probe capable of hybridizing to one of the plurality of additional RNAs to form a plurality of additional different hybridized complexes; and further detecting and quantitating the plurality of additional different hybridized complexes and comparing to a standard control, thereby detecting additional RNA levels in the additional RNAs in the subject.

Embodiment 31

The method of embodiment 29, wherein the RNA and the plurality of additional RNAs comprise all the proteins set forth in Table 12A and Table 12B.

Embodiment 32

The method of embodiment 29, wherein the RNA and the plurality of additional RNAs comprise at least 50 of the RNA set forth in Table 12A and Table 12B.

Embodiment 33

The method of any one of embodiment 29-32, wherein the RNA levels of the RNAs set forth in Table 12B are lower than in a subject that does not have acute myeloid leukemia; and the RNA levels of the RNA set forth in Table 12A are higher than in a subject that does not have acute myeloid leukemia.

Embodiment 34

A method of detecting a long-coding RNA level in a subject having an age-related disease, the method comprising (i) obtaining a biological sample from the subject; (ii) contacting the biological sample with a probe capable of hybridizing to the RNA set forth in Table 7A and/or Table 7B and/or Table 10, thereby forming a hybridized complex; (iii) detecting and quantitating the hybridized complex; and (iv) comparing to a standard control, thereby detecting the protein level of the protein in the subject.

Embodiment 35

The method of embodiment 34, further comprising detecting additional RNA levels for a plurality of additional RNAs set forth in Table 7A and/or Table 7B and/or Table 10 by further contacting the biological sample with a plurality of additional different probes, each additional different probe capable of hybridizing to one of the plurality of additional RNAs to form a plurality of additional different hybridized complexes; and further detecting and quantitating the plurality of additional different hybridized complexes and comparing to a standard control, thereby detecting additional RNA levels in the additional RNAs in the subject.

Embodiment 36

The method of embodiment 34, wherein the RNA and the plurality of additional RNAs comprise all the RNAs set forth in Table 7A, Table 7B, and Table 10.

Embodiment 37

The method of embodiment 34, wherein the RNA and the plurality of additional RNAs comprise at least 25 of the RNAs set forth in Table 7A and/or Table 7B and/or Table 10.

Embodiment 38

The method of any one of embodiments 23-37, wherein the age-related disease is bone marrow failure.

Embodiment 39

The method of any one of embodiments 23-37, wherein the age-related disease is aplastic anemia, myelodysplastic syndrome, paroxysmal nocturnal hemoglobinuria, or large granular lymphocytic leukemia.

Embodiment 40

The method of any one of embodiments 22-39, further comprising administering an effective amount of a splicing modulator.

Embodiment 41

A solid support comprising a plurality of detection agents that each bind to a protein encoded by the RNA set forth in Table 12A and/or 12B.

Embodiment 42

A solid support comprising one or more probes that hybridize to one or more RNA sequences selected from the group consisting of: Table 12A and/or Table 12B.

Embodiment 43

A solid support comprising a plurality of detection agents that each bind to a protein encoded by the RNA set forth in Table 7A and/or Table 7B and/or Table 10.

Embodiment 44

A solid support comprising one or more probes that hybridize to one or more RNA sequences selected from the group consisting of: Table 7A and/or Table 7B and/or Table 10.

Embodiment 45

A method for modulating bone marrow stromal cells, the method comprising contacting bone marrow stromal cells with an effective amount of a splicing modulator, thereby modulating the bone marrow stromal cells.

Embodiment 46

A method of correcting human stem cell function in an aged microenvironment, the method comprising increasing production of one or more proteins encoded by the RNA in Table 15B in bone marrow stromal cells; and optionally further administering an effective amount of a splicing modulator to the aged microenvironment.

Embodiment 47

A method of detecting a protein level in a subject having an age-related disorder, the method comprising (i) obtaining a biological sample from the subject; (ii) contacting the biological sample with a detection agent capable of binding a protein encoded by an RNA in Table 15A and/or Table 15B, thereby forming a detectable complex; (iii) detecting and quantitating the detectable complex; and (iv) comparing to a standard control, thereby detecting the protein level of the protein in the subject.

Embodiment 48

The method of embodiment 47, further comprising detecting additional protein levels for a plurality of additional proteins encoded by RNA in Table 15A and/or Table 15B by further contacting the biological sample with a plurality of additional different detection agents, each additional different detection agent capable of binding to one of the plurality of additional proteins to form a plurality of additional different detectable complexes; and further detecting and quantitating the plurality of additional different detectable complexes and comparing to a standard control, thereby detecting additional protein levels the protein in the additional proteins in the subject.

Embodiment 49

The method of embodiment 47, wherein the protein and the plurality of additional proteins comprise all the proteins encoded by RNA in Table 15A and Table 15.

Embodiment 50

The method of any one of embodiment 47-49, wherein the protein levels of the proteins set forth in Table 15B are lower than in a subject that does not have acute myeloid leukemia; and the protein levels of the proteins set forth in Table 15A are higher than in a subject that does not have acute myeloid leukemia.

Embodiment 51

A method of detecting an RNA level in a subject having an age-related disease, the method comprising (i) obtaining a biological sample from the subject; (ii) contacting the biological sample with a probe capable of hybridizing to the RNA set forth in Table 15A and/or Table 15B, thereby forming a hybridized complex; (iii) detecting and quantitating the hybridized complex; and (iv) comparing to a standard control, thereby detecting the protein level of the protein in the subject.

Embodiment 52

The method of embodiment 51, further comprising detecting additional RNA levels for a plurality of additional RNAs set forth in Table 15A and/or Table 15B by further contacting the biological sample with a plurality of additional probes, each additional different probe capable of hybridizing to one of the plurality of additional RNAs to form a plurality of additional different hybridized complexes; and further detecting and quantitating the plurality of additional different hybridized complexes and comparing to a standard control, thereby detecting additional RNA levels in the additional RNAs in the subject.

Embodiment 53

The method of embodiment 51, wherein the RNA and the plurality of additional RNAs comprise all the RNA set forth in Table 15A and Table 15B.

Embodiment 54

The method of embodiment 51, wherein the RNA and the plurality of additional RNAs comprise at least 20 of the RNA set forth in Table 15A and/or Table 15B.

Embodiment 55

The method of any one of embodiment 51-54, wherein the RNA levels of the RNAs set forth in Table 15B are lower than in a subject that does not have acute myeloid leukemia; and the RNA levels of the RNAs set forth in Table 15A are higher than in a subject that does not have acute myeloid leukemia.

Embodiment 56

A method of detecting a protein level in a subject having an age-related disorder, the method comprising (i) obtaining a biological sample from the subject; (ii) contacting the biological sample with a detection agent capable of binding a cytokines selected from the group consisting of BDNF, IL-17, IL-12p40, IL-23, ICAM-1, Eotaxin-1, B2M, AAT, SCF, MCP-1, VEGF, C3, RANTES, and IL-4, thereby forming a detectable complex; (iii) detecting and quantitating the detectable complex; and (iv) comparing to a standard control, thereby detecting the protein level of the protein in the subject.

Embodiment 57

The method of embodiment 47-56, wherein the age-related disease is bone marrow failure.

Embodiment 58

The method of embodiment 47-56, wherein the age-related disease is aplastic anemia, myelodysplastic syndrome, or paroxysmal nocturnal hemoglobinuria.

Embodiment 59

A method of correcting human stem cell function in an aged microenvironment, the method comprising increasing production of one or more cytokines selected from the group consisting of BDNF, IL-17, IL-12p40, IL-23, ICAM-1, Eotaxin-1, B2M, AAT, SCF, MCP-1, VEGF, C3, RANTES, and IL-4 in bone marrow stromal cells; and optionally further administering an effective amount of a splicing modulator to the aged microenvironment.

Embodiment 60

The method of any embodiment 46 or 59, wherein the aged microenvironment is the area adjacent to the bone marrow stromal cells and/or the area in which the bone marrow stromal cells originate and grow.

Embodiment 61

The method of any one of embodiments 45-60, further comprising administering to the subject an effective amount of a splicing modulator.

Embodiment 62

A solid support comprising a plurality of detection agents that each bind to a protein encoded by the RNA set forth in Table 15A and/or Table 15B.

Embodiment 63

A solid support comprising a plurality of detection agents that each bind to a cytokines selected from the group consisting of BDNF, IL-17, IL-12p40, IL-23, ICAM-1, Eotaxin-1, B2M, AAT, SCF, MCP-1, VEGF, C3, RANTES, and IL-4.

Embodiment 64

A solid support comprising one or more probes that hybridize to one or more RNA sequences selected from the group consisting of: Table 15A and/or Table 15B.

Embodiment 65

The method of any one of embodiments 1, 2, 19, 22, 23, 40, 45, 46, 59, and 61, wherein the splicing modulator is a compound of Formula (I):

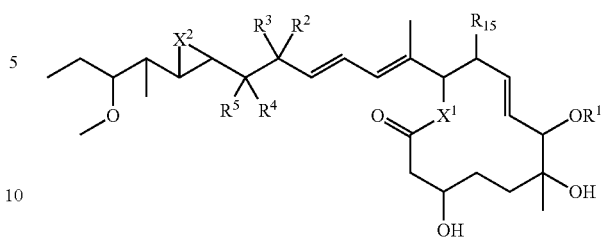

(I)

wherein, $X^1$ is N, O, or $CH_2$; $X^2$ is O or $C(R^6)(R^7)$; $R^6$ and $R^7$ are independently hydrogen, halogen, substituted or unsubstituted alkyl, substituted or unsubstituted aryl, $-OR^{12}$, $-OC(O)R^{12}$, $-OC(O)OR^{12}$, or $-OC(O)NR^{13}R^{14}$; $R^1$ is hydrogen, $-C(O)R^8$, $-OC(O)R^8$, $-OC(O)OR^8$, or $-NHC(O)NHR^8$; $R^2$, $R^3$, $R^4$, and $R^5$ are each independently selected from hydrogen, substituted or unsubstituted alkyl, $-OR^9$, $-OC(O)R^9$, $-OC(O)OR^9$, or $-OC(O)NR^{10}R^{11}$; $R^8$, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{15}$ is hydrogen, halogen, $CF_3$, $CCl_3$, $CBr_3$, $Cl_3$, substituted or unsubstituted alkyl.

Embodiment 66

The method of embodiment 65, wherein $X^2$ is O and the chiral carbon at $R^2$ has (R) stereochemistry and the chiral carbon at $R^4$ has (S) stereochemistry.

Embodiment 67

The method of embodiment 65, wherein $X^2$ is O and the chiral carbon at $R^2$ has (S) stereochemistry and the chiral carbon at $R^4$ has (R) stereochemistry.

Embodiment 68

The method of embodiment 65, wherein when $R^2$ is attached to a chiral carbon having (S) stereochemistry, $R^4$ is attached to a chiral carbon having (S) or (R) stereochemistry.

Embodiment 69

The method of embodiment 65, wherein $X^2$ is $C(R^6)(R^7)$ and the chiral carbon at $R^2$ has (R) stereochemistry and the chiral carbon at $R^4$ has (S) stereochemistry.

Embodiment 70

The method of embodiment 65, wherein $X^2$ is $C(R^6)(R^7)$ and the chiral carbon at $R^2$ has (S) stereochemistry and the chiral carbon at $R^4$ has (R) stereochemistry.

Embodiment 71

The method of embodiment 65, wherein the compound of Formula (I) is a compound selected from the group consisting of:

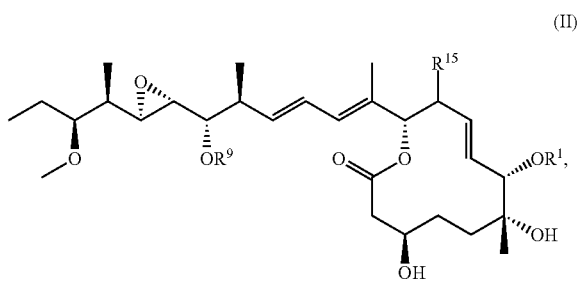
(II)

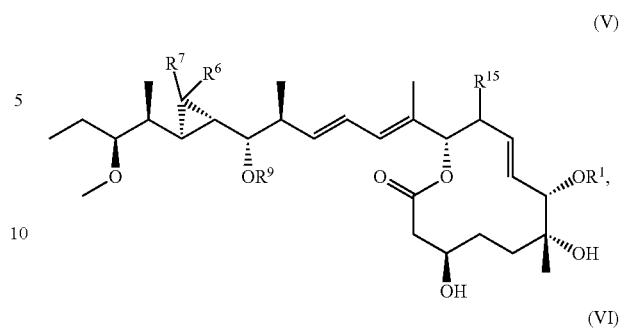
(V)

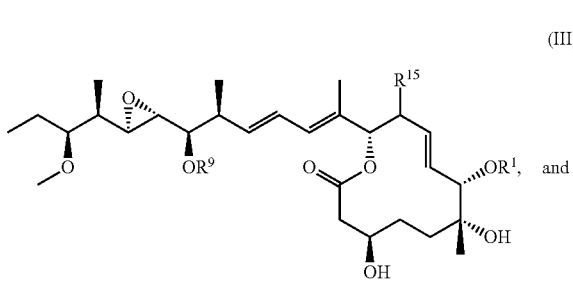
(III)

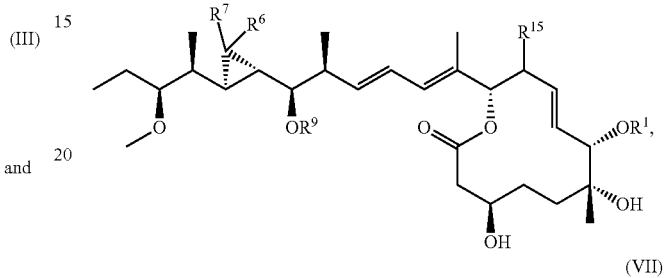
(VI)

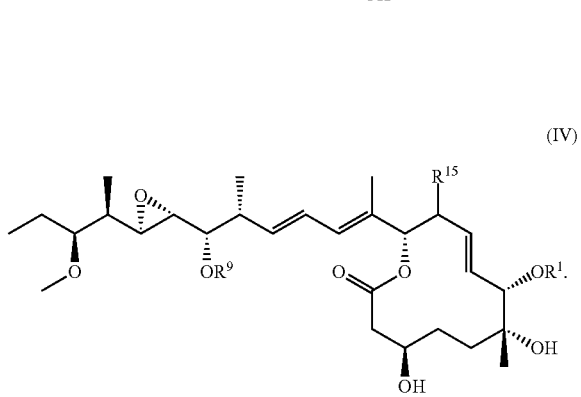
(IV)

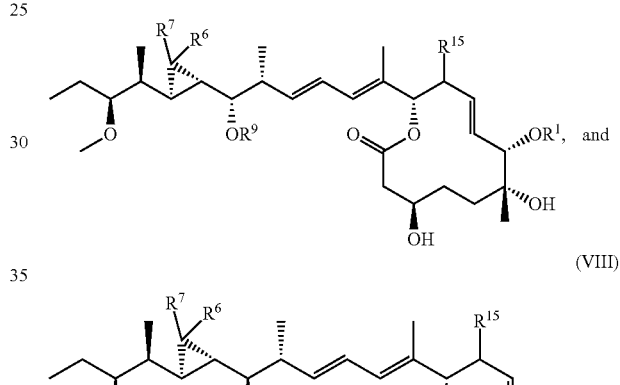
(VII)

and (VIII)

Embodiment 72

The method of embodiment 65, wherein the compound of Formula (I) is:

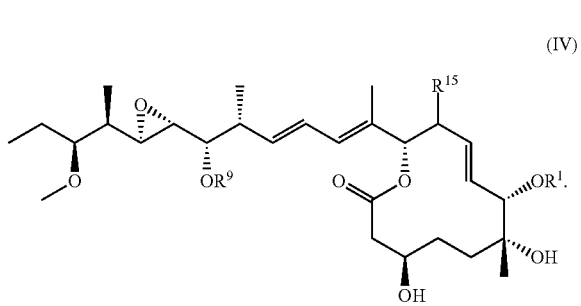
(IV)

Embodiment 73

The method of embodiment 65, wherein the compound of Formula (I) is a compound selected from the group consisting of:

Embodiment 74

The method of any one of embodiments 65-73, wherein $R^{15}$ is hydrogen or $C_1$-$C_4$ unsubstituted alkyl.

Embodiment 75

The method of any one of embodiments 65-73, wherein $R^{15}$ is hydrogen or methyl.

Embodiment 76

The method of any one of embodiments 65-73, wherein $R^{15}$ is methyl.

Embodiment 77

The method of any one of embodiments 65-73, wherein $R^9$ is hydrogen.

Embodiment 78

The method of any one of embodiments 65, 68, and 74-77, wherein X is O.

Embodiment 79

The method of any one of embodiments 65, 68, and 74-77, wherein $X^2$ is $C(R^6)(R^7)$.

Embodiment 80

The method of any one of embodiments 65, 68-70, 73-77, and 79, wherein $R^6$ and $R^7$ are independently hydrogen, halogen, or methyl.

Embodiment 81

The method of any one of embodiments 65, 68-70, 73-77, and 79, wherein $R^6$ and $R^7$ are hydrogen.

Embodiment 82

The method of any one of embodiments 65, 68-70, 73-77, and 79, wherein $R^6$ and $R^7$ are fluoride.

Embodiment 83

The method of embodiment 65, wherein the compound of Formula (I) is selected from the group consisting of:

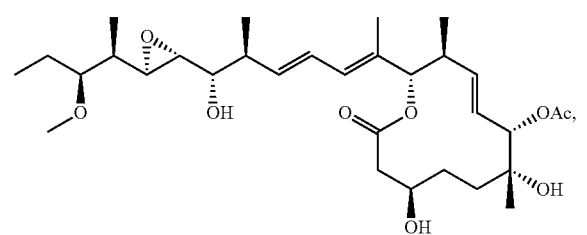
(IX)

(X)

(XI)

Embodiment 84

The method of embodiment 65, wherein the compound of Formula (I) is:

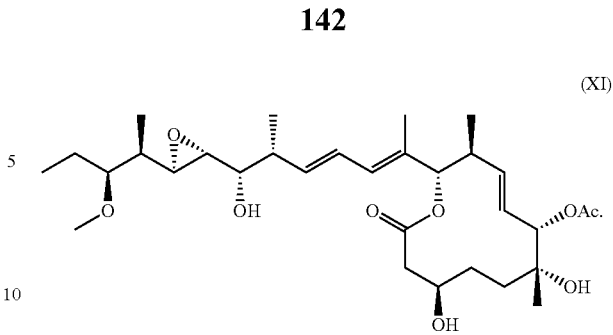
(XI)

Embodiment 85

The method of embodiment 65. wherein the compound of Formula (I) is selected from the group consisting of:

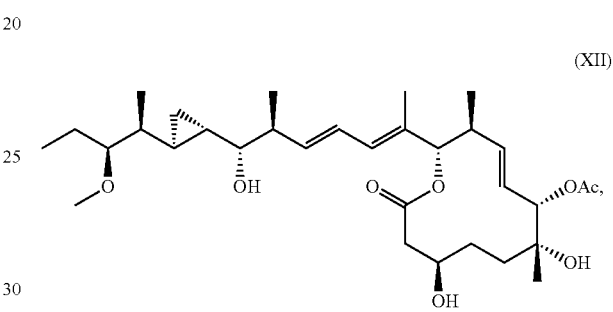
(XII)

(XIII)

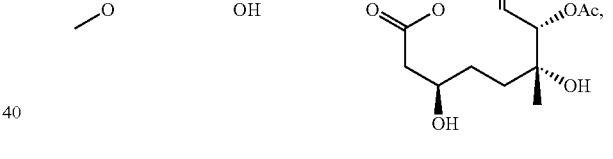
(XIV)

What is claimed is:

1. A method for treating acute myeloid leukemia in a subject in need thereof by modulation of acute myeloid leukemia stem cells, the method comprising administering to the subject an effective amount of a splicing modulator selected from a compound of Formula (I) or a pharmaceutically acceptable salt thereof; wherein the compound of Formula (I) is:

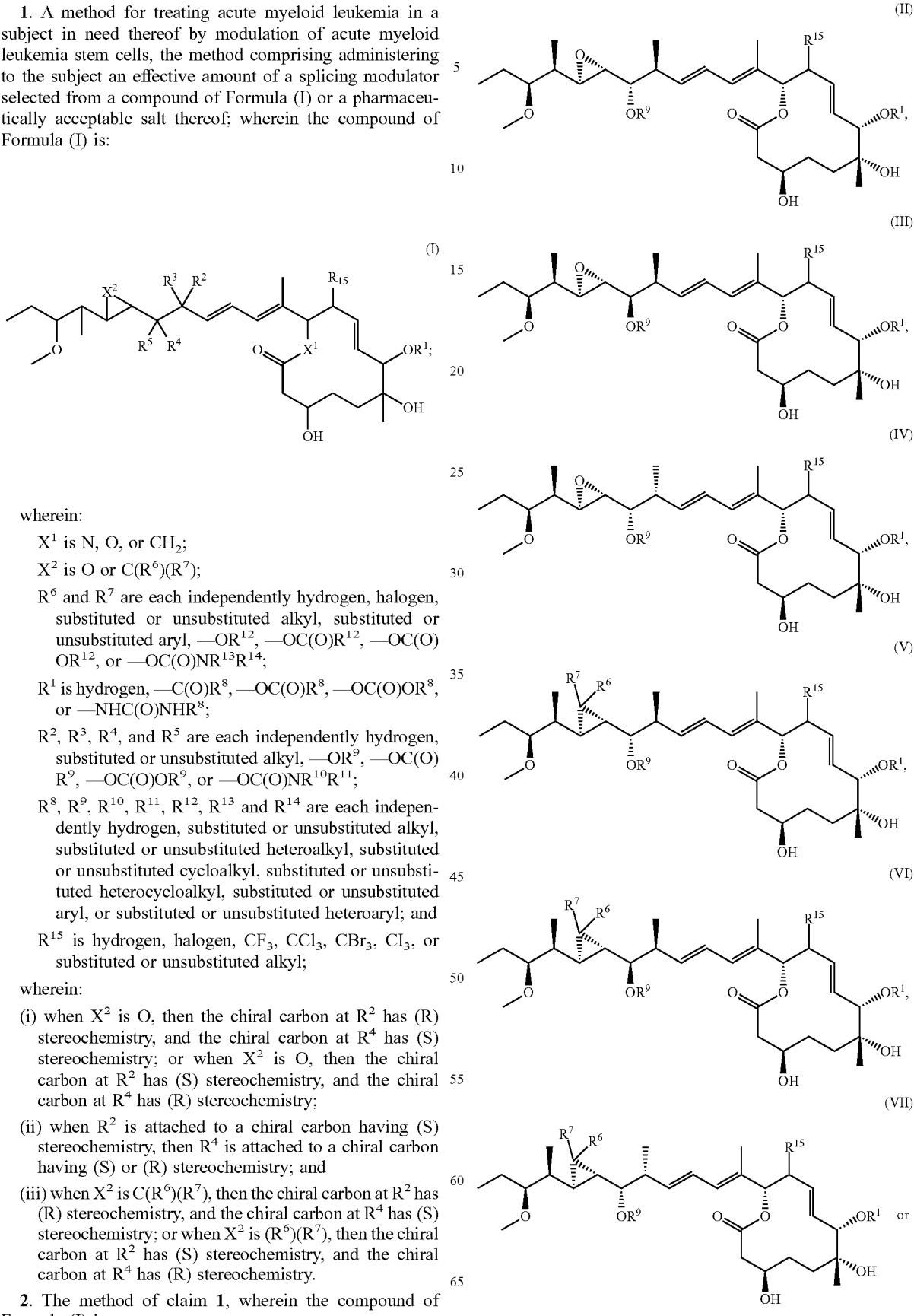

wherein:

$X^1$ is N, O, or $CH_2$;

$X^2$ is O or $C(R^6)(R^7)$;

$R^6$ and $R^7$ are each independently hydrogen, halogen, substituted or unsubstituted alkyl, substituted or unsubstituted aryl, —$OR^{12}$, —$OC(O)R^{12}$, —$OC(O)OR^{12}$, or —$OC(O)NR^{13}R^{14}$;

$R^1$ is hydrogen, —$C(O)R^8$, —$OC(O)R^8$, —$OC(O)OR^8$, or —$NHC(O)NHR^8$;

$R^2$, $R^3$, $R^4$, and $R^5$ are each independently hydrogen, substituted or unsubstituted alkyl, —$OR^9$, —$OC(O)R^9$, —$OC(O)OR^9$, or —$OC(O)NR^{10}R^{11}$;

$R^8$, $R^9$, $R^{10}$, $R^{11}$, $R^{12}$, $R^{13}$ and $R^{14}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{15}$ is hydrogen, halogen, $CF_3$, $CCl_3$, $CBr_3$, $CI_3$, or substituted or unsubstituted alkyl;

wherein:

(i) when $X^2$ is O, then the chiral carbon at $R^2$ has (R) stereochemistry, and the chiral carbon at $R^4$ has (S) stereochemistry; or when $X^2$ is O, then the chiral carbon at $R^2$ has (S) stereochemistry, and the chiral carbon at $R^4$ has (R) stereochemistry;

(ii) when $R^2$ is attached to a chiral carbon having (S) stereochemistry, then $R^4$ is attached to a chiral carbon having (S) or (R) stereochemistry; and (iii) when $X^2$ is $C(R^6)(R^7)$, then the chiral carbon at $R^2$ has (R) stereochemistry, and the chiral carbon at $R^4$ has (S) stereochemistry; or when $X^2$ is $(R^6)(R^7)$, then the chiral carbon at $R^2$ has (S) stereochemistry, and the chiral carbon at $R^4$ has (R) stereochemistry.

2. The method of claim 1, wherein the compound of Formula (I) is:

-continued (VIII)

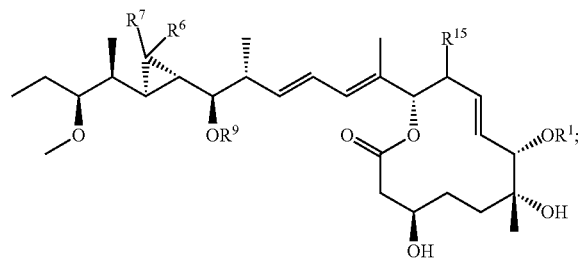

wherein R¹ is hydrogen or acetyl; R⁶ and R⁷ are each independently hydrogen, halogen, or methyl; R⁹ is hydrogen or $C_1$-$C_4$ unsubstituted alkyl; and R¹⁵ is hydrogen or $C_1$-$C_4$ unsubstituted alkyl.

3. The method of claim 1, wherein the compound of Formula (I) is:

(IX)

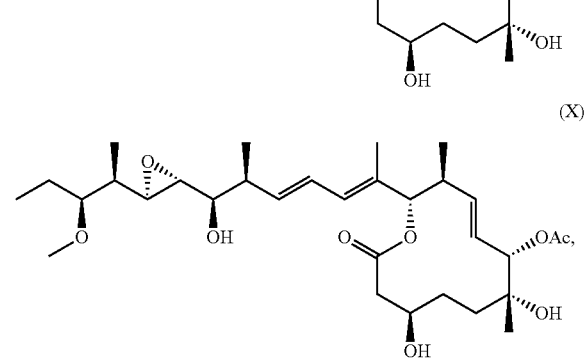

(X)

(XI)

(XII)

-continued (XIII)

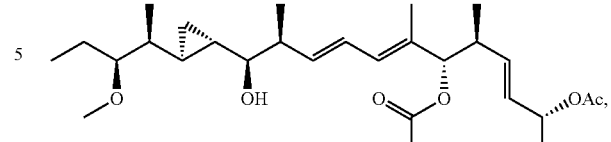

(XIV)

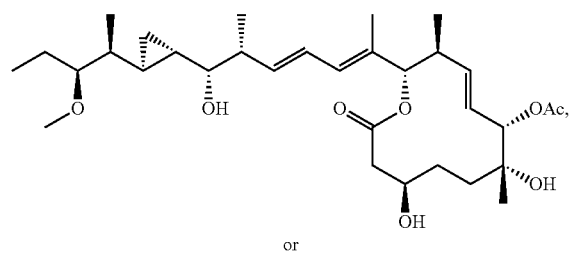

or (XII)

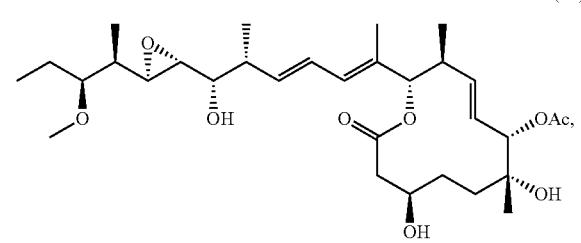

4. The method of claim 1, wherein the acute myeloid leukemia is secondary acute myeloid leukemia, refractory acute myeloid leukemia, or relapsed acute myeloid leukemia.

5. The method of claim 1, further comprising
  (i) obtaining a biological sample from the subject prior to administering the compound of Formula (I) or the pharmaceutically acceptable salt thereof;
  (ii) detecting a protein expression level of 1 to 100 proteins encoded by an RNA by contacting the biological sample with a detection agent capable of binding the one or more proteins, thereby forming a detectable complex; wherein the 1 to 100 proteins are encoded by an RNA selected from a first set or RNA and/or a second set of RNA, wherein
    (a) the first set of RNA comprises FXYD5-009, RPS3-023, RPS24-002, NAP1L1-018, TRGC2-001, CD44-012, ACTG1-014, S100A10-001, EIF3A-201, ACTG1-006, NRD1-005, ITGB2-201, PTPN6-003, TYROBP-002, ARPC1B-001, ANPEP-001, LMAN1-005, TAC3-010, C1orf228-020, CEP57-011, TWF2-001, ARRB2-003, PTK2B-202, C1orf228-011, DCP2-008, PPP1R18-003, RPL37P2-001, TMUB2-002, OAZ2-001, PTK2B-001, RP11-7707.1-001, XPC-007, SDR39U1-003, MACF1-014, SWSAP1-001, MGA-002, FHL3-002, ZC3H15-005, GPSM3-001, RBM28-003, LPIN2-002, PXN-002, WASF2-001, EIF4A1-001, RN7SL182P-201, SSBP4-008, PRR12-001, GOLGA4-004, ANKRD11-011, and C1orf228-005;
    (b) the second set of RNA comprises TMEM106C-007, RABL5-007, EIF4G2-022, HNRNPA1P7-001, RPLP0-008, CANX-005, TMEM106C-020, CTNNAL1-003, NPM1P27-001, NCAPH2-016, SRRM1-017, FAM129C-007, HMGB1-012, RC3H1-201, UGT3A2-001, WIPF3-002, RP11-315A17.1-001, ING3-006, ING3-005, CA1-009, IGHV5-78-001, CAST-038, CDH1-001, ING3-002, CXADR-001, HMHB1-001, AC015987.2-201, TYMS-002, ZFP36L2-001, CAST-039, VPREB1-002, EWSR1-019, FAM134A-004, AC096579.7-001, RNU1-78P-201, SELENBP1-001, HBB-001, EBF1-001, CLC-001, RGS2-001, UCA1-001, FTH1-002, AHSP-001, SNORA22-201, TMBIM6-006, NPY-001, RGS1-001, BLOC1S1-001, VPREB3-001, and RPL14-003; and (iii) detecting and quantitating the detectable complex to detect the protein expression level.

6. The method of claim 5, further comprising comparing the protein expression level to a subject that does not have acute myeloid leukemia.

7. The method of claim 6, wherein the acute myeloid leukemia is responsive to treatment with the compound of Formula (I) if the protein expression level of the first set of RNA is higher than in the subject that does not have acute myeloid leukemia; or wherein the acute myeloid leukemia is responsive to treatment with the compound of Formula (I) if the protein expression level of the second set of RNA is lower than in the subject that does not have acute myeloid leukemia.

8. The method of claim 5, wherein the 1 to 100 proteins is PTK2B, CD44, or a combination thereof.

9. The method of claim 5, comprising detecting the expression level of 5 to 100 proteins encoded by the RNA selected from the first set or RNA and/or the second set of RNA.

10. The method of claim 9, comprising detecting the expression level of 50 to 100 proteins encoded by the RNA selected from the first set or RNA and/or the second set of RNA.

11. The method of claim 1, further comprising
(i) obtaining a biological sample from the subject prior to administering the compound of Formula (I) or the pharmaceutically acceptable salt thereof;
(ii) detecting an expression level in 1 to 100 RNA by contacting the biological sample with one or more probes capable of hybridizing the 1 to 100 RNA, thereby forming a hybridized complex; wherein the one or more RNA are selected from a first set of RNA and/or a second set of RNA, wherein:
(a) the first set of RNA comprises FXYD5-009, RPS3-023, RPS24-002, NAP1L1-018, TRGC2-001, CD44-012, ACTG1-014, S100A10-001, EIF3A-201, ACTG1-006, NRD1-005, ITGB2-201, PTPN6-003, TYROBP-002, ARPC1B-001, ANPEP-001, LMAN1-005, TAC3-010, C1orf228-020, CEP57-011, TWF2-001, ARRB2-003, PTK2B-202, C1orf228-011, DCP2-008, PPP1R18-003, RPL37P2-001, TMUB2-002, OAZ2-001, PTK2B-001, RP11-7707.1-001, XPC-007, SDR39U1-003, MACF1-014, SWSAP1-001, MGA-002, FHL3-002, ZC3H15-005, GPSM3-001, RBM28-003, LPIN2-002, PXN-002, WASF2-001, EIF4A1-001, RN7SL182P-201, SSBP4-008, PRR12-001, GOLGA4-004, ANKRD11-011, and C1orf228-005,
(b) the second set of RNA comprises TMEM106C-007, RABL5-007, EIF4G2-022, HNRNPA1P7-001, RPLP0-008, CANX-005, TMEM106C-020, CTNNAL1-003, NPM1P27-001, NCAPH2-016, SRRM1-017, FAM129C-007, HMGB1-012, RC3H1-201, UGT3A2-001, WIPF3-002, RP11-315A17.1-001, ING3-006, ING3-005, CA1-009, IGHV5-78-001, CAST-038, CDH1-001, ING3-002, CXADR-001, HMHB1-001, AC015987.2-201, TYMS-002, ZFP36L2-001, CAST-039, VPREB1-002, EWSR1-019, FAM134A-004, AC096579.7-001, RNU1-78P-201, SELENBP1-001, HBB-001, EBF1-001, CLC-001, RGS2-001, UCA1-001, FTH1-002, AHSP-001, SNORA22-201, TMBIM6-006, NPY-001, RGS1-001, BLOC1S1-001, VPREB3-001, and RPL14-003, (iii) detecting and quantitating the hybridized complex to detect the RNA expression level.

12. The method of claim 11, further comprising comparing the RNA expression level to a subject that does not have acute myeloid leukemia.

13. The method of claim 12, wherein the acute myeloid leukemia is responsive to treatment with the compound of Formula (I) if the RNA expression level of the first set of RNA is higher than in the subject that does not have acute myeloid leukemia; or wherein the acute myeloid leukemia is responsive to treatment with the compound of Formula (I) if the RNA expression level of the second set of RNA is lower than in the subject that does not have acute myeloid leukemia.

14. The method of claim 11, comprising detecting the expression level of 5 to 100 RNA selected from the first set or RNA and/or the second set of RNA.

15. The method of claim 14, comprising detecting the expression level of 50 to 100 RNA selected from the first set or RNA and/or the second set of RNA.

16. A method for modulating acute myeloid leukemia stem cells, the method comprising contacting the acute myeloid leukemia stem cells with an effective amount of a splicing modulator selected from a compound of Formula (I) or a pharmaceutically acceptable salt thereof, thereby modulating the acute myeloid leukemia stem cells; wherein the compound of Formula (I) is:

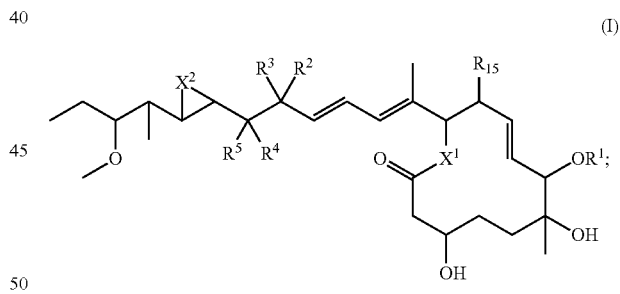

wherein:
$X^1$ is N, O, or $CH_2$;
$X^2$ is O or $C(R^6)(R^7)$;
$R^6$ and $R^7$ are each independently hydrogen, halogen, substituted or unsubstituted alkyl, substituted or unsubstituted aryl, $-OR^{12}$, $-OC(O)R^{12}$, $-OC(O)OR^{12}$, or $-OC(O)NR^{13}R^{14}$;
$R^1$ is hydrogen, $-C(O)R^8$, $-OC(O)R^8$, $-OC(O)OR^8$, or $-NHC(O)NHR^8$;
$R^2$, $R^3$, $R^4$, and $R^5$ are each independently hydrogen, substituted or unsubstituted alkyl, $-OR^9$, $-OC(O)R^9$, $-OC(O)OR^9$, or $-OC(O)NR^{10}R^{11}$;
$R^8$, $R^9$, $R^{10}$, $R^{11}$, $R^{12}$, $R^{13}$ and $R^{14}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{15}$ is hydrogen, halogen, $CF_3$, $CCl_3$, $CBr_3$, $CI_3$, or substituted or unsubstituted alkyl;

wherein:
(i) when $X^2$ is O, then the chiral carbon at $R^2$ has (R) stereochemistry, and the chiral carbon at $R^4$ has (S) stereochemistry; or when $X^2$ is O, then the chiral carbon at $R^2$ has (S) stereochemistry, and the chiral carbon at $R^4$ has (R) stereochemistry;
(ii) when $R^2$ is attached to a chiral carbon having (S) stereochemistry, then $R^4$ is attached to a chiral carbon having (S) or (R) stereochemistry; and
(iii) when $X^2$ is $C(R^6)(R^7)$, then the chiral carbon at $R^2$ has (R) stereochemistry, and the chiral carbon at $R^4$ has (S) stereochemistry; or when $X^2$ is $(R^6)(R^7)$, then the chiral carbon at $R^2$ has (S) stereochemistry, and the chiral carbon at $R^4$ has (R) stereochemistry.

17. The method of claim 15, wherein the compound of Formula (I) is:

(II)

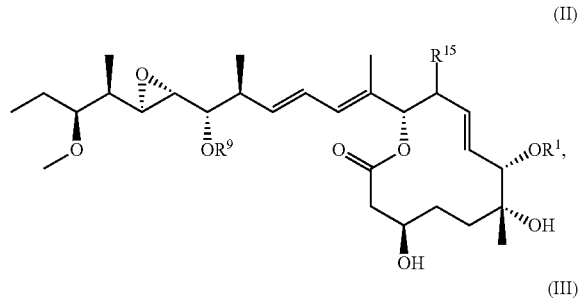

(III)

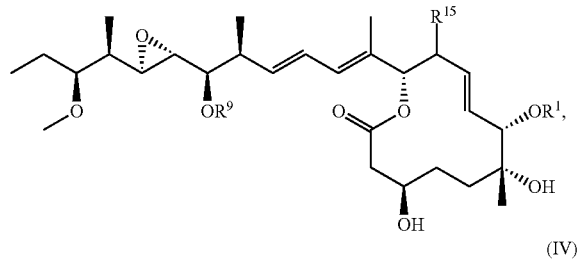

(IV)

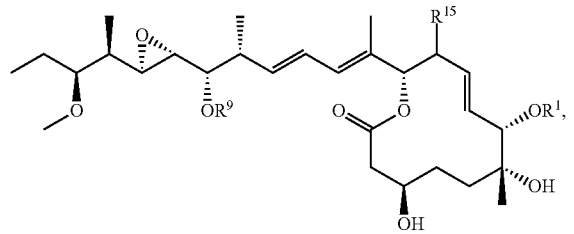

(V)

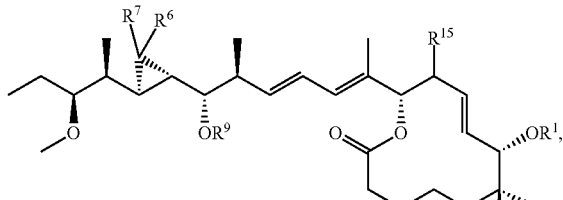

(VI)

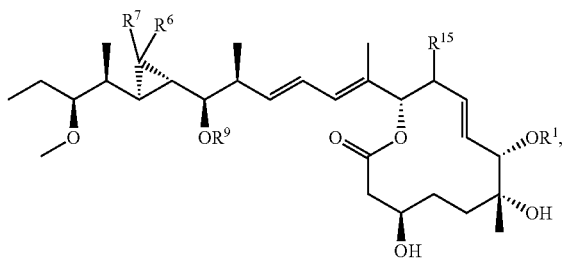

(VII)

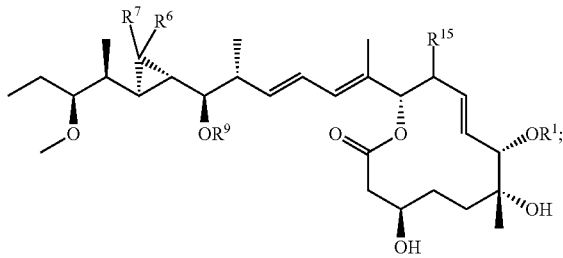

or (VIII)

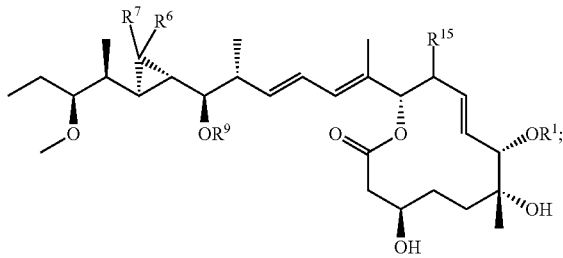

wherein $R^1$ is hydrogen or acetyl; $R^6$ and $R^7$ are each independently hydrogen, halogen, or methyl; $R^9$ is hydrogen or $C_1$-$C_4$ unsubstituted alkyl; and $R^{15}$ is hydrogen or $C_1$-$C_4$ unsubstituted alkyl.

* * * * *

SEQUENCE LISTING

<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 1
tcagggattt gaatcatgtt tgtg                                          24

<210> SEQ ID NO 2
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 2
cgatgtcaat aggactccag atg                                           23

<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3
agcttttgct gttgtagcct ctg                                           23

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
gcttgccagg acttcttgct                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
atgtgtgtgg agagcgtcaa                                               20

<210> SEQ ID NO 6
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 6
ttcagagaca gccaggagaa a                                             21

<210> SEQ ID NO 7
<211> LENGTH: 20
<212> TYPE: DNA
<213> ORGANISM: Artificial Sequence

```
<220> FEATURE:
<223> OTHER INFORMATION: Synthetic polynucleotide

<400> SEQUENCE: 7
atgtgtgtgg agagcgtcaa                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
ctcagcccag actcacatca                                                20

<210> SEQ ID NO 9
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 9
agaccttacg acgggttgg                                                 19

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
aatcctgccc cagtttgtta                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
gaggaggacg agttgtaccg                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
actccacaaa cccatccttg                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
catggcagca gtaaagcaag                                                20
```

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
gaaggagaaa aaggccacaa                    20

<210> SEQ ID NO 15
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 15
ctgcagttcc aggaggag                      18

<210> SEQ ID NO 16
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 16
ctgtgaactc caggtagcc                     19

<210> SEQ ID NO 17
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 17
ggcctgatgg gtcttatcta tgg                23

<210> SEQ ID NO 18
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 18
ttagatggaa gctggctcaa gag                23

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 19
tgaccagcca tctggaaatc                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
caccatctgt cccacaacac                                               20

<210> SEQ ID NO 21
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 21
gaaccaaaat cactttcccc aaggaagg                                      28

<210> SEQ ID NO 22
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 22
aatgaggtcc ccacgtttct cgggtgt                                       27

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 23
ctcggtacct tcgggagcag gc                                            22

<210> SEQ ID NO 24
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 24
ccagcagcac attcctgatg cc                                            22